US012758628B2

(12) United States Patent
Lauterbach et al.

(10) Patent No.: US 12,758,628 B2
(45) Date of Patent: Oct. 13, 2026

(54) RECOMBINANT MVA VIRUSES FOR INTRATUMORAL AND/OR INTRAVENOUS ADMINISTRATION FOR TREATING CANCER

(71) Applicant: Bavarian Nordic A/S, Hellerup (DK)

(72) Inventors: Henning Lauterbach, Herrsching am Ammersee (DE); Maria Hinterberger, Sauerlach (DE); José Medina Echeverz, Munich (DE); Matthias Habjan, Puchheim (DE); Jürgen Hausmann, Gundelfingen (DE); Markus Kalla, Penzberg (DE)

(73) Assignee: Bavarian Nordic A/S, Hellerup (DK)

( * ) Notice: Subject to any disclaimer, the term of this patent is extended or adjusted under 35 U.S.C. 154(b) by 1042 days.

(21) Appl. No.: 17/778,374

(22) PCT Filed: Nov. 20, 2020

(86) PCT No.: PCT/EP2020/082926

§ 371 (c)(1),
(2) Date: May 19, 2022

(87) PCT Pub. No.: WO2021/099586

PCT Pub. Date: May 27, 2021

(65) Prior Publication Data

US 2023/0190922 A1 Jun. 22, 2023

(30) Foreign Application Priority Data

Nov. 20, 2019 (EP) .................................... 19210369
Aug. 31, 2020 (EP) .................................... 20193706

(51) Int. Cl.

| | |
|---|---|
| ***A61K 39/285*** | (2006.01) |
| ***A61K 9/00*** | (2006.01) |
| ***A61K 39/00*** | (2006.01) |
| ***A61K 40/11*** | (2025.01) |
| ***A61K 40/42*** | (2025.01) |
| ***A61P 37/04*** | (2006.01) |

(52) U.S. Cl.

CPC .......... *A61K 39/285* (2013.01); *A61K 9/0019* (2013.01); *A61K 39/0011* (2013.01); *A61K 39/001117* (2018.08); *A61K 40/11* (2025.01); *A61K 40/42* (2025.01); *A61P 37/04* (2018.01); *A61K 2039/5254* (2013.01)

(58) Field of Classification Search

None

See application file for complete search history.

(56) References Cited

U.S. PATENT DOCUMENTS 11,351,247 B2 * 6/2022 Holst ..................... C12N 15/86
12,390,515 B2 * 8/2025 Lauterbach .... A61K 39/001102

FOREIGN PATENT DOCUMENTS

| | | | |
|---|---|---|---|
| WO | 2014037124 | A1 | 3/2014 |
| WO | WO 2015175334 | A2 | 11/2015 |
| WO | WO 2019038388 | A1 | 2/2019 |
| WO | 2019043127 | A9 | 3/2019 |
| WO | 2020104531 | A1 | 5/2020 |

OTHER PUBLICATIONS

Kraus et al. (PLOS, 2013, vol. 8, p. 3-8).*
Kraus et al. (Virology Journal, 2014, p. 1-7).*
Kim et al. (PloSOne, 2018, p. 1-10).*
Maisinger-Henschel et al. (Journal of Virology, 2010, p. 9907-9919).*
Kim et al., "Host lymphodepletion enhances the therapeutic activity of an oncolytic vaccinia virus expressing 4-1BB ligand," Cancer Res., 2009, pp. 8516-8525, vol. 69.
Kraus et al., "Vaccination directed against the human endogenous retrovirus-K (HERV-K) gag protein . . . ," Virol. J., 2014, pp. 58, vol. 11.
Kudo-Saito et al., "4-1BB ligand enhances tumor-specific immunity of poxvirus vaccines," Vaccine, 2006, pp. 4975-4986, vol. 24.
Medina Echeverz et al., "Synergistic cancer immunotherapy combines MVA-CD40L induced innate and adaptive immunity with tumor targeting antibodies," Nature Comm., 2019, pp. 5041, vol. 10.
Ragonnaud et al., "An adenoviral cancer vaccine co-encoding a tumor associated antigen together with secreted 4-1BBL leads to delayed tumor progression," Vaccine, 2016, pp. 2147-2156, vol. 34.
Spencer et al., "4-1BBL enhances CD8+ T cell responses induced by vectored vaccines in mice but fails to improve immunogenicity in Rhesus macaques," PLoS One, 2014, pp. 1-12, vol. 9.
Kraus et al., "Vaccination directed against the Human Endogenous Retrovirus-K Envelope Protein Inhibits Tumor Growth . . . ," PLoS One, 2013, e72756, vol. 8.
Sacha et al., "Vaccination with Cancer- and HIV Infection-associated Endogenous Retrotransposable Elements . . . ," J. Immunol., 2012, pp. 1467-1479, vol. 189.
Kalli et al., "Folate Receptor Alpha Peptide Vaccine Generates Immunity in Breast and Ovarian Cancer Patients," Clin. Cancer Res., 2018, pp. 3014-3025, vol. 24, AACR Journals, Philadelphia, PA.
Krishnamurthy et al., "Genetic Engineering of T Cells to Target HERV-K, an Ancient Retrovirus on Melanoma," Clin. Cancer Res., 2015, pp. 3241-3251, vol. 21, AACR Journals, Philadelphia, PA.

* cited by examiner

*Primary Examiner* — Agnieszka Boesen

(57) ABSTRACT

The invention relates to a composition and related methods for reducing tumor volume and/or increasing the survival of a cancer patient. The composition comprises a recombinant MVA encoding a Tumor Associated Antigen ("TAA") as well as 4-1BBL and/or CD40L and can be administered to a subject in any suitable manner, including by intravenous and/or intratumoral administration.

8 Claims, 38 Drawing Sheets

Specification includes a Sequence Listing.

SEQUENCE LISTING

<160> NUMBER OF SEQ ID NOS: 12

<210> SEQ ID NO 1
<211> LENGTH: 261
<212> TYPE: PRT
<213> ORGANISM: Homo sapiens

<400> SEQUENCE: 1

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60
```

```
Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260
```

<210> SEQ ID NO 2
<211> LENGTH: 792
<212> TYPE: DNA
<213> ORGANISM: Homo sapiens

<400> SEQUENCE: 2

```
atgatcgaga catacaacca gacaagccct agaagcgccg ccacaggact gcctatcagc      60

atgaagatct tcatgtacct gctgaccgtg ttcctgatca cccagatgat cggcagcgcc     120

ctgtttgccg tgtacctgca cagacggctg gacaagatcg aggacgagag aaacctgcac     180

gaggacttcg tgttcatgaa gaccatccag cggtgcaaca ccggcgagag aagtctgagc     240

ctgctgaact gcgaggaaat caagagccag ttcgagggct tcgtgaagga catcatgctg     300

aacaaagagg aaacgaagaa agagaactcc ttcgagatgc agaagggcga ccagaatcct     360

cagatcgccg ctcacgtgat cagcgaggcc agcagcaaga caacaagcgt gctgcagtgg     420

gccgagaagg gctactacac catgagcaac aacctggtca ccctggagaa cggcaagcag     480

ctgacagtga agcggcaggg cctgtactac atctacgccc aagtgacctt ctgcagcaac     540

agagaggcca gctctcaggc tcctttcatc gccagcctgt gcctgaagtc tcctggcaga     600

ttcgagcgga ttctgctgag agccgccaac acacacagca gcgccaaacc ttgtggccag     660

cagtctattc acctcggcgg agtgtttgag ctgcagcctg gcgcaagcgt gttcgtgaat     720

gtgacagacc ctagccaggt gtcccacggc accggcttta catctttcgg actgctgaag     780

ctgtgatgat ag                                                         792
```

<210> SEQ ID NO 3
<211> LENGTH: 254
<212> TYPE: PRT

<213> ORGANISM: Homo sapiens

<400> SEQUENCE: 3

Met Glu Tyr Ala Ser Asp Ala Ser Leu Asp Pro Glu Ala Pro Trp Pro
1 5 10 15

Pro Ala Pro Arg Ala Arg Ala Cys Arg Val Leu Pro Trp Ala Leu Val
20 25 30

Ala Gly Leu Leu Leu Leu Leu Leu Leu Ala Ala Ala Cys Ala Val Phe
35 40 45

Leu Ala Cys Pro Trp Ala Val Ser Gly Ala Arg Ala Ser Pro Gly Ser
50 55 60

Ala Ala Ser Pro Arg Leu Arg Glu Gly Pro Glu Leu Ser Pro Asp Asp
65 70 75 80

Pro Ala Gly Leu Leu Asp Leu Arg Gln Gly Met Phe Ala Gln Leu Val
85 90 95

Ala Gln Asn Val Leu Leu Ile Asp Gly Pro Leu Ser Trp Tyr Ser Asp
100 105 110

Pro Gly Leu Ala Gly Val Ser Leu Thr Gly Gly Leu Ser Tyr Lys Glu
115 120 125

Asp Thr Lys Glu Leu Val Val Ala Lys Ala Gly Val Tyr Tyr Val Phe
130 135 140

Phe Gln Leu Glu Leu Arg Arg Val Val Ala Gly Glu Gly Ser Gly Ser
145 150 155 160

Val Ser Leu Ala Leu His Leu Gln Pro Leu Arg Ser Ala Ala Gly Ala
165 170 175

Ala Ala Leu Ala Leu Thr Val Asp Leu Pro Pro Ala Ser Ser Glu Ala
180 185 190

Arg Asn Ser Ala Phe Gly Phe Gln Gly Arg Leu Leu His Leu Ser Ala
195 200 205

Gly Gln Arg Leu Gly Val His Leu His Thr Glu Ala Arg Ala Arg His
210 215 220

Ala Trp Gln Leu Thr Gln Gly Ala Thr Val Leu Gly Leu Phe Arg Val
225 230 235 240

Thr Pro Glu Ile Pro Ala Gly Leu Pro Ser Pro Arg Ser Glu
245 250

<210> SEQ ID NO 4
<211> LENGTH: 768
<212> TYPE: DNA
<213> ORGANISM: Homo sapiens

<400> SEQUENCE: 4
atggaatacg ccagcgacgc ctctctggac cctgaagctc cttggcctcc agctcctaga 60
gccagggctt gtagagtgct gccttgggct cttgtggctg gacttctgct tctgttgctc 120
ctggctgctg cctgcgcagt gtttcttgct tgtccatggg ctgtgtcagg agccagagca 180
tctcctggat ctgccgcttc tcccagactg agagagggac ctgaactgag ccctgatgat 240
cctgctggac tgctcgacct gagacagggc atgtttgccc agctggtggc ccagaatgtg 300
ctgctgattg atggccctct gagctggtac agcgatcctg gacttgctgg cgttagcctg 360
actggaggcc tgagctacaa ggaggacacc aaagaactgg tggtggccaa ggctggcgtg 420
tactacgtgt tctttcagct ggaactgcgg agagtggtgg caggcgaagg atctggatcc 480
gtgtctctgg cactgcatct gcagcctctg agatctgctg ctggtgcagc tgccctggct 540
ctgacagttg atctgcctcc tgcctccagc gaagccagaa acagcgcctt tggcttccaa 600
ggcagactgc tgcacctgtc tgctggccag agactgggag tgcacctcca cacagaagca 660
agagcaagac acgcctggca gcttacacaa ggcgctacag tgctgggcct gttcagagtg 720
acacctgaga ttccagctgg cttgccatct cctcgcagcg agtaatga 768

<210> SEQ ID NO 5
<211> LENGTH: 666
<212> TYPE: PRT
<213> ORGANISM: Artificial sequence
<220> FEATURE:
<223> OTHER INFORMATION: Synthetic ERV-K-gag protein consensus sequence

<400> SEQUENCE: 5

Met Gly Gln Thr Lys Ser Lys Ile Lys Ser Lys Tyr Ala Ser Tyr Leu
1 5 10 15

Ser Phe Ile Lys Ile Leu Leu Lys Arg Gly Gly Val Lys Val Ser Thr
20 25 30

Lys Asn Leu Ile Lys Leu Phe Gln Ile Ile Glu Gln Phe Cys Pro Trp
35 40 45

Phe Pro Glu Gln Gly Thr Leu Asp Leu Lys Asp Trp Lys Arg Ile Gly
50 55 60

Lys Glu Leu Lys Gln Ala Gly Arg Lys Gly Asn Ile Ile Pro Leu Thr
65 70 75 80

Val Trp Asn Asp Trp Ala Ile Ile Lys Ala Ala Leu Glu Pro Phe Gln
85 90 95

Thr Glu Glu Asp Ser Val Ser Val Ser Asp Ala Pro Gly Ser Cys Ile
100 105 110

Ile Asp Cys Asn Glu Asn Thr Arg Lys Lys Ser Gln Lys Glu Thr Glu
115 120 125

Ser Leu His Cys Glu Tyr Val Ala Glu Pro Val Met Ala Gln Ser Thr
130 135 140

Gln Asn Val Asp Tyr Asn Gln Leu Gln Glu Val Ile Tyr Pro Glu Thr
145 150 155 160

Leu Lys Leu Glu Gly Lys Gly Pro Glu Leu Val Gly Pro Ser Glu Ser
165 170 175

Lys Pro Arg Gly Thr Ser Pro Leu Pro Ala Gly Gln Val Pro Val Thr
180 185 190

Leu Gln Pro Gln Lys Gln Val Lys Glu Asn Lys Thr Gln Pro Pro Val
195 200 205

Ala Tyr Gln Tyr Trp Pro Pro Ala Glu Leu Gln Tyr Arg Pro Pro Pro
210 215 220

Glu Ser Gln Tyr Gly Tyr Pro Gly Met Pro Pro Ala Pro Gln Gly Arg
225 230 235 240

Ala Pro Tyr Pro Gln Pro Pro Thr Arg Arg Leu Asn Pro Thr Ala Pro
245 250 255

Pro Ser Arg Gln Gly Ser Glu Leu His Glu Ile Ile Asp Lys Ser Arg
260 265 270

Lys Glu Gly Asp Thr Glu Ala Trp Gln Phe Pro Val Thr Leu Glu Pro
275 280 285

Met Pro Pro Gly Glu Gly Ala Gln Glu Gly Glu Pro Pro Thr Val Glu
290 295 300

Ala Arg Tyr Lys Ser Phe Ser Ile Lys Met Leu Lys Asp Met Lys Glu
305 310 315 320

Gly Val Lys Gln Tyr Gly Pro Asn Ser Pro Tyr Met Arg Thr Leu Leu
325 330 335

```
Asp Ser Ile Ala His Gly His Arg Leu Ile Pro Tyr Asp Trp Glu Ile
            340                 345                 350

Leu Ala Lys Ser Ser Leu Ser Pro Ser Gln Phe Leu Gln Phe Lys Thr
        355                 360                 365

Trp Trp Ile Asp Gly Val Gln Glu Gln Val Arg Arg Asn Arg Ala Ala
    370                 375                 380

Asn Pro Pro Val Asn Ile Asp Ala Asp Gln Leu Leu Gly Ile Gly Gln
385                 390                 395                 400

Asn Trp Ser Thr Ile Ser Gln Gln Ala Leu Met Gln Asn Glu Ala Ile
                405                 410                 415

Glu Gln Val Arg Ala Ile Cys Leu Arg Ala Trp Glu Lys Ile Gln Asp
            420                 425                 430

Pro Gly Ser Thr Cys Pro Ser Phe Asn Thr Val Arg Gln Gly Ser Lys
        435                 440                 445

Glu Pro Tyr Pro Asp Phe Val Ala Arg Leu Gln Asp Val Ala Gln Lys
    450                 455                 460

Ser Ile Ala Asp Glu Lys Ala Arg Lys Val Ile Val Glu Leu Met Ala
465                 470                 475                 480

Tyr Glu Asn Ala Asn Pro Glu Cys Gln Ser Ala Ile Lys Pro Leu Lys
                485                 490                 495

Gly Lys Val Pro Ala Gly Ser Asp Val Ile Ser Glu Tyr Val Lys Ala
            500                 505                 510

Cys Asp Gly Ile Gly Gly Ala Met His Lys Ala Met Leu Met Ala Gln
        515                 520                 525

Ala Ile Thr Gly Val Val Leu Gly Gly Gln Val Arg Thr Phe Gly Gly
    530                 535                 540

Lys Cys Tyr Asn Cys Gly Gln Ile Gly His Leu Lys Lys Asn Cys Pro
545                 550                 555                 560

Val Leu Asn Lys Gln Asn Ile Thr Ile Gln Ala Thr Thr Thr Gly Arg
                565                 570                 575

Glu Pro Pro Asp Leu Cys Pro Arg Cys Lys Lys Gly Lys His Trp Ala
            580                 585                 590

Ser Gln Cys Arg Ser Lys Phe Asp Lys Asn Gly Gln Pro Leu Ser Gly
        595                 600                 605

Asn Glu Gln Arg Gly Gln Pro Gln Ala Pro Gln Gln Thr Gly Ala Phe
    610                 615                 620

Pro Ile Gln Pro Phe Val Pro Gln Gly Phe Gln Gly Gln Gln Pro Pro
625                 630                 635                 640

Leu Ser Gln Val Phe Gln Gly Ile Ser Gln Leu Pro Gln Tyr Asn Asn
                645                 650                 655

Cys Pro Pro Pro Gln Ala Ala Val Gln Gln
            660                 665
```

<210> SEQ ID NO 6
<211> LENGTH: 2004
<212> TYPE: DNA
<213> ORGANISM: Artificial sequence
<220> FEATURE:
<223> OTHER INFORMATION: Synthetic ERV-K-gag nucleotide sequence

<400> SEQUENCE: 6

```
atgggacaga ccaagagtaa gatcaagtct aagtacgcca gctacctcag cttcatcaag     60

atcctgctga agagaggagg cgtgaaagtg tccaccaaga acctgatcaa gctgttccag    120

atcatcgagc agttctgtcc ctggtttcct gagcagggca ccctggatct gaaggactgg    180
```

```
aagcggatcg gcaaagagct gaagcaggct ggcagaaagg gcaacatcat ccctctgacc    240

gtgtggaacg actgggccat catcaaagca gctctggaac ccttccagac cgaagaggat    300

agcgtgtccg tgtctgatgc tcctggcagc tgcatcatcg actgcaacga gaacacccgg    360

aagaagtccc agaaagagac agagagcctg cactgcgagt acgtggccga acctgtgatg    420

gctcagagca cccagaacgt ggactacaac cagctccaag aagtgatcta tcccgaaaca    480

ctgaagctgg aaggcaaggg acctgaactc gtgggtcctt ctgagtctaa gcccagaggc    540

acatctcctc tgcctgcagg acaggtgcca gtgacactgc agcctcagaa acaagtgaaa    600

gagaacaaga cccagcctcc tgtggcctac cagtattggc ctccagccga gctgcagtac    660

agacctcctc cagagagcca gtacggctac cctggaatgc ctcctgctcc tcaaggcaga    720

gctccttatc ctcagcctcc taccagacgg ctgaacccta cagctcctcc tagcagacag    780

ggctctgagc tgcacgagat cattgacaag agccggaaag agggcgacac cgaggcttgg    840

cagtttcccg ttacactgga acccatgcct ccaggcgaag gcgctcaaga aggcgaacct    900

cctacagtgg aagccaggta caagagcttc agcatcaaga tgctgaagga catgaaggaa    960

ggcgtcaagc agtacggacc taacagccca tacatgcgga ccctgctgga ttctattgcc   1020

cacggccacc ggctgatccc ttacgattgg gagatcctgg ctaagtcctc tctgagccct   1080

agccagttcc tgcagttcaa gacctggtgg atcgacggcg tgcaagaaca agtgagacgg   1140

aacagagctg ccaatcctcc tgtgaacatc gacgccgacc agctcctcgg aatcggccag   1200

aattggagca ccatctctca gcaggctctg atgcagaacg aggccattga acaagtcaga   1260

gccatctgcc tgagagcttg ggagaagatt caggacccag gcagcacatg tcccagcttc   1320

aataccgttc ggcagggcag caaagagccc tatcctgact ttgtggctag actgcaggat   1380

gtggcccaga agtctattgc cgacgagaag gctcggaaag tgatcgtgga actgatggcc   1440

tacgagaacg ctaatccaga gtgccagagc gccatcaagc ccttgaaggg caaagtgcct   1500

gccggatccg atgtgatcag cgagtatgtg aaggcctgcg acggaatcgg aggtgccatg   1560

cacaaagcca tgctgatggc acaggccatc actggcgttg tgctcggagg acaagttcgg   1620

acctttggag gcaagtgcta caactgtggc cagatcggac acctgaagaa gaactgccct   1680

gtgctgaaca agcagaacat caccatccag gccaccacca ccggcagaga acctccagat   1740

ctgtgcccta gatgcaagaa gggcaagcac tgggccagcc agtgcagaag caagttcgac   1800

aagaacggcc agcctctgag cggcaacgaa caaagaggac agcctcaggc tcctcagcag   1860

actggcgcat ttccaatcca gcccttcgtg cctcaaggct tccagggaca acagcctcca   1920

ctgtctcagg tgttccaggg cattagccag ctccctcagt acaacaactg ccctccacct   1980

caggctgctg tgcagcagtg atga                                          2004
```

<210> SEQ ID NO 7
<211> LENGTH: 699
<212> TYPE: PRT
<213> ORGANISM: Artificial sequence
<220> FEATURE:
<223> OTHER INFORMATION: Synthetic ERV-K-env/MEL protein sequence

<400> SEQUENCE: 7

```
Met Asn Pro Ser Glu Met Gln Arg Lys Ala Pro Pro Arg Arg Arg Arg
1               5                   10                  15

His Arg Asn Arg Ala Pro Leu Thr His Lys Met Asn Lys Met Val Thr
            20                  25                  30
```

```
Ser Glu Glu Gln Met Lys Leu Pro Ser Thr Lys Lys Ala Glu Pro Pro
        35                  40                  45

Thr Trp Ala Gln Leu Lys Lys Leu Thr Gln Leu Ala Thr Lys Tyr Leu
    50                  55                  60

Glu Asn Thr Lys Val Thr Gln Thr Pro Glu Ser Met Leu Leu Ala Ala
65                  70                  75                  80

Leu Met Ile Val Ser Met Val Val Ser Leu Pro Met Pro Ala Gly Ala
                85                  90                  95

Ala Ala Ala Asn Tyr Thr Tyr Trp Ala Tyr Val Pro Phe Pro Pro Met
            100                 105                 110

Ile Arg Ala Val Thr Trp Met Asp Asn Pro Ile Glu Val Tyr Val Asn
        115                 120                 125

Asp Ser Val Trp Val Pro Gly Pro Ile Asp Asp Arg Cys Pro Ala Lys
    130                 135                 140

Pro Glu Glu Glu Gly Met Met Ile Asn Ile Ser Ile Gly Tyr Arg Tyr
145                 150                 155                 160

Pro Pro Ile Cys Leu Gly Arg Ala Pro Gly Cys Leu Met Pro Ala Val
                165                 170                 175

Gln Asn Trp Leu Val Glu Val Pro Thr Val Ser Pro Ile Ser Arg Phe
            180                 185                 190

Thr Tyr His Met Val Ser Gly Met Ser Leu Arg Pro Arg Val Asn Tyr
        195                 200                 205

Leu Gln Asp Phe Ser Tyr Gln Arg Ser Leu Lys Phe Arg Pro Lys Gly
    210                 215                 220

Lys Pro Cys Pro Lys Glu Ile Pro Lys Glu Ser Lys Asn Thr Glu Val
225                 230                 235                 240

Leu Val Trp Glu Glu Cys Val Ala Asn Ser Ala Val Ile Leu Gln Asn
                245                 250                 255

Asn Glu Phe Gly Thr Ile Ile Asp Trp Ala Pro Arg Gly Gln Phe Tyr
            260                 265                 270

His Asn Cys Ser Gly Gln Thr Gln Ser Cys Pro Ser Ala Gln Val Ser
        275                 280                 285

Pro Ala Val Asp Ser Asp Leu Thr Glu Ser Leu Asp Lys His Lys His
    290                 295                 300

Lys Lys Leu Gln Ser Phe Tyr Pro Trp Glu Trp Gly Glu Lys Gly Ile
305                 310                 315                 320

Ser Thr Pro Arg Pro Lys Ile Ile Ser Pro Val Ser Gly Pro Glu His
                325                 330                 335

Pro Glu Leu Trp Arg Leu Thr Val Ala Ser His His Ile Arg Ile Trp
            340                 345                 350

Ser Gly Asn Gln Thr Leu Glu Thr Arg Asp Arg Lys Pro Phe Tyr Thr
        355                 360                 365

Val Asp Leu Asn Ser Ser Leu Thr Val Pro Leu Gln Ser Cys Val Lys
    370                 375                 380

Pro Pro Tyr Met Leu Val Val Gly Asn Ile Val Ile Lys Pro Asp Ser
385                 390                 395                 400

Gln Thr Ile Thr Cys Glu Asn Cys Arg Leu Leu Thr Cys Ile Asp Ser
                405                 410                 415

Thr Phe Asn Trp Gln His Arg Ile Leu Leu Val Arg Ala Arg Glu Gly
            420                 425                 430

Val Trp Ile Pro Val Ser Met Asp Arg Pro Trp Glu Ala Ser Pro Ser
        435                 440                 445

Val His Ile Leu Thr Glu Val Leu Lys Gly Val Leu Asn Arg Ser Lys
```

```
    450                 455                 460

Arg Phe Ile Phe Thr Leu Ile Ala Val Ile Met Gly Leu Ile Ala Val
465                 470                 475                 480

Thr Ala Thr Ala Ala Val Ala Gly Val Ala Leu His Ser Ser Val Gln
                485                 490                 495

Ser Val Asn Phe Val Asn Asp Trp Gln Lys Asn Ser Thr Arg Leu Trp
            500                 505                 510

Asn Ser Gln Ser Ser Ile Asp Gln Lys Met Leu Ala Val Ile Ser Cys
        515                 520                 525

Ala Val Gln Thr Val Ile Trp Met Gly Asp Arg Leu Met Ser Leu Glu
    530                 535                 540

His Arg Phe Gln Leu Gln Cys Asp Trp Asn Thr Ser Asp Phe Cys Ile
545                 550                 555                 560

Thr Pro Gln Ile Tyr Asn Glu Ser Glu His His Trp Asp Met Val Arg
                565                 570                 575

Arg His Leu Gln Gly Arg Glu Asp Asn Leu Thr Leu Asp Ile Ser Lys
            580                 585                 590

Leu Lys Glu Gln Ile Phe Glu Ala Ser Lys Ala His Leu Asn Leu Val
        595                 600                 605

Pro Gly Thr Glu Ala Ile Ala Gly Val Ala Asp Gly Leu Ala Asn Leu
    610                 615                 620

Asn Pro Val Thr Trp Val Lys Thr Ile Gly Ser Thr Thr Ile Ile Asn
625                 630                 635                 640

Leu Ile Leu Ile Leu Val Cys Leu Phe Cys Leu Leu Leu Val Cys Arg
                645                 650                 655

Cys Thr Gln Gln Leu Arg Arg Asp Ser Asp His Arg Glu Arg Ala Met
            660                 665                 670

Met Thr Met Ala Val Leu Ser Lys Arg Lys Gly Gly Asn Val Gly Lys
        675                 680                 685

Ser Lys Arg Asp Gln Ile Val Thr Val Ser Val
    690                 695
```

<210> SEQ ID NO 8
<211> LENGTH: 2103
<212> TYPE: DNA
<213> ORGANISM: Artificial sequence
<220> FEATURE:
<223> OTHER INFORMATION: Synthetic ERV-K-env/MEL nucleotide sequence

<400> SEQUENCE: 8

```
atgaacccta gcgagatgca gagaaaggct ccacctagac ggagaagaca cagaaacagg     60

gctcctctga cacacaagat gaacaagatg gtcaccagcg aggaacagat gaaactgccc    120

agcaccaaga aggccgagcc tccaacatgg gctcagctga agaaactgac ccagctggcc    180

accaagtacc tggagaacac caaagtgacc cagacacctg agagcatgct gctggcagct    240

ctgatgatcg tgtccatggt ggtgtccctg cctatgcctg ctggtgctgc cgctgccaac    300

tacacatact gggcctacgt gccctttcct cctatgatca gagccgtgac ctggatggac    360

aaccctattg aggtgtacgt gaacgacagc gtgtgggtgc caggacctat cgacgataga    420

tgtcctgcca aacctgagga agagggcatg atgatcaaca tcagcatcgg ctaccggtat    480

cctccaatct gcctgggcag agcacctggc tgtcttatgc cagctgtgca gaattggctg    540

gtggaagtgc ctaccgtgtc tcccatcagc cggttcacct accacatggt gtccggcatg    600

agcctcagac ctagagtgaa ctacttgcag gacttcagct atcagcggag cctgaagttc    660
```

```
agacccaagg gaaagccctg tcctaaagag attcccaaag agtccaagaa caccgaggtg    720
ctcgtgtggg aagagtgcgt ggccaattct gccgtgatcc tgcagaacaa cgagttcggc    780
accatcattg actgggctcc tagaggccag ttctaccaca attgcagcgg acagacacag    840
agctgtccta gcgcacaagt gtcaccagcc gtggatagcg atctgaccga gagcctggac    900
aagcacaaac acaagaaact tcagagcttc tatccctggg agtggggaga gaagggcatc    960
tctacaccaa ggcctaagat cattagccct gtgtctggac cagaacatcc cgaactttgg   1020
agactgacag tggccagcca ccacatcaga atctggagcg gcaatcagac cctggaaaca   1080
cgggacagaa agcccttcta caccgtcgat ctgaacagca gcctgaccgt gcctctccag   1140
agctgtgtga agcctcctta catgctggtc gtgggcaaca ttgtgatcaa gcccgactcc   1200
cagaccatca catgcgagaa ctgcagactg ctgacctgca tcgacagcac cttcaactgg   1260
cagcaccgga tcctgctcgt gcgagctaga gaaggcgtgt ggatccctgt ctctatggac   1320
aggccttggg aagccagccc tagcgtgcac attctgacag aggtgctgaa gggcgtgctc   1380
aacagatcca agcggttcat cttcaccctg atcgccgtca tcatgggcct gattgctgtg   1440
acagccacag ctgctgttgc tggcgtggcc ctgcatagct ctgtgcagag cgtgaacttc   1500
gtgaacgatt ggcagaagaa cagcacacgg ctgtggaaca gccagagcag catcgaccag   1560
aagatgctgg ccgtgatctc ctgtgccgtg cagacagtta tctggatggg cgacagactg   1620
atgagcctgg aacaccggtt ccagctgcag tgcgactgga ataccagcga cttctgcatc   1680
acacctcaga tctacaacga gagcgagcac cactgggata tggtccgaag gcatctgcag   1740
ggcagagagg acaacctgac actggacatc agcaagctga aagagcagat cttcgaggcc   1800
agcaaggctc acctgaatct ggtgcctgga accgaagcta ttgctggagt tgcagatggc   1860
ctggccaatc tgaatcctgt gacctgggtc aagaccatcg gcagcaccac aatcatcaac   1920
ctgatcctga tcctcgtgtg cctgttttgc ctgctgcttg tgtgcagatg cacccagcag   1980
ctgagaagag acagcgacca tagagaaaga gccatgatga ccatggccgt cctgagcaag   2040
agaaagggag gcaacgtggg caagagcaag cgggatcaga tcgtgaccgt gtccgtttga   2100
taa                                                                 2103
```

```
<210> SEQ ID NO 9
<211> LENGTH: 741
<212> TYPE: PRT
<213> ORGANISM: Artificial sequence
<220> FEATURE:
<223> OTHER INFORMATION: Synthetic hFOLR1/hPRAME fusion protein sequence

<400> SEQUENCE: 9

Met Ala Gln Arg Met Thr Thr Gln Leu Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
```

```
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
    130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Ala Met Glu Arg Arg Arg Leu Trp Gly
225                 230                 235                 240

Ser Ile Gln Ser Arg Tyr Ile Ser Met Ser Val Trp Thr Ser Pro Arg
                245                 250                 255

Arg Leu Val Glu Leu Ala Gly Gln Ser Leu Leu Lys Asp Glu Ala Leu
            260                 265                 270

Ala Ile Ala Ala Leu Glu Leu Leu Pro Arg Glu Leu Phe Pro Pro Leu
        275                 280                 285

Phe Met Ala Ala Phe Asp Gly Arg His Ser Gln Thr Leu Lys Ala Met
    290                 295                 300

Val Gln Ala Trp Pro Phe Thr Cys Leu Pro Leu Gly Val Leu Met Lys
305                 310                 315                 320

Gly Gln His Leu His Leu Glu Thr Phe Lys Ala Val Leu Asp Gly Leu
                325                 330                 335

Asp Val Leu Leu Ala Gln Glu Val Arg Pro Arg Arg Trp Lys Leu Gln
            340                 345                 350

Val Leu Asp Leu Arg Lys Asn Ser His Gln Asp Phe Trp Thr Val Trp
        355                 360                 365

Ser Gly Asn Arg Ala Ser Leu Tyr Ser Phe Pro Glu Pro Glu Ala Ala
    370                 375                 380

Gln Pro Met Thr Thr Lys Ala Lys Val Asp Gly Leu Ser Thr Glu Ala
385                 390                 395                 400

Glu Gln Pro Phe Ile Pro Val Glu Val Leu Val Asp Leu Phe Leu Lys
                405                 410                 415

Glu Gly Ala Cys Asp Glu Leu Phe Ser Tyr Leu Ile Glu Lys Val Ala
            420                 425                 430

Ala Lys Lys Asn Val Leu Arg Leu Cys Cys Lys Lys Leu Lys Ile Phe
        435                 440                 445

Ala Met Pro Met Gln Asp Ile Lys Met Ile Leu Lys Met Val Gln Leu
    450                 455                 460

Asp Ser Ile Glu Asp Leu Glu Val Thr Cys Thr Trp Lys Leu Pro Thr
465                 470                 475                 480

Leu Ala Lys Phe Ser Pro Tyr Leu Gly Gln Met Ile Asn Leu Arg Arg
                485                 490                 495

Leu Leu Leu Ser His Ile His Ala Ser Ser Tyr Ile Ser Pro Glu Lys
            500                 505                 510

Glu Glu Gln Tyr Ile Ala Gln Phe Thr Ser Gln Phe Leu Ser Leu Gln
        515                 520                 525
```

Cys Leu Gln Ala Leu Tyr Val Asp Ser Leu Phe Phe Leu Arg Gly Arg
    530                 535                 540

Leu Asp Gln Leu Leu Arg His Val Met Asn Pro Leu Glu Thr Leu Ser
545                 550                 555                 560

Ile Thr Asn Cys Arg Leu Ser Glu Gly Asp Val Met His Leu Ser Gln
                565                 570                 575

Ser Pro Ser Val Ser Gln Leu Ser Val Leu Ser Leu Ser Gly Val Met
            580                 585                 590

Leu Thr Asp Val Ser Pro Glu Pro Leu Gln Ala Leu Leu Glu Arg Ala
        595                 600                 605

Ser Ala Thr Leu Gln Asp Leu Val Phe Asp Glu Cys Gly Ile Thr Asp
    610                 615                 620

Asp Gln Leu Leu Ala Leu Leu Pro Ser Leu Ser His Cys Ser Gln Leu
625                 630                 635                 640

Thr Thr Leu Ser Phe Tyr Gly Asn Ser Ile Ser Ile Ser Ala Leu Gln
                645                 650                 655

Ser Leu Leu Gln His Leu Ile Gly Leu Ser Asn Leu Thr His Val Leu
            660                 665                 670

Tyr Pro Val Pro Leu Glu Ser Tyr Glu Asp Ile His Gly Thr Leu His
        675                 680                 685

Leu Glu Arg Leu Ala Tyr Leu His Ala Arg Leu Arg Glu Leu Leu Cys
    690                 695                 700

Glu Leu Gly Arg Pro Ser Met Val Trp Leu Ser Ala Asn Pro Cys Pro
705                 710                 715                 720

His Cys Gly Asp Arg Thr Phe Tyr Asp Pro Glu Pro Ile Leu Cys Pro
                725                 730                 735

Cys Phe Met Pro Asn
            740

<210> SEQ ID NO 10
<211> LENGTH: 2228
<212> TYPE: DNA
<213> ORGANISM: Artificial sequence
<220> FEATURE:
<223> OTHER INFORMATION: Synthetic hFOLR1/hPRAME fusion nucleotide
      sequence

<400> SEQUENCE: 10
tggcccagag aatgaccaca caactgctgc tgctcctggt gtgggttgcc gttgttggag     60
aggcccagac cagaattgcc tgggccagaa ccgagctgct gaacgtgtgc atgaacgcca    120
agcatcacaa agagaagcct ggacctgaag acaagctgca tgaacagtgt cggccttgga    180
gaaagaatgc ttgctgtagc accaacacca gccaagaggc ccacaaggac gtgtcctacc    240
tgtaccggtt caactggaac cactgcggag aaatggctcc tgcctgcaag agacacttca    300
tccaggatac ctgcctgtac gagtgctctc ccaatctcgg accttggatc cagcaagtgg    360
accagagctg gcggaaagaa cgggtgctga atgtgccctt gtgcaaagag gattgcgagc    420
agtggtggga agattgccgg accagctaca catgtaagag caactggcac aaaggctgga    480
actggaccag cggcttcaac aagtgtgccg tgggagctgc ctgccagcct ttccacttct    540
acttcccaac acctaccgtg ctgtgcaacg aaatctggac ccacagctac aaggtgtcca    600
actacagcag aggcagcggc aggtgtatcc agatgtggtt cgatcccgct cagggcaatc    660
ccaatgagga agtggctaga ttctacgctg ctgccatgga aagaagaagg ctctggggca    720
gcatccagag ccggtacatt agcatgagcg tgtggacaag ccctagacgg ctggttgaac    780

```
tggctggaca gagcctgctc aaggatgagg ccctggccat tgctgctctg gagctgctgc    840

ctagagagct gttccctcct ctgttcatgg ctgccttcga cggcagacac agccagacac    900

tgaaagccat ggtgcaggcc tggcctttca cctgtctgcc tctgggagtg ctgatgaagg    960

gccagcatct gcacctggaa accttcaagg ccgtgctgga cggcctggat gttctcctgg   1020

ctcaagaggt gaggcctcgg cgttggaaac tgcaggttct ggatctgcgg aagaactctc   1080

accaggattt ctggaccgtt tggtccggca acagagccag cctgtacagc tttcctgaac   1140

ctgaggctgc ccagcccatg accacaaagg ccaaagtgga tggcctgagc acagaggccg   1200

agcagccttt cattcccgtc gaagtgctgg tggacctgtt cctgaaagaa ggagcctgcg   1260

atgagctgtt cagctacctg attgagaagg tggcagccaa gaagaacgtg ctgcggctgt   1320

gctgcaagaa gctgaagatc tttgccatgc ctatgcagga tatcaagatg atcctgaaga   1380

tggtgcagct ggacagcatc gaggacctgg aagtgacctg tacctggaag ctgcccacac   1440

tggccaagtt cagcccttac ctgggacaga tgattaacct gcggaggctg ctgctgtctc   1500

acatccacgc cagctcctac atcagccctg agaaagagga acagtatatc gcccagttca   1560

caagccagtt tctgagcctg cagtgtctgc aggccctgta cgtggacagc ctgttctttc   1620

tgagaggcag gctggatcag ctgctgcggc acgtgatgaa ccctctggaa accctgagca   1680

tcaccaactg tagactgagc gagggcgacg tgatgcacct gtctcagagc ccatctgtgt   1740

ctcagctgag cgtgctgtct ctgtctggcg tgatgctgac cgatgtgagc cctgaacctc   1800

tgcaggcact gctggaaaga gcctccgcta ctctgcagga cctggtgttc gatgagtgcg   1860

gcatcaccga tgaccagctg cttgctctgc tgccaagcct gagccactgt agccagctga   1920

caaccctgtc cttctacggc aacagcatct ccatctctgc cctgcagtct ctcctgcagc   1980

atctgatcgg cctgtccaat ctgacccacg tgctgtaccc tgtgccactg gaaagctacg   2040

aggacatcca cggaaccctg cacctcgaga gactggccta tctgcatgct cggctgagag   2100

aactgctgtg cgaactgggc agacccagca tggtttggct gagcgccaat ccatgtcctc   2160

actgtggcga ccggaccttc tacgaccctg agcctatcct gtgtccttgc ttcatgccca   2220

actaatag                                                            2228
```

```
<210> SEQ ID NO 11
<211> LENGTH: 517
<212> TYPE: PRT
<213> ORGANISM: Artificial sequence
<220> FEATURE:
<223> OTHER INFORMATION: ERV-K-env/MEL_03 protein sequence

<400> SEQUENCE: 11

Met Asn Pro Ser Glu Met Gln Arg Lys Ala Pro Pro Arg Arg Arg Arg
1               5                   10                  15

His Arg Asn Arg Ala Pro Leu Thr His Lys Met Asn Lys Met Val Thr
            20                  25                  30

Ser Glu Glu Gln Met Lys Leu Pro Ser Thr Lys Lys Ala Glu Pro Pro
        35                  40                  45

Thr Trp Ala Gln Leu Lys Lys Leu Thr Gln Leu Ala Thr Lys Tyr Leu
    50                  55                  60

Glu Asn Thr Lys Val Thr Gln Thr Pro Glu Ser Met Leu Leu Ala Ala
65                  70                  75                  80

Leu Met Ile Val Ser Met Val Val Ser Leu Pro Met Pro Ala Gly Ala
                85                  90                  95
```

```
Ala Ala Ala Asn Tyr Thr Tyr Trp Ala Tyr Val Pro Phe Pro Pro Met
            100                 105                 110

Ile Arg Ala Val Thr Trp Met Asp Asn Pro Ile Glu Val Tyr Val Asn
        115                 120                 125

Asp Ser Val Trp Val Pro Gly Pro Ile Asp Asp Arg Cys Pro Ala Lys
    130                 135                 140

Pro Glu Glu Glu Gly Met Met Ile Asn Ile Ser Ile Gly Tyr Arg Tyr
145                 150                 155                 160

Pro Pro Ile Cys Leu Gly Arg Ala Pro Gly Cys Leu Met Pro Ala Val
                165                 170                 175

Gln Asn Trp Leu Val Glu Val Pro Thr Val Ser Pro Ile Ser Arg Phe
            180                 185                 190

Thr Tyr His Met Val Ser Gly Met Ser Leu Arg Pro Arg Val Asn Tyr
        195                 200                 205

Leu Gln Asp Phe Ser Tyr Gln Arg Ser Leu Lys Phe Arg Pro Lys Gly
    210                 215                 220

Lys Pro Cys Pro Lys Glu Ile Pro Lys Glu Ser Lys Asn Thr Glu Val
225                 230                 235                 240

Leu Val Trp Glu Glu Cys Val Ala Asn Ser Ala Val Ile Leu Gln Asn
                245                 250                 255

Asn Glu Phe Gly Thr Ile Ile Asp Trp Ala Pro Arg Gly Gln Phe Tyr
            260                 265                 270

His Asn Cys Ser Gly Gln Thr Gln Ser Cys Pro Ser Ala Gln Val Ser
        275                 280                 285

Pro Ala Val Asp Ser Asp Leu Thr Glu Ser Leu Asp Lys His Lys His
    290                 295                 300

Lys Lys Leu Gln Ser Phe Tyr Pro Trp Glu Trp Gly Glu Lys Gly Ile
305                 310                 315                 320

Ser Thr Pro Arg Pro Lys Ile Ile Ser Pro Val Ser Gly Pro Glu His
                325                 330                 335

Pro Glu Leu Trp Arg Leu Thr Val Ala Ser His His Ile Arg Ile Trp
            340                 345                 350

Ser Gly Asn Gln Thr Leu Glu Thr Arg Asp Arg Lys Pro Phe Tyr Thr
        355                 360                 365

Val Asp Leu Asn Ser Ser Leu Thr Val Pro Leu Gln Ser Cys Val Lys
    370                 375                 380

Pro Pro Tyr Met Leu Val Val Gly Asn Ile Val Ile Lys Pro Asp Ser
385                 390                 395                 400

Gln Thr Ile Thr Cys Glu Asn Cys Arg Leu Leu Thr Cys Ile Asp Ser
                405                 410                 415

Thr Phe Asn Trp Gln His Arg Ile Leu Leu Val Arg Ala Arg Glu Gly
            420                 425                 430

Val Trp Ile Pro Val Ser Met Asp Arg Pro Trp Glu Ala Ser Pro Ser
        435                 440                 445

Val His Ile Leu Thr Glu Val Leu Lys Gly Val Leu Asn Met Leu Ala
    450                 455                 460

Val Ile Ser Cys Ala Val Ala Gly Val Ala Leu His Gly Ser Ala Gly
465                 470                 475                 480

Ser Ala Ala Gly Ser Gly Glu Phe Val Val Ile Ser Ala Ile Leu Ala
                485                 490                 495

Leu Val Val Leu Thr Ile Ile Ser Leu Ile Ile Leu Ile Met Leu Trp
            500                 505                 510

Gln Lys Lys Pro Arg
```

515

<210> SEQ ID NO 12
<211> LENGTH: 1557
<212> TYPE: DNA
<213> ORGANISM: Artificial sequence
<220> FEATURE:
<223> OTHER INFORMATION: ERV-K-env/MEL_03 nucleotide sequence

<400> SEQUENCE: 12
atgaacccta gcgagatgca gagaaaggct ccacctagac ggagaagaca cagaaacagg 60
gctcctctga cacacaagat gaacaagatg gtcaccagcg aggaacagat gaaactgccc 120
agcaccaaga aggccgagcc tccaacatgg gctcagctga agaaactgac ccagctggcc 180
accaagtacc tggagaacac caaagtgacc cagacacctg agagcatgct gctggcagct 240
ctgatgatcg tgtccatggt ggtgtccctg cctatgcctg ctggtgctgc cgctgccaac 300
tacacatact gggcctacgt gccctttcct cctatgatca gagccgtgac ctggatggac 360
aaccctattg aggtgtacgt gaacgacagc gtgtgggtgc caggacctat cgacgataga 420
tgtcctgcca aacctgagga agagggcatg atgatcaaca tcagcatcgg ctaccggtat 480
cctccaatct gcctgggcag agcacctggc tgtcttatgc cagctgtgca gaattggctg 540
gtggaagtgc ctaccgtgtc tcccatcagc cggttcacct accacatggt gtccggcatg 600
agcctcagac ctagagtgaa ctacttgcag gacttcagct atcagcggag cctgaagttc 660
agacccaagg gaaagccctg tcctaaagag attcccaaag agtccaagaa caccgaggtg 720
ctcgtgtggg aagagtgcgt ggccaattct gccgtgatcc tgcagaacaa cgagttcggc 780
accatcattg actgggctcc tagaggccag ttctaccaca attgcagcgg acagacacag 840
agctgtccta gcgcacaagt gtcaccagcc gtggatagcg atctgaccga gagcctggac 900
aagcacaaac acaagaaact tcagagcttc tatccctggg agtggggaga gaagggcatc 960
tctacaccaa ggcctaagat cattagccct gtgtctggac cagaacatcc cgaactttgg 1020
agactgacag tggccagcca ccacatcaga atctggagcg gcaatcagac cctggaaaca 1080
cgggacagaa agcccttcta caccgtcgat ctgaacagca gcctgaccgt gcctctccag 1140
agctgtgtga agcctcctta catgctggtc gtgggcaaca ttgtgatcaa gcccgactcc 1200
cagaccatca catgcgagaa ctgcagactg ctgacctgca tcgacagcac cttcaactgg 1260
cagcaccgga tcctgctcgt gcgagctaga gaaggcgtgt ggatccctgt ctctatggac 1320
aggccttggg aagccagccc tagcgtgcac attctgacag aggtgctgaa gggcgtgctc 1380
aacatgctgg ccgtgatctc ctgtgccgtg gctggcgtgg ccctgcatgg ctctgctgga 1440
tctgctgctg gaagcggcga gttcgtggtc atctctgcca ttctggctct ggtggtgctg 1500
accatcatca gcctgatcat cctgattatg ctgtggcaga agaagccccg gtgataa 1557

RECOMBINANT MVA VIRUSES FOR INTRATUMORAL AND/OR INTRAVENOUS ADMINISTRATION FOR TREATING CANCER

FIELD OF THE INVENTION

The present invention relates to a therapy for the treatment of cancers; the treatment includes an intravenously or intratumorally administered recombinant modified vaccinia Ankara (MVA) virus comprising a nucleic acid encoding 4-1BBL (CD137L). Recombinant modified vaccinia Ankara (MVA) virus as used herein (also "recombinant MVA" or "rMVA") refers to an MVA comprising at least one polynucleotide encoding a tumor associated antigen (TAA). In a more particular aspect, the invention includes intravenously or intratumorally administered recombinant MVA comprising a nucleic acid encoding a TAA and a nucleic acid encoding 4-1BBL. In additional aspects, the invention includes an intravenously or intratumorally administered recombinant MVA comprising a nucleic acid encoding a TAA and a nucleic acid encoding CD40L. In additional aspects, the invention includes an intravenously and/or intratumorally administered recombinant MVA comprising nucleic acids encoding a TAA, 4-1BBL (CD137L), and CD40L.

BACKGROUND OF THE INVENTION

Recombinant poxviruses have been used as immunotherapy vaccines against infectious organisms and, more recently, against tumors (Mastrangelo et al. (2000) *J Clin Invest.* 105(8):1031-1034).

One poxviral strain that has proven useful as an immunotherapy vaccine against infectious disease and cancer is the Modified Vaccinia Ankara (MVA) virus (sometimes referred to simply as "MVA"). MVA was generated by 516 serial passages on chicken embryo fibroblasts of the Ankara strain of vaccinia virus (CVA) (for review see Mayr et al. (1975) *Infection* 3: 6-14). As a consequence of these long-term passages, the genome of the resulting MVA virus had about 31 kilobases of its genomic sequence deleted and, therefore, was described as highly host cell restricted for replication to avian cells (Meyer et al. (1991) *J. Gen. Virol.* 72: 1031-1038). It was shown in a variety of animal models that the resulting MVA was significantly avirulent (Mayr & Danner (1978) *Dev. Biol. Stand.* 41: 225-34). Strains of MVA having enhanced safety profiles for the development of safer products, such as vaccines or pharmaceuticals, have been described (see International PCT publication WO2002042480; see also, e.g., U.S. Pat. Nos. 6,761,893 and 6,913,752, all of which are incorporated by reference herein). Such variants are capable of reproductive replication in non-human cells and cell lines, especially in chicken embryo fibroblasts (CEF), but are replication incompetent in human cell lines, in particular including HeLa, HaCat and 143B cell lines. Such strains are also not capable of reproductive replication in vivo, for example, in certain mouse strains, such as the transgenic mouse model AGR 129, which is severely immune-compromised and highly susceptible to a replicating virus (see U.S. Pat. Nos. 6,761,893). Such MVA variants and its derivatives, including recombinants, referred to as "MVA-BN," have been described (see International PCT publication WO2002/042480; see also, e.g., U.S. Pat. Nos. 6,761,893 and 6,913,752).

The use of poxviral vectors that encode tumor-associated antigens (TAAs) have been shown to successfully reduce tumor size as well as increase overall survival rate of cancer patients (see, e.g., WO 2014/062778). It has been demonstrated that when a cancer patient is administered a poxviral vector encoding a TAA, such as HER2, CEA, MUC1, and/or Brachyury, a robust and specific T-cell response is generated by the patient to fight the cancer (Id.; see also, Guardino et al. ((2009) *Cancer Res.* 69 (24), doi 10.1158/0008-5472.SABCS-09-5089), Heery et al. (2015) *JAMA Oncol.* 1: 1087-95).

One type of TAA that was found to be expressed on many cancer and tumor cells are Endogenous Retroviral (ERV) proteins. ERVs are remnants of former exogenous forms that invaded the germ line of the host and have since been vertically transmitted through a genetic population (see Bannert et al. (2018) *Frontiers in Microbiology*, Volume 9, Article 178). ERV-induced genomic recombination events and dysregulation of normal cellular genes have been documented to have contributory effects to tumor formation (Id.). Further, there is evidence that certain ERV proteins have oncogenic properties (Id.). ERVs have been found to be expressed in a large variety of cancers including, e.g., breast, ovarian, melanoma, prostate, pancreatic, and lymphoma. (See, e.g., Bannert et al. (2018) *Front. Microbiol.* 9: 178; Cegolon et al. (2013) *BMC Cancer* 13: 4; Wang-Johanning et al. (2003) *Oncogene* 22: 1528-35; Wang-Johanning et al. (2007) *Int. J. Cancer* 120: 81-90; Wang-Johanning et al. (2008) *Cancer Res.* 68: 5869-77; Wang-Johanning et al. (2018) *Cancer Res.* 78 (13 Suppl.), *AACR Annual Meeting April* 2018, *Abstract* 1257; Contreras-Galindo et al. (2008) *J. Virol.* 82: 9329-36; Schiavetti et al. (2002) *Cancer Res.* 62: 5510-16; Maliniemi et al. (2013) *PLoS One* 8: e76281; Fava et al. (2017) *Genes Dev.* 31: 34-45, Muster et al. (2003) *Cancer Res.* 63: 8735-41; Buscher et al. (2005) *Cancer Res.* 65: 4172-80; Serafino et al. (2009) *Expt'l. Cell Res.* 315: 849-62; Iramaneerat et al. (2011) *Int. J. Gynecol. Cancer* 21: 51-7; Ishida et al. (2006) *Cancer Sci.* 97: 1139-46; Goering et al. (2011) *Carcinogenesis* 32: 1484-92; Agoni et al. (2013) *Front. Oncol.* 9: 180; Li et al. (2017) *J. Mol. Diagn.* 19: 4-23).

In addition to their effectiveness with TAAs, poxviruses such as MVA have been shown to have enhanced efficacy when combined with a CD40 agonist such as CD40 Ligand (CD40L) (see WO 2014/037124) or with a 4-1BB agonist such as 4-1BB Ligand (4-1BBL) (Spencer et al. (2014) *PLoS One* 9: e105520).

CD40/CD40L is a member of the tumor necrosis factor receptor/tumor necrosis factor ("TNFR/TNF") superfamily. While CD40 is constitutively expressed on many cell types, including B cells, macrophages and DCs, its ligand CD40L is predominantly expressed on activated CD4+ T-cells (Lee et al. (2002) *J. Immunol.* 171(11): 5707-5717; Ma and Clark (2009) *Semin. Immunol.* 21(5): 265-272). The cognate interaction between DCs and CD4+ T-cells early after infection or immunization 'licenses' DCs to prime CD8+ T-cell responses (Ridge et al. (1998) *Nature* 393: 474-478). DC licensing results in the upregulation of co-stimulatory molecules, increased survival and better cross-presenting capabilities of DCs. This process is mainly mediated via CD40/CD40L interaction (Bennet et al. (1998) *Nature* 393: 478-480; Schoenberger et al. (1998) *Nature* 393: 480-483), but CD40/CD40L-independent mechanisms also exist (CD70, LT.beta.R). Interestingly, a direct interaction between CD40L expressed on DCs and CD40 expressed on CD8+ T-cells has also been suggested, providing a possible explanation for the generation of helper-independent CTL responses (Johnson et al. (2009) *Immunity* 30: 218-227).

4-1BB/4-1BBL is a member of the TNFR/TNF superfamily. 4-1BBL is a costimulatory ligand expressed in activated B cells, monocytes and DCs. 4-1BB is constitutively expressed by natural killer (NK) and natural killer T (NKT) cells, Tregs and several innate immune cell populations, including DCs, monocytes and neutrophils. Interestingly, 4-1BB is expressed on activated, but not resting, T cells (Wang et al. (2009) *Immunol. Rev.* 229: 192-215). 4-1BB ligation induces proliferation and production of interferon gamma (IFN-γ) and interleukin 2 (IL-2), as well as enhances T cell survival through the upregulation of antiapoptotic molecules such as Bcl-xL (Snell et al. (2011) *Immunol. Rev.* 244: 197-217). Importantly, 4-1BB stimulation enhances NK cell proliferation, IFN-γ production and cytolytic activity through enhancement of Antibody-Dependent Cell Cytotoxicity (ADCC) (Kohrt et al. (2011) *Blood* 117: 2423-32).

The 4-1BB/4-1BBL axis of immunity is currently being explored by different immunotherapeutic strategies. As an example, autologous transfer of Chimeric Antigen Receptor (CAR) T cells shows clinical benefit in large B cell lymphomas, being approved by the FDA in 2017. Patient autologous T cells are transduced with CARs that combine an extracellular domain derived from a tumor-specific antibody, the CD3ζ intracellular signaling domain and the 4-1BB costimulatory motif. The addition of 4-1BB is crucial for in vivo persistence and antitumor toxicity of CAR T cells (Song et al. (2011) *Cancer Res.* 71: 4617e27). Antibodies targeting 4-1BB are currently being investigated.

Several studies have shown that agonistic antibodies targeting 4-1BB/4-1BBL pathway show anti-tumor activity when utilized as a monotherapy (Palazón et al. (2012) Cancer Discovery 2: 608-23). Agonistic antibodies targeting 4-1BB (Urelumab, BMS; Utolimumab, Pfizer) are currently in clinical development. In recent years, studies that have combined 4-1BBL with other therapies have shown varied success. For example, when mice with preexisting MC38 (murine adenocarcinoma) tumors, but not B16 melanoma tumors, were administered with antibodies to CTLA-4 and anti-4-1BB, significant CD8+ T cell-dependent tumor regression was observed, together with long-lasting immunity to these tumors. In another example, treatment with anti-4-1BB (Bristol-Myers Squibb (BMS)-469492) led to only modest regression of M109 tumors, but significantly delayed the growth of EMT6 tumors.

The tumor microenvironment is composed of a large variety of cell types, from immune cell infiltrates to cancer cells, extracellular matrix, endothelial cells, and other cellular players that influence tumor progression. This complex and entangled equilibrium changes not only from patient to patient, but within lesions in the same subject (Jiménez-Sánchez et al. (2017) *Cell* 170(5): 927-938). Stratification of tumors based on Tumor Infiltrating Lymphocytes (TIL) and Programmed Death Ligand 1 (PD-L1) expression emphasizes the importance of an inflammatory environment to achieve objective responses against cancer (Teng et al. (2015) *Cancer Res.* 75(11): 2139-45). Pan-cancer analysis of gene expression profiles form the Cancer Genome Atlas (TCGA) support that a tumor inflammation signature correlates with objective responses to immunotherapy (Danaher et al. (2018) *J. Immunother. Cancer* 6(1): 63).

In recent years, attempts to improve cancer therapies routes of administration of vaccines have been expanded from subcutaneous injection to an intravenous route of administration. For example, it was demonstrated that an intravenous administration of an MVA vaccine encoding a heterologous antigen was able to induce a strong specific immune response to the antigen (see WO 2014/037124). Further, enhanced immune response were generated when the MVA vaccine included CD40L.

The inoculation of bacterial-derived material (Coley's toxin) into tumor lesions achieving curative responses has long been reported, highlighting the role of local infection in promoting antitumor responses (Coley (1906) *Proc. R. Soc. Med.* 3 (Surg Sect): 1-48). The local administration of Pathogen Associated Molecular Patterns (PAMPs), bacterial products, and viruses into tumor lesions induces an antimicrobial program that results in a cascade of events following the administration, including: i) secretion of pro-inflammatory cytokines as Type I, II and III interferons and Tumor necrosis Factor alpha (TNF-alpha); ii) danger signals such as alarmins and heat-shock proteins; and iii) release of tumor antigens (Aznar et al. (2017) *J. Immunol.* 198: 31-39). Local administration of immunotherapy into the tumor induces systemic immune responses, as regressions have been assessed in non-treated tumor lesions ((2018) *Cancer Discov.* 8(6): 67).

Intratumoral administration of MVA vaccines has been reported in the past few years. It was found that intratumoral injections of MVA expressing GM-CSF and immunization with DNA vaccine prolonged the survival of mice bearing HPV16 E7 tumors (Nemeckova et al. (2007) *Neoplasma* 54: 4). Other studies of intratumoral injection of MVA were unable to demonstrate inhibition of pancreatic tumor growth (White et al. (2018) *PLoS One* 13(2): e0193131). Intratumoral injection of heat-inactivated MVA induced antitumor immune responses dependent in the generation of danger signals, type I interferon, and antigen cross-presentation by dendritic cells (Dai et al. (2017) *Sci. Immunol.* 2(11): eaal1713).

The activity of many cancer vaccines involves the induction of an adaptive immune response against the tumor. Effective activation of tumor-specific T cells comprises: First, the exclusive and high expression of the antigen in the tumor but not in healthy tissue to minimize tolerance induction and favor a competent T cell repertoire. Second, the effective processing of the tumor antigen and loading on HLA molecules within the cell. And finally, the presentation of immunogenic HLA/peptide complexes on the cell surface and their recognition by tumor-specific T cells.

There is clearly a substantial unmet medical need for additional cancer treatments, including active immunotherapies and cancer vaccines. Additionally, there is a need for therapies that can induce enhanced immune responses in multiple areas of a patient's immune response. In many aspects, the embodiments of the present disclosure address these needs by providing vaccines, therapies, and combination therapies that increase and improve the cancer treatments currently available.

BRIEF SUMMARY OF THE INVENTION

It was determined in the various embodiments of the present invention that a recombinant MVA encoding a tumor-associated antigen (TAA) and a 4-1BB Ligand (also referred to herein as 41BBL, 4-1BBL, or CD137L) when administered intratumorally or intravenously increases the effectiveness of and/or enhances treatment of a cancer patient. More particularly, it was determined that the various embodiments of the present disclosure resulted in increased inflammation in the tumor, decreases in regulatory T cells (Tregs) and T cell exhaustion in the tumor, expansion of tumor-specific T cells and activation of NK cells, increases in reduction in tumor volume, and/or increases in the survival of a cancer subject as compared to an administration of a recombinant MVA by itself.

It was determined in the various embodiments of the present invention that a recombinant MVA encoding a tumor-associated antigen (TAA) and a CD40 Ligand (CD40L) when administered intratumorally or intravenously enhances treatment of a cancer patient. More particularly, it was determined that the various embodiments of the present disclosure resulted in increased inflammation in the tumor, decreases in regulatory T cells (Tregs) and T cell exhaustion in the tumor, expansion of tumor-specific T cells and activation of NK cells, increases in reduction in tumor volume, and/or increases in the survival of a cancer subject as compared to an administration of a recombinant MVA by itself.

In additional embodiments, the invention includes a recombinant modified vaccinia Ankara (MVA) virus comprising a nucleic acid encoding 4-1BBL (CD137L) and a nucleic acid encoding CD40L that when administered intravenously and/or intratumorally enhances treatment of a cancer patient.

Accordingly, in one embodiment, the present invention includes a method for reducing tumor size and/or increasing survival in a subject having a cancerous tumor, the method comprising intratumorally administering to the subject a recombinant modified Vaccinia Ankara (MVA) comprising a first nucleic acid encoding a tumor-associated antigen (TAA) and a second nucleic acid encoding 4-1BBL, wherein the intratumoral administration of the recombinant MVA enhances an inflammatory response in the cancerous tumor, increases tumor reduction, and/or increases overall survival of the subject as compared to a non-intratumoral injection of a recombinant MVA virus comprising a first and second nucleic acid encoding a TAA and a 4-1BBL antigen.

In an additional embodiment, the present invention includes a method for reducing tumor size and/or increasing survival in a subject having a cancerous tumor, the method comprising intratumorally administering to the subject a recombinant modified Vaccinia Ankara (MVA) comprising a first nucleic acid encoding a tumor-associated antigen (TAA) and a second nucleic acid encoding CD40L, wherein the intratumoral administration of the recombinant MVA enhances an inflammatory response in the cancerous tumor, increases tumor reduction, and/or increases overall survival of the subject as compared to a non-intratumoral injection of a recombinant MVA virus comprising a first and second nucleic acid encoding a TAA and a CD40L antigen.

In an additional embodiment, the present invention includes a method for reducing tumor size and/or increasing survival in a subject having a cancerous tumor, the method comprising intratumorally and/or intravenously administering to the subject a recombinant modified Vaccinia Ankara (MVA) comprising a first nucleic acid encoding a tumor-associated antigen (TAA), a second nucleic acid encoding CD40L, and a third nucleic acid encoding 4-1BBL (CD137L) wherein the administration of the recombinant MVA enhances an inflammatory response in the cancerous tumor, increases tumor reduction, and/or increases overall survival of the subject as compared to an injection of a recombinant MVA virus comprising a first and second nucleic acid encoding a TAA, a CD40L antigen, and a 4-1BBL antigen by a different route of injection (i.e., non-intratumoral or non-intravenous injection).

In an additional embodiment, the present invention includes a method for reducing tumor size and/or increasing survival in a subject having a cancerous tumor, the method comprising intravenously administering to the subject a recombinant modified Vaccinia Ankara (MVA) comprising a first nucleic acid encoding a tumor-associated antigen (TAA) and a second nucleic acid encoding 4-1BBL, wherein the intravenous administration of the recombinant MVA enhances Natural Killer (NK) cell response and enhances CD8 T-cell responses specific to the TAA as compared to a non-intravenous injection of a recombinant MVA virus comprising a first and second nucleic acid encoding a TAA and a 4-1BBL antigen.

In an additional embodiment, the present invention includes a method for reducing tumor size and/or increasing survival in a subject having a cancerous tumor, the method comprising intravenously administering to the subject a recombinant modified Vaccinia Ankara (MVA) comprising a first nucleic acid encoding a tumor-associated antigen (TAA) and a second nucleic acid encoding CD40L, wherein the intravenous administration of the recombinant MVA enhances Natural Killer (NK) cell response and enhances CD8 T cell responses specific to the TAA as compared to a non-intravenous injection of a recombinant MVA virus comprising a first and second nucleic acid encoding a TAA and a CD40L antigen.

In an additional embodiment, the present invention includes a method for reducing tumor size and/or increasing survival in a subject having a cancerous tumor, the method comprising intravenously and/or intratumorally administering to the subject a recombinant modified Vaccinia Ankara (MVA) comprising a first nucleic acid encoding a tumor-associated antigen (TAA), a second nucleic acid encoding CD40L, and a third nucleic acid encoding 4-1BBL, wherein the intravenous and/or intratumoral administration of the recombinant MVA enhances Natural Killer (NK) cell response and enhances CD8 T cell responses specific to the TAA as compared to a non-intravenous or non-intratumoral injection of a recombinant MVA virus comprising a first nucleic acid encoding a TAA, a second nucleic acid encoding a CD40L antigen, and a third nucleic acid encoding a 4-1BBL antigen.

In yet another embodiment, the present invention includes a method of inducing an enhanced inflammatory response in a cancerous tumor of a subject, the method comprising intratumorally administering to the subject a recombinant modified Vaccinia Ankara (MVA) comprising a first nucleic acid encoding a first heterologous tumor-associated antigen (TAA) and a second nucleic acid encoding a 4-1BBL antigen, wherein the intratumoral administration of the recombinant MVA generates an enhanced inflammatory response in the tumor as compared to an inflammatory response generated by a non-intratumoral injection of a recombinant MVA virus comprising a first and second nucleic acid encoding a heterologous tumor-associated antigen and a 4-1BBL antigen.

In yet another embodiment, the present invention includes a method of inducing an enhanced inflammatory response in a cancerous tumor of a subject, the method comprising intratumorally administering to the subject a recombinant modified Vaccinia Ankara (MVA) comprising a first nucleic acid encoding a first heterologous tumor-associated antigen (TAA) and a second nucleic acid encoding a CD40L antigen, wherein the intratumoral administration of the recombinant MVA generates an enhanced inflammatory response in the tumor as compared to an inflammatory response generated by a non-intratumoral injection of a recombinant MVA virus comprising a first and second nucleic acid encoding a heterologous tumor-associated antigen and a CD40L antigen.

In yet another embodiment, the present invention includes a method of inducing an enhanced inflammatory response in a cancerous tumor of a subject, the method comprising intratumorally and/or intravenously administering to the subject a recombinant modified Vaccinia Ankara (MVA) comprising a first nucleic acid encoding a first heterologous tumor-associated antigen (TAA), a second nucleic acid encoding a CD40L antigen, and a third nucleic acid encoding a 4-1BBL antigen, wherein the intratumoral and/or intravenous administration of the recombinant MVA generates an enhanced inflammatory response in the tumor as compared to an inflammatory response generated by a non-intratumoral or non-intravenous injection of a recombinant MVA virus comprising a first nucleic acid encoding a heterologous tumor-associated antigen, a second nucleic acid encoding a CD40L antigen, and a third nucleic acid encoding a 4-1BBL antigen.

In various additional embodiments, the present invention provides a recombinant modified Vaccinia Ankara (MVA) for treating a subject having cancer, the recombinant MVA comprising a) a first nucleic acid encoding a tumor-associated antigen (TAA) and b) a second nucleic acid encoding 4-1BBL.

In various additional embodiments, the present invention includes a recombinant modified Vaccinia Ankara (MVA) for treating a subject having cancer, the recombinant MVA comprising a) a first nucleic acid encoding a tumor-associated antigen (TAA) and b) a second nucleic acid encoding CD40L.

In various additional embodiments, the present invention includes a recombinant modified Vaccinia Ankara (MVA) for treating a subject having cancer, the recombinant MVA comprising: a) a first nucleic acid encoding a tumor-associated antigen (TAA); b) a second nucleic acid encoding CD40L; and c) a third nucleic acid encoding 4-1BBL.

In yet another embodiment, a recombinant MVA encoding a 4-1BBL antigen, when administered intratumorally to a patient in combination with an administration of a checkpoint inhibitor antagonist enhances treatment of a cancer patient, more particularly increases reduction in tumor volume and/or increases survival of the cancer patient.

In yet another embodiment, a recombinant MVA encoding a CD40L antigen, when administered intratumorally to a patient in combination with an administration of a checkpoint inhibitor antagonist enhances treatment of a cancer patient, more particularly increases reduction in tumor volume and/or increases survival of the cancer patient.

In yet another embodiment, a recombinant MVA encoding a CD40L and 4-1BBL antigen, when administered intratumorally and/or intravenously to a patient in combination with an administration of a checkpoint inhibitor antagonist enhances treatment of a cancer patient, more particularly increases reduction in tumor volume and/or increases survival of the cancer patient.

In another embodiment, the recombinant MVA of the present invention is administered at the same time or after administration of the antibody. In a more preferred embodiment, the recombinant MVA is administered after the antibody.

In another embodiment, the recombinant MVA of the present invention is administered by the same route(s) of administration and at the same time or after administration of the antibody. In another embodiment, the recombinant MVA is administered by a different route or routes of administration or after administration of the antibody.

In yet another embodiment, the present invention includes a method for enhancing antibody therapy in a cancer patient, the method comprising administering the pharmaceutical combination of the present invention to a cancer patient, wherein administering the pharmaceutical combination enhances antibody dependent cell-mediated cytotoxicity (ADCC) induced by the antibody therapy, as compared to administering the antibody therapy alone.

In preferred embodiments, the first nucleic acid encodes a TAA that is an endogenous retroviral (ERV) protein. In more preferred embodiments, the ERV protein is from the human endogenous retroviral protein K (HERV-K) family. In more preferred embodiments, the ERV protein is selected from a HERV-K envelope and a HERV-K gag protein.

In preferred embodiments, the first nucleic acid encodes a TAA that is an endogenous retroviral (ERV) peptide. In more preferred embodiments, the ERV peptide is from the human endogenous retroviral protein K (HERV-K) family. In more preferred embodiments, the ERV peptide is selected from a pseudogene of a HERV-K envelope protein (HERV-K-MEL).

In other preferred embodiments, the first nucleic acid encodes a TAA selected from the group consisting of: carcinoembryonic antigen (CEA), mucin 1 cell surface associated (MUC-1), prostatic acid phosphatase (PAP), prostate specific antigen (PSA), human epidermal growth factor receptor 2 (HER-2), survivin, tyrosine related protein 1 (TRP1), tyrosine related protein 1 (TRP2), Brachyury, Preferentially Expressed Antigen in Melanoma (PRAME), Folate receptor 1 (FOLR1), and combinations thereof.

In one or more preferred embodiments, the recombinant MVA is MVA-BN or a derivative thereof.

In various additional embodiments, the recombinant MVAs and methods described herein are administered to a cancer subject in combination with either an immune checkpoint molecule antagonist or agonist. In further embodiments, the recombinant MVAs and methods described herein are administered to a cancer subject in combination with an antibody specific for a TAA to treat a subject with cancer. In a more preferred embodiment, the recombinant MVAs and methods described herein are administered in combination with an antagonist or agonist of an immune checkpoint molecule selected from CTLA-4, PD-1, PD-L1, LAG-3, TIM-3, and ICOS. In most preferred embodiments, the immune checkpoint molecule antagonist or agonist comprises an antibody. In a most preferred embodiment, the immune checkpoint molecule antagonist or agonist comprises a PD-1 or PD-L1 antibody.

Additional objects and advantages of the invention will be set forth in part in the description which follows, and in part will be obvious from the description or may be learned by practice of the invention. The objects and advantages of the invention will be realized and attained by means of the elements and combinations particularly pointed out in the appended claims.

The accompanying drawings, which are incorporated in and constitute a part of this specification, illustrate one or more embodiments of the invention and together with the description, serve to explain the principles of the invention.

BRIEF DESCRIPTION OF THE DRAWINGS

FIG. 2A shows GMFI of T-bet on OT-I CD8+ T cells (indicated as "CD8+" in the figure); FIG. 2B shows percentage of CD44+Granzyme B+IFNγ+ TNFα+ of OT-I CD8+ T cells. Data are shown as Mean±SEM.

FIGS. 3A, 3C, 3D, and 3E show the percentage of dead cells ("Live/Dead+"). FIG. 3B: HMGB1 in the supernatants from FIG. 3A was quantified by ELISA. FIG. 3E: Bone marrow-derived macrophages (BMDMs) were infected at the indicated MOI for 20 hours. Cells were analyzed for their viability by flow cytometry. Data are presented as Mean±SEM.

FIG. 5A: 6 hours later, mice were bled, serum was isolated from whole blood and IFN-γ concentration in serum determined by Luminex. FIG. 5B: 3, 21 and 45 hours later, mice were intravenously injected with Brefeldin A to stop protein secretion. Mice were sacrificed 6, 24 and 48 hours after immunization and splenocytes analyzed by flow cytometry. Data are shown as Mean±SEM.

FIG. 7A shows percentage of antigen (OVA)-specific CD8+ T cells among Peripheral Blood Leukocytes (PBL); FIG. 7B shows the percentage of vector (B8R)-specific CD8+ T cells among PBL. Mice were sacrificed on day 70 after prime immunization. Spleens were harvested and flow cytometry analysis performed. FIG. 7C shows percentage of antigen (OVA)-specific CD8+ T cells among live cells; and FIG. 7D shows percentage of vector (B8R)-specific CD8+ T cells among live cells. Data are shown as Mean±SEM.

In FIG. 12A, tumor mean volume is shown. FIG. 12B: On day 12 after prime, peripheral blood lymphocytes were stained with OVA-dextramer and analyzed by FACS. Percentage OVA dextramer+CD44+ T cells among CD8+ T cells is shown.

FIG. 13C: 7 days after immunization, blood cells were restimulated and the percentage of CD8+CD44+IFN-γ+ cells in blood upon stimulation is shown.

FIG. 15 shows cytokine/chemokines being upregulated in immunized mice.

FIG. 16 shows those cytokine/chemokines that are upregulated in MVA-OVA-4-1BBL immunized mice compared to MVA-BN.

FIG. 18A: Percentage of Ki67+ cells among OVA-specific CD8+ T cells in tumor (left panel) and TdLN (right panel) is shown. FIG. 18B: GMFI of PD1 among OVA-specific CD8+ T cells in the tumor seven days after i.t. immunization is shown. FIG. 18C: OVA-specific Teff/Treg ratio in the tumor seven days after i.t. immunization is shown.

FIG. 21A: tumor mean diameter is shown. FIG. 21B: 11 days after the first immunization blood was withdrawn and analyzed for the presence of antigen-specific T cells (i.e., $OVA_{257-264}$-specific T cells). The percentage of OVA-specific T cells within CD8+ T cells is shown.

FIG. 23 shows those cytokine/chemokines that are decreased in the absence of IL15Rα after MVA-OVA-4-1BBL intratumoral (i.t.) immunization.

FIG. 24A shows tumor mean diameter, and FIG. 24B shows the appearance of vitiligo in mice treated with MVA-gp70-4-1BBL. 11 days after the first immunization, blood was withdrawn and analyzed for the presence of antigen-specific T cells. The percentage of IFNγ producing CD44+ T cells within CD8+ T cells upon p15E restimulation is shown in FIG. 24C.

FIG. 26A shows tumor mean diameter and FIG. 26B shows percent survival. FIG. 26C: Eleven days after the first immunization, blood was withdrawn and restimulated with AH1 peptide; the percentage of IFNγ+CD44+ T cells within CD8+ T cells is shown.

FIG. 27 shows number of $CD8^+$ T cells, p15E-specific $CD8^+$ T cells, and $Ki67^+$ p15E-specific $CD8^+$ T cells per mg tumor and per TdLN. Data represent Mean±SEM.

FIG. 29A shows tumor mean diameter and FIG. 29B shows percent survival. Seven days after the first immunization, blood was withdrawn and restimulated with AH1 peptide; FIG. 29C shows the percentage of $IFN\gamma^+$ $CD44^+$ T cells within $CD8^+$ T cells as Mean±SEM.

DETAILED DESCRIPTION OF THE INVENTION

Figure 1A:
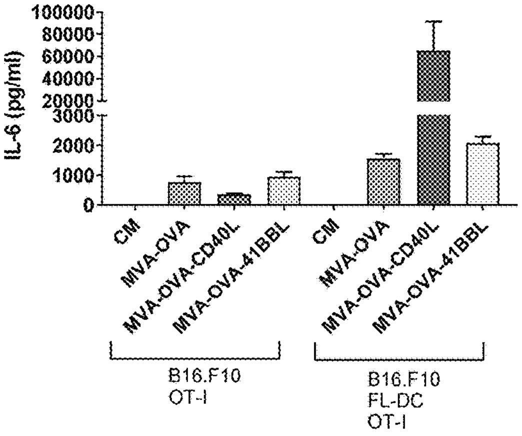
FIGS. 1A, 1B, 1C, and 1D illustrate that 4-1BBL-mediated costimulation of CD8 T cells by MVA-OVA-4-1BBL infected tumor cells influences cytokine production without the need of DC. MVA-OVA-CD40L in contrast only enhances cytokine production in the presence of DC. As described in Example 2, dendritic cells (DCs) were generated after culturing bone marrow cells from C57BL/6 mice in the presence of recombinant Flt3L for 14 days. B16.F10 cells were infected with MVA-OVA, MVA-OVA-CD40L, or MVA-OVA-4-1BBL and infected tumor cells were harvested and cocultured when indicated in the presence of DCs. Naïve OVA(257-264) specific CD8+ T cells were magnetically purified from OT-I mice and added to the coculture. Cells were cultured and the supernatant was collected for cytokine concentration analysis by Luminex. Supernatant concentration of IL-6 (FIG. 1A), GM-CSF (FIG. 1B), IL-2 (FIG. 1C) and IFN-γ (FIG. 1D) is shown. Data are shown as Mean±SEM.

It is to be understood that both the foregoing Summary and the following Detailed Description are exemplary and explanatory only and are not restrictive of the invention, as claimed.

Described and illustrated in the present application, the recombinant MVA and methods of the present invention enhance multiple aspects of a cancer patient’s immune response. In various aspects, the present invention demonstrates that when a recombinant MVA comprising a tumor-associated antigen (TAA) and a 4-1BBL antigen is administered intratumorally or intravenously to a cancer subject, there is an increased anti-tumor effect realized in the subject. As described in more detail herein, this increased anti-tumor effect includes a higher reduction in tumor volume, increased overall survival rate, an enhanced CD8 T cell response to the TAA, and enhanced inflammatory responses such as increased NK cell activity, increases in cytokine production, and so forth.

Described and illustrated in the present application, the recombinant MVA and methods of the present invention enhance multiple aspects of a cancer patient’s immune response. In various aspects, the present invention demonstrates that when a recombinant MVA comprising a tumor-associated antigen (TAA) and a CD40L antigen is administered intratumorally or intravenously to a cancer subject, there is an increased anti-tumor effect realized in the subject. As described in more detail herein, this increased anti-tumor effect includes a higher reduction in tumor volume, increased overall survival rate, an enhanced CD8 T cell response to the TAA, and enhanced inflammatory responses such as increased NK cell activity, increases in cytokine production, and so forth.

In additional aspects, various embodiments of the present invention demonstrate that when a recombinant MVA comprising a tumor-associated antigen (TAA) and a 4-1BBL antigen is administered intratumorally in combination with at least one immune checkpoint molecule antagonist/agonist there is increased tumor reduction and an increase in overall survival rate in cancer subjects.

In still further aspects, various embodiments of the present invention demonstrate that when a recombinant MVA comprising a tumor-associated antigen (TAA) and a 4-1BBL antigen is administered intratumorally in combination with a tumor specific antibody there is increased tumor reduction and an increase in overall survival rate in cancer subjects.

While recombinant MVA viruses have previously encoded a 4-1BBL antigen, the immunogenic benefits of an MVA encoding 4-1BBL was unclear (see, e.g., Spencer et al. (2014) *PLoS One* 9(8): e105520). In Spencer, co-expression of 4-1BBL and a transgenic antigen in either an MVA vector or an Adenovirus vector resulted in an increase in mouse CD8 T cell responses; however, after an intra-muscular administration with the Adenovirus vector encoding 4-1BBL, there was not any increase seen in IFN-γ responses in non-human primates (Id. at pages 2, 6). Furthermore, the immunogenic benefits of utilizing an MVA encoding 4-1BBL as part of treating cancer and destroying tumor and/or tumor cells was unknown.

The various embodiments of the present disclosure demonstrate that an MVA encoding 4-1BBL and a TAA (referred to herein as MVA-TAA-4-1BBL) can be effective in treating cancer in a subject, such as a human. Shown and described herein, administration of MVA-TAA-4-1BBL can enhance multiple aspects of a cancer subject’s immune response and can effectively reduce and kill tumor cells. One or more of the enhanced anti-tumor effects of the various embodiments of the present disclosure are summarized as follows.

Intravenous administration of recombinant MVA encoding 4-1BBL generates an enhanced antitumor effect. In at least one aspect, the present invention includes a recombinant MVA encoding a TAA and a 4-1BBL antigen (rMVA-TAA-4-1BBL) that is administered intravenously, wherein the intravenous administration enhances an anti-tumor effect, as compared to an intravenous administration of a recombinant MVA without 4-1BBL, or as compared to a non-intravenous administration of a recombinant MVA encoding 4-1BBL (for example, such as a subcutaneous administration of a recombinant MVA encoding 4-1BBL). These enhanced antitumor effects include an enhanced NK cell response (shown in FIGS. 4A and 4B), an enhanced inflammatory response as shown by an increase in IFN-γ secretion (shown in FIGS. 5A, 5B, and 6), an increased antigen and vector-specific CD8 T cell expansion (shown in FIGS. 7A, 7B, 7C, and 7D), and an increased tumor reduction (shown in FIG. 8).

Intratumoral administration of recombinant MVA encoding 4-1BBL enhances inflammation in the tumor. In another aspect of the present invention, it was determined that infection of tumor cells with MVA-OVA-4-1BBL, but not with MVA-OVA-CD40L, activated antigen-specific CD8+ T cells to produce T cell-derived cytokines such as GM-CSF, IL-2 and IFN-γ in the absence of antigen cross-presenting DCs (FIGS. 1A-1D). This was unexpected in the case of GM-CSF, a growth factor produced by naïve T cells upon activation that induces maturation of dendritic cell and myeloid cell subsets (Min et al. (2010) *J. Immunol.* 184: 4625-4629). In the presence of antigen-cross-presenting DCs, antigen-specific CD8+ T cells stimulated by infected tumor cells with rMVA-CD40L produced IFN-γ, but not IL-2 or GM-CSF as rMVA-4-1BBL (FIGS. 1A-1D). Interestingly, large amounts of IL-6, a key cytokine produced by DCs, were detected (FIG. 1A).

In one advantageous aspect, enhanced inflammation in the tumor can result in having large numbers of TILs (tumor infiltrating lymphocytes) killing tumor cells at the site of the tumor (see, e.g., Lanitis et al. (2017) *Annals Oncol.* 28 (suppl 12): xii18-xii32). These inflamed tumors, also known as “hot” tumors, enable enhanced tumor cell destruction in view of the increased numbers of TILs, cytokines, and other inflammatory molecules.

Intratumoral administration of recombinant MVA encoding 4-1BBL reduces tumor volume and increase overall survival rate. In one aspect, the present invention includes a recombinant MVA encoding a 4-1BBL antigen (MVA-4-1BBL) that is administered intratumorally, wherein the intratumoral administration enhances anti-tumor effects in a cancer subject, as compared to an intratumoral administration of a recombinant MVA without 4-1BBL.

While recombinant MVA viruses have been previously administered intratumorally (see e.g., White et al. (2018) *PLoS One* 13: e0193131, and Nemeckova et al. (2007) *Neoplasma* 54: 326-33), the studies have produced diverse results. For example, in Nemeckova, it was found that intratumoral injections of vaccinia virus MVA expressing GM-CSF and immunization with DNA vaccine prolonged the survival of mice bearing HPV16 induced tumors (see Nemeckova at Abstract). Alternatively, White et al. were unable to demonstrate inhibition of pancreatic tumor growth following intratumoral injection of MVA (see White at Abstract).

As part of the present disclosure, a recombinant MVA comprising one or more nucleic acids encoding a TAA and 4-1BBL was administered intratumorally to a subject. Shown in FIG. 9, an intratumoral injection of MVA-TAA-4-1BBL demonstrated a significant decrease in tumor volume as compared to recombinant MVA TAA.

Intratumoral administration of recombinant MVA encoding 4-1BBL administered in combination with an immune checkpoint molecule antagonist or agonist generates an increased anti-tumor effect. In various embodiments, the present invention includes an administration of MVA-TAA-4-1BBL in combination with an immune checkpoint antagonist or agonist. Preferably the administration of the MVA-TAA-4-1BBL is intravenous or intratumoral. The MVAs of the present invention in combination with an immune checkpoint antagonist or agonist is advantageous as the combination provides a more effective cancer treatment. For example, the combination and/or combination therapy of the present invention enhances multiple aspects of a cancer patient's immune response. In at least one aspect, the combination synergistically enhances both the innate and adaptive immune responses and, when combined with an antagonist or agonist of an immune checkpoint molecule, reduces tumor volume and increase survival of a cancer patient.

The data presented in this application demonstrate that MVA-TAA-4-1BBL when combined with an immune checkpoint antagonist or agonist generates an increased anti-tumor effect. Indeed, shown in FIG. 11, when an intratumoral administration of MVA-OVA-4-1BBL was combined with a PD-1 antibody intraperitoneally, there was a decrease in tumor volume as compared to PD-1 by itself.

Intratumoral administration of recombinant MVA encoding 4-1BBL administered in combination with an antibody specific for a tumor associated antigen (TAA) generates an increased anti-tumor effect. In various embodiments, the present invention includes an administration of MVA-TAA-4-1BBL in combination with an antibody specific for a TAA. Preferably the administration of the MVA-TAA-4-1BBL is intravenous or intratumoral. The MVAs of the present invention in combination with an TAA specific antibody is advantageous and can work together to provide a more effective cancer treatment.

In one exemplary aspect, the enhanced NK cells response induced by the administration of the MVA-TAA-4-1BBL works synergistically with the TAA specific antibody to enhance antibody dependent cytotoxicity (ADCC) in a subject. This enhanced ADCC in a cancer subject leads to an increase in tumor cell killing and tumor destruction.

The data presented in the present application demonstrate that MVA-TAA-4-1BBL when combined with an TAA specific antibody generates an increased anti-tumor effect. Indeed, shown in FIG. 11, when an intratumoral administration of MVA-OVA-4-1BBL was combined with intraperitoneal TRP-1 antibody, there was a decrease in tumor volume as compared to the TRP-1 antibody by itself.

Administration of MVA-TAA-4-1BBL as part of a prime and boost immunization according to the invention increases antigen and vector-specific CD8+ T cell expansion. In other aspects, the invention provides a method in which MVA-TAA-4-1BBL is administered as part of a homologous and/or heterologous prime-boost regimen. Preferably the administration of the MVA-TAA-4-1BBL is intravenous or intratumoral. Illustrated in FIGS. 7A-7D, antigen and vector-specific CD8+ T cell expansion was increased during a priming and boosting by intravenous administration of MVA-TAA-4-1BBL.

Definitions

As used herein, the singular forms "a," "an," and "the" include plural references unless the context clearly indicates otherwise. Thus, for example, reference to "a nucleic acid" includes one or more of the nucleic acid and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise," and variations such as "comprises" and "comprising," will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having." Any of the aforementioned terms (comprising, containing, including, having), though less preferred, whenever used herein in the context of an aspect or embodiment of the present invention can be substituted with the term "consisting of. When used herein "consisting of" excludes any element, step, or ingredient not specified in the claim element. When used herein, "consisting essentially of" does not exclude materials or steps that do not materially affect the basic and novel characteristics of the claim.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

"Mutated" or "modified" protein or antigen as described herein is as defined herein any a modification to a nucleic acid or amino acid, such as deletions, additions, insertions, and/or substitutions.

"Percent (%) sequence homology or identity" with respect to nucleic acid sequences described herein is defined as the percentage of nucleotides in a candidate sequence that are identical with the nucleotides in the reference sequence (i.e., the nucleic acid sequence from which it is derived), after aligning the sequences and introducing gaps, if necessary, to achieve the maximum percent sequence identity, and not considering any conservative substitutions as part of the sequence identity. Alignment for purposes of determining percent nucleotide sequence identity or homology can be achieved in various ways that are within the skill in the art, for example, using publicly available computer software such as BLAST, ALIGN, or Megalign (DNASTAR) software. Those skilled in the art can determine appropriate parameters for measuring alignment, including any algorithms needed to achieve maximum alignment over the full length of the sequences being compared.

For example, an appropriate alignment for nucleic acid sequences is provided by the local homology algorithm of Smith and Waterman ((1981) *Advances in Applied Mathematics* 2: 482-489). This algorithm can be applied to amino acid sequences by using the scoring matrix developed by Dayhoff, *Atlas of Protein Sequences and Structure*, M. O. Dayhoff ed., 5 suppl. 3: 353-358, National Biomedical Research Foundation, Washington, D.C., USA, and normalized by Gribskov ((1986) *Nucl. Acids Res.* 14(6): 6745-6763). An exemplary implementation of this algorithm to determine percent identity of a sequence is provided by the Genetics Computer Group (Madison, Wisconsin, USA) in the "BestFit" utility application. The default parameters for this method are described in the Wisconsin Sequence Analysis Package Program Manual, Version 8 (1995) (available from Genetics Computer Group, Madison, Wisconsin, USA). A preferred method of establishing percent identity in the context of the present invention is to use the MPSRCH package of programs copyrighted by the University of Edinburgh, developed by Collins and Sturrok, and distributed by IntelliGenetics, Inc. (Mountain View, California, USA). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+ GenBank CDS translations+Swiss protein+Spupdate+PIR. Details of these programs can be found at the following internet address: blast.ncbi.nlm.nih.gov/.

The term "prime-boost vaccination" or "prime-boost regimen" refers to a vaccination strategy or regimen using a first priming injection of a vaccine targeting a specific antigen followed at intervals by one or more boosting injections of the same vaccine. Prime-boost vaccination may be homologous or heterologous. A homologous prime-boost vaccination uses a vaccine comprising the same antigen and vector for both the priming injection and the one or more boosting injections. A heterologous prime-boost vaccination uses a vaccine comprising the same antigen for both the priming injection and the one or more boosting injections but different vectors for the priming injection and the one or more boosting injections. For example, a homologous prime-boost vaccination may use a recombinant poxvirus comprising nucleic acids expressing one or more antigens for the priming injection and the same recombinant poxvirus expressing one or more antigens for the one or more boosting injections. In contrast, a heterologous prime-boost vaccination may use a recombinant poxvirus comprising nucleic acids expressing one or more antigens for the priming injection and a different recombinant poxvirus expressing one or more antigens for the one or more boosting injections.

The term "recombinant" means a polynucleotide, virus or vector of semisynthetic, or synthetic origin which either does not occur in nature or is linked to another polynucleotide in an arrangement not found in nature. By "recombinant MVA" or "rMVA" as used herein is generally intended a modified vaccinia Ankara (MVA) that comprises at least one polynucleotide encoding a tumor associated antigen (TAA).

As used herein, reducing tumor volume or a reduction in tumor volume can be characterized as a reduction in tumor volume and/or size but can also be characterized in terms of clinical trial endpoints understood in the art. Some exemplary clinical trial endpoints associated with a reduction in tumor volume and/or size can include, but are not limited to, Response Rate (RR), Objective response rate (ORR), and so forth.

As used herein an increase in survival rate can be characterized as an increase in survival of a cancer patient, but can also be characterized in terms of clinical trial endpoints understood in the art. Some exemplary clinical trial endpoints associated with an increase in survival rate include, but are not limited to, Overall Survival rate (OS), Progression Free Survival (PFS) and so forth.

As used herein, a "transgene" or "heterologous" gene is understood to be a nucleic acid or amino acid sequence which is not present in the wild-type poxviral genome (e.g., Vaccinia, Fowlpox, or MVA). The skilled person understands that a "transgene" or "heterologous gene", when present in a poxvirus, such as Vaccinia Virus, is to be incorporated into the poxviral genome in such a way that, following administration of the recombinant poxvirus to a host cell, it is expressed as the corresponding heterologous gene product, i.e., as the "heterologous antigen" and\or "heterologous protein." Expression is normally achieved by operatively linking the heterologous gene to regulatory elements that allow expression in the poxvirus-infected cell. Preferably, the regulatory elements include a natural or synthetic poxviral promoter.

A "vector" refers to a recombinant DNA or RNA plasmid or virus that can comprise a heterologous polynucleotide. The heterologous polynucleotide may comprise a sequence of interest for purposes of prevention or therapy, and may optionally be in the form of an expression cassette. As used herein, a vector needs not be capable of replication in the ultimate target cell or subject. The term includes cloning vectors and viral vectors.

Combinations and Methods

In various embodiments, the present invention comprises a recombinant MVA comprising a first nucleic acid encoding a tumor-associated antigen (TAA) and a second nucleic acid encoding 4-1BBL, that when administered intratumorally induces both an inflammatory response and an enhanced T cell response as compared to an inflammatory response and a T cell response induced by a non-intratumoral administration of a recombinant MVA virus comprising a first nucleic acid encoding a TAA and a second nucleic acid encoding 4-1BBL.

In various additional embodiments, the present invention comprises a first nucleic acid encoding a tumor-associated antigen (TAA) and a second nucleic acid encoding 4-1BBL, that when administered intratumorally induces both an enhanced intratumoral inflammatory response and an enhanced T cell response as compared to an intratumoral inflammatory response and a T cell response induced by an intratumoral administration of a recombinant MVA virus comprising a first nucleic acid encoding a TAA.

Enhanced Inflammation Response in the Tumor. In various aspects of the present disclosure it was determined that an intratumoral administration of a recombinant MVA encoding a TAA and a 4-1BBL induces an enhanced inflammatory response in a tumor, as compared to an administration of a recombinant MVA by itself. In at least one aspect, an "enhanced inflammation response" in a tumor according to present disclosure is characterized by one or more of the following: 1) an increase in expression of IFN-γ and/or 2) an increase in expression of Granzyme B (GraB) in the tumor and/or tumor cells. Thus, whether an inflammatory response is enhanced in a tumor and/or tumor cells in accordance with present disclosure can be determined by measuring to determine whether there is an increase in expression of one or more molecules which are indicative of an increased inflammatory response, including the secretion of chemokines and cytokines as is known in the art. Exemplary inflammatory response markers include one or more of markers that are useful in measuring NK cell frequency and/or activity include one or more of: IFN-γ and/or Granzyme B (GraB). These molecules and the measurement thereof are validated assays that are understood in the art and can be carried out according to known techniques. See, e.g., Borrego et al. ((1999) *Immunology* 7(1): 159-165).

Enhanced NK cell response. In various additional aspects of the present disclosure it was determined that an intratumoral administration or an intravenous administration of a recombinant MVA encoding a TAA and a 4-1BBL induces an enhanced NK Cells response in a tumor or tumor environment, as compared an administration of a recombinant MVA by itself. In one aspect, an "enhanced NK cell response" according to the present disclosure is characterized by one or more of the following: 1) an increase in NK cell frequency, 2) an increase in NK cell activation, and/or 3) an increase in NK cell proliferation. Thus, whether an NK cell response is enhanced in accordance with the present disclosure can be determined by measuring the expression of one or more molecules which are indicative of an increased NK cell frequency, increased NK cell activation, and/or increased NK cell proliferation. Exemplary markers that are useful in measuring NK cell frequency and/or activity include one or more of: NKp46, IFN-γ, CD69, CD70, NKG2D, FasL, granzyme B, CD56, and/or Bcl-XL. Exemplary markers that are useful in measuring NK cell activation include one or more of IFN-γ, CD69, CD70, NKG2D, FasL, granzyme B and/or Bcl-XL. Exemplary markers that are useful in measuring NK cell proliferation include: Ki67. These molecules and the measurement thereof are validated assays that are understood in the art and can be carried out according to known techniques (see, e.g., Borrego et al. (1999) *Immunology* 7(1): 159-165). Additionally, assays for measuring the molecules can be found in Examples 5 and 6 of the present disclosure. At least in one aspect, 1) an increase in NK cell frequency can be defined as at least a 2-fold increase in CD3-NKp46+ cells compared to pre-treatment/baseline; 2) an increase in NK cell activation can be defined as at least a 2-fold increase in IFN-γ, CD69, CD70, NKG2D, FasL, granzyme B and/or Bcl-XL expression compared to pre-treatment/baseline expression; and/or 3) an increase in NK cell proliferation is defined as at least a 1.5 fold increase in Ki67 expression compared to pre-treatment/baseline expression.

Enhanced T Cell response. In accordance with the present application, an "enhanced T cell response" is characterized by one or more of the following: 1) an increase in frequency of CD8 T cells; 2) an increase in CD8 T cell activation; and/or 3) an increase in CD8 T cell proliferation. Thus, whether a T cell response is enhanced in accordance with the present application can be determined by measuring the expression of one or more molecules which are indicative of 1) an increase in CD8 T cell frequency 2) an increase in CD8 T cell activation; and/or 3) an increase CD8 T cell proliferation. Exemplary markers that are useful in measuring CD8 T cell frequency, activation, and proliferation include CD3, CD8, IFN-γ, TNF-α, IL-2, CD69 and/or CD44, and Ki67, respectively. Measuring antigen specific T cell frequency can also be measured by MHC Multimers such as pentamers or dextramers as shown by the present application. Such measurements and assays as well as others suitable for use in evaluating methods and compositions of the invention are validated and understood in the art.

In one aspect, an increase in CD8 T cell frequency is characterized by an at least a 2-fold increase in IFN-γ and/or dextramer+CD8 T cells compared to pre-treatment/baseline. An increase in CD8 T cell activation is characterized as at least a 2-fold increase in CD69 and/or CD44 expression compared to pre-treatment/baseline expression. An increase in CD8 T cell proliferation is characterized as at least a 2-fold increase in Ki67 expression compared to pre-treatment/baseline expression.

In an alternative aspect, an enhanced T cell response is characterized by an increase in CD8 T cell expression of effector cytokines and/or an increase of cytotoxic effector functions. An increase in expression of effector cytokines can be measured by expression of one or more of IFN-γ, TNF-α, and/or IL-2 compared to pre-treatment/baseline. An increase in cytotoxic effector functions can be measured by expression of one or more of CD107a, granzyme B, and/or perforin and/or antigen-specific killing of target cells.

The assays, cytokines, markers, and molecules described herein and the measurement thereof are validated and understood in the art and can be carried out according to known techniques. Additionally, assays for measuring the T cells responses can be found in the working examples, wherein T cell responses were analyzed, including but not limited to Examples 2, 3, 8, 13 and 14.

The enhanced T cell response realized by the present invention is particularly advantageous in combination with the enhanced NK cell response, and the enhanced inflammatory response as the enhanced T cells effectively target and kill those tumor cells that have evaded and/or survived past the initial innate immune responses in the cancer patient.

In yet additional embodiments, the combinations and methods described herein are for use in treating a human cancer patient. In preferred embodiments, the cancer patient is suffering from and/or is diagnosed with a cancer selected from the group consisting of: breast cancer, lung cancer, head and neck cancer, thyroid, melanoma, gastric cancer, bladder cancer, kidney cancer, liver cancer, melanoma, pancreatic cancer, prostate cancer, ovarian cancer, urothelial, cervical, or colorectal cancer. In yet additional embodiments, the combinations and methods described herein are for use in treating a human cancer patient suffering from and/or diagnosed with a breast cancer, colorectal cancer or melanoma, preferably a melanoma, more preferably a colorectal cancer or most preferably a colorectal cancer.

Certain Exemplary Tumor-Associated Antigens. In certain embodiments, an immune response is produced in a subject against a cell-associated polypeptide antigen. In certain such embodiments, a cell-associated polypeptide antigen is a tumor-associated antigen (TAA).

The term "polypeptide" refers to a polymer of two or more amino acids joined to each other by peptide bonds or modified peptide bonds. The amino acids may be naturally occurring as well as non-naturally occurring, or a chemical analogue of a naturally occurring amino acid. The term also refers to proteins, i.e. functional biomolecules comprising at least one polypeptide; when comprising at least two polypeptides, these may form complexes, be covalently linked, or may be non-covalently linked. The polypeptide(s) in a protein can be glycosylated and/or lipidated and/or comprise prosthetic groups.

Endogenous Retroviral Proteins (ERVs). Preferably, the TAA is embodied in an Endogenous Retroviral Proteins (ERVs). More preferably, the ERV is an ERV from the Human HERV-K protein family. Most preferably, the HERV-K protein is selected from a HERV-K envelope (env) protein, a HERV-K group specific antigen (gag) protein, and a HERV-K "marker of melanoma risk" (mel) protein (see, e.g., Cegolon et al. (2013) *BMC Cancer* 13:4).

ERVs constitute 8% of the human genome and are derived from germline infections million years ago. The majority of those elements inserted into our genome are heavily mutated and thus are not transcribed or translated. However, a small, rather recently acquired fraction of ERVs is still functional and translated and in some cases even produce viral particles. The transcription of ERVs is very restricted as the locus is usually highly methylated and consequently not transcribed in somatic cells (Kassiotis (2016) *Nat. Rev. Immunol.* 16: 207-19). Only under some circumstances such as cellular stress (chemicals, UV radiation, hormones, cytokines) ERVs can be reactivated. Importantly, ERVs are also expressed in many different types of cancer but not in normal tissues (Cegolon et al. (2013) *BMC Cancer* 13: 4; Wang-Johanning et al. (2003) *Oncogene* 22: 1528-35). This very restricted expression pattern ensures that ERVs are not or rarely exposed to immunological tolerance mechanisms which presumably results in a competent ERV-specific T cell repertoire. In this manner, ERVs can be used in MVAs as tumor antigens ("TAAs").

In various additional embodiments, the TAA includes, but is not limited to, HER2, PSA, PAP, CEA, MUC-1, FOLR1, PRAME, survivin, TRP1, TRP2, or Brachyury alone or in combinations. Such exemplary combination may include CEA and MUC-1, for example in an MVA also known as CV301. Other exemplary combinations may include PAP and PSA.

In still further embodiments, additional TAAs may include, but are not limited to, 5 alpha reductase, alpha-fetoprotein, AM-1, APC, April, BAGE, beta-catenin, Bcl12, bcr-abl, CA-125, CASP-8/FLICE, Cathepsins, CD19, CD20, CD21, CD23, CD22, CD33 CD35, CD44, CD45, CD46, CD5, CD52, CD55, CD59, CDC27, CDK4, CEA, c-myc, Cox-2, DCC, DcR3, E6/E7, CGFR, EMBP, Dna78, farnesyl transferase, FGF8b, FGF8a, FLK-1/KDR, folic acid receptor, G250, GAGE-family, gastrin 17, gastrin-releasing hormone, GD2/GD3/GM2, GnRH, GnTV, GP1, gp100/Pme117, gp-100-in4, gp15, gp75/TRP1, hCG, heparanase, Her2/neu, HMTV, Hsp70, hTERT, IGFR1, IL-13R, iNOS, Ki67, KIAA0205, K-ras, H-ras, N-ras, KSA, LKLR-FUT, MAGE-family, mammaglobin, MAP17, melan-A/MART-1, mesothelin, MIC A/B, MT-MMPs, mucin, NY-ESO-1, osteonectin, p15, P170/MDR1, p53, p97/melanotransferrin, PAI-1, PDGF, uPA, PRAME, probasin, progenipoietin, PSA, PSM, RAGE-1, Rb, RCAS1, SART-1, SSX-family, STAT3, STn, TAG-72, TGF-alpha, TGF-beta, Thymosin-beta-15, TNF-alpha, TRP1, TRP2, tyrosinase, VEGF, ZAG, p16INK4, and glutathione-S-transferase.

A preferred PSA antigen comprises the amino acid change of isoleucine to leucine at position 155 (see U.S. Pat. No. 7,247,615, which is incorporated herein by reference).

In one or more preferred embodiments of present invention, the heterologous TAA is selected from HER2 and/or Brachyury.

Any TAA may be used so long as it accomplishes at least one objective or desired end of the invention, such as, for example, stimulating an immune response following administration of the MVA containing it. Exemplary sequences of TAAs, including TAAs mentioned herein, are known in the art and are suitable for use in the compositions and methods of the invention. Sequences of TAAs for use in the compositions and methods of the invention may be identical to sequences known in the art or disclosed herein, or they may share less than 100% identity, such as at least 90%, 91%, 92%, 95%, 97%, 98%, or 99% or more sequence identity to either a nucleotide or amino acid sequence known in the art or disclosed herein. Thus, a sequence of a TAA for use in a composition or method of the invention may differ from a reference sequence known in the art and/or disclosed herein by less than 20, or less than 19, 18, 15, 14, 13, 12, 11, 10, 9, 8, 7, 6, 5, 4, 3, 2, or 1 nucleotides or amino acids, so long as it accomplishes at least one objective or desired end of the invention. One of skill in the art is familiar with techniques and assays for evaluating TAAs to ensure their suitability for use in an MVA or method of the invention.

Modified Tumor-Associated Antigens. In certain embodiments, a cell-associated polypeptide antigen is modified such that a CTL response is induced against a cell which presents epitopes derived from a polypeptide antigen on its surface, when presented in association with an MHC Class I molecule on the surface of an APC. In certain such embodiments, at least one first foreign TH epitope, when presented, is associated with an MHC Class II molecule on the surface of the APC. In certain such embodiments, a cell-associated antigen is a tumor-associated antigen.

Exemplary APCs capable of presenting epitopes include dendritic cells and macrophages. Additional exemplary APCs include any pino- or phagocytizing APC, which is capable of simultaneously presenting: 1) CTL epitopes bound to MHC class I molecules; and 2) TH epitopes bound to MHC class II molecules.

In certain embodiments, modifications to one or more of the TAAs, such as, but not limited to, HERV-K env, HERV-K gag, HERV-K mel, CEA, MUC-1, PAP, PSA, PRAME, FOLR1, HER2, survivin, TRP1, TRP2, or Brachyury, are made such that, after administration to a subject, polyclonal antibodies are elicited that predominantly react with the one or more of the TAAs described herein. Such antibodies could attack and eliminate tumor cells as well as prevent metastatic cells from developing into metastases. The effector mechanism of this anti-tumor effect would be mediated via complement and antibody dependent cellular cytotoxicity. In addition, the induced antibodies could also inhibit cancer cell growth through inhibition of growth factor dependent oligo-dimerisation and internalization of the receptors. In certain embodiments, such modified TAAs could induce CTL responses directed against known and/or predicted TAA epitopes displayed by the tumor cells.

In certain embodiments, a modified TAA polypeptide antigen comprises a CTL epitope of the cell-associated polypeptide antigen and a variation, wherein the variation comprises at least one CTL epitope or a foreign TH epitope. Certain such modified TAAs can include in one non-limiting example one or more HER2 polypeptide antigens comprising at least one CTL epitope and a variation comprising at least one CTL epitope of a foreign TH epitope, and methods of producing the same, are described in U.S. Pat. No. 7,005,498 and U.S. Patent Pub. Nos. 2004/0141958 and 2006/0008465.

Certain such modified TAAs can include in one non-limiting example one or more MUC-1 polypeptide antigens comprising at least one CTL epitope and a variation comprising at least one CTL epitope of a foreign epitope, and methods of producing the same, are described in U.S. Patent Pub. Nos. 2014/0363495.

Additional promiscuous T-cell epitopes include peptides capable of binding a large proportion of HLA-DR molecules encoded by the different HLA-DR. See, e.g., WO 98/23635 (Frazer I H et al., assigned to The University of Queensland); Southwood et. al. (1998) *J. Immunol.* 160: 3363 3373; Sinigaglia et al. (1988) *Nature* 336: 778 780; Rammensee et al. (1995) *Immunogenetics* 41: 178 228; Chicz et al. (1993) *J. Exp. Med.* 178: 27 47; Hammer et al. (1993) *Cell* 74: 197 203; and Falk et al. (1994) *Immunogenetics* 39: 230 242. The latter reference also deals with HLA-DQ and -DP ligands. All epitopes listed in these references are relevant as candidate natural epitopes as described herein, as are epitopes which share common motifs with these.

In certain other embodiments, the promiscuous T-cell epitope is an artificial T-cell epitope which is capable of binding a large proportion of haplotypes. In certain such embodiments, the artificial T-cell epitope is a pan DR epitope peptide ("PADRE") as described in WO 95/07707 and in the corresponding paper Alexander et al. (1994) *Immunity* 1: 751 761.

4-1BBL (also referred to herein as "41BBL" or "4-1BB ligand"). As illustrated by the present disclosure, the inclusion of 4-1BBL as part of the recombinant MVA and related methods induces increased and enhanced anti-tumor effects upon an intratumoral or intravenous administration in a cancer subject. Thus, in various embodiments, in addition to encoding a TAA, there is a recombinant MVA encoding a 4-1BBL antigen.

4-1BB/4-1BBL is a member of the TNFR/TNF superfamily. 4-1BBL is a costimulatory ligand expressed in activated B cells, monocytes and DCs. 4-1BB is constitutively expressed by natural killer (NK) and natural killer T (NKT) cells, Tregs and several innate immune cell populations, including DCs, monocytes and neutrophils. Interestingly, 4-1BB is expressed on activated, but not resting, T cells (Wang et al. (2009) *Immunol. Rev.* 229: 192-215). 4-1BB ligation induces proliferation and production of interferon gamma (IFN-γ) and interleukin 2 (IL-2), as well as enhances T cell survival through the upregulation of antiapoptotic molecules such as Bcl-xL (Snell et al. (2011) *Immunol. Rev.* 244: 197-217). Importantly, 4-1BB stimulation enhances NK cell proliferation, IFN-γ production and cytolytic activity through enhancement of Antibody-Dependent Cell Cytotoxicity (ADCC) (Kohrt et al. (2011) *Blood* 117: 2423-32).

In one or more preferred embodiments, 4-1BBL is encoded by the MVA of the present invention. In one or more other preferred embodiments, 4-1BBL is a human 4-1BBL. In still more preferred embodiments, the 4-1BBL comprises a nucleic acid encoding an amino acid sequence having a sequence with at least 90%, 95%, 97% 98%, or 99% identity to SEQ ID NO:3, i.e., differing from the amino acid sequence set forth in SEQ ID NO:3 by less than 10, 9, 8, 7, 6, 5, 4, 3, 2, or 1 amino acids. In even more preferred embodiments, the 4-1BBL comprises a nucleic acid encoding an amino acid sequence comprising SEQ ID NO: 3. In additional embodiments, a nucleic acid encoding 4-1BBL comprises a nucleic acid sequence having at least 90%, 95%, 97% 98%, or 99% identity to SEQ ID NO:4, i.e., differing from the nucleic acid sequence set forth in SEQ ID NO:4 by less than 20, 10, 5, 4, 3, 2, or 1 nucleic acid in the sequence. In more preferred embodiments, the 4-1BBL comprises a nucleic acid comprising SEQ ID NO: 4.

CD40L. As illustrated by the present disclosure the inclusion of CD40L as part of the combination and related method further enhances the decrease in tumor volume, prolongs progression-free survival and increase survival rate realized by the present invention. Thus, in various embodiments, the combination further comprises administering CD40L to a cancer patient. In preferred embodiments, the CD40L is encoded as part of a recombinant MVA as described herein.

While CD40 is constitutively expressed on many cell types, including B cells, macrophages, and dendritic cells, its ligand CD40L is predominantly expressed on activated T helper cells. The cognate interaction between dendritic cells and T helper cells early after infection or immunization 'licenses' dendritic cells to prime CTL responses. Dendritic cell licensing results in the up-regulation of co-stimulatory molecules, increased survival and better cross-presenting capabilities. This process is mainly mediated via CD40/CD40L interaction. However, various configurations of CD40L are described, from membrane bound to soluble (monomeric to trimeric) which induce diverse stimuli, either inducing or repressing activation, proliferation, and differentiation of APCs.

In one or more preferred embodiments, CD40L is encoded by the MVA of the present invention. In one or more other preferred embodiments, CD40L is a human CD40L. In still more preferred embodiments, the CD40L comprises a nucleic acid encoding an amino acid sequence having a sequence with at least 90%, 95%, 97% 98%, or 99% identity to SEQ ID NO:1, i.e., differing from the amino acid sequence set forth in SEQ ID NO:1 by less than 10, 9, 8, 7, 6, 5, 4, 3, 2, or 1 amino acids. In even more preferred embodiments, the CD40L comprises a nucleic acid encoding an amino acid sequence comprising SEQ ID NO: 1. In additional embodiments, a nucleic acid encoding CD40L comprises a nucleic acid sequence having at least 90%, 95%, 97% 98%, or 99% identity to SEQ ID NO:2, i.e., differing from the nucleic acid sequence set forth in SEQ ID NO:2 by less than 20, 10, 5, 4, 3, 2, or 1 nucleic acid in the sequence. In more preferred embodiments, the CD40L comprises a nucleic acid comprising SEQ ID NO: 2.

Antagonists of Immune Checkpoint Molecules. As described herein, at least in one aspect, the invention encompasses the use of immune checkpoint antagonists. Such immune checkpoint antagonists function to interfere with and/or block the function of the immune checkpoint molecule. Some preferred immune checkpoint antagonists include antagonists of Cytotoxic T-Lymphocyte Antigen 4 (CTLA-4), Programmed Cell Death Protein 1 (PD-1), Programmed Death-Ligand 1 (PD-L1), Lymphocyte-activation gene 3 (LAG-3), and T-cell immunoglobulin and mucin domain 3 (TIM-3).

Additionally, exemplary immune checkpoint antagonists can include, but are not limited to CTLA-4, PD-1, PD-L1, PD-L2, LAG-3, TIM-3, T cell Immunoreceptor with Ig and ITIM domains (TIGIT) and V-domain Ig Suppressor of T cell activation (VISTA).

Such antagonists of the immune checkpoint molecules can include antibodies which specifically bind to immune checkpoint molecules and inhibit and/or block biological activity and function of the immune checkpoint molecule.

Other antagonists of the immune checkpoint molecules can include antisense nucleic acid RNAs that interfere with the expression of the immune checkpoint molecules; and small interfering RNAs that interfere with the expression of the immune checkpoint molecules.

Antagonists can additionally be in the form of small molecules that inhibit or block the function of the immune checkpoint. Some non-limiting examples of these include NP12 (Aurigene), (D) PPA-1 by Tsinghua Univ, high affinity PD-1 (Stanford); BMS-202 and BMS-8 (Bristol Myers Squibb (BMS), and CA170/CA327 (Curis/Aurigene); and small molecule inhibitors of CTLA-4, PD-1, PD-L1, LAG-3, and TIM-3.

Antagonists can additionally be in the form of Anticalins® that inhibit or block the function of the immune checkpoint molecule. See, e.g., Rothe et al. ((2018) *BioDrugs* 32(3): 233-243).

It is contemplated that antagonists can additionally be in the form of Affimers®. Affimers are Fc fusion proteins that inhibit or block the function of the immune checkpoint molecule. Other fusion proteins that can serve as antagonists of immune checkpoints are immune checkpoint fusion proteins (e.g., anti-PD-1 protein AMP-224) and anti-PD-L1 proteins such as those described in US2017/0189476.

Candidate antagonists of immune checkpoint molecules can be screened for function by a variety of techniques known in the art and/or disclosed within the instant application, such as for the ability to interfere with the immune checkpoint molecules function in an in vitro or mouse model.

Agonist of ICOS. The invention further encompasses agonists of ICOS. An agonist of ICOS activates ICOS. ICOS is a positive co-stimulatory molecule expressed on activated T cells and binding to its' ligand promotes their proliferation (Dong (2001) *Nature* 409: 97-101).

In one embodiment, the agonist is ICOS-L, an ICOS natural ligand. The agonist can be a mutated form of ICOS-L that retains binding and activation properties. Mutated forms of ICOS-L can be screened for activity in stimulating ICOS in vitro.

Antibodies to an Immune Checkpoint Antagonist or Agonist. In preferred embodiments, the antagonist and/or agonist of an immune checkpoint molecules each comprises an antibody. As described herein, in various embodiments, the antibodies can be synthetic, monoclonal, or polyclonal and can be made by techniques well known in the art. Such antibodies specifically bind to the immune checkpoint molecule via the antigen-binding sites of the antibody (as opposed to non-specific binding). Immune checkpoint peptides, fragments, variants, fusion proteins, etc., can be employed as immunogens in producing antibodies immunoreactive therewith. More specifically, the polypeptides, fragment, variants, fusion proteins, etc. contain antigenic determinants or epitopes that elicit the formation of antibodies.

In more preferred embodiments, the antibodies of present invention are those that are approved, or in the process of approval by the government of a sovereign nation, for the treatment of a human cancer patient. Some non-limiting examples of these antibodies already approved, or in the approval process include antibodies to the following: CTLA-4 (Ipilimumab® and Tremelimumab); PD-1 (Pembrolizumab, Lambrolizumab, Amplimmune-224 (AMP-224)), Amplimmune-514 (AMP-514), Nivolumab, MK-3475 (Merck). BI 754091 (Boehringer Ingelheim)), and PD-L1 (Atezolizumab, Avelulmab, Durvalumab, MPDL3280A (Roche), MED14736 (AZN), MSB0010718C (Merck)); LAG-3 (IMP321, BMS-986016, BI754111 (Boehringer Ingelheim), LAG525 (Novartis), MK-4289 (Merck), TSR-033 (Tesaro).

In one exemplary aspect, the immune checkpoint molecules CTLA-4, PD-1, PD-L1, LAG-3, TIM-3, and ICOS and peptides based on the amino acid sequence of CTLA-4, PD-1, PD-L1, LAG-3, TIM-3, and ICOS can be utilized to prepare antibodies that specifically bind to CTLA-4, PD-1, PD-L1, LAG-3, TIM-3, or ICOS. The term "antibodies" is meant to include polyclonal antibodies, monoclonal antibodies, fragments thereof, such as F(ab')2 and Fab fragments, single-chain variable fragments (scFvs), single-domain antibody fragments (VHHs or Nanobodies), bivalent antibody fragments (diabodies), as well as any recombinantly and synthetically produced binding partners.

Antibodies Specific to a Tumor Associated Antigen (TAA). In various embodiments of the present invention the recombinant MVAs and methods described herein are combined with, or administered in combination with, an antibody specific to a TAA. In more particular embodiments, the recombinant MVAs and methods described herein are combined with or administered in combination with an antibody specific to an antigen that is expressed on the cell membrane of a tumor cell. It is understood in the art that in many cancers, one or more antigens are expressed or overexpressed on the tumor cell membrane. See, e.g. Durig et al. (2002) *Leukemia* 16: 30-5; Mocellin et al. (2013) *Biochim. Biophys. Acta* 1836: 187-96; Arteaga (2011) *Nat. Rev. Clin. Oncol.*, doi:10.1038/nrclinonc.2011.177; Finn (2017) *Cancer Immunol. Res.* 5: 347-54; Ginaldi et al. (1998) *J. Clin. Pathol.* 51: 364-9. Assays for determining whether an antigen is expressed or overexpressed on a tumor cells are readily understood in the art (Id.), as well as methods for producing antibodies to a particular antigen.

In more specific embodiments, the pharmaceutical combination and related methods include an antibody, wherein in the antibody is a) specific to an antigen that is expressed on a cell membrane of a tumor and b) comprises an Fc domain. In at least one aspect, the characteristics of the antibody (e.g., a) and b)) enable the antibody to bind to and interact with an effector cell, such as an NK cell, macrophage, basophil, neutrophil, eosinophil, monocytes, mast cells, and/or dendritic cells, and enable the antibody to bind a tumor antigen that is expressed on a tumor cell. In a preferred embodiment, the antibody comprises an Fc domain. In an additional preferred embodiment, the antibody is able to bind and interact with an NK cell.

Some exemplary antibodies to antigens expressed on tumor cells that are contemplated by the present disclosure include, but are not limited to, Anti-CD20 (e.g., rituximab; ofatumumab; tositumomab), Anti-CD52 (e.g., alemtuzumab Campath®), Anti-EGFR (e.g., cetuximab Erbitux®, panitumumab), Anti-CD2 (e.g., Siplizumab), Anti-CD37 (e.g., BI836826), Anti-CD123 (e.g., JNJ-56022473), Anti-CD30 (e.g., XmAb2513), Anti-CD38 (e.g., daratumumab Darzalex®), Anti-PDL1 (e.g., avelumab, atezolilzumab, durvalumab), Anti-GD2 (e.g., 3F8, ch14.18, KW-2871, dinutuximab), Anti-CEA, Anti-MUC1, Anti-FLT3, Anti-CD19, Anti-CD40, Anti-SLAMF7, Anti-CCR4, Anti-B7-H3, Anti-ICAM1, Anti-CSF1R, anti-CA125 (e.g. Oregovomab), anti-FRα (e.g. MOv18-IgG1, Mirvetuximab soravtansine (IMGN853), MORAb-202), anti-mesothelin (e.g. MORAb-009), anti-TRP2, and Anti-HER2 (e.g., trastuzumab, Herzuma, ABP 980, and/or Pertuzumab).

In a more preferred embodiment, the antibody included as part of present invention includes an antibody that when administered to a patient binds to the corresponding antigen on a tumor cell and induces antibody dependent cell-mediated cytotoxicity (ADCC). In an even more preferred embodiment, the antibody comprises an antibody that is approved or in pre-approval for the treatment of a cancer.

In even more preferred embodiments, the antibody is an anti-HER2 antibody, an anti-EGFR antibody, and/or an anti-CD20 antibody.

In a most preferred embodiment, an anti-HER2 antibody is selected from Pertuzumab, Trastuzumab, Herzuma, ABP 980, and Ado-trastuzumab emtansine.

In a most preferred embodiment, an anti-EGFR antibody and an anti-CD20 is cetuximab and rituximab, respectively.

As described herein, in various embodiments, the antibodies can be synthetic, monoclonal, or polyclonal and can be made by techniques well known in the art. Such antibodies specifically bind to the TAA via the antigen-binding sites of the antibody (as opposed to non-specific binding). TAA peptides, fragments, variants, fusion proteins, etc., can be employed as immunogens in producing antibodies immunoreactive therewith. More specifically, the polypeptides, fragment, variants, fusion proteins, etc. contain antigenic determinants or epitopes that elicit the formation of antibodies.

Antibodies. In various embodiments of the present invention, the recombinant MVAs and methods described herein are combined with and/or administered in combination with either 1) an immune checkpoint antagonist or agonist antibody or 2) a TAA-specific antibody.

It is contemplated that the antibodies can be synthetic, monoclonal, or polyclonal and can be made by techniques well known in the art. Such antibodies specifically bind to the immune checkpoint molecule or TAA via the antigen-binding sites of the antibody (as opposed to non-specific binding). Immune checkpoint and/or TAA peptides, fragments, variants, fusion proteins, etc., can be employed as immunogens in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (Janeway, Jr. and Travers, *Immuno Biology* 3:9 (Garland Publishing Inc., 2nd ed. 1996)). Because folded proteins have complex surfaces, the number of epitopes available is quite numerous; however, due to the conformation of the protein and steric hindrances, the number of antibodies that actually bind to the epitopes is less than the number of available epitopes (Janeway, Jr. and Travers, *Immuno Biology* 2:14 (Garland Publishing Inc., 2nd ed. 1996)). Epitopes can be identified by any of the methods known in the art.

Antibodies, including scFV fragments, which bind specifically to the TAAs or the immune checkpoint molecules such as CTLA-4, PD-1, PD-L1, LAG-3, TIM-3, or ICOS and either block its function ("antagonist antibodies") or enhance/activate its function ("agonist antibodies"), are encompassed by the invention. Such antibodies can be generated by conventional means.

In one embodiment, the invention encompasses monoclonal antibodies against a TAA or immune checkpoint molecules or that either block ("antagonist antibodies") or enhance/activate ("agonist antibodies") the function of the immune checkpoint molecules or TAAs.

Antibodies are capable of binding to their targets with both high avidity and specificity. They are relatively large molecules (~150 kDa), which can sterically inhibit interactions between two proteins (e.g. PD-1 and its target ligand) when the antibody binding site falls within proximity of the protein-protein interaction site. The invention further encompasses antibodies that bind to epitopes within close proximity to an immune checkpoint molecule ligand binding site.

In various embodiments, the invention encompasses antibodies that interfere with intermolecular interactions (e.g. protein-protein interactions), as well as antibodies that perturb intramolecular interactions (e.g. conformational changes within a molecule). Antibodies can be screened for the ability to block or enhance/activate the biological activity of an immune checkpoint molecule. Both polyclonal and monoclonal antibodies can be prepared by conventional techniques.

In one exemplary aspect, the TAAs or immune checkpoint molecules CTLA-4, PD-1, PD-L1, LAG-3, TIM-3, and ICOS and peptides based on the amino acid sequence of the TAAs or CTLA-4, PD-1, PD-L1, LAG-3, TIM-3, and ICOS can be utilized to prepare antibodies that specifically bind to the TAA or CTLA-4, PD-1, PD-L1, LAG-3, TIM-3, or ICOS. The term "antibodies" is meant to include polyclonal antibodies, monoclonal antibodies, fragments thereof, such as F(ab')2 and Fab fragments, single-chain variable fragments (scFvs), single-domain antibody fragments (VHHs or nanobodies), bivalent antibody fragments (diabodies), as well as any recombinantly and synthetically produced binding partners. In another exemplary aspect, antibodies are defined to be specifically binding if they to an immune checkpoint molecule if they bind with a Kd of greater than or equal to about $10^7$ $M^{-1}$. Affinities of binding partners or antibodies can be readily determined using conventional techniques, for example those described by Scatchard et al. ((1949) *Ann. N.Y. Acad Sci.* 51: 660).

Polyclonal antibodies can be readily generated from a variety of sources, for example, horses, cows, goats, sheep, dogs, chickens, rabbits, mice, or rats, using procedures that are well known in the art. In general, purified TAAs or CTLA-4, PD-1, PD-L1, LAG-3, TIM-3, and ICOS or a peptide based on the amino acid sequence of CTLA-4, PD-1, PD-L1, LAG-3, TIM-3, and ICOS that is appropriately conjugated is administered to the host animal typically through parenteral injection. Following booster immunizations, small samples of serum are collected and tested for reactivity to CTLA-4, PD-1, PD-L1, LAG-3, TIM-3, and ICOS polypeptide. Examples of various assays useful for such determination include those described in Antibodies: A Laboratory Manual, Harlow and Lane (eds.), Cold Spring Harbor Laboratory Press, 1988; as well as procedures, such as countercurrent immuno-electrophoresis (CIEP), radioimmunoassay, radio-immunoprecipitation, enzyme-linked immunosorbent assays (ELISA), dot blot assays, and sandwich assays. See U.S. Pat. Nos. 4,376,110 and 4,486,530.

Monoclonal antibodies can be readily prepared using well known procedures. See, for example, the procedures described in U.S. Pat. Nos. RE 32,011, 4,902,614, 4,543, 439, and 4,411,993; *Monoclonal Antibodies, Hybridomas: A New Dimension in Biological Analyses*, Plenum Press, Kennett, McKeam, and Bechtol (eds.) (1980).

For example, the host animals, such as mice, can be injected intraperitoneally at least once and preferably at least twice at about 3 week intervals with isolated and purified immune checkpoint molecule. Mouse sera are then assayed by conventional dot blot technique or antibody capture (ABC) to determine which animal is best to fuse. Approximately two to three weeks later, the mice are given an intravenous boost of the immune checkpoint molecule. Mice are later sacrificed and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG). Fusion is plated out into plates containing media that allows for the selective growth of the fused cells. The fused cells can then be allowed to grow for approximately eight days. Supernatants from resultant hybridomas are collected and added to a plate that is first coated with goat anti-mouse Ig. Following washes, a label, such as a labeled immune checkpoint molecule polypeptide, is added to each well followed by incubation. Positive wells can be subsequently detected. Positive clones can be grown in bulk culture and supernatants are subsequently purified over a Protein A column (Pharmacia).

The monoclonal antibodies of the invention can be produced using alternative techniques, such as those described by Alting-Mees et al. ((1990) *Strategies in Mol. Biol.* 3: 1-9, "Monoclonal Antibody Expression Libraries: A Rapid Alternative to Hybridomas"), which is incorporated herein by reference. Similarly, binding partners can be constructed using recombinant DNA techniques to incorporate the variable regions of a gene that encodes a specific binding antibody. Such a technique is described in Larrick et al. ((1989) *Biotechnology* 7: 394).

Antigen-binding fragments of such antibodies, which can be produced by conventional techniques, are also encompassed by the present invention. Examples of such fragments include, but are not limited to, Fab and F(ab')2 fragments. Antibody fragments and derivatives produced by genetic engineering techniques are also provided.

The monoclonal antibodies of the present invention include chimeric antibodies, e.g., humanized versions of murine monoclonal antibodies. Such humanized antibodies can be prepared by known techniques, and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment can comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. ((1988) *Nature* 332: 323), Liu et al. ((1987) *Proc. Nat'l. Acad. Sci.* 84: 3439), Larrick et al. ((1989) *Bio/Technology* 7: 934), and Winter and Harris ((1993) *TIPS* 14: 139). Procedures to generate antibodies transgenically can be found in GB 2,272,440, U.S. Pat. Nos. 5,569,825 and 5,545,806 both of which are incorporated by reference herein.

Antibodies produced by genetic engineering methods, such as chimeric and humanized monoclonal antibodies, comprising both human and non-human portions, which can be made using standard recombinant DNA techniques, can be used. Such chimeric and humanized monoclonal antibodies can be produced by genetic engineering using standard DNA techniques known in the art, for example using methods described in Robinson et al. International Publication No. WO 87/02671; Akira et al. European Patent Application 0184187; Taniguchi, M., European Patent Application 0171496; Morrison et al. European Patent Application 0173494; Neuberger et al. PCT International Publication No. WO 86/01533; Cabilly et al. U.S. Pat. No. 4,816,567; Cabilly et al. European Patent Application 0125023; Better et al., (1988) *Science* 240: 1041-1043; Liu et al. (1987) *Proc. Nat'l. Acad. Sci.* 84: 3439-3443; Liu et al. (1987) *J. Immunol.* 139: 3521-3526; Sun et al. (1987) *Proc. Nat'l. Acad. Sci.* 84: 214-218; Nishimura et al. (1987) *Cancer Res.* 47: 999-1005; Wood et al. (1985) *Nature* 314: 446-449; and Shaw et al. (1988) *J. Natl. Cancer Inst.* 80: 1553-1559); Morrison (1985) *Science* 229: 1202-1207; Oi et al. (1986) *BioTechniques* 4: 214; Winter U.S. Pat. No. 5,225,539; Jones et al. (1986) *Nature* 321: 552 525; Verhoeyan et al. (1988) *Science* 239: 1534; and Beidler et al. (1988) *J. Immunol.* 141: 4053-4060.

In connection with synthetic and semi-synthetic antibodies, such terms are intended to cover but are not limited to antibody fragments, isotype switched antibodies, humanized antibodies (e.g., mouse-human, human-mouse), hybrids, antibodies having plural specificities, and fully synthetic antibody-like molecules.

For therapeutic applications, "human" monoclonal antibodies having human constant and variable regions are often preferred so as to minimize the immune response of a patient against the antibody. Such antibodies can be generated by immunizing transgenic animals which contain human immunoglobulin genes. See Jakobovits et al. Ann NY Acad Sci 764:525-535 (1995).

Human monoclonal antibodies against a TAA or an immune checkpoint molecule can also be prepared by constructing a combinatorial immunoglobulin library, such as a Fab phage display library or a scFv phage display library, using immunoglobulin light chain and heavy chain cDNAs prepared from mRNA derived from lymphocytes of a subject. See, e.g., McCafferty et al. PCT publication WO 92/01047; Marks et al. (1991) *J. Mol. Biol.* 222: 581-597; and Griffths et al. (1993) *EMBO J.* 12: 725-734. In addition, a combinatorial library of antibody variable regions can be generated by mutating a known human antibody. For example, a variable region of a human antibody known to bind the immune checkpoint molecule can be mutated, by for example using randomly altered mutagenized oligonucleotides, to generate a library of mutated variable regions which can then be screened to bind to the immune checkpoint molecule. Methods of inducing random mutagenesis within the CDR regions of immunoglobin heavy and/or light chains, methods of crossing randomized heavy and light chains to form pairings and screening methods can be found in, for example, Barbas et al. PCT publication WO 96/07754; Barbas et al. (1992) *Proc. Nat'l Acad. Sci. USA* 89: 4457-4461.

An immunoglobulin library can be expressed by a population of display packages, preferably derived from filamentous phage, to form an antibody display library. Examples of methods and reagents particularly amenable for use in generating antibody display library can be found in, for example, Ladner et al. U.S. Pat. No. 5,223,409; Kang et al. PCT publication WO 92/18619; Dower et PCT publication WO 91/17271; Winter et al. PCT publication WO 92/20791; Markland et al. PCT publication WO 92/15679; Breitling et al. PCT publication WO 93/01288; McCafferty et al. PCT publication WO 92/01047; Garrard et al. PCT publication WO 92/09690; Ladner et al. PCT publication WO 90/02809; Fuchs et al. (1991) Bio/Technology 9: 1370 1372; Hay et al. (1992) *Hum Antibod Hybridomas* 3: 81-85; Huse et al. (1989) Science 246: 1275-1281; Griffths et al. (1993) supra;

Hawkins et al. (1992) *J. Mol. Biol.* 226: 889-896; Clackson et al. (1991) *Nature* 352: 624-628; Gram et al. (1992) *Proc. Nat'l. Acad. Sci.* 89: 3576-3580; Garrad et al. (1991) *Bio/Technology* 9: 1373-1377; Hoogenboom et al. (1991) *Nucl. Acid Res.* 19: 4133-4137; and Barbas et al. (1991) *Proc. Nat'l. Acad. Sci.* 88: 7978-7982. Once displayed on the surface of a display package (e.g., filamentous phage), the antibody library is screened to identify and isolate packages that express an antibody that binds a TAA or an immune checkpoint molecule.

Recombinant MVA. In more preferred embodiments of the present invention, the one or more proteins and nucleotides disclosed herein are included in a recombinant MVA. As described and illustrated by the present disclosure, the intravenous administration of the recombinant MVAs of the present disclosure induces in various aspects an enhanced immune response in cancer patients. Thus, in one or more preferred embodiments, the invention includes a recombinant MVA comprising a first nucleic acid encoding one or more of the TAAs described herein and a second nucleic acid encoding CD40L.

Example of MVA virus strains that are useful in the practice of the present invention and that have been deposited in compliance with the requirements of the Budapest Treaty are strains MVA 572, deposited at the European Collection of Animal Cell Cultures (ECACC), Vaccine Research and Production Laboratory, Public Health Laboratory Service, Centre for Applied Microbiology and Research, Porton Down, Salisbury, Wiltshire SP4 0JG, United Kingdom, with the deposition number ECACC 94012707 on Jan. 27, 1994, and MVA 575, deposited under ECACC 00120707 on Dec. 7, 2000, MVA-BN, deposited on Aug. 30, 2000 at the European Collection of Cell Cultures (ECACC) under number V00083008, and its derivatives, are additional exemplary strains.

"Derivatives" of MVA-BN refer to viruses exhibiting essentially the same replication characteristics as MVA-BN, as described herein, but exhibiting differences in one or more parts of their genomes. MVA-BN, as well as derivatives thereof, are replication incompetent, meaning a failure to reproductively replicate in vivo and in vitro. More specifically in vitro, MVA-BN or derivatives thereof have been described as being capable of reproductive replication in chicken embryo fibroblasts (CEF), but not capable of reproductive replication in the human keratinocyte cell line HaCat (Boukamp et al. (1988) *J. Cell Biol.* 106: 761-771), the human bone osteosarcoma cell line 143B (ECACC Deposit No. 91112502), the human embryo kidney cell line 293 (ECACC Deposit No. 85120602), and the human cervix adenocarcinoma cell line HeLa (ATCC Deposit No. CCL-2). Additionally, MVA-BN or derivatives thereof have a virus amplification ratio at least two-fold less, more preferably three-fold less than MVA-575 in Hela cells and HaCaT cell lines. Tests and assay for these properties of MVA-BN and derivatives thereof are described in WO 02/42480 (U.S. Patent Application No. 2003/0206926) and WO 03/048184 (U.S. Patent App. No. 2006/0159699).

The term "not capable of reproductive replication" or "no capability of reproductive replication" in human cell lines in vitro as described in the previous paragraphs is, for example, described in WO 02/42480, which also teaches how to obtain MVA having the desired properties as mentioned above. The term applies to a virus that has a virus amplification ratio in vitro at 4 days after infection of less than 1 using the assays described in WO 02/42480 or in U.S. Pat. No. 6,761,893.

The term "failure to reproductively replicate" refers to a virus that has a virus amplification ratio in human cell lines in vitro as described in the previous paragraphs at 4 days after infection of less than 1. Assays described in WO 02/42480 or in U.S. Pat. No. 6,761,893 are applicable for the determination of the virus amplification ratio.

The amplification or replication of a virus in human cell lines in vitro as described in the previous paragraphs is normally expressed as the ratio of virus produced from an infected cell (output) to the amount originally used to infect the cell in the first place (input) referred to as the "amplification ratio". An amplification ratio of "1" defines an amplification status where the amount of virus produced from the infected cells is the same as the amount initially used to infect the cells, meaning that the infected cells are permissive for virus infection and reproduction. In contrast, an amplification ratio of less than 1, i.e., a decrease in output compared to the input level, indicates a lack of reproductive replication and therefore attenuation of the virus.

By "adjuvantation" herein is intended that a particular encoded protein or component of a recombinant MVA increases the immune response produced by the other encoded protein(s) or component(s) of the recombinant MVA.

Expression Cassettes/Control Sequences. In various aspects, the one or more nucleic acids described herein are embodied in in one or more expression cassettes in which the one or more nucleic acids are operatively linked to expression control sequences. "Operably linked" means that the components described are in relationship permitting them to function in their intended manner e.g., a promoter to transcribe the nucleic acid to be expressed. An expression control sequence operatively linked to a coding sequence is joined such that expression of the coding sequence is achieved under conditions compatible with the expression control sequences. The expression control sequences include, but are not limited to, appropriate promoters, enhancers, transcription terminators, a start codon at the beginning a protein-encoding open reading frame, splicing signals for introns, and in-frame stop codons. Suitable promoters include, but are not limited to, the SV40 early promoter, an RSV promoter, the retrovirus LTR, the adenovirus major late promoter, the human CMV immediate early I promoter, and various poxvirus promoters including, but not limited to the following vaccinia virus or MVA-derived and FPV-derived promoters: the 30K promoter, the 13 promoter, the PrS promoter, the PrS5E promoter, the Pr7.5K, the PrHyb promoter, the Pr13.5 long promoter, the 40K promoter, the MVA-40K promoter, the FPV 40K promoter, 30 k promoter, the PrSynIIm promoter, the PrLE1 promoter, and the PR1238 promoter. Additional promoters are further described in WO 2010/060632, WO 2010/102822, WO 2013/189611, WO 2014/063832, and WO 2017/021776 which are incorporated fully by reference herein.

Additional expression control sequences include, but are not limited to, leader sequences, termination codons, polyadenylation signals and any other sequences necessary for the appropriate transcription and subsequent translation of the nucleic acid sequence encoding the desired recombinant protein (e.g., HER2, Brachyury, and/or CD40L) in the desired host system. The poxvirus vector may also contain additional elements necessary for the transfer and subsequent replication of the expression vector containing the nucleic acid sequence in the desired host system. It will further be understood by one skilled in the art that such vectors are easily constructed using conventional methods (Ausubel et al., (1987) in "Current Protocols in Molecular Biology," John Wiley and Sons, New York, N.Y.) and are commercially available.

Methods and Dosing regimens for administering the Combination. In one or more aspects, the combinations of the present invention can be administered as part of a homologous and/or heterologous prime-boost regimen. Illustrated in part by data shown in FIG. 7A-7D, a homologous prime boost regimen increases a subject's specific CD8 and CD4 T cell responses. Thus, in one or more embodiments there is a combination and/or method for a reducing tumor size and/or increasing survival in a cancer patient comprising administering to the cancer patient a combination of the present disclosure, wherein the combination is administered as part of a homologous or heterologous prime-boost regimen.

Generation of Recombinant MVA Viruses Comprising Transgenes

The recombinant MVA viruses provided herein can be generated by routine methods known in the art. Methods to obtain recombinant poxviruses or to insert exogenous coding sequences into a poxviral genome are well known to the person skilled in the art. For example, methods for standard molecular biology techniques such as cloning of DNA, DNA and RNA isolation, Western blot analysis, RT-PCR and PCR amplification techniques are described in *Molecular Cloning, A Laboratory Manual* (2nd ed., Sambrook et al., Cold Spring Harbor Laboratory Press (1989)), and techniques for the handling and manipulation of viruses are described in *Virology Methods Manual* (Mahy et al. (eds.), Academic Press (1996)). Similarly, techniques and know-how for the handling, manipulation and genetic engineering of MVA are described in *Molecular Virology: A Practical Approach* (Davison & Elliott (eds.), *The Practical Approach Series*, IRL Press at Oxford University Press, Oxford, UK (1993)(see, e.g., "Chapter 9: Expression of genes by Vaccinia virus vectors")) and *Current Protocols in Molecular Biology* (John Wiley & Son, Inc. (1998) (see, e.g., Chapter 16, Section IV: "Expression of proteins in mammalian cells using vaccinia viral vector")).

For the generation of the various recombinant MVA viruses disclosed herein, different methods may be applicable. The DNA sequence to be inserted into the virus can be placed into an *E. coli* plasmid construct into which DNA homologous to a section of DNA of the poxvirus has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of poxviral DNA containing a non-essential locus. The resulting plasmid construct can be amplified by propagation within *E. coli* bacteria and isolated. The isolated plasmid containing the DNA gene sequence to be inserted can be transfected into a cell culture, e.g., of chicken embryo fibroblasts (CEFs), at the same time the culture is infected with MVA virus. Recombination between homologous MVA viral DNA in the plasmid and the viral genome, respectively, can generate a poxvirus modified by the presence of foreign DNA sequences.

According to a preferred embodiment, a cell of a suitable cell culture as, e.g., CEF cells, can be infected with an MVA virus. The infected cell can be, subsequently, transfected with a first plasmid vector comprising a foreign or heterologous gene or genes, such as one or more of the nucleic acids provided in the present disclosure; preferably under the transcriptional control of a poxvirus expression control element. As explained above, the plasmid vector also comprises sequences capable of directing the insertion of the exogenous sequence into a selected part of the MVA viral genome. Optionally, the plasmid vector also contains a cassette comprising a marker and/or selection gene operably linked to a poxviral promoter. Suitable marker or selection genes are, e.g., the genes encoding the green fluorescent protein, β-galactosidase, neomycin-phosphoribosyltransferase or other markers. The use of selection or marker cassettes simplifies the identification and isolation of the generated recombinant poxvirus. However, a recombinant poxvirus can also be identified by PCR technology. Subsequently, a further cell can be infected with the recombinant poxvirus obtained as described above and transfected with a second vector comprising a second foreign or heterologous gene or genes. In case, this gene shall be introduced into a different insertion site of the poxviral genome, the second vector also differs in the poxvirus-homologous sequences directing the integration of the second foreign gene or genes into the genome of the poxvirus. After homologous recombination has occurred, the recombinant virus comprising two or more foreign or heterologous genes can be isolated. For introducing additional foreign genes into the recombinant virus, the steps of infection and transfection can be repeated by using the recombinant virus isolated in previous steps for infection and by using a further vector comprising a further foreign gene or genes for transfection.

Alternatively, the steps of infection and transfection as described above are interchangeable, i.e., a suitable cell can at first be transfected by the plasmid vector comprising the foreign gene and, then, infected with the poxvirus. As a further alternative, it is also possible to introduce each foreign gene into different viruses, co-infect a cell with all the obtained recombinant viruses and screen for a recombinant including all foreign genes. A third alternative is ligation of DNA genome and foreign sequences in vitro and reconstitution of the recombined vaccinia virus DNA genome using a helper virus. A fourth alternative is homologous recombination in *E. coli* or another bacterial species between a MVA virus genome cloned as a bacterial artificial chromosome (BAC) and a linear foreign sequence flanked with DNA sequences homologous to sequences flanking the desired site of integration in the MVA virus genome.

The one or more nucleic acids of the present disclosure may be inserted into any suitable part of the MVA virus or MVA viral vector. Suitable parts of the MVA virus are non-essential parts of the MVA genome. Non-essential parts of the MVA genome may be intergenic regions or the known deletion sites 1-6 of the MVA genome. Alternatively, or additionally, non-essential parts of the recombinant MVA can be a coding region of the MVA genome which is non-essential for viral growth. However, the insertion sites are not restricted to these preferred insertion sites in the MVA genome, since it is within the scope of the present invention that the nucleic acids of the present invention (e.g., HER2, Brachyury, HERV-K-env, HERV-K-gag, PRAME, FOLR1, and CD40L and/or 4-1BBL) and any accompanying promoters as described herein may be inserted anywhere in the viral genome as long as it is possible to obtain recombinants that can be amplified and propagated in at least one cell culture system, such as Chicken Embryo Fibroblasts (CEF cells).

Preferably, the nucleic acids of the present invention may be inserted into one or more intergenic regions (IGR) of the MVA virus. The term "intergenic region" refers preferably to those parts of the viral genome located between two adjacent open reading frames (ORF) of the MVA virus genome, preferably between two essential ORFs of the MVA virus genome. For MVA, in certain embodiments, the IGR is selected from IGR 07/08, IGR 44/45, IGR 64/65, IGR 88/89, IGR 136/137, and IGR 148/149.

For MVA virus, the nucleotide sequences may, additionally or alternatively, be inserted into one or more of the known deletion sites, i.e., deletion sites I, II, III, IV, V, or VI of the MVA genome. The term "known deletion site" refers to those parts of the MVA genome that were deleted through continuous passaging on CEF cells characterized at passage 516 with respect to the genome of the parental virus from which the MVA is derived from, in particular the parental chorioallantois vaccinia virus Ankara (CVA), e.g., as described in Meisinger-Henschel et al. ((2007) *J. Gen. Virol.* 88: 3249-3259).

Vaccines

In certain embodiments, the recombinant MVA of the present disclosure can be formulated as part of a vaccine. For the preparation of vaccines, the MVA virus can be converted into a physiologically acceptable form.

An exemplary preparation follows. Purified virus is stored at −80° C. with a titer of $5\times10^8$ TCID50/ml formulated in 10 mM Tris, 140 mM NaCl, pH 7.4. For the preparation of vaccine shots, e.g., $1\times10^8$-$1\times10^9$ particles of the virus can be lyophilized in phosphate-buffered saline (PBS) in the presence of 2% peptone and 1% human albumin in an ampoule, preferably a glass ampoule. Alternatively, the vaccine shots can be prepared by stepwise, freeze-drying of the virus in a formulation. In certain embodiments, the formulation contains additional additives such as mannitol, dextran, sugar, glycine, lactose, polyvinylpyrrolidone, or other additives, such as, including, but not limited to, antioxidants or inert gas, stabilizers or recombinant proteins (e.g. human serum albumin) suitable for in vivo administration. The ampoule is then sealed and can be stored at a suitable temperature, for example, between 4° C. and room temperature for several months. However, as long as no need exists, the ampoule is stored preferably at temperatures below −20° C., most preferably at about −80° C.

In various embodiments involving vaccination or therapy, the lyophilisate is dissolved in 0.1 to 0.5 ml of an aqueous solution, preferably physiological saline or Tris buffer such as 10 mM Tris, 140 mM NaCl pH 7.7. It is contemplated that the recombinant MVA, vaccine or pharmaceutical composition of the present disclosure can be formulated in solution in a concentration range of $10^4$ to $10^{10}$ TCID50/ml, $10^5$ to $5\times10^9$ TCID50/ml, $10^6$ to $5\times10^9$ TCID50/ml, or $10^7$ to $5\times10^9$ TCID50/ml. A preferred dose for humans comprises between $10^6$ to $10^{10}$ TCID50, including a dose of $10^6$ TCID50, $10^7$ TCID50, $10^8$ TCID50, $5\times10^8$TCID50, $10^9$ TCID50, $5\times10^9$ TCID50, or $10^{10}$ TCID50. Optimization of dose and number of administrations is within the skill and knowledge of one skilled in the art.

In one or more preferred embodiments, as set forth herein, the recombinant MVA is administered to a cancer patient intravenously. In other embodiments, the recombinant MVA is administered to a cancer patient intratumorally. In other embodiments, the recombinant MVA is administered to a cancer patient both intravenously and intratumorally at the same time or at different times.

In some embodiments, MVAs are designed to contain both TAAs as well as co-stimulatory molecules, and is intended to be suitable for administration either intravenously or intratumorally, or via both routes of administration. Such MVAs can express one or more TAAs, including proteins of the K superfamily of human endogenous retroviruses (HERV-K), such as, for example, HERV-K-env, HERV-K-gag, or HERV-K-mel, or synthetic variants thereof such as those described in Example 38.

In additional embodiments, the recombinant MVA is administered to the patient and also an immune checkpoint antagonist or agonist, or preferably antibody can be administered either systemically or locally, i.e., by intraperitoneal, parenteral, subcutaneous, intravenous, intramuscular, intranasal, intradermal, or any other path of administration known to a skilled practitioner.

Kits, Compositions, and Methods of Use. In various embodiments, the invention encompasses kits, pharmaceutical combinations, pharmaceutical compositions, and/or immunogenic combination, comprising the a) recombinant MVA that includes the nucleic acids described herein and/or b) one or more antibodies described herein.

It is contemplated that the kit and/or composition can comprise one or multiple containers or vials of a recombinant poxvirus of the present disclosure, one or more containers or vials of an antibody of the present disclosure, together with instructions for the administration of the recombinant MVA and antibody. It is contemplated that in a more particular embodiment, the kit can include instructions for administering the recombinant MVA and antibody in a first priming administration and then administering one or more subsequent boosting administrations of the recombinant MVA and antibody.

The kits and/or compositions provided herein may generally include one or more pharmaceutically acceptable and/or approved carriers, additives, antibiotics, preservatives, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like.

Certain Exemplary Embodiments

Embodiment 1 is a method for reducing tumor size and/or increasing survival in a subject having a cancerous tumor, the method comprising intratumorally administering to the subject a recombinant modified Vaccinia Ankara (MVA) comprising a first nucleic acid encoding a tumor-associated antigen (TAA) and a second nucleic acid encoding 4-1BBL, wherein the intratumoral administration of the recombinant MVA enhances an inflammatory response in the cancerous tumor, increases tumor reduction, and/or increases overall survival of the subject as compared to a non-intratumoral injection of a recombinant MVA virus comprising a first and second nucleic acid encoding a TAA and a 4-1BBL antigen.

Embodiment 2 is a method for reducing tumor size and/or increasing survival in a subject having a cancerous tumor, the method comprising intravenously administering to the subject a recombinant modified Vaccinia Ankara (MVA) comprising a first nucleic acid encoding a tumor-associated antigen (TAA) and a second nucleic acid encoding 4-1BBL, wherein the intravenous administration of the recombinant MVA enhances Natural Killer (NK) cell response and enhances CD8 T cell responses specific to the TAA as compared to a non-intravenous injection of a recombinant MVA virus comprising a first and second nucleic acid encoding a TAA and a 4-1BBL antigen.

Embodiment 3 is a method for reducing tumor size and/or increasing survival in a subject having a cancerous tumor, the method comprising administering to the subject a recombinant modified Vaccinia Ankara (MVA) comprising a first nucleic acid encoding a tumor-associated antigen (TAA) and a second nucleic acid encoding 4-1BBL, wherein the administration of the recombinant MVA increases tumor reduction and/or increases overall survival of the subject as compared to administration of a recombinant MVA and 4-1BBL antigen by themselves.

Embodiment 4 is a method of inducing an enhanced inflammatory response in a cancerous tumor of a subject, the method comprising intratumorally administering to the subject a recombinant modified Vaccinia Ankara (MVA) comprising a first nucleic acid encoding a first heterologous tumor-associated antigen (TAA) and a second nucleic acid encoding a 4-1BBL antigen, wherein the intratumoral administration of the recombinant MVA generates an enhanced inflammatory response in the tumor as compared to an inflammatory response generated by a non-intratumoral injection of a recombinant MVA virus comprising a first and second nucleic acid encoding a heterologous tumor-associated antigen and a 4-1BBL antigen. Such an enhanced inflammatory response is discussed elsewhere herein and can include, for example, the induction of NK cells and T cells.

Embodiment 5 is a method for reducing tumor size and/or increasing survival in a subject having a cancerous tumor, the method comprising administering to the subject a recombinant modified Vaccinia Ankara (MVA) comprising a first nucleic acid encoding a an endogenous retroviral antigen (ERV) and a second nucleic acid encoding 4-1BBL, wherein the administration of the recombinant MVA increases tumor reduction and/or increases overall survival of the subject as compared to administration of a recombinant MVA and 4-1BBL antigen by themselves.

Embodiment 6 is a method according to any one of embodiments 1-5, wherein the subject is human.

Embodiment 7 is a method according to any one of embodiments 1-4, wherein the TAA is an endogenous retroviral (ERV) protein.

Embodiment 8 is a method according to embodiment 7, wherein the ERV is an ERV protein expressed in at tumor cell.

Embodiment 9 is a method according to any one of embodiments 7-8, wherein the ERV is from the human endogenous retroviral protein K (HERV-K) family.

Embodiment 10 is a method according to embodiment 9, wherein the HERV-K protein is selected from a HERV-K envelope protein, a HERV-K gag protein, and a HERV-K mel protein.

Embodiment 11 is a method according to embodiment 9, wherein the HERV-K protein is selected from a HERV-K envelope protein, a HERV-K gag protein, a HERV-K mel peptide, and an immunogenic fragment thereof.

Embodiment 12 is a method according to any one of embodiments 1-6, wherein the TAA is selected from the group consisting of carcinoembryonic antigen (CEA), mucin 1 cell surface associated (MUC-1), prostatic acid phosphatase (PAP), prostate specific antigen (PSA), human epidermal growth factor receptor 2 (HER-2), survivin, tyrosine related protein 1 (TRP1), tyrosine related protein 1 (TRP2), Brachyury, FOLR1, PRAME, p15, and combinations thereof.

Embodiment 13 is a method according to any one of embodiments 1-6 and 12, wherein the TAA is selected from the group consisting of carcinoembryonic antigen (CEA) and mucin 1 cell surface associated (MUC-1), or is a TAA that is a composite or combination of AH1A5, p15E, and TRP2, for example such as described in Example 1.

Embodiment 14 is a method according to any one of embodiments 1-6 and 12, wherein the TAA is selected from the group consisting of PAP or PSA.

Embodiment 15 is a method according to any one of embodiments 1-6, 12, and 14, wherein the TAA is PSA.

Embodiment 16 is a method according to any one of embodiments 1-6, wherein the TAA is selected from the group consisting of: 5-α-reductase, α-fetoprotein (AFP), AM-1, APC, April, B melanoma antigen gene (BAGE), β-catenin, Bcl12, bcr-abl, Brachyury, CA-125, caspase-8 (CASP-8, also known as FLICE), Cathepsins, CD19, CD20, CD21/complement receptor 2 (CR2), CD22/BL-CAM, CD23/FcεRII, CD33, CD35/complement receptor 1 (CR1), CD44/PGP-1, CD45/leucocyte common antigen ("LCA"), CD46/membrane cofactor protein (MCP), CD52/CAMPATH-1, CD55/decay accelerating factor (DAF), CD59/protectin, CDC27, CDK4, carcinoembryonic antigen (CEA), c-myc, cyclooxygenase-2 (cox-2), deleted in colorectal cancer gene ("DCC"), DcR3, E6/E7, CGFR, EMBP, Dna78, farnesyl transferase, fibroblast growth factor-8a (FGF8a), fibroblast growth factor-8b (FGF8b), FLK-1/KDR, folic acid receptor, G250, G melanoma antigen gene family (GAGE-family), gastrin 17, gastrin-releasing hormone, ganglioside 2 (GD2)/ganglioside 3 (GD3)/ganglioside-monosialic acid-2 ("GM2"), gonadotropin releasing hormone (GnRH), UDP-G1cNAc:R1Man(α1-6)R2 [GlcNAc to Man(α1-6)] β1,6-N¬-acetylglucosaminyltransferase V (GnT V), GP1, gp100/Pme117, gp-100-in4, gp15, gp75/tyrosine-related protein-1 (gp75/TRP-1), human chorionic gonadotropin (hCG), heparanase, HER2, human mammary tumor virus (HMTV), 70 kiloDalton heat-shock protein ("HSP70"), human telomerase reverse transcriptase (hTERT), insulin-like growth factor receptor-1 (IGFR-1), interleukin-13 receptor (IL-13R), inducible nitric oxide synthase (iNOS), Ki67, KIAA0205, K-ras, H-ras, N-ras, KSA, LKLR-FUT, melanoma antigen-encoding gene 1 (MAGE-1), melanoma antigen-encoding gene 2 (MAGE-2), melanoma antigen-encoding gene 3 (MAGE-3), melanoma antigen-encoding gene 4 (MAGE-4), mammaglobin, MAP17, Melan-A/melanoma antigen recognized by T-cells-1 (MART-1), mesothelin, MIC A/B, MT-MMPs, mucin, testes-specific antigen NY-ESO-1, osteonectin, p15, P170/MDR1, p53, p97/melanotransferrin, PAI-1, platelet-derived growth factor (PDGF), μPA, PRAME, probasin, progenipoietin, prostate-specific antigen (PSA), prostate-specific membrane antigen (PSMA), RAGE-1, Rb, RCAS1, SART-1, SSX-family, STAT3, STn, TAG-72, transforming growth factor-alpha (TGF-α), transforming growth factor-beta (TGF-β), Thymosin-beta-15, tumor necrosis factor-alpha (TNF-α), TP1, TRP-2, tyrosinase, vascular endothelial growth factor (VEGF), ZAG, p16INK4, and glutathione-S-transferase (GST). the group consisting of carcinoembryonic antigen (CEA), mucin 1 cell surface associated (MUC-1), prostatic acid phosphatase (PAP), prostate specific antigen (PSA), human epidermal growth factor receptor 2 (HER-2), survivin, tyrosine related protein 1 (TRP1), tyrosine related protein 1 (TRP2), Brachyury, and combinations thereof.

Embodiment 17 is a method according to any one of embodiments 1-16, wherein the recombinant MVA further comprises a third nucleic acid encoding a CD40L antigen.

Embodiment 18 is a method according to any one of embodiments 1-17, further comprising administering to the subject at least one immune checkpoint molecule antagonist or agonist.

Embodiment 19 is a method according to embodiment 18, wherein the immune checkpoint molecule is selected from CTLA-4, PD-1, PD-L1, LAG-3, TIM-3, and ICOS.

Embodiment 20 is a method according to any one of embodiments 18-19, wherein the immune checkpoint molecule is PD-1 and/or PD-L1.

Embodiment 21 is a method according to embodiment 20, wherein the immune checkpoint molecule antagonist further comprises an antagonist of LAG-3.

Embodiment 22 is a method according to any one of embodiments 18-21, wherein the immune checkpoint molecule antagonist comprises an antibody.

Embodiment 23 is a method according to any one of embodiments 1-17, further comprising administering to the subject an antibody specific for a second TAA.

Embodiment 24 is a method according to embodiment 23, wherein the antibody specific for a second TAA is specific to an antigen that is expressed on a cell membrane of a tumor.

Embodiment 25 is a method according to embodiment 23, wherein the antibody specific for a second TAA is a) specific to an antigen that is expressed on a cell membrane of a tumor and b) comprises an Fc domain.

Embodiment 26 is a pharmaceutical composition for use in a method according to any one of embodiments 1-25.

Embodiment 27 is a vaccine for use in a method according to any one of embodiments 1-25.

Embodiment 28 is a recombinant modified Vaccinia Ankara (MVA) for treating a subject having cancer, the recombinant MVA comprising a) a first nucleic acid encoding a tumor-associated antigen (TAA) and b) a second nucleic acid encoding 4-1BBL.

Embodiment 29 is a recombinant MVA according to embodiment 28, wherein the TAA is an endogenous retroviral (ERV) protein.

Embodiment 30 is a recombinant MVA according to embodiment 29, wherein the ERV protein is from the human endogenous retroviral protein K (HERV-K) family.

Embodiment 31 is a recombinant MVA according to embodiment 30, wherein the retroviral protein K is selected from HERV-K envelope protein, a HERV-K gag protein, and a HERV-K mel protein.

Embodiment 32 is a recombinant MVA according to any one of embodiments 28-31 further comprising a third nucleic acid encoding CD40L.

Embodiment 33 is a pharmaceutical combination comprising a) a recombinant MVA of any one of embodiments 28-32 and b) at least one of an immune checkpoint molecule antagonist or agonist.

Embodiment 34 is a pharmaceutical combination according to embodiment 33, wherein the immune checkpoint molecule antagonist or agonist is selected from an antagonist or agonist of CTLA-4, PD-1, PD-L1, LAG-3, TIM-3, and ICOS.

Embodiment 35 is a pharmaceutical combination according to embodiment 34, wherein the immune checkpoint molecule antagonist is an antagonist of PD-1 and/or PD-L1.

Embodiment 36 is a pharmaceutical combination according to embodiment 35, wherein the immune checkpoint molecule antagonist further comprises an antagonist of LAG-3.

Embodiment 37 is a pharmaceutical combination according to any one of embodiments 33-36, wherein the immune checkpoint molecule antagonist comprises an antibody.

Embodiment 38 is a pharmaceutical combination comprising a) a recombinant MVA of any one of embodiments 28-32 b) an antibody specific for a second TAA.

Embodiment 39 is a pharmaceutical combination according to embodiment 38, wherein the antibody specific for a second TAA is specific to an antigen that is expressed on a cell membrane of a tumor.

Embodiment 40 is a pharmaceutical combination according to embodiment 39, wherein the antibody specific for a second TAA is a) specific to an antigen that is expressed on a cell membrane of a tumor and b) comprises an Fc domain.

Embodiment 41 is a recombinant MVA according to any one of embodiments 28-32, a vaccine according to embodiment 27, a pharmaceutical composition according to embodiment 26, a pharmaceutical combination according to any one of embodiments 33-40, for use in reducing tumor size and/or increasing survival in a subject having a cancerous tumor.

Embodiment 42 is a recombinant MVA according to any one of embodiments 28-32, a vaccine according to embodiment 27, a pharmaceutical composition according to embodiment 26, a pharmaceutical combination according to any one of embodiments 33-40, for use in method for reducing tumor size and/or increasing survival in a subject having a cancerous tumor, the method comprising intratumorally administering to the subject the recombinant MVA of embodiments 28-32, the vaccine according to embodiment 27, the pharmaceutical composition according to embodiment 26, or the pharmaceutical combination according to any one of embodiments 33-40, wherein the intratumoral administration of enhances an inflammatory response in the cancerous tumor, increases tumor reduction, and/or increases overall survival of the subject as compared to a non-intratumoral injection of a recombinant MVA virus comprising a first and second nucleic acid encoding a TAA and a 4-1BBL antigen.

Embodiment 43 is a recombinant MVA according to any one of embodiments 28-32, a vaccine according to embodiment 27, a pharmaceutical composition according to embodiment 26, a pharmaceutical combination according to any one of embodiments 33-40, for use in method for reducing tumor size and/or increasing survival in a subject having a cancerous tumor, the method comprising intravenously administering to the subject the recombinant MVA of embodiments 28-32, the vaccine according to embodiment 27, the pharmaceutical composition according to embodiment 26, or the pharmaceutical combination according to any one of embodiments 33-40, wherein the intravenous administration increases tumor reduction, and/or increases overall survival of the subject as compared to a non-intravenous administration of a recombinant MVA virus comprising a first and second nucleic acid encoding a TAA and a 4-1BBL antigen.

Embodiment 44 is a recombinant MVA according to any one of embodiments 28-32, a vaccine according to embodiment 27, a pharmaceutical composition according to embodiment 26, a pharmaceutical combination according to any one of embodiments 33-40, for use in method for inducing an enhanced inflammatory response in a cancerous tumor of a cancer subject, the method comprising intratumorally administering to the subject the recombinant MVA of embodiments 28-32, the vaccine according to embodiment 27, the pharmaceutical composition according to embodiment 26, or the pharmaceutical combination according to any one of embodiments 33-40, wherein the intratumoral administration enhances an inflammatory response in the cancerous tumor of the subject as compared to a non-intratumoral injection of a recombinant MVA virus comprising a first and second nucleic acid encoding a TAA and a 4-1BBL antigen.

Embodiment 45 is a recombinant MVA according to any one of embodiments 28-32, a vaccine according to embodiment 27, a pharmaceutical composition according to embodiment 26, a pharmaceutical combination according to any one of embodiments 33-40, for use in method for treating cancer in subject.

Embodiment 46, is a recombinant MVA according to any one of embodiments 28-32, a vaccine according to embodiment 27, a pharmaceutical composition according to embodiment 26, a pharmaceutical combination according to any one of embodiments 33-40, for use in method for treating cancer, wherein the cancer is selected from the group consisting of: breast cancer, lung cancer, head and neck cancer, thyroid, melanoma, gastric cancer, bladder cancer, kidney cancer, liver cancer, melanoma, pancreatic cancer, prostate cancer, ovarian cancer, urothelial, cervical, or colorectal cancer.

Embodiment 47 is a recombinant MVA according to embodiment 44, wherein the enhanced inflammatory response is localized to the tumor.

Embodiment 48 is a method for reducing tumor size and/or increasing survival in a subject having a cancerous tumor, the method comprising intratumorally administering to the subject a recombinant modified Vaccinia Ankara (MVA) comprising a first nucleic acid encoding a tumor-associated antigen (TAA) and a second nucleic acid encoding CD40L, wherein the intratumoral administration of the recombinant MVA enhances an inflammatory response in the cancerous tumor, increases tumor reduction, and/or increases overall survival of the subject as compared to a non-intratumoral injection of a recombinant MVA virus comprising a first and second nucleic acid encoding a TAA and a CD40L.

Embodiment 49 is a method for reducing tumor size and/or increasing survival in a subject having a cancerous tumor, the method comprising intravenously administering to the subject a recombinant modified Vaccinia Ankara (MVA) comprising a first nucleic acid encoding a tumor-associated antigen (TAA) and a second nucleic acid encoding CD40L, wherein the intravenous administration of the recombinant MVA enhances Natural Killer (NK) cell response and enhances CD8 T cell responses specific to the TAA as compared to a non-intravenous injection of a recombinant MVA virus comprising a first and second nucleic acid encoding a TAA and a CD40L antigen.

Embodiment 50 is a method for reducing tumor size and/or increasing survival in a subject having a cancerous tumor, the method comprising administering to the subject a recombinant modified Vaccinia Ankara (MVA) comprising a first nucleic acid encoding a tumor-associated antigen (TAA) and a second nucleic acid encoding CD40L, wherein the administration of the recombinant MVA increases tumor reduction and/or increases overall survival of the subject as compared to administration of a recombinant MVA and CD40L antigen by themselves.

Embodiment 51 is a recombinant MVA according to any one of embodiments 28-32, a vaccine according to embodiment 27, a pharmaceutical composition according to embodiment 26, a pharmaceutical combination according to any one of embodiments 33-40, for use in method for reducing tumor size and/or increasing survival in a subject having a cancerous tumor, the method comprising intravenously and/or intratumorally administering to the subject the recombinant MVA of embodiments 28-32, the vaccine according to embodiment 27, the pharmaceutical composition according to embodiment 26, or the pharmaceutical combination according to any one of embodiments 33-40, wherein said intravenous and/or intratumoral administration increases tumor reduction, and/or increases overall survival of the subject as compared to a non-intravenous or non-intratumoral administration of any MVA selected from the group of: 1) a recombinant MVA virus comprising a first nucleic acid encoding a TAA and second nucleic acid encoding a 4-1BBL antigen; 2) a recombinant MVA virus comprising a first nucleic acid encoding a TAA and second nucleic acid encoding a CD40L antigen; or 3) a recombinant MVA virus comprising a first nucleic acid encoding a TAA, a second nucleic acid encoding a 4-1BBL antigen, and a third nucleic acid encoding a CD40L antigen.

Embodiment 52 is a recombinant MVA according to any one of embodiments 28-32, a vaccine according to embodiment 27, a pharmaceutical composition according to embodiment 26, a pharmaceutical combination according to any one of embodiments 33-40, for use in method for reducing tumor size and/or increasing survival in a subject having a cancerous tumor, the method comprising intravenously and intratumorally administering to the subject the recombinant MVA of embodiments 28-32, the vaccine according to embodiment 27, the pharmaceutical composition according to embodiment 26, or the pharmaceutical combination according to any one of embodiments 33-40, wherein said intravenous and intratumoral administration increases tumor reduction, and/or increases overall survival of the subject as compared to a non-intravenous or non-intratumoral administration of any MVA selected from the group of: 1) a recombinant MVA virus comprising a first nucleic acid encoding a TAA and second nucleic acid encoding a 4-1BBL antigen; 2) a recombinant MVA virus comprising a first nucleic acid encoding a TAA and second nucleic acid encoding a CD40L antigen; or 3) a recombinant MVA virus comprising a first nucleic acid encoding a TAA, a second nucleic acid encoding a 4-1BBL antigen, and a third nucleic acid encoding a CD40L antigen. Said intravenous and intratumoral administration can be performed at the same time or at different times, as is evident to one of skill in the art.

Still Further Embodiments

In one aspect, the invention provides a recombinant modified Vaccinia virus Ankara (MVA) comprising:

(a) a first nucleic acid encoding a tumor-associated antigen (TAA);

(b) a second nucleic acid encoding a 4-1BB ligand (4-1BBL); and (c) at least one further nucleic acid encoding a TAA.

In one embodiment, the recombinant MVA further comprises:

(d) a nucleic acid encoding a CD40 ligand (CD40L).

In one embodiment, the recombinant MVA comprises two, three, four, five, six, or more nucleic acids each encoding a different TAA.

In one embodiment of the recombinant MVA, the TAA is selected from the group consisting of an endogenous retroviral (ERV) protein, an endogenous retroviral (ERV) peptide, carcinoembryonic antigen (CEA), mucin 1 cell surface associated (MUC-1), prostatic acid phosphatase (PAP), prostate specific antigen (PSA), human epidermal growth factor receptor 2 (HER-2), survivin, tyrosine related protein 1 (TRP1), tyrosine related protein 1 (TRP2), Brachyury, p15, AH1A5, folate receptor alpha (FOLR1), preferentially expressed antigen of melanoma (PRAME), and MEL; and combinations thereof.

In one embodiment of the recombinant MVA, the ERV protein is from the human endogenous retroviral K (HERV-K) family, preferably is selected from a HERV-K envelope (HERV-K-env) protein and a HERV-K gag protein.

In one embodiment of the recombinant MVA, the ERV peptide is from the human endogenous retroviral K (HERV-K) family, preferably is selected from a pseudogene of a HERV-K envelope protein (HERV-K-env/MEL).

In another aspect, the invention provides a recombinant modified Vaccinia virus Ankara (MVA) comprising:

(i) a nucleic acid encoding HERV-K-env/MEL;

(ii) a nucleic acid encoding HERV-K gag;

(iii) a nucleic acid encoding FOLR1 and PRAME, preferably expressed as a fusion protein; and (iv) a nucleic acid encoding 4-1BBL.

In one embodiment, the recombinant MVA further comprises:

(v) a nucleic acid encoding CD40L.

In one embodiment, the nucleic acid in (i) encodes a HERV-K-env/MEL comprising a HERV-K-env surface (SU) and transmembrane (TM) unit, wherein the TM unit is mutated, preferably wherein the TM unit is mutated such that an immunosuppressive domain is inactivated. Preferably, HERVK-MEL is inserted within the mutated TM unit. More preferably, HERVK-MEL replaces a portion of the immunosuppressive domain of the TM unit.

In one embodiment, the nucleic acid sequence in (i) encodes an amino acid sequence comprising or consisting of an amino acid sequence as depicted in SEQ ID NO: 7.

In one embodiment, the nucleic acid sequence in (i) comprises or consists of a nucleic acid sequence as depicted in SEQ ID NO: 8.

In one embodiment, the nucleic acid in (i) encodes a HERVK-env/MEL comprising a HERV-K-env surface (SU) and transmembrane (TM) unit, wherein the TM unit is shortened to less than 20 amino acids, preferably less than 10 amino acids, more preferably less than 8 amino acids, most preferably 6 amino acids.

In one embodiment, the nucleic acid in (i) encodes a HERVK-env/MEL comprising a HERV-K-env surface (SU) unit, wherein the RSKR furin cleavage site of the HERV-K-env SU unit is deleted. Preferably, HERVK-MEL is attached to the C-terminus of the HERV-Kenv SU unit.

In one embodiment, the nucleic acid in (i) encodes a HERVK-env/MEL comprising a heterologous membrane anchor, preferably derived from the human PDGF (platelet-derived growth factor) receptor.

In one embodiment, the nucleic acid sequence in (i) encodes an amino acid sequence comprising or consisting of an amino acid sequence as depicted in SEQ ID NO: 11.

In one embodiment, the nucleic acid sequence in (i) comprises or consists of a nucleic acid sequence as depicted in SEQ ID NO: 12.

In one embodiment, the recombinant MVA is derived from MVA-BN.

In another aspect, the invention provides a pharmaceutical preparation or composition comprising the recombinant MVA of the invention.

In one embodiment, the pharmaceutical preparation or composition is adapted to intratumoral and/or intravenous administration, preferably intratumoral administration.

In another aspect the invention provides the recombinant MVA for use as a medicament or a vaccine.

In another aspect, the invention provides the recombinant MVA for use in the treatment of cancer, preferably melanoma, breast cancer, colon cancer, or ovarian cancer.

In another aspect, the invention provides the recombinant MVA of the invention for use in enhancing an inflammatory response in a cancerous tumor, reducing the size of a cancerous tumor, retarding or arresting the growth of a cancerous tumor and/or increasing the overall survival of a subject, preferably a human.

In one embodiment, the recombinant MVA for use is administered intratumorally and/or intravenously, preferably intratumorally.

23. In one embodiment, the recombinant MVA for use is used in combination with a TAA specific antibody.

24. In one embodiment, the recombinant MVA for use is used in combination with either an immune checkpoint molecule antagonist or agonist.

In yet another aspect, the invention provides a method of treatment wherein the administered recombinant MVA is a recombinant MVA according to the invention.

EXAMPLES

The following examples illustrate the invention but should not be construed as in any way limiting the scope of the claims.

Example 1: Construction of Recombinant MVA-TAA-4-1BBL and MVA-TAA-CD40L

Generation of recombinant MVA viruses that embody elements of the present disclosure was done by insertion of the indicated transgenes with their promoters into the vector MVA-BN. Transgenes were inserted using recombination plasmids containing the transgenes and a selection cassette, as well as sequences homologous to the targeted loci within MVA-BN. Homologous recombination between the viral genome and the recombination plasmid was achieved by transfection of the recombination plasmid into MVA-BN infected CEF cells. The selection cassette was then deleted during a second step with help of a plasmid expressing CRE-recombinase, which specifically targets loxP sites flanking the selection cassette, therefore excising the intervening sequence. Alternatively, deletion of the selection cassette was achieved by MVA-mediated recombination using MVA-derived internal repeat sequences.

For construction of MVA-OVA and MVA-OVA-4-1BBL the recombination plasmid included the transgenes OVA or OVA and 4-1BBL, each preceded by a promoter sequence, as well as sequences which are identical to the targeted insertion site within MVA-BN to allow for homologous recombination into the viral genome.

For construction of MVA-OVA-CD40L the recombination plasmid included the transgenes OVA and CD40L, each preceded by a promoter sequence, as well as sequences which are identical to the targeted insertion site within MVA-BN to allow for homologous recombination into the viral genome.

For the construction of MVA-gp70-4-1BBL the recombination plasmid includes two transgenes gp70 and 4-1BBL, each preceded by a promoter sequence, as well as sequences which are identical to the targeted insertion site within MVA-BN to allow for homologous recombination into the viral genome.

For the construction of MVA-HERV-K, MVA-HERV-K-4-1BBL, and MVA-HERV-K-4-1BBL-CD40L, the recombination plasmid included the HERV-K, HERV-K and 4-1BBL, and HERV-K, 4-1BBL, and CD40L transgenes, respectively. Each transgene or set of transgenes was preceded by a promoter sequence, as well as sequences which are identical to the targeted insertion site within MVA-BN to allow for homologous recombination into the viral genome.

For the construction of MVA-AH1A5-p15E-TRP2 and MVA-AH1A5-p15E-TRP2-CD40L the recombination plasmid included the transgenes AH1A5-p15E-TRP2 or AH1A5-p15E-TRP2 and CD40L, each preceded by a promoter sequence, as well as sequences which are identical to the targeted insertion site within MVA-BN to allow for homologous recombination into the viral genome.

For generation of the above described mBN MVAs, CEF cell cultures were each inoculated with MVA-BN and transfected each with the corresponding recombination plasmid. In turn, samples from these cell cultures were inoculated into CEF cultures in medium containing drugs inducing selective pressure, and fluorescence-expressing viral clones were isolated by plaque purification. Loss of the fluorescent-protein-containing selection cassette from these viral clones was mediated in a second step by CRE-mediated recombination involving two loxP sites flanking the selection cassette in each construct or MVA-mediated internal recombination. After the second recombination step only the transgene sequences (e.g., OVA, 4-1BBL, gp70, HERV-K, and/or CD40L) with their promoters inserted in the targeted loci of MVA-BN were retained. Stocks of plaque-purified virus lacking the selection cassette were prepared.

Expression of the identified transgenes is demonstrated in cells inoculated with the described construct.

Generation of the constructs described herein was carried out by using a cloned version of MVA-BN in a bacterial artificial chromosome (BAC). Recombination plasmids contained the described transgene sequences, each downstream of a promoter. The plasmids included sequences that are also present in MVA and therefore allow for specific targeting of the integration site. Briefly, infectious viruses were reconstituted from BACs by transfecting BAC DNA into BHK-21 cells and superinfecting them with Shope fibroma virus as a helper virus. After three additional passages on CEF cell cultures, helper-virus-free versions of the constructs were obtained. An exemplary MVA generation is also found in Baur et al. ((2010) *Virol.* 84: 8743-52, "Immediate-early expression of a recombinant antigen by modified vaccinia virus Ankara breaks the immunodominance of strong vector-specific B8R antigen in acute and memory CD8 T-cell responses").

Figure 1B:
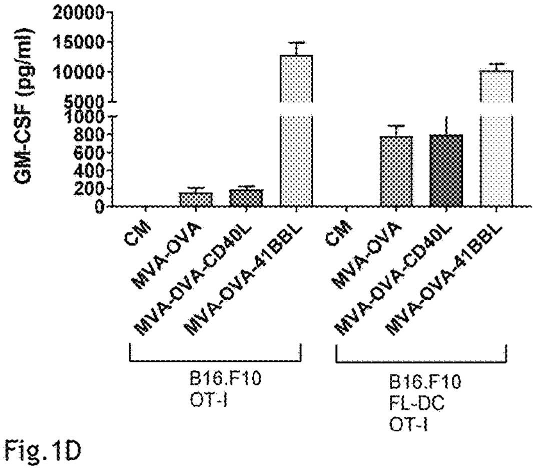
Figure 1C:
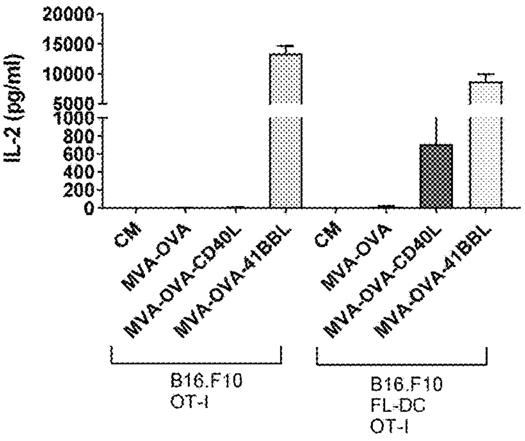
Figure 1D:
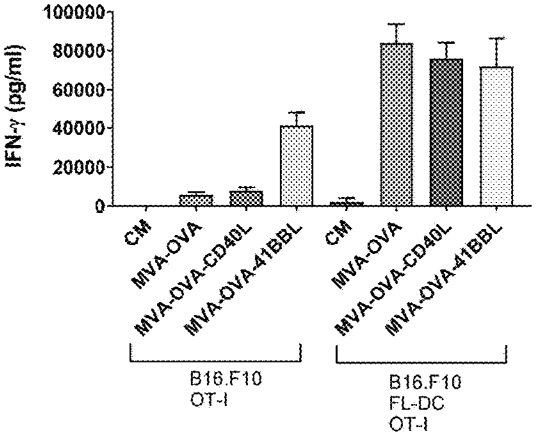

Example 2: 4-1BBL-Mediated Costimulation of CD8 T Cells by MVA-OVA-4-1BBL Infected Tumor Cells Influences Cytokine Production without the Need of DCs Dendritic cells (DCs) were generated after culturing bone marrow cells from C57BL/6 mice in the presence of recombinant Flt3L for 14 days. B16.F10 (melanoma model) cells were infected with MVA-OVA, MVA-OVA-CD40L, or MVA-OVA-4-1BBL at a MOI of 10 and cultured overnight at 37° C. with 5% CO2. The next day, infected tumor cells were harvested and cocultured when indicated in the presence of DCs at a 1:1 ratio for 4 hours at 37° C. with 5% CO2. Naïve OVA(257-264) specific CD8+ T cells were magnetically purified from OT-I mice and added to the coculture at a ratio of 1:5. Cells were cultured at 37° C. with 5% CO2 for 48 hours. Then, culture supernatant was collected for cytokine concentration analysis by Luminex. Results are shown as supernatant concentration of: IL-6 (FIG. 1A); GM-CSF (FIG. 1B); IL-2 (FIG. 1C); and IFN-γ (FIG. 1D). Data are represented as Mean±SEM.

In line with what has been previously reported, MVA-OVA-CD40L had a great impact on the activation of DC and their antigen presentation capabilities. Thus, MVA-OVA-CD40L-infected FLDC produced large amounts of IL-6 (FIG. 1A). Importantly, OVA-specific T cell responses could be exclusively induced in the presence of DC but not directly by MVA-CD40L infected B16.F10 cells themselves (FIGS. 1B and 1C). These results show a clear requirement of DC to unfold the benefits of MVA-OVA-CD40L. In contrast, MVA-OVA-4-1BBL did not induce IL-6 production in DC, but MVA-OVA-4-1BBL-infected B16.F10 cells elicited the secretion of T cell activation cytokines IFN-γ, IL-2 and GM-CSF in a DC-independent manner (FIG. 1A-1D).

Figure 2B:
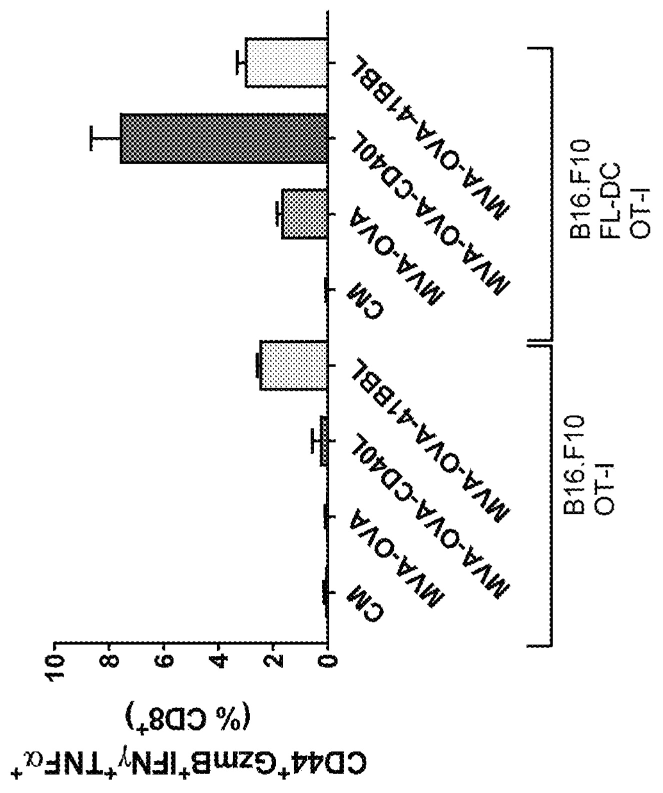
FIG. 2A and FIG. 2B show that MVA-OVA-4-1BBL infected tumor cells directly, i.e., without the need of DC, drive differentiation of antigen-specific CD8 T cells into activated effector T cells, whereas CD40L-mediated costimulation of MVA-OVA-CD40L infected tumor cells is dependent on the presence of DC. As described in Example 3, dendritic cells (DCs) were generated after culturing bone marrow cells from C57BL/6 mice in the presence of recombinant Flt3L for 14 days. B16.F10 (melanoma model) cells were infected with MVA-OVA, MVA-OVA-CD40L or MVA-OVA-4-1BBL. The next day, infected tumor cells were harvested and cocultured (when indicated) in the presence of DCs. Naïve OVA(257-264)-specific CD8+ T cells were magnetically purified from OT-I mice and added to the coculture at a ratio of 1:5. Cells were cultured at 37° C. 5% CO2 for 48 hours. Cells were then stained and analyzed by flow cytometry.
Figure 2A:
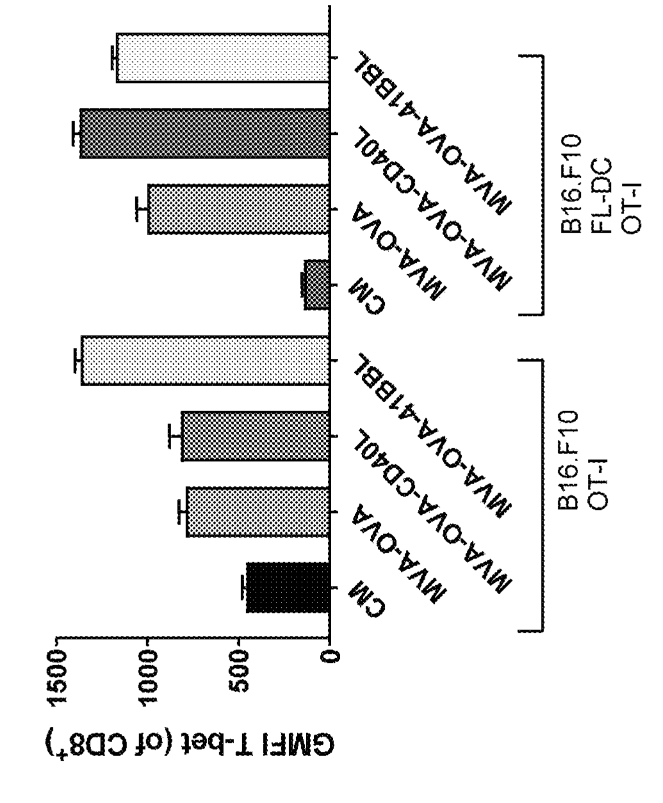

Example 3: MVA-OVA-4-1BBL Infected Tumor Cells Directly (i.e., without the Need of DC) Drive Differentiation of Antigen-Specific CD8 T Cells into Activated Effector T Cells Dendritic cells (DCs) were generated after culturing bone marrow cells from C57BL/6 mice in the presence of recombinant Flt3L for 14 days. B16.F10 (melanoma model) cells were infected with MVA-OVA, MVA-OVA-CD40L, or MVA-OVA-4-1BBL at a MOI of 10 and cultured overnight at 37° C. with 5% CO2. The next day, infected tumor cells were harvested and cocultured when indicated in the presence of DCs at a 1:1 ratio for 4 hours at 37° C. with 5% CO2. Meanwhile, naïve OVA(257-264) specific CD8+ T cells were magnetically purified from OT-I mice and added to the coculture at a ratio of 1:5. Cells were cultured at 37° C. 5% CO2 for 48 hours. Cells were then stained and analyzed by flow cytometry. Results are shown as GMFI of T-bet on OT-I CD8+ T cells (FIG. 2A) and percentage of CD44+Granzyme B+IFN-γ+ TNFα+ of OT-I CD8+ T cells (FIG. 2B). Data are shown as Mean±SEM.

The results show that in the absence of cross-presenting DC, the induction of Granzyme B+ and IFNγ+ cytotoxic effector T cells was dependent on 4-1BBL (FIG. 2B). Collectively with the results presented in FIG. 1A-1D, these findings document that, in contrast to MVA-encoded CD40L, which operates through the activation of DCs, 4-1BBL encoded by MVA acts directly on T cells in a DC-independent manner.

Example 4: Infection with MVAs Encoding Either CD40L or 4-1BBL Induce Tumor Cell Death in Tumor Cell Lines and Macrophages Tumor cell lines B16.OVA (FIGS. 3A and 3B), MC38 (FIG. 3C) and B16.F10 (FIG. 3D) were infected at the indicated MOI for 20 hours. Then, cells were analyzed for their viability by flow cytometry. Serum HMGB1 in the samples from FIG. 3A was quantified by ELISA (FIG. 3B). Bone-marrow-derived macrophages (BMDMs) were infected at the indicated MOI for 20 hours. Cells were then analyzed for their viability by flow cytometry. Results are shown in FIGS. 3A-3E. Data are presented as Mean±SEM.

Figure 3A:
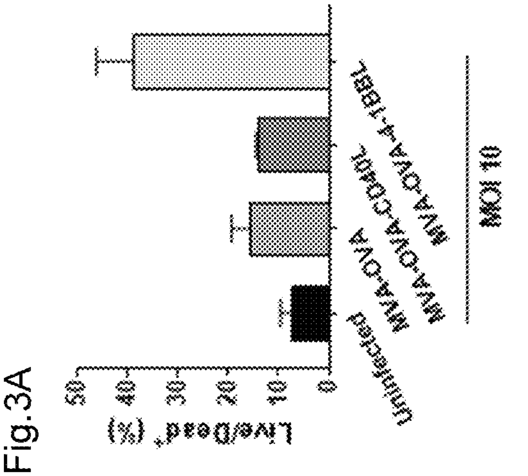
FIGS. 3A, 3B, 3C, 3D, and 3E illustrate that infection with MVAs encoding either CD40L or 4-1BBL induce tumor cell death in tumor cell lines and macrophages. As described in Example 4, tumor cell lines B16.OVA (FIGS. 3A and 3B), MC38 (FIG. 3C) and B16.F10 (FIG. 3D) were infected with vectors at the indicated MOI for 20 hours. Cells were analyzed for their viability by flow cytometry.
Figure 3B:
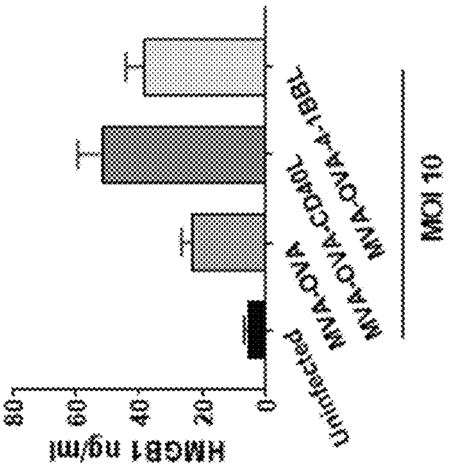
Figure 3C:
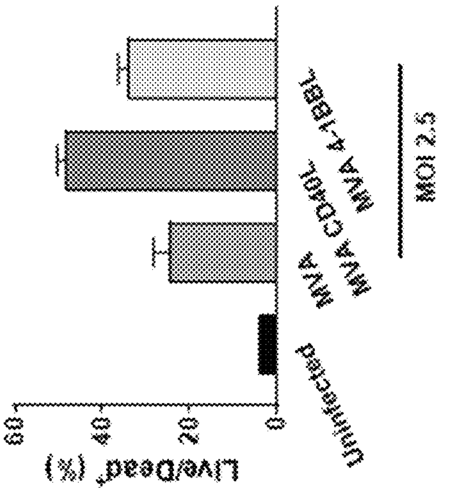
Figure 3D:
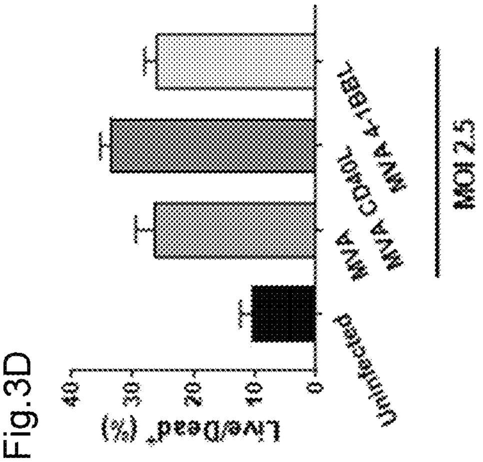

As shown in FIGS. 3A and 3B, infection with MVA-OVA or MVA-OVA-CD40L resulted in mild induction of cell death compared to PBS-treated tumor cells. Interestingly, infection with MVA-OVA-4-1BBL significantly enhanced tumor cell death 18 hours post infection.

Figure 3E:
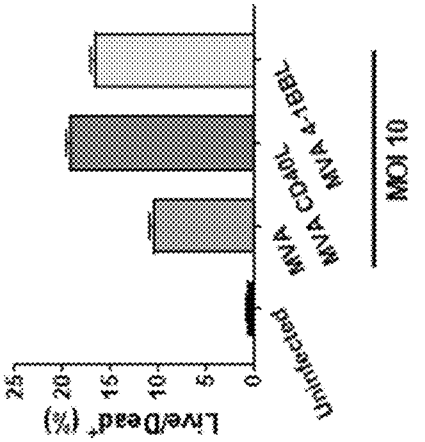

To further confirm these results in non-antigenic cell lines, we performed similar assays using MC38 (FIG. 3C) and B16.F10 (FIG. 3D) tumor cells infected with MVA, MVA-CD40L, and MVA-4-1BBL (none of which encoded TAAs). Consistently, infection with these MVAs induced cell death in these tumor cell lines and efficiently killed bone marrow-derived macrophages (BMDMs) (FIG. 3E). Altogether, these data demonstrated that MVA infection resulted in tumor cell and macrophage death that were increased when CD40L or 4-1BBL were expressed by the recombinant MVA.

Oncolytic virus infection of tumor cells results in the induction of so-called immunogenic cell death (ICD) (Workenhe et al. (2014) *Mol. Ther.* 22: 251-56). ICD comprises the release of intracellular proteins such as calreticulin, ATP, or HMGB1 that act as alarmins to the immune system, leading to enhanced antigen-presentation and thereby inducing anti-tumor immunity. We tested whether MVA infection would result in induction of ICD by means of secreted HMGB1. Unexpectedly, we found that MVA-OVA-4-1BBL and MVA-OVA-CD40L induced a significant increase of HMGB1 in comparison to MVA-OVA (FIG. 3B).

Example 5: MVA Encoding 4-1BBL Induces NK Cell Activation In Vivo

Figure 4B:
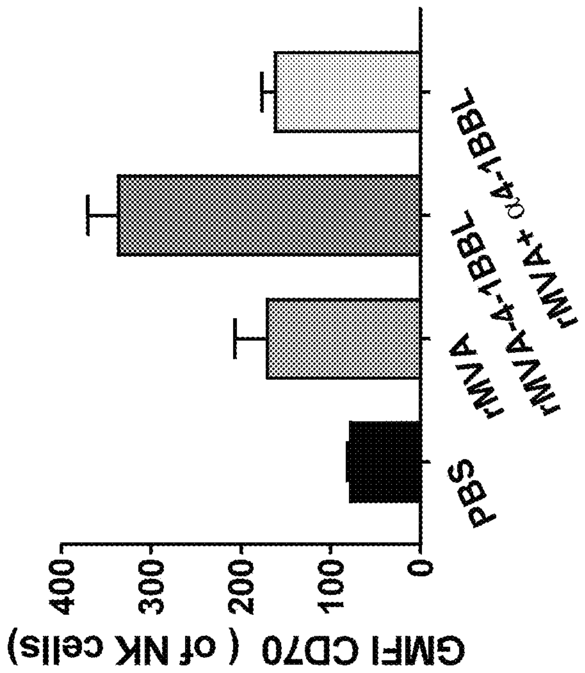
FIGS. 4A and 4B show that rMVA-4-1BBL induces NK cell activation in vivo. As described in Example 5, C57BL/6 mice (n=5/group) were immunized intravenously either with saline or $5\times10^7$ TCID50 "rMVA" (=MVA-OVA), "rMVA-4-1BBL" (=MVA-OVA-4-1BBL) or $5\times10^7$ TCID50 rMVA combined with 200 μg anti 4-1BBL antibody (clone TKS-1). 24 hours later, mice were sacrificed and spleens processed for flow cytometry analysis. Geometric Mean Fluorescence Intensity (GMFI) of CD69 (FIG. 4A) and CD70 (FIG. 4B) is shown. Data are shown as Mean±SEM.
Figure 4A:
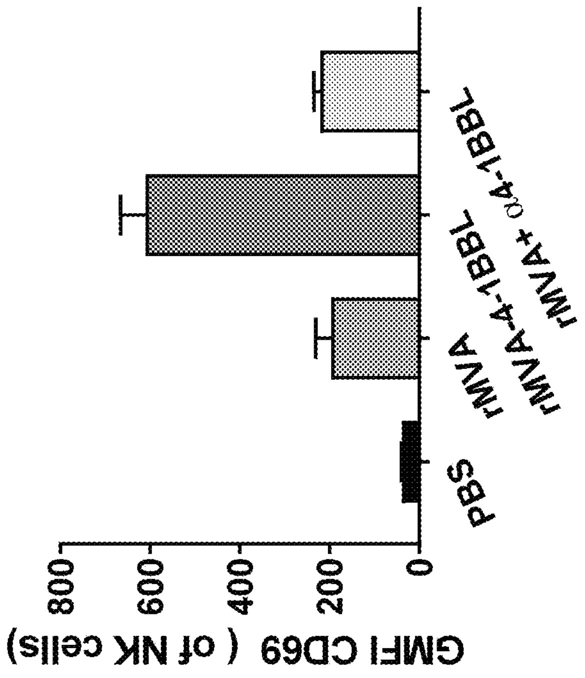

C57BL/6 mice (n=5/group) were immunized intravenously either with saline or $5\times10^7$ TCID50 MVA-OVA ("rMVA" in FIGS. 4A and 4B), $5\times10^7$ TCID50 MVA-OVA-4-1BBL ("rMVA-4-1BBL" in FIGS. 4A and 4B), or $5\times10^7$ TCID50 MVA-OVA combined with 200 μs anti 4-1BBL antibody (clone TKS-1). 24 hours later, mice were sacrificed and spleens processed for flow cytometry analysis. Results are shown in FIG. 4A and FIG. 4B. Geometric Mean Fluorescence Intensity (GMFI) of CD69 (FIG. 4A) and CD70 (FIG. 4B) is shown. Data are shown as Mean±SEM, representative of two independent experiments.

The results showed that the quality of the NK cell response was enhanced by the addition of 4-1BBL to MVA-OVA as compared to the IV administration of MVA-OVA without 4-1BBL, and both NK cell activation markers, CD69 and CD70, were strongly upregulated as compared to MVA-OVA (FIGS. 4A and 4B). Coinjection of blocking 4-1BBL antibody showed that MVA-OVA-induced NK cell activation was completely 4-1BBL-independent, but could be enhanced when excessive 4-1BBL signal was delivered by MVA-OVA-4-1BBL.

Figure 5B:
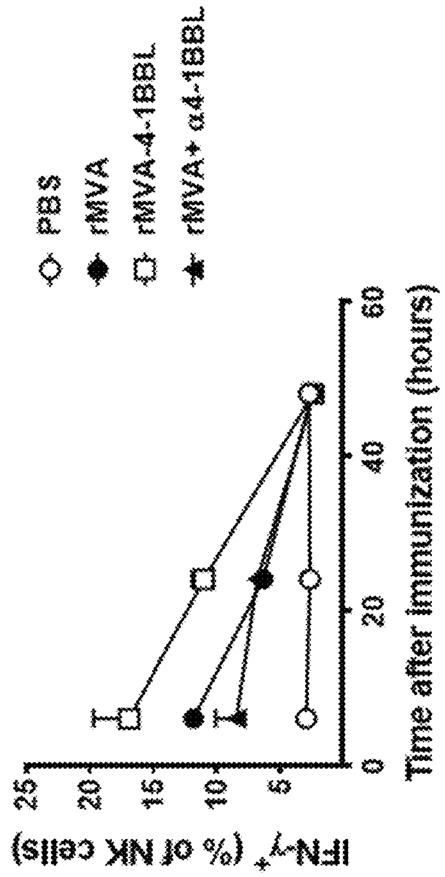
FIGS. 5A and 5B show that intravenous rMVA-4-1BBL immunization promotes serum IFN-γ secretion in vivo. As described in Example 6, C57BL/6 mice (n=5/group) were immunized intravenously either with saline or $5\times10^7$ TCID50 "rMVA" (=MVA-OVA), "rMVA 1BBL" (=MVA-OVA-4-1BBL), or $5\times10^7$ TCID50 rMVA combined with 200 μg anti 4-1BBL antibody (clone TKS-1).
Figure 5A:
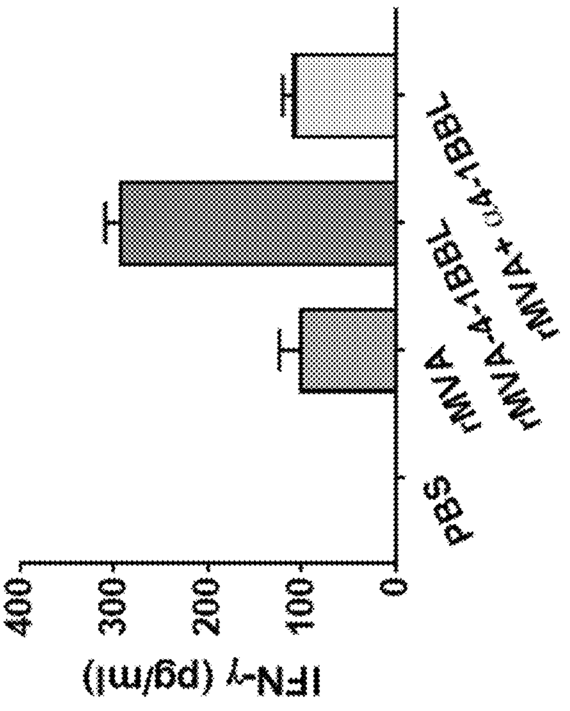

Example 6: Intravenous Immunization with MVA Encoding 4-1BBL Promotes Serum IFN-γ Secretion In Vivo C57BL/6 mice (n=5/group) were immunized intravenously either with saline or $5\times10^7$ TCID50 "rMVA" (=MVA-OVA), $5\times10^7$ TCID50 "rMVA-4-1BBL" (=MVA-OVA-4-1BBL), or $5\times10^7$ TCID50 MVA-OVA combined with 200 μg anti 4-1BBL antibody (clone TKS-1). Results are shown in FIGS. 5A and 5B. Data are shown as Mean±SEM. FIG. 5A: 6 hours later, mice were bled, serum was isolated from whole blood and IFN-γ concentration in serum determined by Luminex. FIG. 5B: 3, 21, and 45 hours later, mice were intravenously injected with Brefeldin A to stop protein secretion. Mice were sacrificed 6, 24 and 48 hours after immunization and splenocytes analyzed by flow cytometry.

The 4-1BB-mediated NK cell activation coincided with increased serum levels of the NK effector cytokine IFNγ (FIG. 5A). NK cells are known to produce high amounts of IFN-γ upon activation. To determine whether the increased IFN-γ levels in the serum could have originated from NK cells, the proportion of IFN-γ-producing NK cells was determined at different timepoints after intravenous injection of the indicated recombinant MVA vectors. 6 h after injection, when high serum levels of IFN-γ were measured, the percentage of IFN-γ+NK cells was highest and slowly decreased thereafter (FIG. 5B). The highest frequency of IFN-γ positive NK cells was observed when MVA-OVA-4-1BBL was used. Taken together, these data show that intravenous immunization of rMVA-4-1BBL leads to the strong activation of NK cells and increased production of the NK cell effector cytokine IFN-γ.

Figure 6:
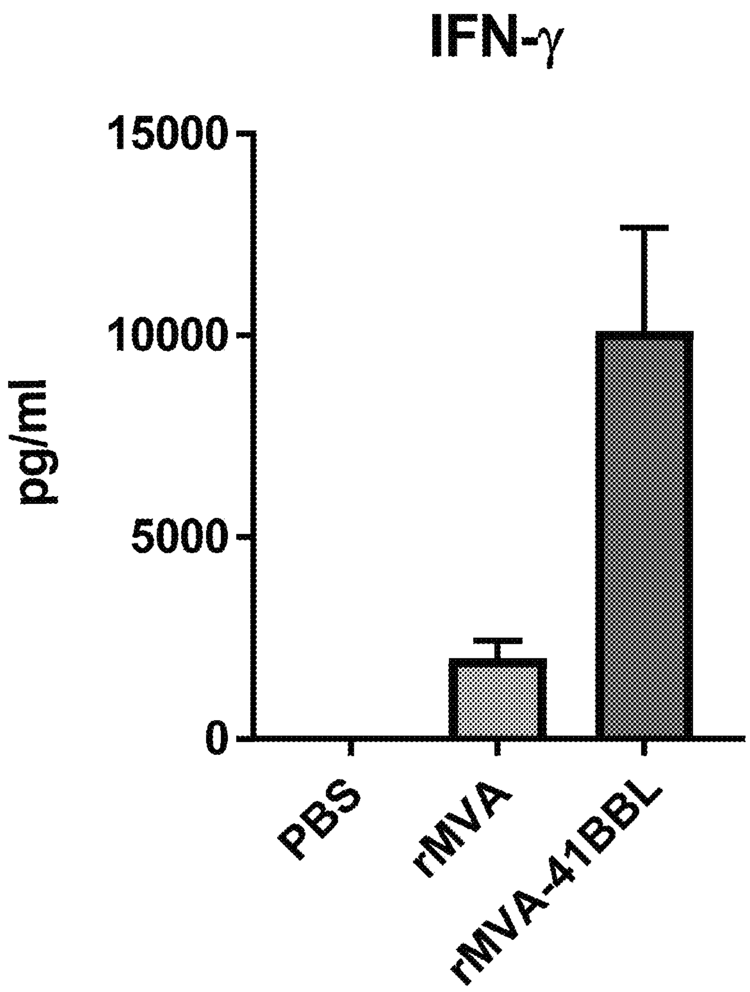
FIG. 6 shows that intravenous "rMVA-4-1BBL" (=MVA-OVA-4-1BBL) immunization promotes serum IFN-γ secretion in B16.OVA tumor-bearing mice. As described in Example 7, B16.OVA tumor-bearing C57BL/6 mice (n=5/group) were grouped and received i.v. (intravenous) PBS or $5\times10^7$ TCID50 rMVA (=MVA-OVA) or rMVA-4-1BBL at day 7 after tumor inoculation. 6 hours later, mice were bled, serum was isolated from whole blood and IFN-γ concentration in serum determined by Luminex. Data are shown as Mean±SEM.

Example 7: Intravenous rMVA-4-1BBL Immunization Promotes Serum IFN-γ Secretion in B16.OVA Tumor-Bearing Mice B16.OVA tumor-bearing C57BL/6 mice (n=5/group) were grouped and received i.v. (intravenous) PBS or $5\times10^7$ TCID50 MVA-OVA ("rMVA" in the figure) or MVA-OVA-4-1BBL ("rMVA-4-1BBL" in the figure) at day 7 after tumor inoculation. 6 hours later, mice were bled, serum was isolated from whole blood, and IFN-γ concentration in serum was determined by Luminex. Results are shown in FIG. 6. Data are shown as Mean±SEM.

The data shown in FIG. 6 demonstrate that similar effects on NK cells to those reported in other experiments could be also obtained in a melanoma tumor model. 6 h after immunization, serum IFN-γ levels were highly increased in MVA-OVA-4-1BBL immunized tumor-bearing mice, indicating strong NK cell activation (FIG. 6).

Example 8: Intravenous rMVA-4-1BBL Prime and Boost Immunizations Enhances Antigen- and Vector-Specific CD8+ T Cell Expansion FIGS. 7A-7D show antigen and vector-specific after intravenous rMVA-4-1BBL prime and boost immunization. C57BL/6 mice (n=4/group) received intravenous prime immunization either with saline or $5\times10^7$ TCID50 rMVA (=MVA-OVA), $5\times10^7$ TCID50 rMVA-4-1BBL (=MVA-OVA-4-1BBL), or $5\times10^7$ TCID50 rMVA combined with 200 μg anti 4-1BBL antibody (clone TKS-1) on day 0 and boost immunization on day 41. Mice were bled on days 6, 21, 35, 48, and 64 after prime immunization, and flow cytometric analysis of peripheral blood was performed. Mice were sacrificed on day 70 after prime immunization. Spleens were harvested and flow cytometry analysis performed.

Figure 7A:
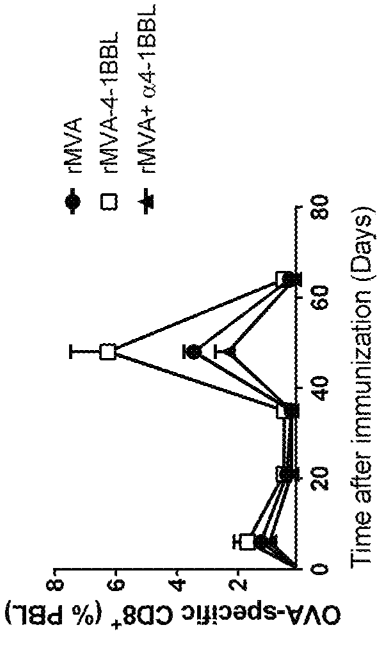
FIGS. 7A, 7B, 7C, and 7D show antigen and vector-specific CD8+ T cell expansion after intravenous "rMVA-4-1BBL" (=MVA-OVA-4-1BBL) prime and boost immunization. As described in Example 8, C57BL/6 mice (n=4/group) received intravenous prime immunization either with saline or $5\times10^7$ TCID50 "rMVA" (=MVA-OVA), rMVA-4-1BBL or $5\times10^7$ TCID50 rMVA combined with 200 μg anti 4-1BBL antibody (clone TKS-1) on day 0 and boost immunization on day 41. Mice were bled on days 6, 21, 35, 48 and 64 after prime immunization, and flow cytometric analysis of peripheral blood was performed.
Figure 7B:
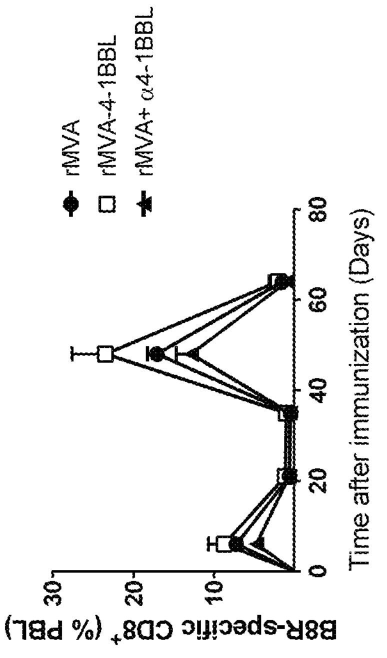
Figure 7C:
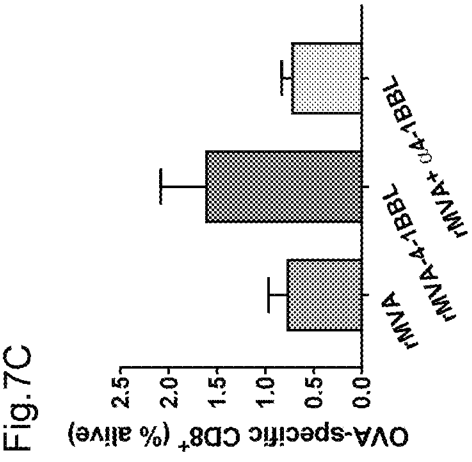
Figure 7D:
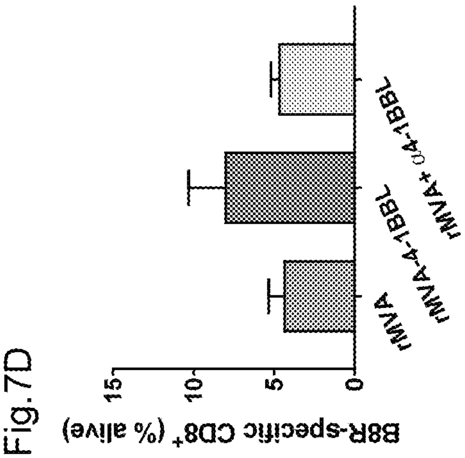
Figure 8:
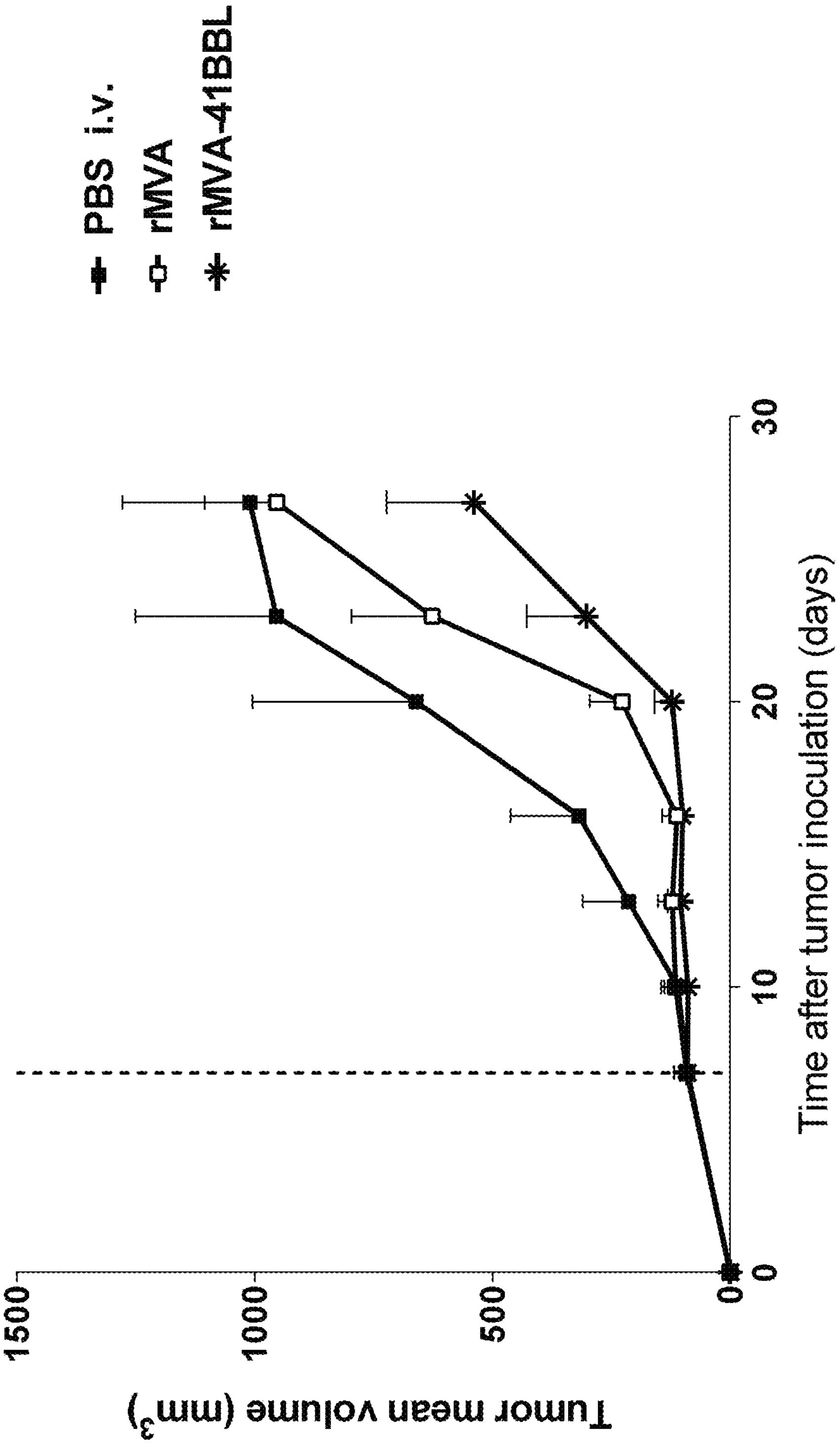
FIG. 8 shows an increased antitumor effect of intravenous injection of MVA virus encoding 4-1BBL as compared to the recombinant MVA without 4-1BBL. As described in Example 9, B16.OVA tumor-bearing C57BL/6 mice (n=5/group) were grouped and received intravenous administrations of PBS or $5\times10^7$ TCID50 MVA-OVA ("rMVA" in figure) or MVA-OVA-4-1BBL ("rMVA-4-1BBL" in figure) at day 7 (black dotted line) after tumor inoculation. Tumor growth was measured at regular intervals.

Results are shown in FIGS. 7A-7D. FIG. 7A shows percentage of antigen (OVA)-specific CD8+ T cells among Peripheral Blood Leukocytes (PBL) and FIG. 7B shows percentage of vector (B8R)-specific CD8+ T cells among PBL. FIG. 7C illustrates percentage of antigen (OVA)-specific CD8+ T cells among live cells. FIG. 7D shows percentage of vector (B8R)-specific CD8+ T cells among live cells. Data are shown as Mean±SEM.

The results show that B8- and OVA-specific CD8 T cells reached a maximum on day 7 after the first immunization and were further expanded after the second immunization on day 41 (FIGS. 7A and 7B). At the day 41 timepoint, there was a clear benefit of rMVA-4-1BBL in terms of antigen-specific T cell response when compared to rMVA, both for B8 and OVA. Interestingly, coinjection of blocking 4-1BBL antibody showed that rMVA-induced T cell responses were completely 4-1BBL-independent, but could be enhanced when excessive 4-1BBL signal was delivered by rMVA-4-1BBL (FIGS. 7A and 7B). In line with these results, rMVA-4-1BBL prime/boost immunization also resulted in an improved OVA- and B8-specific T cell response in the spleen 70 days after the first immunization (FIGS. 7C and 7D).

Example 9: Increased Antitumor Effect of Intravenous Injection of MVA Virus Encoding a TAA and 4-1BBL B16.OVA tumor-bearing C57BL/6 mice (n=5/group) were grouped and received i.v. (intravenous) PBS or $5\times10^7$ TCID50 MVA-OVA or $5\times10^7$ TCID50 MVA-OVA-4-1BBL at day 7 (black dotted line) after tumor inoculation. Tumor growth was measured at regular intervals. Shown in FIG. 8, an intravenous administration of MVA virus encoding 4-1BBL resulted in a reduction in tumor volume as compared to MVA or the control (PBS) as a consequence of prolonged delay in growth of the tumors.

Example 10: Enhanced Antitumor Effect of Intratumoral Injection of MVA Virus Encoding 4-1BBL or CD40L B16.OVA tumor-bearing C57BL/6 mice (n=4-5/group) were grouped and received intratumoral (i.t.) PBS or $5\times10^7$ TCID50 of MVA-OVA ("rMVA" in the figure), MVA-OVA-CD40L ("rMVA-CD40L" in the figure), or MVA-OVA-4-1BBL ("rMVA-4-1BBL" in the figure) at days 7 (black dotted line), 12 and 15 (grey dashed lines) after tumor inoculation. Tumor growth was measured at regular intervals. Shown in FIGS. 9A-9D, an enhanced antitumor effect was realized via an intratumoral injection of MVA virus encoding a TAA and either 4-1BBL or CD40L. More particularly, shown in FIG. 9, a significantly greater reduction in tumor growth was seen with MVA virus encoding 4-1BBL. While the invention is not bound by any particular mechanism or mode of action, one hypothesis for the differences observed between 4-1BBL and CD40L is that 4-1BBL aims to activate NK cells and T cells, whereas CD40L aims to activate DCs. B16 melanoma tumors are more infiltrated with T cells (Mosely et al. (2016) *Cancer Immunol. Res.* 5(1): 29-41); therefore an MVA encoding 4-1BBL is more effective than an MVA encoding CD40L in this setting.

Figure 9:
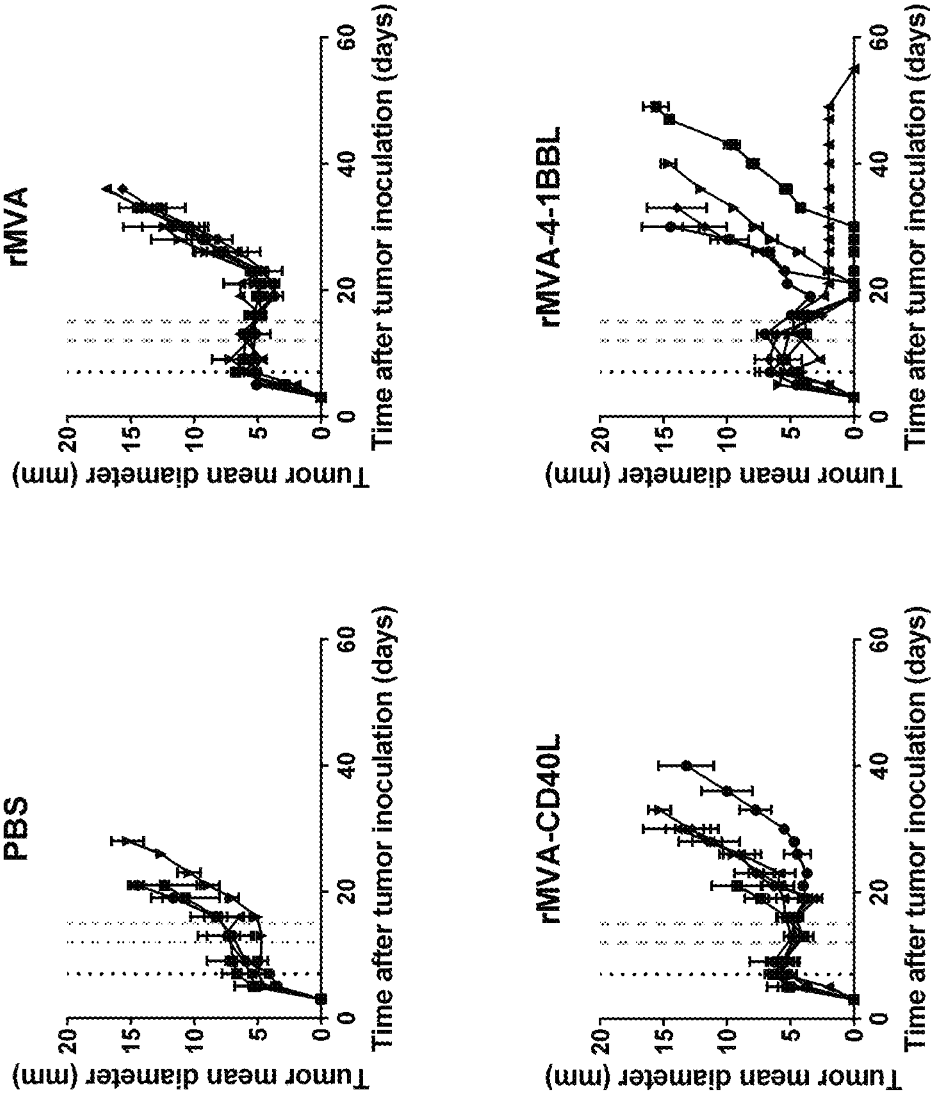
FIG. 9 shows an enhanced antitumor effect of intratumoral injection of MVA virus encoding 4-1BBL or CD40L. As described in Example 10, B16.OVA tumor-bearing C57BL/6 mice (n=4-5/group) were grouped and received intratumoral administrations of PBS or $5\times10^7$ TCID50 of MVA-OVA (labelled "rMVA" in figure), MVA-OVA-CD40L (labelled "rMVA-CD40L" in figure), or MVA-OVA-4-1BBL (labelled "rMVA-4-1BBL" in figure) at days 7 (black dotted line), 12, and 15 (grey dashed lines) after tumor inoculation. Tumor growth was measured at regular intervals.

Regardless of the exact mechanism or pathway by which 4-1BBL and CD40L exert their effects on tumor growth or diameter, the data in FIG. 9 showed that intratumoral injection of MVA encoding 4-1BBL resulted in prolonged tumor growth control and in some cases even in complete rejection of the tumor.

Figure 10:
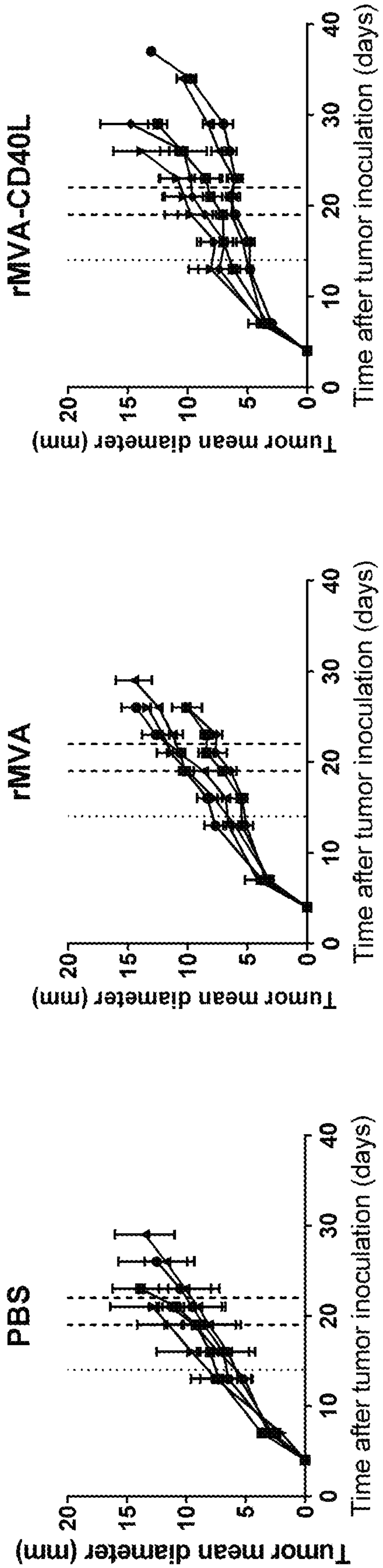
FIG. 10 shows the antitumor effect of intratumoral injection of MVA virus encoded with CD40L against established colon cancer. As described in Example 11, MC38-tumor-bearing C57BL/6 mice (n=5/group) were grouped and received intratumoral (i.t.) administrations of PBS or $5\times10^7$ TCID50 MVA-TAA (labelled "rMVA" in the figure) or MVA-TAA-CD40L (labelled "rMVA-CD40L" in the figure) at days 14 (black dotted line), 19, and 22 (black dashed lines) after tumor inoculation. Tumor growth was measured at regular intervals. In these experiments, the TAA encoded by the recombinant MVAs comprised antigens AH1A5, p15E, and TRP2.

Example 11: Enhanced Antitumor Effect of Intratumoral Injection of MVA Virus Encoded with a TAA and CD40L Against Established Colon Cancer MC38 tumor-bearing C57BL/6 mice (n=5/group) were grouped and received intratumoral (i.t.) PBS or $5\times10^7$ TCID50 MVA-AH1A5-p15E-TRP2 (labelled "rMVA" in figure) or MVA-AH1A5-p15E-TRP2-CD40L (labelled "rMVA-CD40L" in figure) at days 14 (black dotted line), 19, and 22 (black dashed lines) after tumor inoculation. Tumor growth was measured at regular intervals. Results are shown in FIG. 10 for the non-antigenic, established MC38 colon carcinomas.

These vectors encode a string of tumor associated epitopes consisting of one melanoma-associated TRP2 derived epitope (SVYDFFVWL, H2-$K^b$) and two murine leukemia virus gp70 derived $CD8^+$ T cell epitopes, p15E (KSPWFTTL, H2-$K^b$) and the modified AH1, AH1A5 (SPSYAYHQF, H2-$L^d$), These results show that intratumoral injection of MVA-CD40L can significantly delay tumor growth in an MC38 colon carcinoma model.

Figure 11:
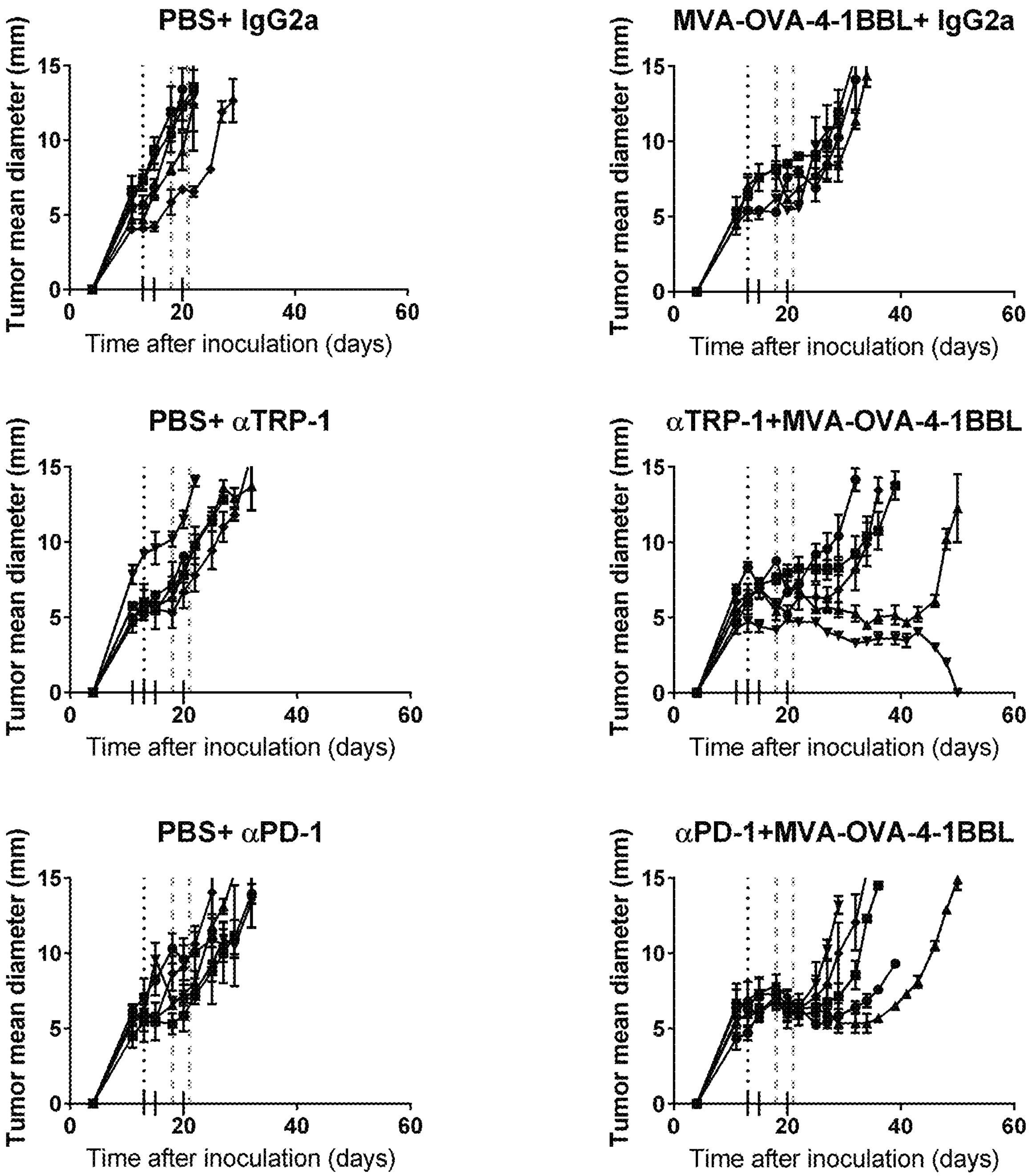
FIG. 11 illustrates that checkpoint blockade and tumor-targeting antibodies synergize with intratumoral (i.t.) administration of rMVA-4-1BBL (also referred to herein as "MVA-OVA-4-1BBL"). As described in Example 12, B16.OVA tumor-bearing C57BL/6 mice (n=5/group) were grouped and received 200 μg IgG2a, anti TRP-1, or anti PD-1 antibody intraperitoneally when indicated (ticks). Mice were immunized intratumorally (i.t.) either with PBS or with 5x$10^7$ TCID50 MVA-OVA-4-1BBL at days 13 (black dotted line), 18 and 21 (grey dashed lines) after tumor inoculation. Tumor growth was measured at regular intervals.

Example 12: Immune Checkpoint Blockade and Tumor Antigen Specific Antibodies Synergize with Intratumoral Administration of MVA-OVA-4-1BBL B16.OVA melanoma cells ($5\times10^5$) were subcutaneously injected into C57BL/6 mice. When tumors reached about 5 mm in diameter, mice were grouped (n=5/group) and received when indicated (ticks) 200 µg IgG2a, anti TRP-1 or anti PD-1 intraperitoneally (i.p.). Mice were immunized intratumorally (i.t.) either with PBS or with $5\times10^7$ TCID50 MVA-OVA-4-1BBL at days 13 (black dotted line), 18 and 21 (grey dashed lines) after tumor inoculation. Tumor growth was measured at regular intervals. Results are shown in FIG. 11. When an antibody specific for the Tumor Associated Antigen (TAA) Trp1 (anti-Trp1) was combined with an intratumoral administration of MVA-OVA-4-1BBL, there was an increased reduction in tumor volume as compared to anti PD-1 by itself (FIG. 11, middle row). When the immune checkpoint molecule antibody PD-1 was combined with an intratumoral administration of MVA-OVA-4-1BBL there was an increased reduction in tumor volume as compared to anti PD-1 by itself (FIG. 11, bottom row).

These experiments demonstrate that anti-PD-1 and anti-TRP-1 antibodies enhanced tumor growth control as single agents, while the combination of either antibody with MVA-OVA-4-1BBL improved the therapeutic effect exerted by MVA-OVA-4-1BBL. Here, combination therapies of intratumoral MVA 4-1BBL with either checkpoint blockade or TAA-targeting antibodies had greater therapeutic activity than any of the monotherapies. This data also indicates that tumor-specific antibodies that potentially induce ADCC may be combined with intratumoral injections of MVA expressing 4-1BBL for a synergistic effect.

Example 13: Superior Anti-Tumor Effect of Intratumoral MVA-OVA-4-1BBL Injection as Compared to Agonistic Anti-CD137 Antibody Treatment B16.OVA tumor-bearing C57BL/6 mice (n=5/group) were grouped and were intratumorally injected with either PBS, $5\times10^7$ TCID50 MVA-OVA-4-1BBL, or 10 µg anti-4-1BB (3H3, BioXcell) on day 7, 12, and 15 (black dashed lines) after tumor inoculation. Tumor growth was measured at regular intervals.

Figure 12B:
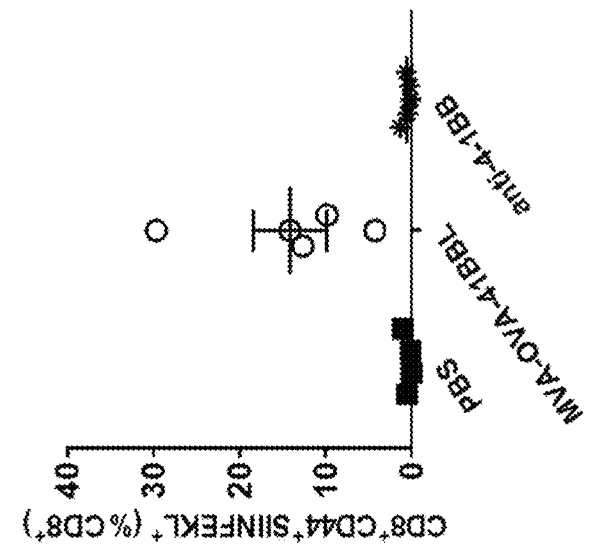
FIGS. 12A and 12B demonstrates that intratumoral MVA-OVA-4-1BBL injection leads to a superior anti-tumor effect when compared to anti-CD137 antibody treatment. As described in Example 13, C57BL/6 mice received 5x$10^5$ B16.OVA cells s.c. (subcutaneously). Seven days later, when tumors measured above 5x5 mm, mice were grouped and intratumorally injected with either PBS, 5x$10^7$ TCID50 MVA-OVA-4-1BBL, or 10 μg anti-4-1BB (3H3) antibody. Tumor growth was measured at regular intervals.
Figure 12A:
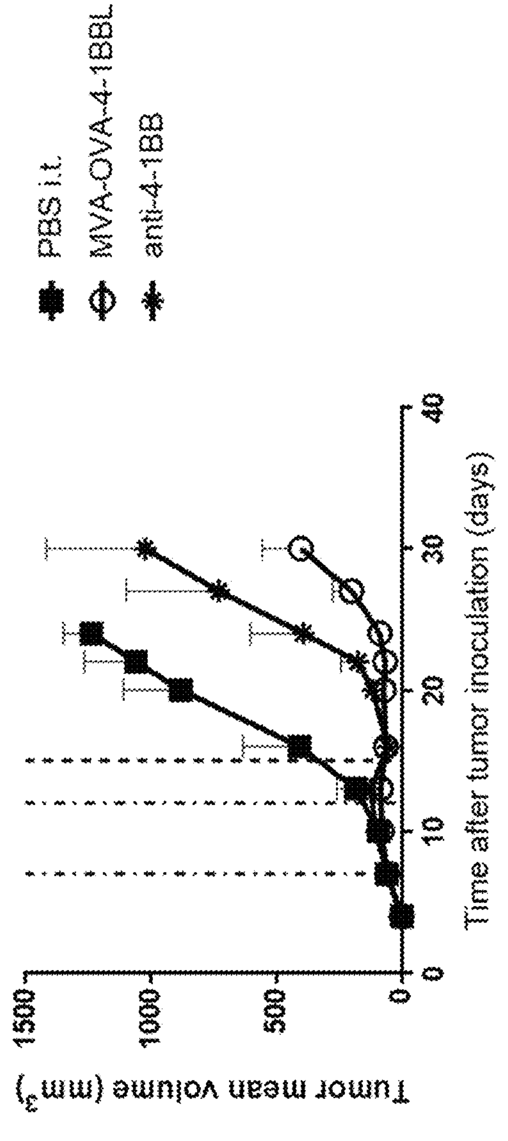

FIG. 12A shows a superior anti-tumor effect of MVA-OVA-4-1BBL as compared to the agonistic anti-4-1BBL antibody (3H3). FIG. 12B shows that intratumoral immunization with MVA-OVA-4-1BBL exclusively induced an OVA-specific T cell response in the blood whereas the agonistic anti-4-1BBL antibody did not induce any OVA-specific T cells in the blood.

Thus, these data show that intratumoral MVA-OVA-4-1BBL treatment is more potent than agonistic anti-CD137 antibodies, both in terms of tumor-specific T cells responses as well as tumor growth control.

Example 14: Increased Antitumor Effect of Intravenous Injection of MVA Encoding the Endogenous Retroviral (ERV) Antigen Gp70 Encoded with CD40L in the CT26 Tumor Model CT26 tumor-bearing Balb/c mice (n=5/group) were grouped and received intravenous (i.v.) PBS or $5\times10^7$ TCID50 MVA-BN, MVA-Gp70, or MVA-Gp70-CD40L at day 12 (black dotted line) after introduction of tumors into the mice. Tumor growth was measured at regular intervals. Shown in FIGS. 13A and 13B, intravenous administration of MVA virus encoding the endogenous retroviral antigen Gp70 resulted in a reduction in tumor volume as compared to MVA or the control (PBS). The anti-tumor effect was further improved when CD40L was additionally encoded by MVA-Gp70-CD40L.

Figure 13A:
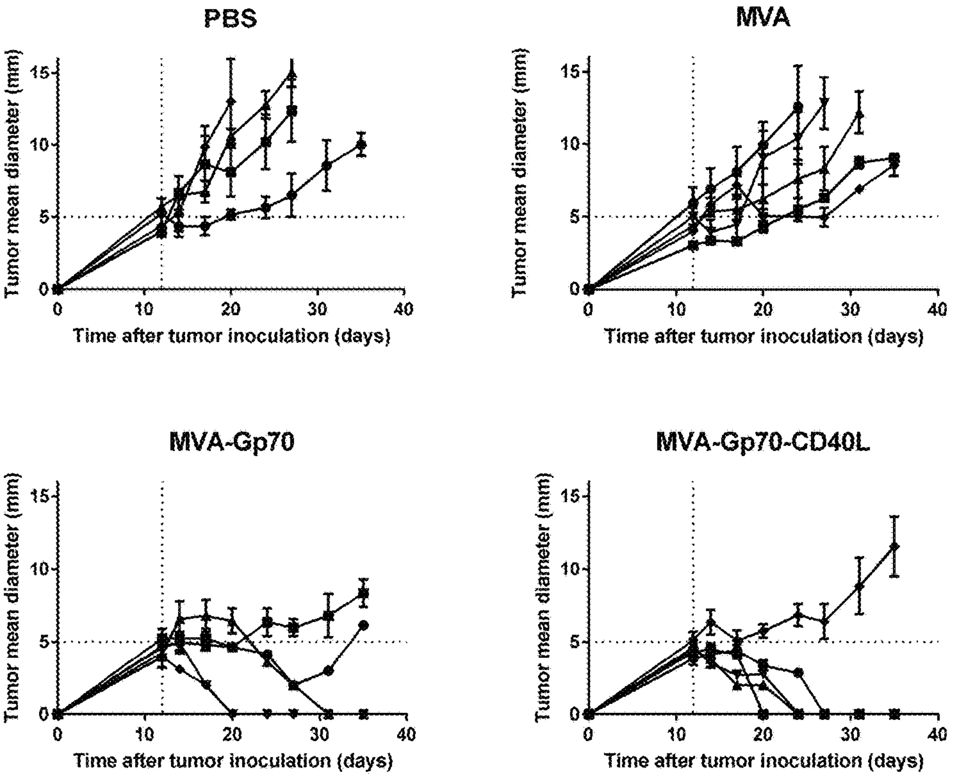
FIGS. 13A, 13B, and 13C show the antitumor effect of intravenous injection of MVA virus encoding the endogenous retroviral antigen Gp70. As described in Example 14, Balb/c mice received 5x$10^5$ CT26.wt cells s.c. (subcutaneously). When tumors measured above 5x5 mm, CT26.wt tumor-bearing mice (n=5/group) were grouped and received i.v. (intravenous) PBS or 5x$10^7$ TCID50 of MVA, rMVA-Gp70, or rMVA-Gp70-CD40L at day 12 after tumor inoculation. Tumor growth was measured at regular intervals. Shown are tumor mean diameter (FIG. 13A) and tumor mean volume (FIG. 13B).
Figure 13B:
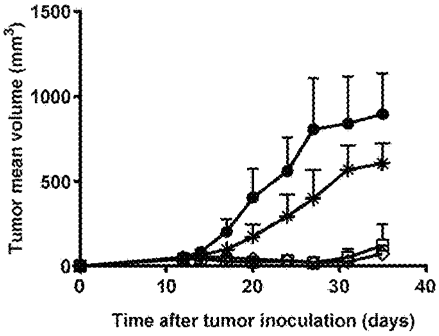
Figure 13C:
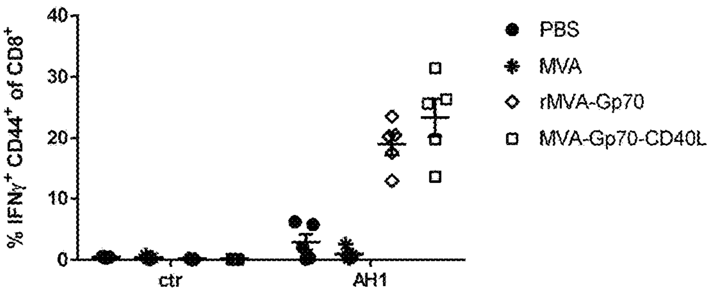

FIG. 13C shows the induction of Gp70 specific CD8 T cells in the blood upon intravenous injection of MVA-Gp70 or MVA-Gp70-CD40L.

Thus, in these experiments, an MVA was constructed encoding a model ERV that is the murine protein gp70 (envelope protein of the murine leukemia virus) ("MVA-gp70"). An MVA further comprising the costimulatory molecule CD40L was also generated ("MVA-gp70-CD40L"). The anti-tumor potential of these new constructs was tested using the CT26.wt colon carcinoma model. CT26.wt cells have been shown to express high levels of gp70 (see, e.g., Scrimieri (2013) *Oncoimmunol* 2: e26889). CT26.wt tumor bearing mice were generated and, when tumors were at least 5 mm×5 mm, were immunized intravenously as indicated above. Immunization with MVA alone induced a mild delay in tumor growth. In contrast, immunization with MVA-gp70 caused the complete rejection of 3/5 tumors (FIGS. 13A and 13B). Even more striking results were obtained with immunization with MVA-Gp70-CD40L, which caused the rejection of 4/5 tumors (FIGS. 13A and 13B).

To determine whether these anti-tumor responses correlated with the induction of gp70-specific T cells following immunization, a blood re-stimulation was performed using the H-2Kd-restricted gp70 epitope AH1. These results (FIG. 13C) show a strong induction of gp70-specific CD8 T cell responses in MVA-Gp70 and MVA-Gp70-CD40L treated mice (FIG. 13 C).

Example 15: Increased Antitumor Effect of Intravenous Injection of MVA Encoding the Endogenous Retroviral Antigen Gp70 Encoded with CD40L in the B16.F10 Tumor Model B16.F10 tumor-bearing C57BL/6 mice (n=5/group) were grouped and received intravenous (i.v.) PBS or $5\times10^7$ TCID50 of MVA-BN, MVA-Gp70, or MVA-Gp70-CD40L at day 7 (black dotted line) after tumor inoculation when tumors measured approximately 5×5 mm. Tumor growth was measured at regular intervals. Shown in FIG. 14A, intravenous administration of MVA virus encoding the endogenous retroviral antigen Gp70 and the CD40L resulted in a reduction in tumor volume as compared to MVA or the control (PBS).

Figure 14A:
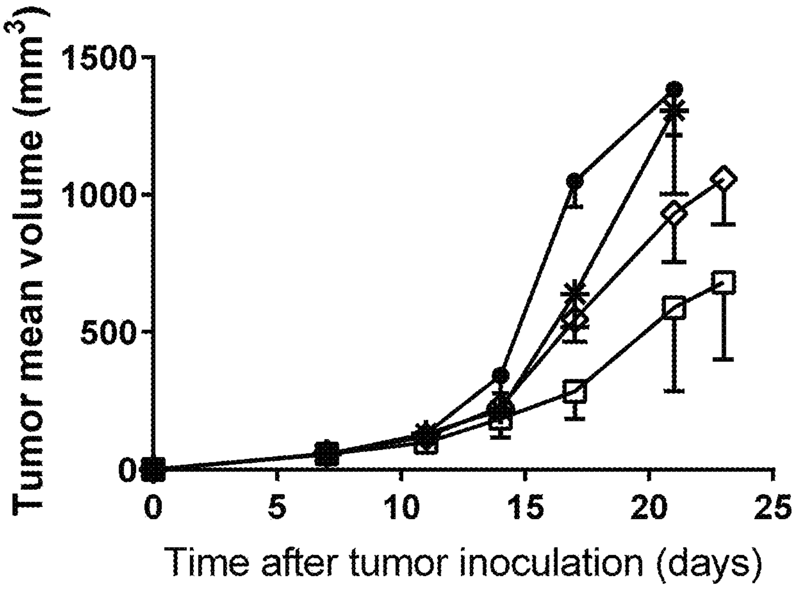
FIGS. 14A and 14B show the antitumor effect of intravenous injection of MVA virus encoding the endogenous retroviral antigen Gp70 plus CD40L. As described in Example 15, C57BL/6 mice received 5x$10^5$ B16.F10 cells s.c. (subcutaneously). Seven days later when tumors measured above 5x5 mm, B16.F10 tumor-bearing C57BL/6 mice (n=5/group) were grouped and received i.v. (intravenous) PBS or 5x$10^7$ TCID50 MVA, rMVA-Gp70, or rMVA-Gp70-CD40L. Tumor growth was measured at regular intervals. Shown are tumor mean volume (FIG. 14A) and percentage of CD8+CD44+IFN-γ+ cells in blood upon stimulation with p15e peptide 7 days after immunization (FIG. 14B).
Figure 14B:
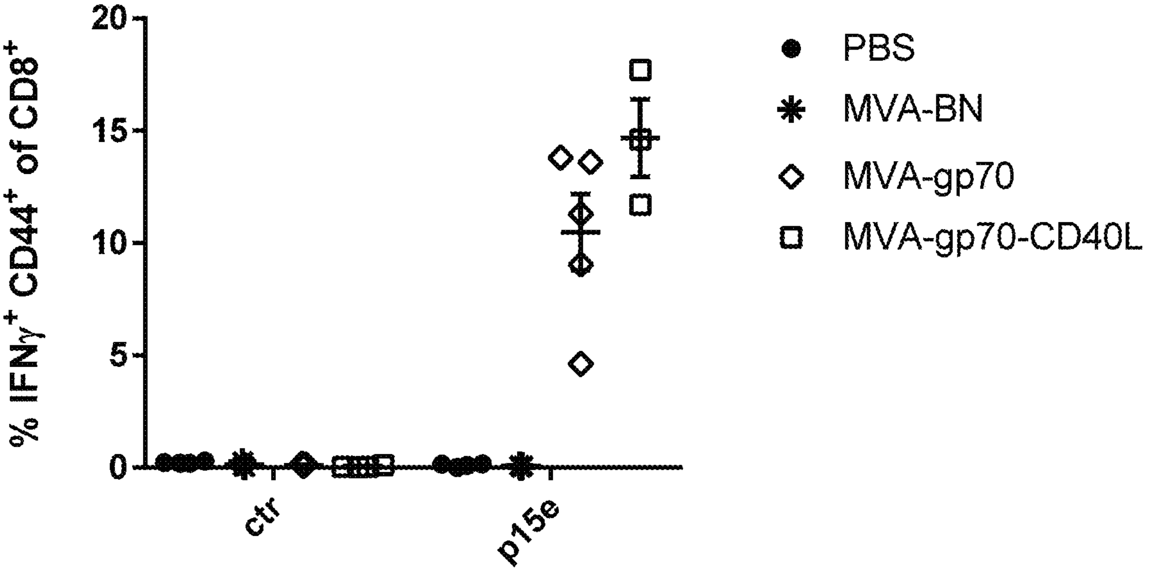

FIG. 14B shows the induction of Gp70 specific CD8 T cells in the blood upon intravenous injection of MVA-Gp70 or MVA-Gp70-CD40L.

Thus, in these experiments, the efficacy of treatment with MVA-Gp70 and MVA-Gp70-CD40L were demonstrated in an additional independent tumor model. B16.F10 is a melanoma cell line derived from C57BL/6 and expresses high levels of Gp70 (Scrimieri (2013) *Oncoimmunol* 2: e26889). Treatment with MVA alone ("MVA-BN") led to some tumor growth delay of B16.F10 tumors, comparable to the effect of non-adjuvanted MVA-Gp70 (FIG. 14A). However, MVA-Gp70-CD40L resulted in a stronger anti-tumor effect than the MVA backbone control alone (FIG. 14A). Additional experiments demonstrated that both groups receiving Gp70-antigen-encoding MVAs exhibited CD8 T cell responses specific for the H-2Kb-restricted gp70 epitope p15e, but no dramatic increase in peripheral T cell responses was observed when CD40L was also encoded by the MVA (FIG. 14B).

Example 16: Increased Antitumor Effect of Intravenous Injection of MVA Virus Encoding Gp70 and 4-1BBL [Prophetic Example]

B16.OVA tumor-bearing C57BL/6 mice (n=5/group) are grouped and receive intravenously PBS or $5\times10^7$ TCID50 MVA-OVA or MVA-gp70-4-1BBL at day 7 (black dotted line) after tumor inoculation. Tumor growth is measured at regular intervals. Because the mouse homologs of human endogenous retroviral (ERV) proteins are neither highly expressed in normal mouse tissues nor predominantly expressed in mouse tumor tissues, the efficacy of human ERVs cannot be studied effectively in a mouse model. Gp70 is a mouse ERV protein that has been well studied (see, e.g., Bronte et al. (2003) *J Immunol.* 171 (12): 6396-6405; Bashratyan et al. (2017) *Eur. J. Immunol.* 47: 575-584; and Nilsson et al. (1999) *Virus Genes* 18: 115-120). Accordingly, the study of a gp70-specific cancer vaccine in mice is very likely to have strong predictive value regarding the efficacy of an ERV-specific cancer vaccine in humans.

Example 17: Enhanced Antitumor Effect of Intratumoral Injection of MVA Virus Encoding Gp70 and Either 4-1BBL or CD40L [Prophetic Example]

B16.OVA tumor-bearing C57BL/6 mice (n=4-5/group) are grouped and receive intratumoral (i.t.) PBS or $5\times10^7$ TCID50 of MVA-OVA, MVA-OVA-CD40L, or MVA-OVA-4-1BBL at days 7 (black dotted line), 12 and 15 (grey dashed lines) after tumor inoculation. Tumor growth was measured at regular intervals.

Example 18: Administration with rMVA-HERV-K-4-1BBL Influences Cytokine Production by Direct Antigen Presentation of Infected Tumor Cells [Prophetic Example]

Dendritic cells (DCs) are generated after culturing bone marrow cells from C57BL/6 mice in the presence of recombinant Flt3L for 14 days. B16.F10 cells are infected with MVA-HERV-K, MVA-HERV—K-CD40L, MVA-HERV-K-4-1BBL, or MVA-HERV-K-4-1BBL-CD40L at a MOI 10 and left overnight. The next day, infected tumor cells are harvested and cocultured when indicated in the presence of DCs at a 1:1 ratio for 4 hours at 37° C. 5% CO2. HERV-K specific CD8+ T cells are magnetically purified from HERV-K immunized mice, and added to the coculture at a ratio of 1:5. Cells are cultured at 37° C. 5% CO2 for 48 hours. Then, culture supernatant is collected for cytokine concentration analysis by Luminex. Cytokine levels measure include (A) IL-6, (B) GM-CSF, (C) IL-2, and (D) IFNγ. Data are represented as Mean±SEM.

Example 19: Administration with rMVA-HERV-K-4-1BBL Directs Antigen-Specific CD8+ T Cells Towards Activated Effector T Cells by Direct Antigen Presentation of Infected Tumor Cells [Prophetic Example]

Dendritic cells (DCs) are generated after culturing bone marrow cells from C57BL/6 mice in the presence of recombinant Flt3L for 14 days. B16.F10 cells are infected with MVA-HERV-K, MVA-HERV—K-CD40L, MVA-HERV-K-4-1BBL, or MVA-HERV-K-4-1BBL-CD40L at a MOI 10 and left overnight. The next day, infected tumor cells are harvested and cocultured when indicated in the presence of DCs at a 1:1 ratio for 4 hours at 37° C. 5% CO2. Meanwhile, HERV-K specific CD8+ T cells are magnetically purified from HERV-K immunized mice, and added to the coculture at a ratio of 1:5. Cells are cultured at 37° C. 5% CO2 for 48 hours. Cells are then stained and analyzed by flow cytometry. Cytokine analysis is done for (A) GMFI of T-bet on OT-I CD8+ T cells and (B) percentage of CD44+Granzyme B+IFNγ+ TNFα+ of OT-I CD8+ T cells. Data are shown as Mean±SEM.

Example 20: Infection with rMVA-HERV-K Encoded Either with CD40L or 4-1BBL Induce Tumor Cell Death in Tumor Cell Lines and Macrophages [Prophetic Example]

Tumor cell lines B16.OVA (A and B), MC38 (C) and B16.F10 (D) are infected at the indicated MOI for 20 hours. Then, cells are analyzed for their viability by flow cytometry. Serum HMGB1 in the samples from (A) is quantified by ELISA. Bone marrow derived macrophages (BMDMs) are infected at the indicated MOI for 20 hours. Cells are then analyzed for their viability by flow cytometry. Data are presented as Mean±SEM.

Example 21: Intratumoral Administration of Recombinant MVA Encoding 4-1BBL Results a Decrease in Treg Cells and a Decrease in Tcell Exhaustion in the Tumor [Prophetic Example]

B16.OVA tumor-bearing C57BL/6 mice (n=5/group) are grouped and receive intratumoral (i.t.) PBS or $5\times10^7$ TCID50 of MVA-OVA or MVA-OVA-4-1BBL at days 7 (black dotted line) after tumor inoculation. Five days later, mice are sacrificed, spleens and tumors harvested and stained to assess Treg infiltration and T cell exhaustion with fluorochrome conjugated antibodies. (A) Percentage of CD4+FoxP3+ T cells among CD45+ tumor-infiltrating leukocytes; Geometric Mean Fluorescence Intensity of PD-1 (B) and Lag-3 (C) on tumor infiltrating CD8 T cells. Data are presented as Mean±SEM.

Example 22: Immune Checkpoint Blockade and Tumor Antigen Specific Antibodies Synergize with Intratumoral Administration of rMVA Gp-70-4-1BBL [Prophetic Example]

B16.OVA tumor-bearing C57BL/6 mice (n=5/group) are grouped and receive when indicated (ticks) 200 μg IgG2a, anti TRP-1 or anti PD-1. Mice are immunized intratumorally either with PBS or with $5\times10^7$ TCID50 MVA-gp70-4-1BBL at days 13 (black dotted line), 18 and 21 (grey dashed lines) after tumor inoculation. Tumor growth is measured at regular intervals.

Example 23: Cytokine/Chemokine MVA-BN Backbone Responses to IT Immunization can be Increased by 4-1BBL Adjuvantation To assess the potential of recombinant MVAs to induce inflammation within the Tumor MicroEnvironment (TME), cytokines and chemokines were analyzed in tissue from B16.OVA tumors. First, $5\times10^5$ B16.OVA cells were subcutaneously (s.c.) implanted into C57BL/6 mice. On day 10, mice were immunized intratumorally (i.t.) with PBS or $2\times10^8$ $TCID_{50}$ MVA-BN, MVA-OVA, or MVA-OVA-4-1BBL (n=5 to 6 mice/group).

Figure 15:
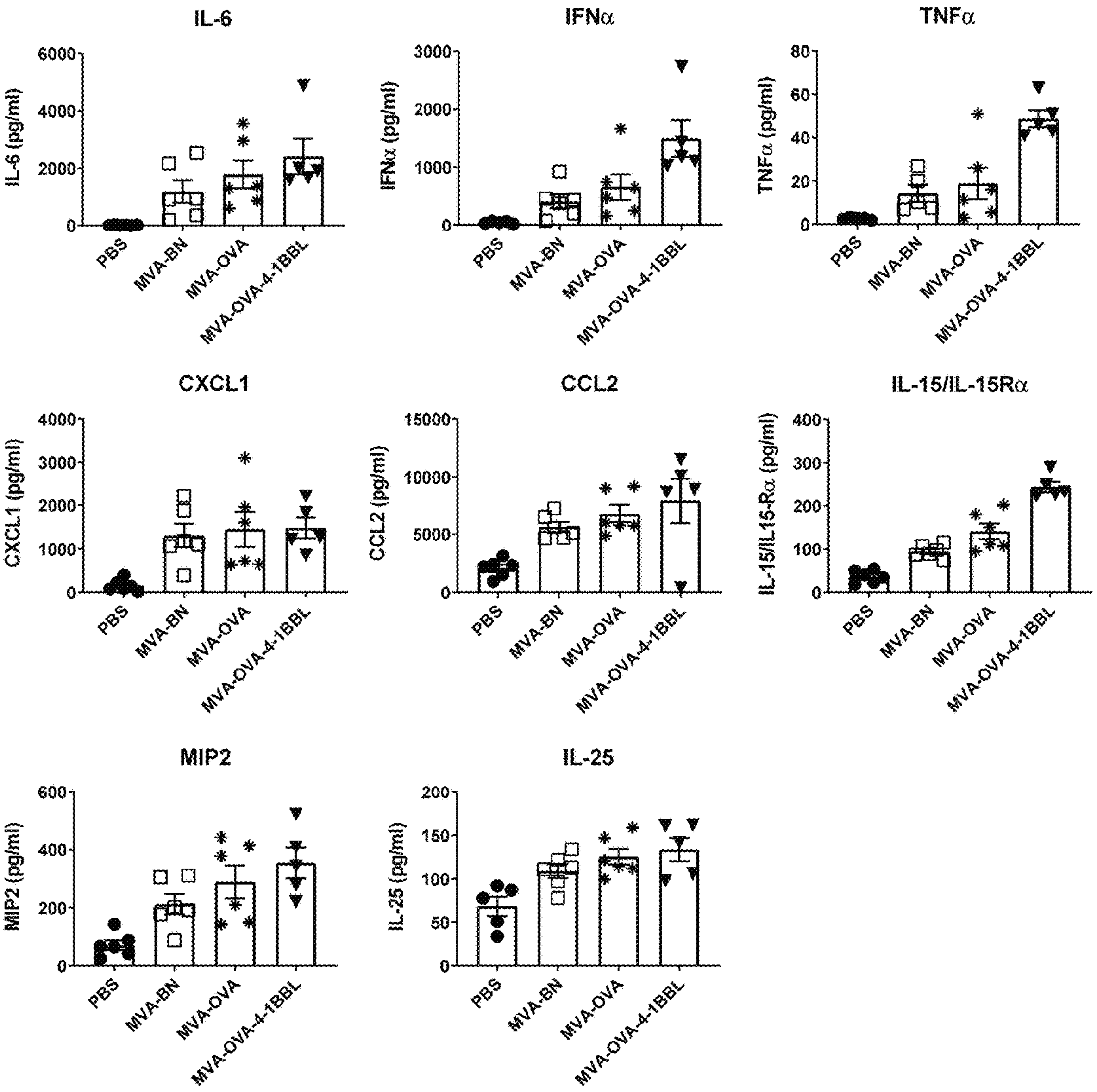
FIG. 15: Cytokine/chemokine MVA-BN backbone responses to IT immunization can be increased by 4-1BBL adjuvantation. By "adjuvantation" herein is intended that a particular encoded protein or component of a recombinant MVA increases the immune response produced by the other encoded protein(s) or component(s) of the recombinant MVA. Here, 5x$10^5$ B16.OVA cells were subcutaneously (s.c.) implanted into C57BL/6 mice (see Example 23). Mice were immunized on day 10 intratumorally (i.t.) with PBS or 2x$10^8$ TCID50 MVA-BN, MVA-OVA, or MVA-OVA-4-1BBL (n=6 mice/group). 6 hours later, tumors were extracted and tumor lysates processed. Cytokine/chemokine profiles were analysed by Luminex.

Six hours after injection, cytokine and chemokine expression was measured (FIG. 15). Cytokine/chemokine expression in tissue treated with PBS represents the basal inflammatory profile induced by insertion of the needle into the tumor and saline shear pressure. Cytokines including IL-6, IFN-α, IL-15, and TNF-α, as well as chemokines such as CXCL1, CCL2, and MIP2 were upregulated (FIG. 15). IL-25 (also known as IL-17E), which is induced by NF-κβ activation and stimulates the production of IL-8 in humans, was also detected (Lee et al. (2001) *J. Biol. Chem.* 276: 1660-64). Interestingly, tumors injected with MVA-OVA-4-1BBL exhibited a significant increase in pro-inflammatory cytokines such as IL-6, IFN-α, or IL-15/IL15Rα compared to tumors injected with MVA-BN or MVA-OVA injected tumor lesions.

Figure 16:
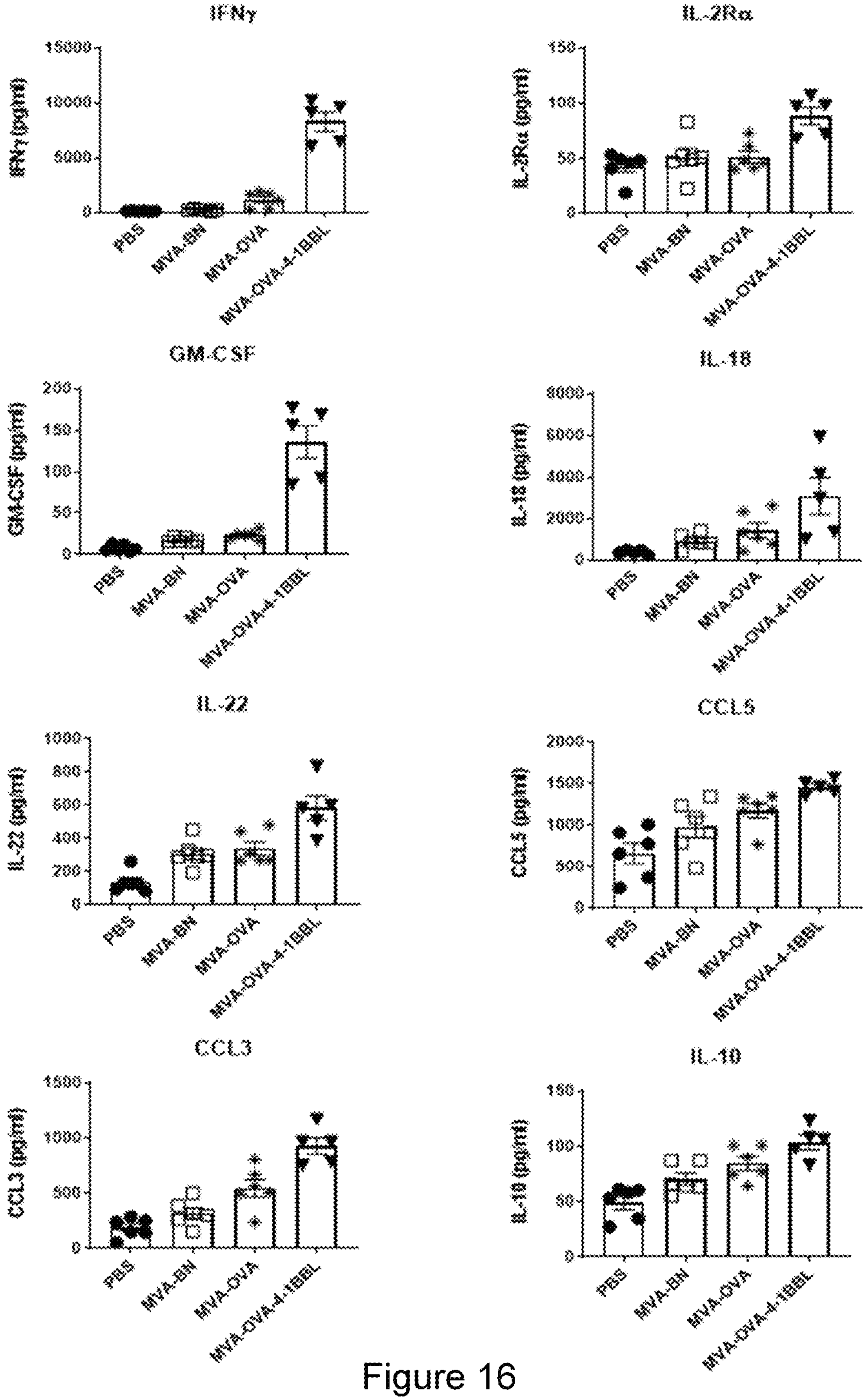
FIG. 16: Cytokine/chemokine pro-inflammatory responses to intratumoral (i.t.) immunization are increased by MVA-OVA-4-1BBL. 5x$10^5$ B16.OVA cells were subcutaneously (s.c.) implanted into C57BL/6 mice (see Examples 23 and 24). Mice were immunized on day 10 intratumorally (i.t.) with PBS or 2x$10^8$ TCID50 of MVA-BN, MVA-OVA, or MVA-OVA-4-1BBL (n=6 mice/group). 6 hours later, tumors were extracted and tumor lysates processed. Cytokine/chemokine profiles were analysed by Luminex.

Example 24: Cytokine/Chemokine Pro-Inflammatory Responses to Intratumoral (i.t.) Immunization are Increased by MVA-OVA-4-1BBL Mice and tumors were treated as described in Example 23. Strikingly, several pro-inflammatory cytokines, including IFN-γ and GM-CSF, were only produced following intratumoral immunization with MVA-OVA-4-1BBL (FIG. 16). Production of other pro-inflammatory cytokines including IL-18, CCL5, CCL3, and IL-22 was enhanced by intratumoral (i.t.) immunization with either MVA-OVA or MVA-OVA-4-1BBL, but not MVA-BN or PBS alone.

Altogether, this data demonstrates that intratumoral (i.t.) MVA immunization can induce an inflammatory cytokine/chemokine shift in the tumor microenvironment (TME), thereby enhancing the inflammatory response. Increased effects were observed for intratumoral immunization with MVA-OVA-4-1BBL compared to MVA or MVA-OVA. In this manner, the addition of 4-1BBL can be said to have "adjuvanted" the recombinant MVA.

Example 25: Quantitative and Qualitative T-Cell Analysis of the TME and Draining LN after Intratumoral Injection of MVA-OVA-4-1BBL To better understand the cellular processes induced by inflammation following intratumoral (i.t.) injection of MVA-OVA and MVA-OVA-4-1BBL, an in-depth analysis of innate and adaptive immune infiltrates at different time points after intratumoral (i.t.) injection was performed. B16.OVA tumor-bearing mice were injected intratumorally (i.t.) with either PBS or $2\times10^8$ $TCID_{50}$ MVA-OVA or MVA-OVA-4-1BBL. Mice were sacrificed 1, 3, and 7 days after prime immunization. Tumors and tumor-draining lymph nodes (TdLN) were removed and treated with collagenase and DNase, and single cells were analyzed by flow cytometry. Immune cell populations were analyzed to determine their size, proliferative behavior, and functional state.

Figure 17:
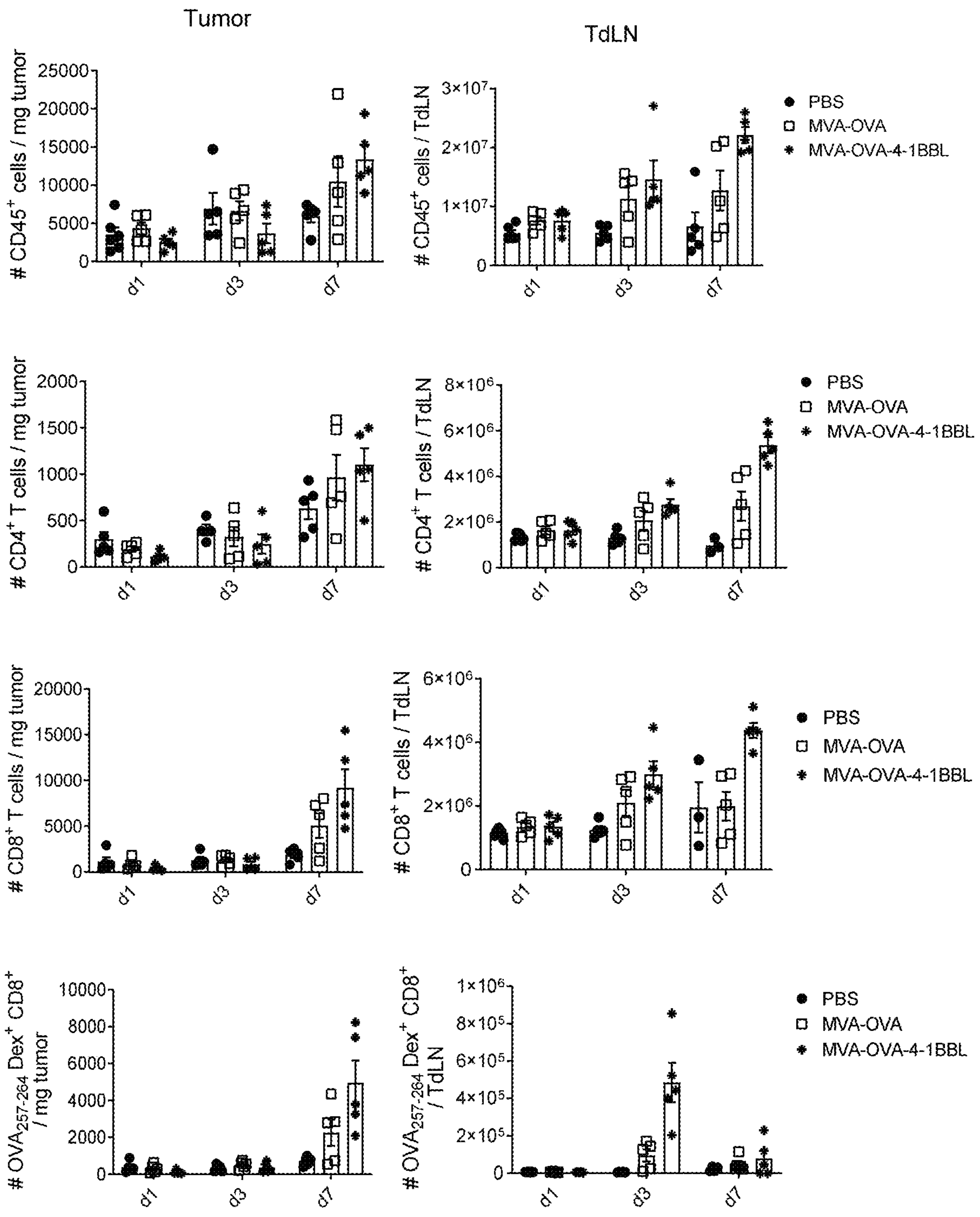
FIG. 17: Quantitative and qualitative T cell analysis of the tumor microenvironment (TME) and Tumor-draining Lymph Node (TdLN) after intratumoral injection of MVA-OVA-4-1BBL. C57BL/6 mice received 5x$10^5$ B16.OVA cells subcutaneously (s.c.). Nine to thirteen days later when tumors measured above 5x5 mm, mice were grouped and intratumorally injected with either PBS, 2x$10^8$ TCID50 MVA-OVA, or MVA-OVA-4-1BBL (see Example 25). One, three and seven days after immunization, mice were sacrificed and tumors as well as tumor draining lymph nodes (TdLN) were digested with Collagenase/DNase and analyzed by flow cytometry. Number of CD45+ cells, CD8+ T cells, CD4+ T cells and OVA-specific CD8+ T cells per mg tumor and per TdLN is shown.

Results showed that injection of B16.OVA tumors either with MVA-OVA or MVA-OVA-4-1BBL induced infiltration of $CD45^+$ leukocytes into the tumor 7 days after intratumoral (i.t.) immunization (FIG. 17, top row, left histogram). Interestingly, an expansion of $CD45^+$ leukocyte numbers in the TdLN was already observed 3 days after the i.t. (intratumoral) immunization (FIG. 17. top row, right histogram), especially following injection of MVA expressing 4-1BBL. This difference was further enlarged in the TdLN seven days after intratumoral (i.t.) immunization, suggesting that MVA immune-mediated antitumor effects start in the TdLN as soon as day 3 after immunization.

One aspect of vaccination-based antitumor therapy is the expansion and reinvigoration of tumor-specific $CD8^+$ and $CD4^+$ T cells and their enrichment in the tumor. Both $CD4^+$ T cells and $CD8^+$ T cells increased in the tumor one week after immunization (FIG. 17, second and third row respectively, left histograms). CD4+ T cells increased in the tumors by day 7 as well as in the TdLN starting at day 3 and peaking at day 7 following i.t. immunization with MVA-OVA-4-1BBL. $CD8^+$ T cells largely contributed to the increase in $CD45^+$ cells in the tumor by day 7. Injection of MVA-OVA-4-1BBL further expanded the $CD8^+$ T cell population as compared to injection of MVA-OVA in both tumor (day 7) and dLN (days 3 and 7).

Quantification of OVA-specific $CD8^+$ T cells revealed an increase within the tumor microenvironment 7 days after intratumoral (i.t.) immunization, particularly in the group treated with MVA-OVA-4-1BBL (FIG. 17, lower left). Strikingly, the expansion of OVA-specific $CD8^+$ T cells in the TdLN peaked on day 3 after immunization, being higher in the MVA-OVA-4-1BBL treated group (FIG. 17, lower right). Altogether, these data indicate that intratumoral immunization with MVA-OVA, especially MVA-OVA-4-1BBL, enhances the generation of adaptive immune responses starting 3 days after treatment in the tumor draining lymph node, resulting in a significant increase of antigen-specific $CD8^+$ T cells in the tumor microenvironment by day 7.

Figure 18A:
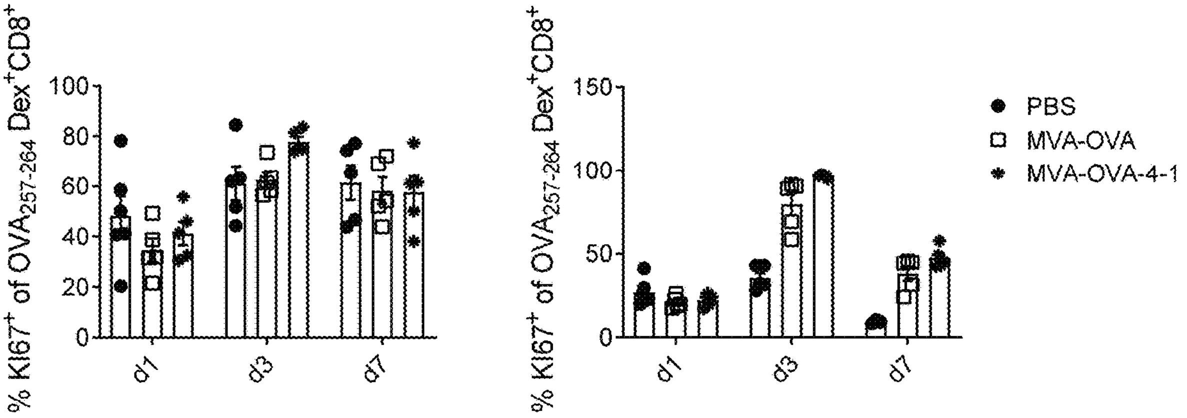
FIGS. 18A, 18B, and 18C: Quantitative and qualitative T cell analysis of the TME and draining LN after intratumoral injection of MVA-OVA-4-1BBL. C57BL/6 mice received 5x$10^5$ B16.OVA cells subcutaneously (s.c.). Nine to thirteen days later when tumors measured above 5.5x5.5 mm, mice were grouped and intratumorally injected with either PBS or 2x$10^8$ TCID50 MVA-OVA or MVA-OVA-4-1BBL (see Example 26). One, three and seven days after immunization, mice were sacrificed and tumors as well as TdLN (tumor draining lymph node) were digested with Collagenase/DNase and analyzed by flow cytometry.
Figure 18B:
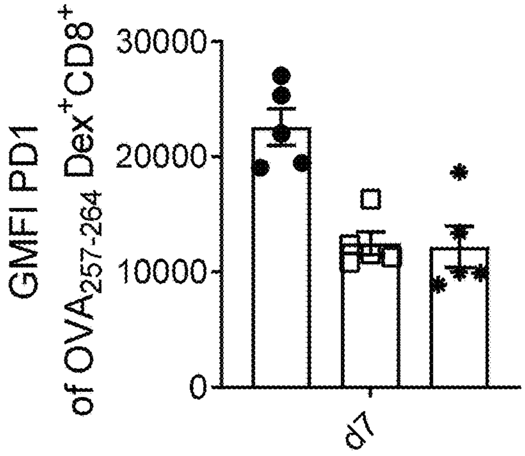

Example 26: Induction of Antigen-Specific CD8+ T Cells by Intratumoral Injection of MVA-OVA-4-1BBL OVA-specific $CD8^+$ T cells in the tumor draining lymph node (TdLN) induced by intratumoral injection of MVA-OVA-4-1BBL exerted a high proliferative capacity. The percentage of OVA-specific $CD8^+$ T cells expressing Ki67 (an indicator of cell proliferation) was higher in the TdLN after MVA-OVA treatment compared to PBS and was further increased in mice immunized with MVA-OVA-4-1BBL (FIG. 18A). Moreover, OVA-specific CD8 T cells in the tumor downregulated the exhaustion marker PD-1 by day 7 after immunization with MVA-OVA as well as MVA-OVA-4-1BBL, suggesting a regain in functionality (FIG. 18B).

Figure 18C:
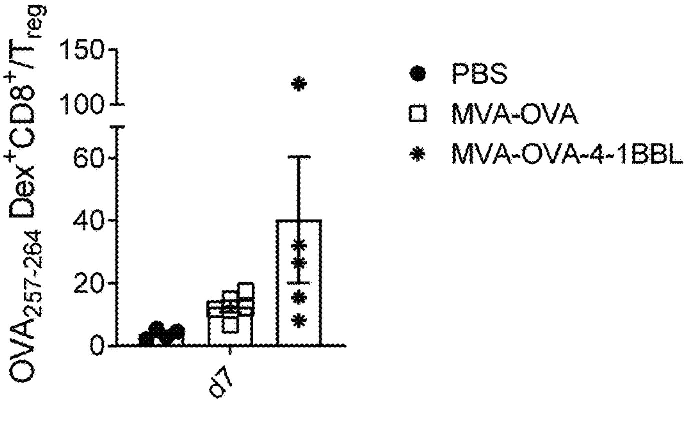

Treg cells (also, "regulatory T cells") are potent inhibitors of anti-tumor immune responses (see, e.g., Tanaka et al. (2017) *Cell Res.* 27: 109-118). Intratumoral injection of MVA-OVA increased the OVA-specific Teff/Treg ratio in the tumor (i.e., the ratio of "Teff" cells, or "effector T cells" to Treg cells), and further increases were seen on day 7 after treatment with MVA-OVA-4-1BBL (FIG. 18C). Thus, intratumoral treatment with MVA-OVA and particularly with MVA-OVA-4-1BBL reduced the frequency of intratumoral Treg in favor of CD8+ T effector cells which is beneficial for anti-tumor immune responses.

Figure 19:
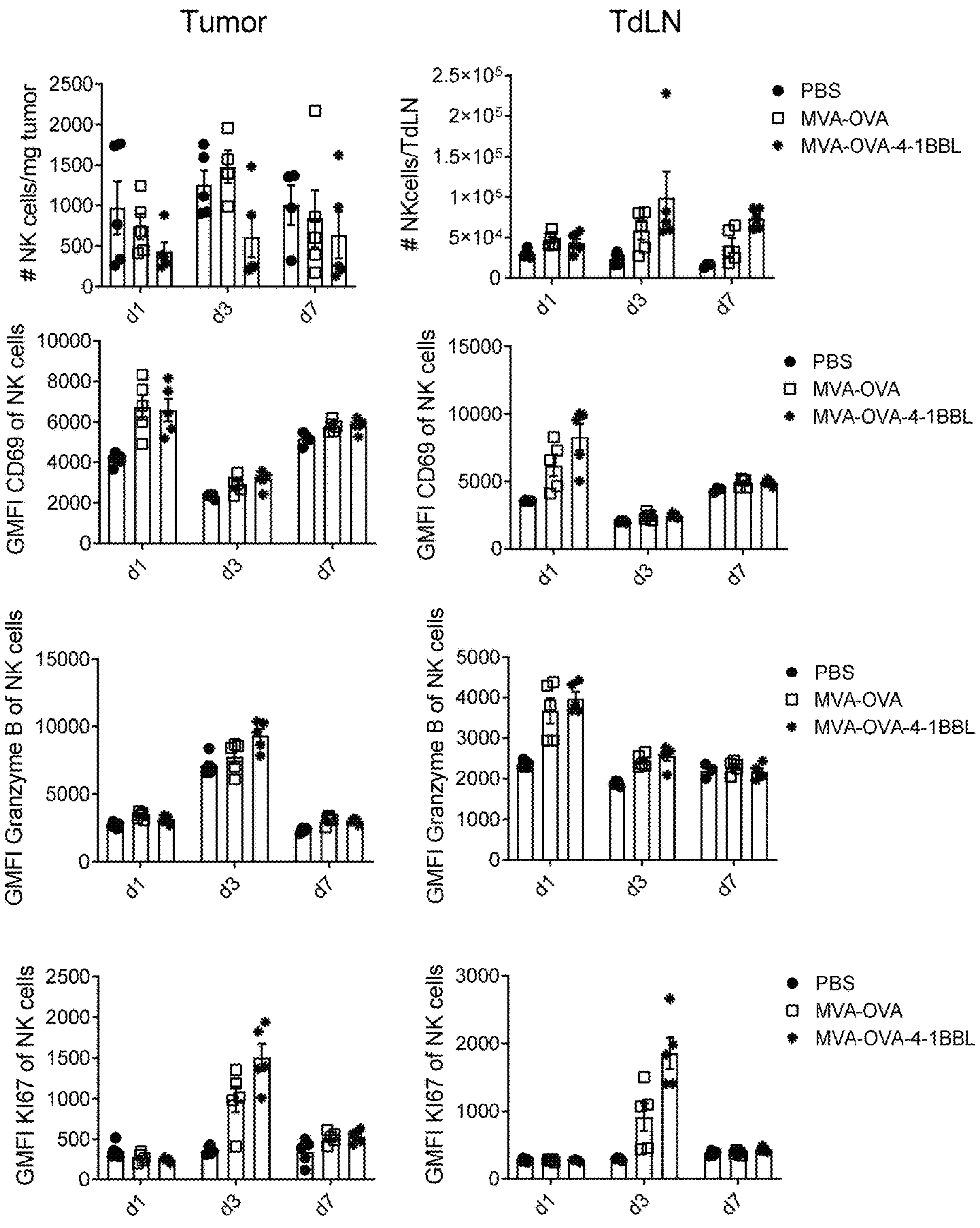
FIG. 19: Quantitative and qualitative NK cell analysis of the TME and tumor-draining lymph node (TdLN) after intratumoral injection of MVA-OVA-4-1BBL. C57BL/6 mice received 5x$10^5$ B16.OVA cells subcutaneously (s.c.). Nine to thirteen days later when tumors measured above 5.5x5.5 mm, mice were grouped and intratumorally injected with either PBS or 2x$10^8$ TCID50 MVA-OVA or MVA-OVA-4-1BBL (see Example 27). Mice were sacrificed one, three and seven days after immunization, and tumors as well as tumor-draining lymph nodes (TdLN) were digested with Collagenase/DNase and analyzed by flow cytometry. Number of NK cells per mg tumor and TdLN and GMFI of CD69, Granzyme B, and Ki67 surface markers of NK cells in tumor and T dLN is shown.

Example 27: Quantitative and Qualitative NK Cell Analysis of the TME and Draining LN after Intratumoral Injection of MVA-OVA-4-1BBL Quantification of NK cells after i.t. immunization with MVA-OVA showed a decrease of NK cells in the tumor on day 1 after intratumoral immunization (FIG. 19, top row, left histogram). These changes were more pronounced when MVA-OVA-4-1BBL was used. Concurrently, NK cells in the tumor draining lymph node (TdLN) were increased at 3 and 7 days after immunization with both MVA-OVA and MVA-OVA-4-1BBL (FIG. 19, top row, right histogram), although MVA-OVA-4-1BBL induced the highest increase of NK cells in the TdLN.

CD69 is a marker of early NK cell activation. Both viral vectors, MVA-OVA and MVA-OVA-4-1BBL, led to the immediate upregulation of the activation marker CD69 in the tumor as well as in the draining lymph node (TdLN; FIG. 19, second row). Furthermore, i.t. immunization resulted in the induction of Granzyme B in NK cells at various timepoints both in tumors and TdLNs, which is indicative of enhanced cytotoxic NK cell function (FIG. 19, third row).

Finally, the proliferative capacity of NK cells by means of Ki67 expression was analyzed. On day 3, Ki67 expression on NK cells was significantly increased in the tumor and the TdLN of mice that were treated intratumorally with either MVA-OVA or MVA-OVA-4-1BBL (FIG. 19, last row).

These results demonstrate that 4-1BBL-adjuvanted MVA-OVA (i.e., MVA-OVA-4-1BBL) further increased the expression of CD69, Granzyme B, and Ki67 surface markers on NK cells following intratumoral injection in comparison to MVA-OVA. These experiments also reveal a significant role of the draining lymph nodes (TdLNs) in mounting anti-tumor T cell and NK cell responses after intratumoral immunotherapy.

While the invention is not bound by any particular mechanism of operation, the expansion of T cells in the TdLN on day 3 and the delayed infiltration of T cells in the tumor on day 7 (see FIG. 17) speaks in favor of a scenario in which tumor-specific T cells are primed and expanded in the TdLN and thereafter migrate to the tumor to kill tumor cells. Intratumoral injection of viral vectors might also lead to NK cell activation directly in the TdLN, thereby inducing further DC activation.

Example 28: Role of CD8 T Cells in Intratumoral MVA Cancer Therapy

Figure 20:
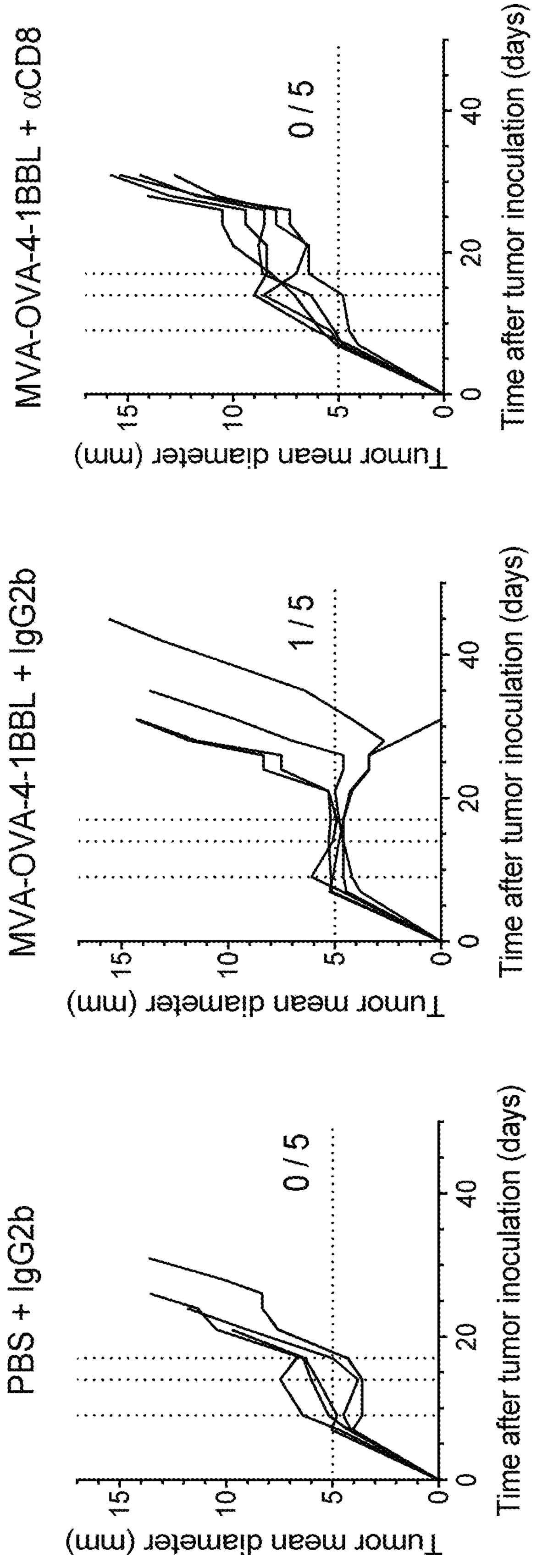
FIG. 20: CD8 T cell-dependency of MVA-OVA-4-1BBL mediated anti-tumor effects. C57BL/6 mice received 5x$10^5$ B16.OVA cells subcutaneously (s.c.). Seven days later, mice were grouped and intratumorally injected with PBS or 2x$10^8$ $TCID_{50}$ MVA-OVA-4-1BBL (see Example 28). On day 5 and day 8 following this first injection, these intratumoral (i.t.) injections were repeated (vertical dashed lines). Additionally, IgG2b isotype control antibody (left and middle panels) or anti-CD8 antibody (2.43; right panel) were injected intraperitoneally (i.p.) on day −1 before and day 1, 4, 7, 11 after the first immunization (100 μg/mouse). Tumor growth was measured at regular intervals, and tumor mean diameter is shown.

The analysis of T cell responses in the tumor and the TdLN (e.g., in FIG. 17) showed an expansion of tumor-specific T cells at both sites after intratumoral (i.t.) treatment. Experiments were conducted to examine the contribution of T cells to MVA-OVA-4-1BBL mediated anti-tumor effects. In these experiments, C57BL/6 mice were injected with B16.OVA melanoma cells ($5\times10^5$ cells) and tumor growth was monitored following one of several treatments. Treatments included intratumoral (i.t.) injection of PBS or MVA-OVA-4-1BBL in the presence or absence of 100 μg CD8-T-cell-depleting antibodies ("αCD8," clone 2.43) or isotype control antibodies. Injection of MVA-OVA-4-1BBL was performed (i.t.) when tumors reached 5 mm in diameter and was repeated twice within a week. One day before the first injection with MVA-OVA-4-BBL, mice were injected i.p. with either anti-CD8 or IgG2b antibodies, and this treatment was repeated four times within the following two weeks. Data presented in FIG. 20 shows that CD8 T cells were essential for effective MVA tumor therapy. Together, these data indicate that MVA-induced activation and expansion of tumor-specific CD8 T cell in the tumor and TdLN are important events for tumor growth control.

Example 29: Batf3+DC-Dependency of MVA-OVA and MVA-OVA-4-1BBL Mediated Anti-Tumor Effects In order to elucidate the underlying cellular and molecular entities that contribute to anti-tumor immune responses induced by MVA-OVA-4-1BBL, we investigated the role of various immune cell players. Dendritic cells (DCs), with their ability to potently sample and present antigens and co-stimulatory signals to cells of the adaptive immune system, are considered a critical factor in antitumor immunity. Various subtypes of DCs have been implicated in the activation of potent immune responses against tumors, including CD8α+ DCs (also known as "cDCl"). This DC subset has the unique ability to cross-present antigens during immune responses, and CD8α+ DCs are the main producers of IL-12 in response to infection (Hochrein et al. (2001) *J. Immunol.* 166: 5448-55; Martinez-López et al. (2014) *Eur. J. Immunol.* 45: 119-29) and cancer (Broz et al. (2014) *Cancer Cell* 26: 638-52). CD8α+ DCs are also potent inducers of antitumor CD8+ T cells by cross-presentation of tumor-associated antigens (Sánchez-Paulete et al., (2015) *Cancer Discovery* 6: 71-79; Salmon et al. (2016) *Immunity* 44: 924-38). CD8α+DC development is crucially dependent on the transcription factor Batf3 (Hildner et al. (2008) *Science* 322: 1097-1100).

Figure 21A:
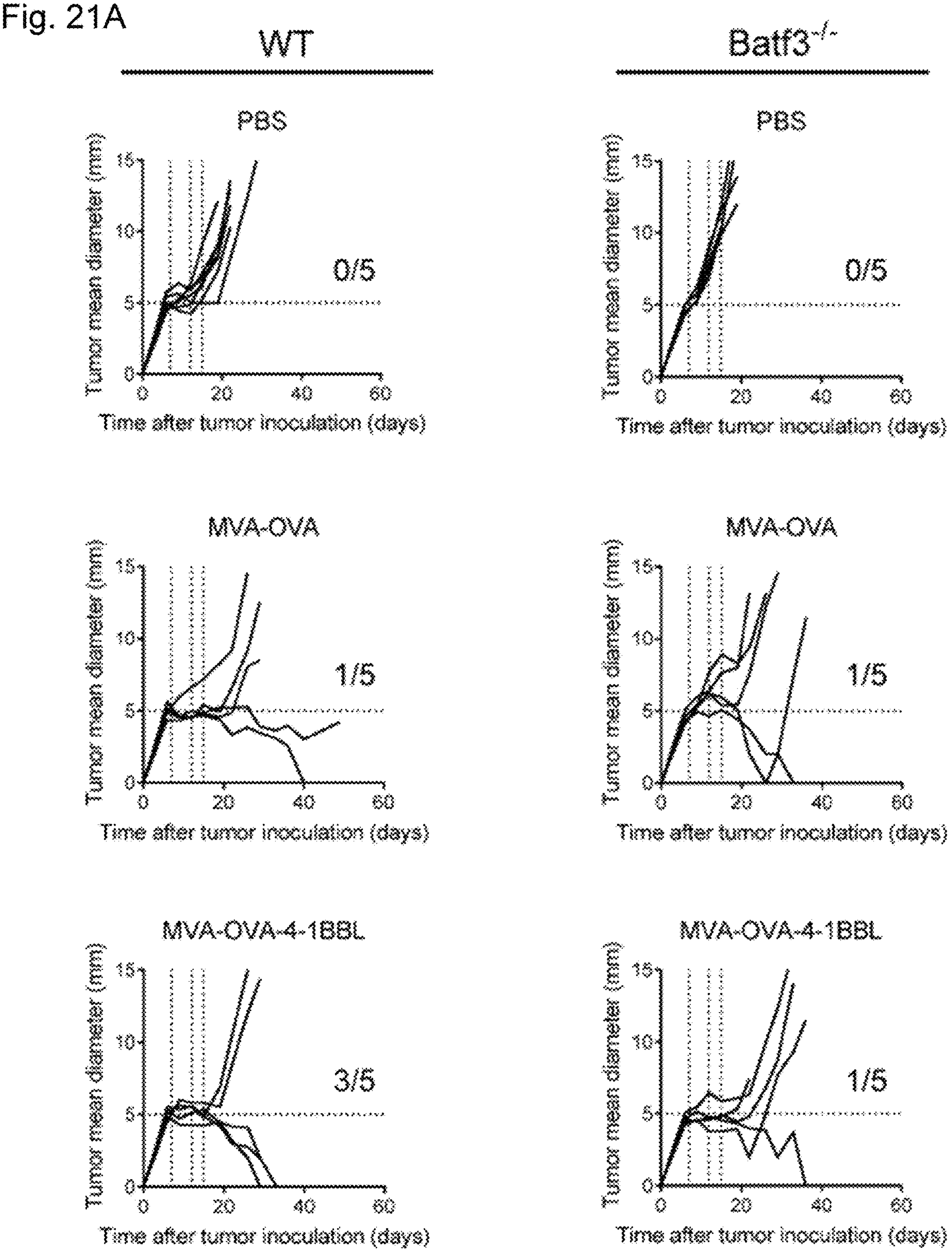
FIGS. 21A and 21B: Batf3+DC-dependency of MVA-OVA and MVA-OVA-4-1BBL mediated anti-tumor effects. C57BL/6 mice or Batf3−/− mice received 5×10$^5$ B16.OVA cells subcutaneously (s.c.). Seven days later (vertical dashed line), mice were grouped and intratumorally injected with PBS or 2×10$^8$ TCID50 of MVA, MVA-OVA, or MVA-OVA-4-1BBL (see Example 29). On day 5 and day 8 following the first intratumoral injection, the i.t. injection was repeated (vertical dashed lines). Tumor growth was measured at regular intervals.

In order to assess the importance of this DC subset for intratumoral MVA cancer therapy, we utilized wildtype and Batf3-deficient (Batf3−/−) B16.OVA tumor-bearing mice. FIG. 21A shows that B16.OVA tumors grew dramatically faster in the absence of cross-presenting DC (Batf3−/−), which indicates an important role of this Antigen Presenting Cell (APC) subset in the induction of tumor-directed immune responses. In line with previous experiments, in wildtype mice, intratumoral injection of MVA-OVA led to tumor growth delay and in one case to the complete clearance of the tumor. This effect was improved when mice were injected with MVA-OVA-4-1BBL; 3 out of 5 mice treated with MVA-OVA-4-1BBL rejected the tumor (FIG. 21A). Intriguingly, in the absence of cross-presenting DC (Batf3−/−), intratumoral MVA immunotherapy was not at all impaired as compared to the WT groups (FIG. 21A). However, Batf3-DC seem to participate in the 4-1BBL induced antitumor responses (FIG. 21A, bottom).

Figure 21B:
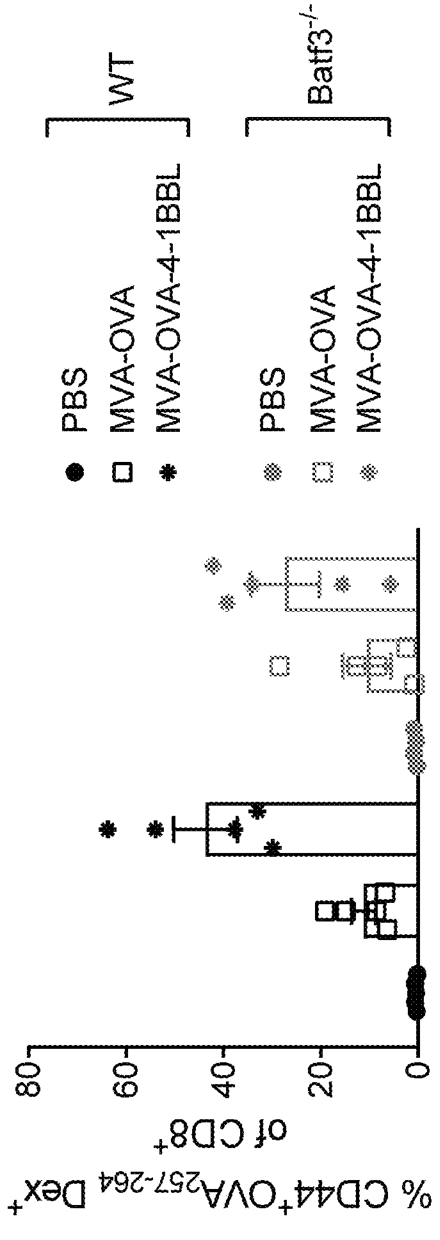

Flow cytometry analysis of $CD8^+$ T lymphocyte populations in peripheral blood 11 days after the first immunization (FIG. 21B) showed that OVA-specific $CD8^+$ T cell frequencies were only mildly diminished in MVA-OVA-4-1BBL immunized $Batf3^{-/-}$ tumor bearers compared to wildtype counterparts. While the invention is not bound by or dependent on any particular mechanism of operation, these data suggest that Batf3-dependent DC play a redundant role for intratumoral cancer therapy with MVA.

Example 30: Role of NK Cells for Intratumoral Administration of MVA-OVA-4-1BBL NK cells are known to express 4-1BB, and ligation of 4-1BB on NK cells has been shown to result in increased proliferation and cytotoxicity of these cells (Muntasell et al. (2017) *Curr. Opin. Immunol.* 45: 73-81). In earlier experiments (see FIG. 19), we found that intratumoral injection of MVA-OVA-4-1BBL strongly upregulated the activation marker CD69 as well as the cytotoxicity marker granzyme B on NK cells concomitant with enhanced proliferation.

Figure 22A:
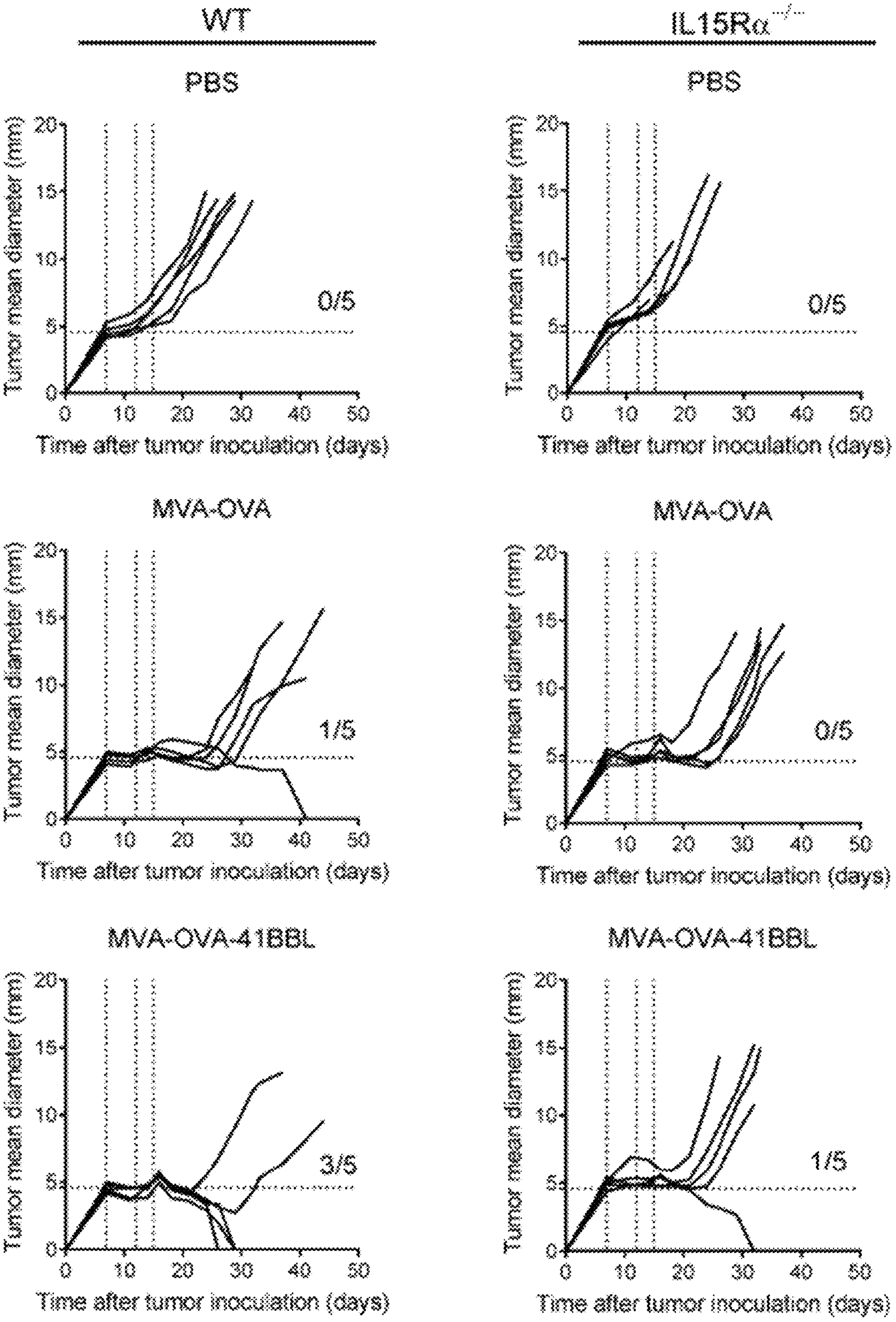
FIGS. 22A, 22B, and 22C: Role of NK cells for intratumoral administration of MVA-OVA-4-1BBL in B16.OVA melanoma bearing mice. C57BL/6 or IL15Rα−/− mice received 5×10$^5$ B16.OVA cells subcutaneously (s.c.). Seven days later, mice were grouped and intratumorally injected with PBS or 2×10$^8$ TCID50 of MVA-OVA or MVA-OVA-4-1BBL (see Example 30). Treatment was repeated on day 5 and 8 after the first injection. Tumor growth was measured at regular intervals. Tumor mean diameter (FIG. 22A) and percent survival is shown (FIG. 22B). 11 days after the first immunization blood was withdrawn and analyzed for the presence of antigen-specific T cells (FIG. 22C). The percentage of $OVA_{257-264}$-dextramer+(SIINFEKL+) CD44+ T cells within CD8+ T cells is shown.
Figure 22B:
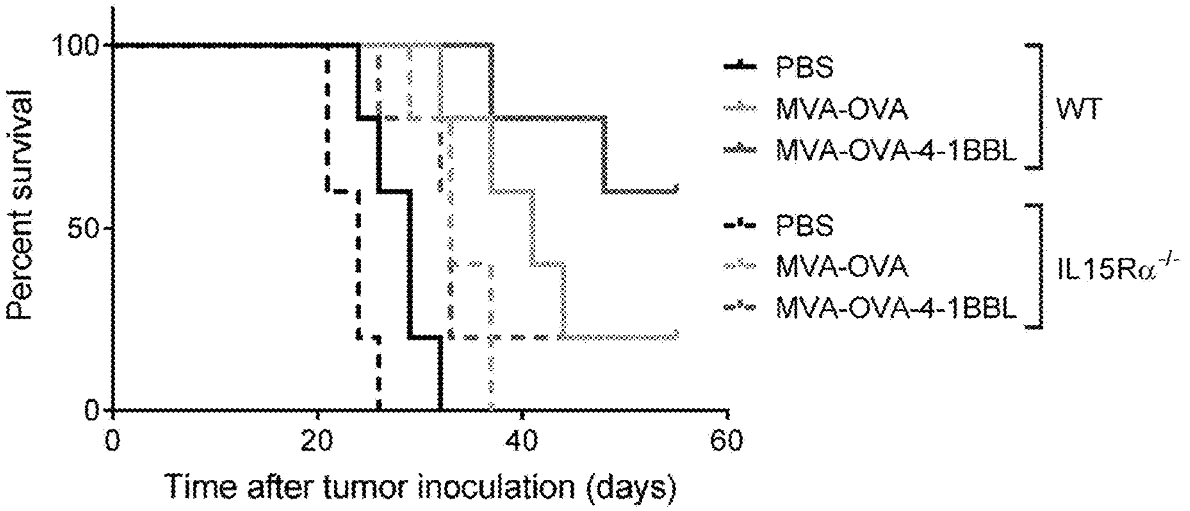

To explore the role of NK cells in the 4-1BBL-induced anti-tumor immune response, we utilized $IL15R\alpha^{-/-}$ mice. The IL-15 receptor alpha subunit (IL-15Rα) mediates high-affinity binding of IL-15, a pleiotropic cytokine shown to be crucial for the development of NK cells (Lodolce et al. (1998) *Immunity* 9: 669-76). Wildtype and IL15Rα-deficient ($IL15R\alpha^{-/-}$) B16.OVA tumor-bearing mice were generated and intratumorally immunized with either MVA-OVA or MVA-OVA 1BBL. Mice treated with MVA-OVA showed a similar therapeutic efficacy irrespective of the presence or absence of IL-15Rα (FIG. 22A). Intriguingly, the benefits that were observed in wildtype mice when using MVA-OVA-4-1BBL (in which 3 of 5 mice rejected the tumor) were completely lost in IL15Rα-deficient tumor bearing mice treated with MVA-OVA-4-1BBL (in which 1 of 5 mice rejected the tumor; see FIG. 22A). These results were also reflected in the survival of the mice following tumor inoculation (FIG. 22B).

Figure 22C:
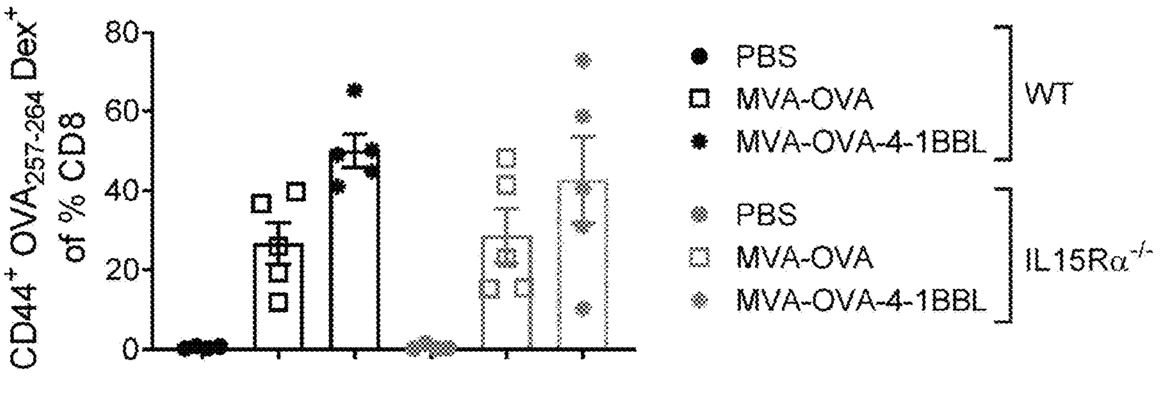

It is known that the absence of IL15Rα not only affects the development of NK cells but also diminishes T cell homeostasis and LN migration, and selectively reduces CD8 memory T cells in mice (Lodolce et al. (1998) *Immunity* 9: 669-76). Therefore, we also investigated T cell responses to these treatments. In line with our previous data, we observed an induction of OVA-specific CD8 T cells upon MVA-OVA intratumoral (i.t.) immunization in wildtype animals which was further increased with MVA-OVA-4-1BBL (FIG. 22C). However, OVA-specific T cell responses in $IL15R\alpha^{-/-}$ mice were similar to the responses found in wildtype mice.

While the invention is not bound by any particular mechanism or mode of operation, these findings indicate that $IL15R\alpha^{-/-}$ tumor bearing mice can mount tumor-specific T cell responses and thus support the notion that 4-1BBL-enhanced NK cell activation and function contributes to the therapeutic efficacy of intratumoral MVA-OVA-4-1BBL treatment.

Example 31: NK Cell-Dependent Cytokine/Chemokine Profile in Response to Intratumoral Immunization with MVA-OVA-4-1BBL To identify cytokines that were selectively induced by 4-1BBL-4-1BB interaction on NK cells, cytokines and chemokines were analyzed in tumor tissue from B16.OVA tumor bearing wildtype or $IL15R\alpha^{-/-}$ mice treated intratumorally with PBS or $5\times10^7$ $TCID_{50}$ MVA-OVA or MVA-OVA-4-1BBL.

Figure 23:
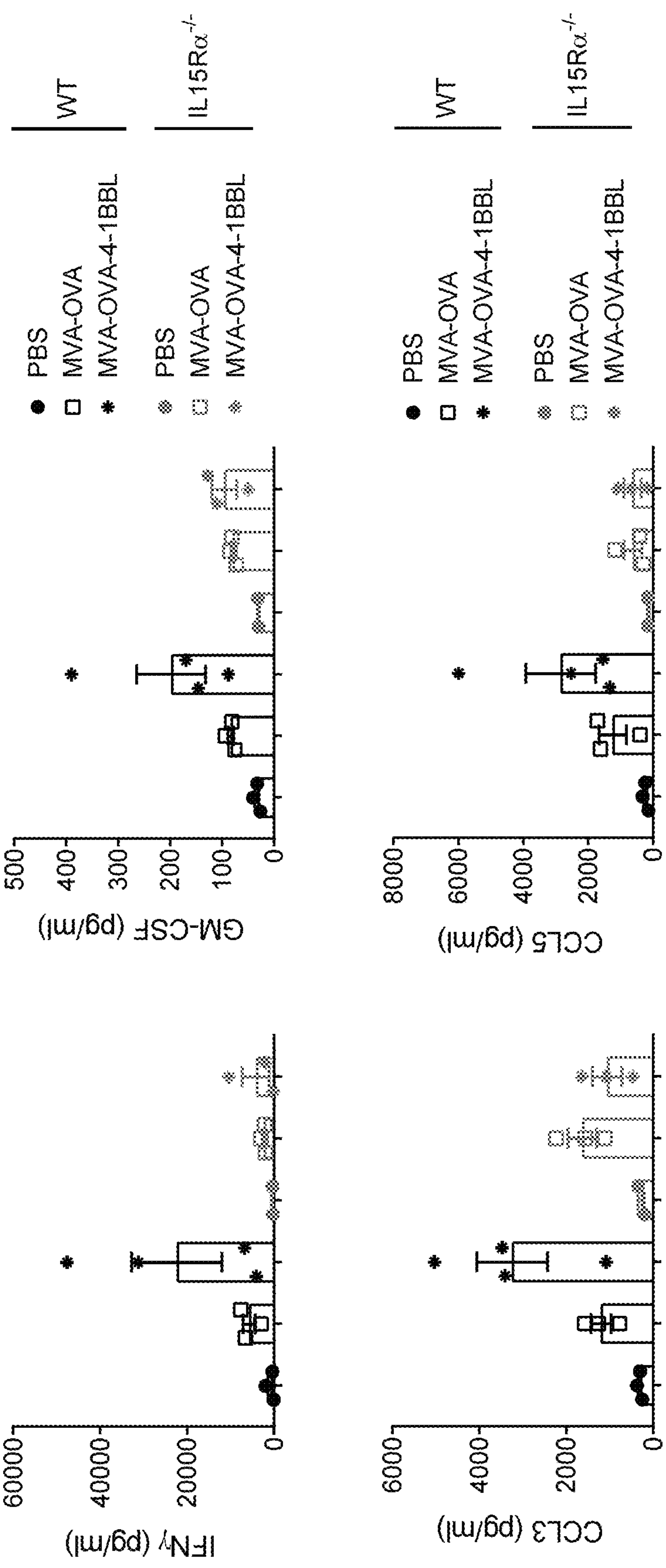
FIG. 23 shows NK cell-dependent cytokine/chemokine profile in response to IT immunization with MVA-OVA-4-1BBL. 5×10$^5$ B16.OVA cells were subcutaneously (s.c.) implanted into C57BL/6 and IL15Rα−/− mice (see Example 31). Mice were immunized intratumorally (i.t.) on day 7 with PBS or 2×10$^8$ TCID50 MVA-OVA or MVA-OVA-4-1BBL (n=2-3 mice/group). 6 hours later, tumors were extracted and tumor lysates processed. Cytokine/chemokine profiles were analysed by Luminex.

Previous experiments showed that a large number of cytokines and chemokines increased six hours after intratumoral injection of recombinant MVA (FIGS. 15 and 16). In these experiments, injection of tumors with MVA-OVA-4-1BBL exhibited a significant increase over injection with MVA-OVA in the production of pro-inflammatory cytokines or chemokines such as IFN-γ, CCL3, and CCL5 known to be produced by NK cells upon stimulation with 4-1BBL (FIG. 23). This 4-1BBL-induced increase was completely abrogated in $IL15R\alpha^{-/-}$ mice, demonstrating that intratumoral injection of rMVA-OVA-4-1BBL induces a distinct cytokine and chemokine profile in the tumor microenvironment 6 h after injection that emanates from NK cells.

Example 32: Anti-Tumor Efficacy of Intratumoral Immunization with MVA-Gp70-CD40L in Comparison to MVA-Gp70-4-1BBL Gp70 is a tumor self-antigen expressed in a number of syngeneic tumor models (B16.F10, CT26, MC38, 4T1, EL4, etc.) all representing distinct tumor microenvironments (TMEs) in terms of stroma and immune cell composition. Here, we tested the potency of MVA encoding the tumor antigen gp70 in addition to either CD40L or 4-1BBL in intratumoral immunization of B16.F10 tumor-bearing mice.

Figure 24A:
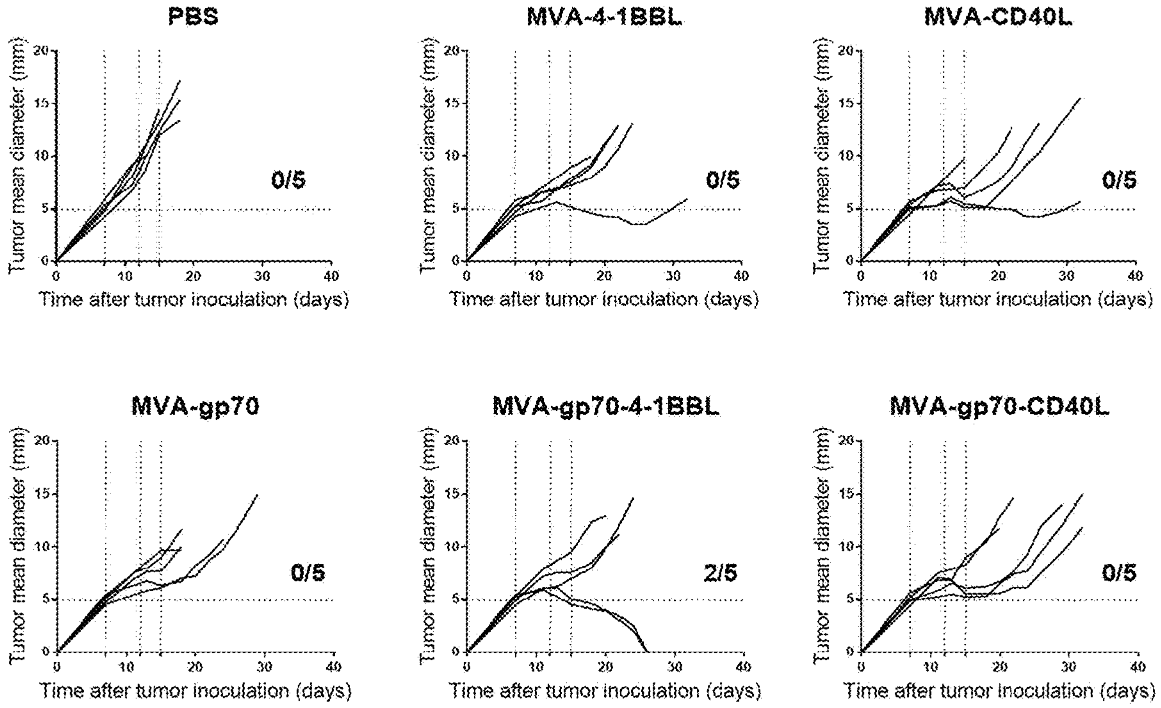
FIGS. 24A, 24B, and 24C show anti-tumor efficacy of intratumoral immunization with MVA-gp70-CD40L in comparison to MVA-gp70-4-1BBL in B16.F10 melanoma bearing mice. C57BL/6 mice received 5×10$^5$ B16.F10 cells subcutaneously (s.c.). Seven days later, mice were grouped and intratumorally injected with PBS or 5×10$^7$ TCID50 of MVA-gp70, MVA-gp70-4-1BBL, MVA-gp70-CD40L, MVA-4-1BBL, or MVA-CD40L (see Example 32). Treatment was repeated on day 5 and 8 after the first injection. Tumor growth was measured at regular intervals.

B16.F10 melanoma cells were subcutaneously injected into C57BL/6 mice. When tumors reached ~50 $mm^3$ in size, mice were immunized intratumorally with PBS, MVA-gp70, MVA-gp70-4-1BBL, MVA-gp70-CD40L, MVA-4-1BBL, or MVA-CD40L; results are shown in FIG. 24A-24C.

Immunization with MVA-gp70 induced transient and mild tumor growth control. This anti-tumor effect could be enhanced when the virus expressed CD40L. However, intratumoral immunization with MVA-gp70-4-1BBL produced the strongest therapeutic effects, resulting in the complete tumor clearance in 2 out of 5 animals treated (FIG. 24A).

Figure 24B:
Figure 24C:
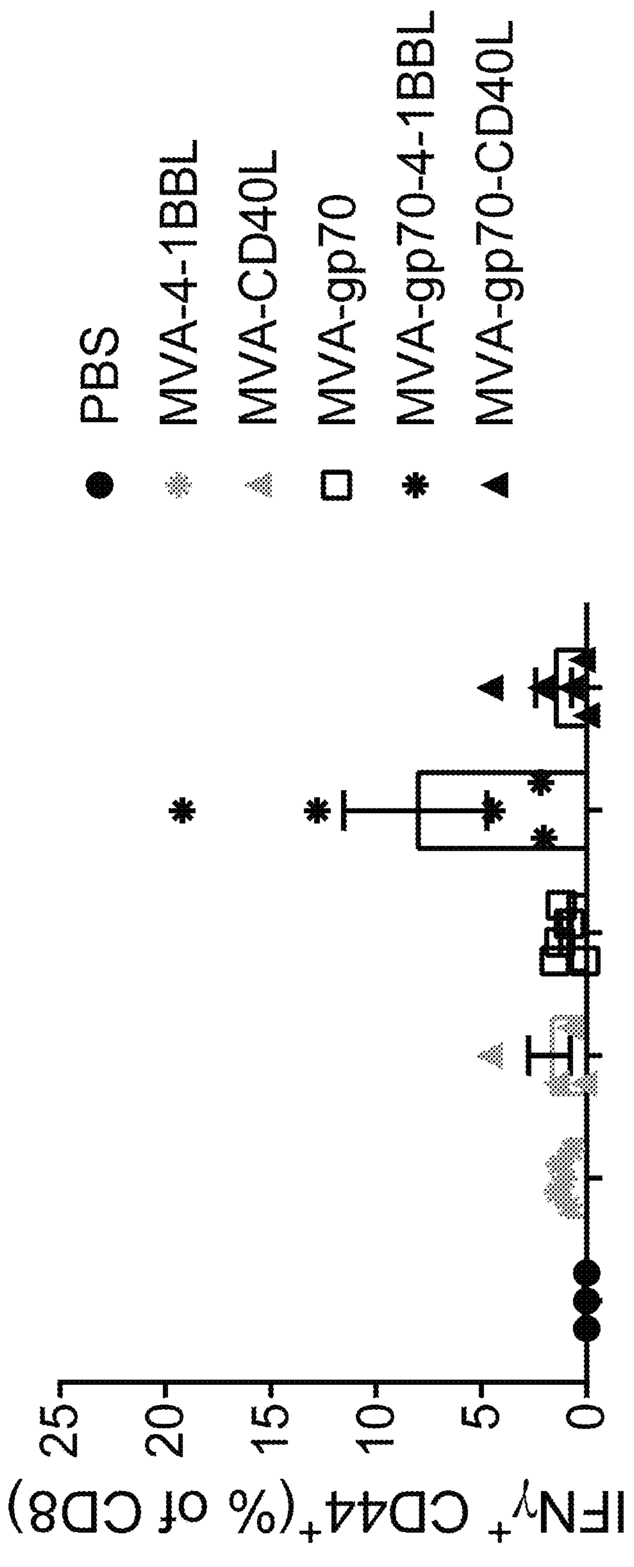

Strikingly, the mice that were cured of tumors after treatment with MVA-gp70-4-1BBL exhibited a loss of pigmentation at the spot where the tumor had been (FIG. 24B). This depigmentation is indicative of the autoimmune condition vitiligo and is a result of melanocyte destruction by self-reactive T cells. This destruction of melanocytes suggests that the activation of the immune system by a recombinant MVA is not restricted to the TAA encoded by the MVA (here, gp70). Rather, this expanded activation of the immune system against other antigens, a phenomenon known as epitope spreading, results in a broader immune response that might provide a better therapeutic outcome.

To assess antigen-specific T cell responses induced by immunization, blood was withdrawn 11 days after the first immunization and analyzed for the presence of antigen-specific T cells. Immunization with both MVA-gp70 and MVA-gp70-CD40L, as well as with MVA-CD40L and MVA-4-1BBL induced a measurable p15E-specific T cell response which ranged between 1-2% (FIG. 24C). Importantly, this response was drastically increased (>5 fold) in mice that received MVA-gp70-4-1BBL. This antigen-specific T cell response to p15E peptide restimulation correlated with the therapeutic efficacy in the different treatment groups.

Example 33: Anti-Tumor Efficacy of Intratumoral Immunization of MVA-Gp70-4-1BBL-CD40L A recombinant MVA was generated expressing the tumor antigen gp70 together with 4-1BBL and CD40L and was tested intratumorally in the B16 melanoma model. B16.F10 melanoma cells were subcutaneously injected into C57BL/6 mice. When tumors reached ~50 $mm^3$, mice were immunized intratumorally with PBS, MVA-gp70, MVA-gp70-4-1BBL, MVA-gp70-CD40L, MVA-gp70-4-1BBL-CD40L, or corresponding MVA constructs not expressing gp70.

Figure 25A:
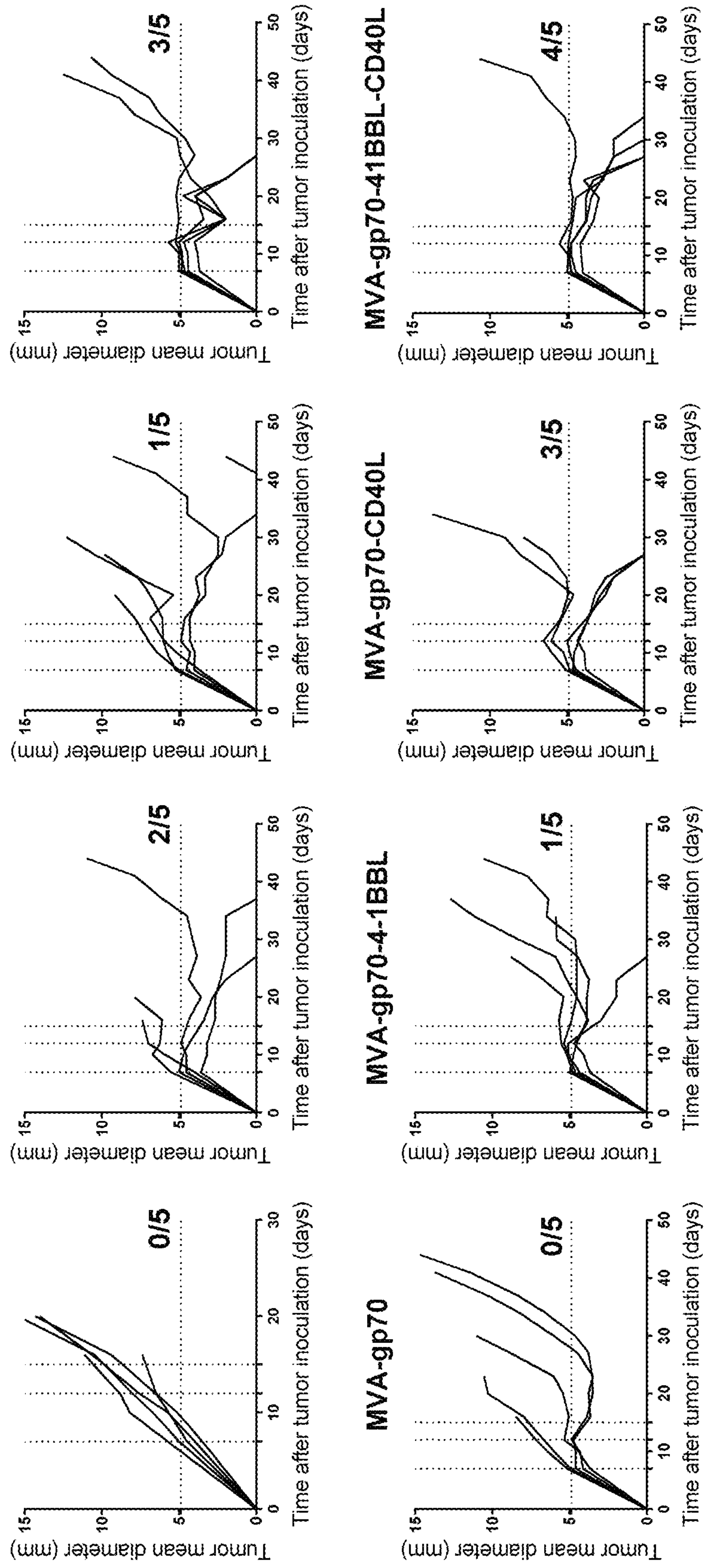
FIGS. 25A and 25B: Anti-tumor efficacy of intratumoral administration of MVA-gp70-4-1BBL-CD40L in B16.F10 melanoma bearing mice. C57BL/6 mice received 5×10$^5$ B16.F10 cells subcutaneously (s.c.). Seven days later, mice were grouped and intratumorally injected with PBS or 5×10$^7$ TCID50 of: MVA-gp70, MVA-gp70-4-1BBL, MVA-gp70-CD40L, MVA-gp70-4-1BBL-CD40L, MVA-4-1BBL, MVA-CD40L, or MVA-4-1BBL-CD40L (see Example 33). Treatment was repeated on day 5 and 8 after the first injection. Tumor growth was measured at regular intervals. Tumor mean diameter is shown in FIG. 25A. Eleven days after the first immunization, blood was withdrawn and restimulated with p15e peptide. The percentage of IFNγ+ CD44+ T cells within CD8+ T cells is shown in FIG. 25B.

Immunization with MVA-gp70 induced transient and significant tumor growth control (FIG. 25A). This anti-tumor effect could be enhanced when the virus expressed CD40L or 4-1BBL. However, intratumoral immunization with MVA-gp70-4-1BBL-CD40L led to the strongest therapeutic effects—complete tumor clearance in 4 out of 5 treated animals (FIG. 25A). Strikingly, three of the four cured mice that were treated with the MVA-gp70-4-1BBL-CD40L showed a loss of pigmentation where the tumor used to be, indicative of the autoimmune condition vitiligo, as discussed above in Example 32.

Figure 25B:
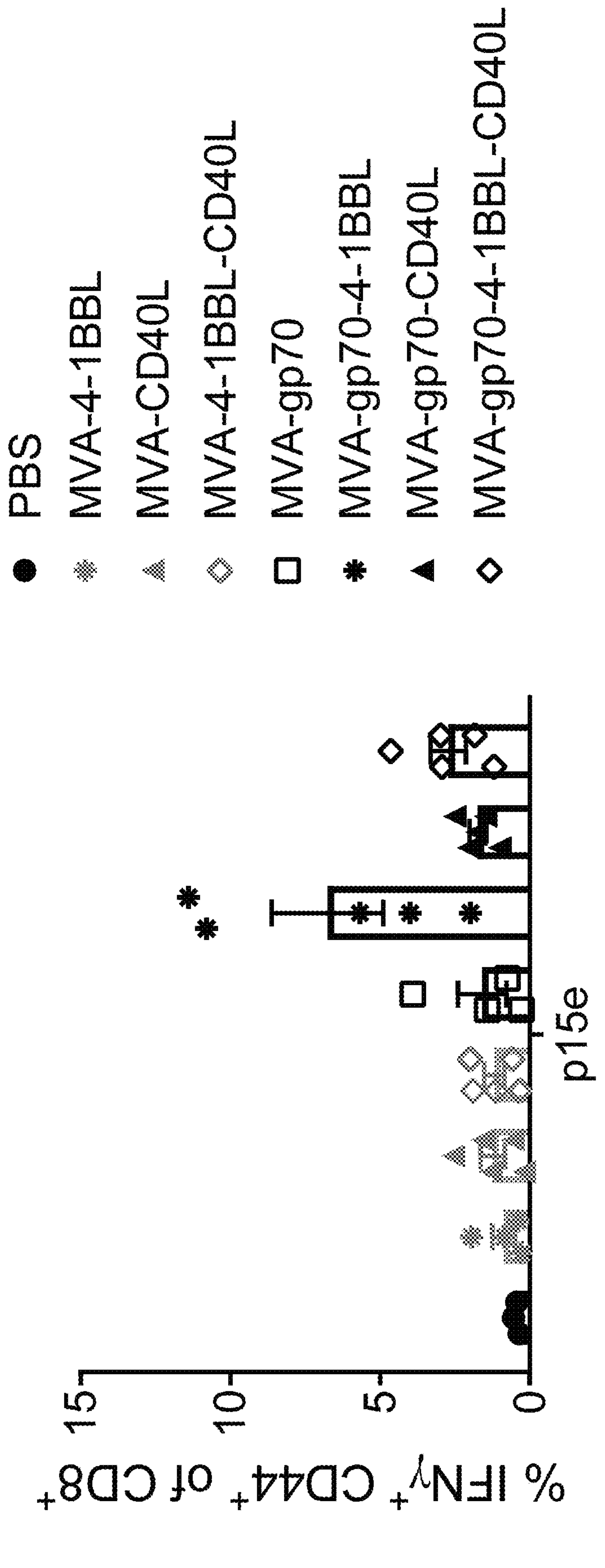

In addition, gp70-specific T cell responses were measured in the blood 11 days after the first immunization. Immunization with MVA-gp70 and MVA-gp70-CD40L as well as with MVA-CD40L and MVA-4-1BBL induced a measurable tumor-specific T cell response which ranged between 1-2%; this response was dramatically increased (>5-fold) in mice that received MVA-gp70-4-1BBL (FIG. 25B).

Taken together, in the B16.F10 melanoma model, anti-tumor efficacy could be enhanced when MVA-gp70 was adjuvanted with either CD40L or 4-1BBL, but even stronger effects were observed when 4-1BBL and CD40L were expressed together in MVA-gp70-4-1BBL-CD40L.

Example 34: Intratumoral Immunotherapy with MVA-Gp70-4-1BBL-CD40L in CT26.WT Tumors Constructs were then tested using the CT26 colon carcinoma model, described to be rich in T cells and myeloid cells and considered immunogenic (see, e.g., Mosely et al. (2016) *Cancer Immunol. Res.* 5: 29-41). Balb/c mice were injected subcutaneously (s.c.) with CT26.wt colon carcinoma cells. When tumors reached ~60 mm3, mice were immunized intratumorally with PBS, MVA-gp70, MVA-gp70-4-1BBL, MVA-gp70-CD40L, MVA-gp70-4-1BBL-CD40L, or MVA 1BBL-CD40L.

Figure 26A:
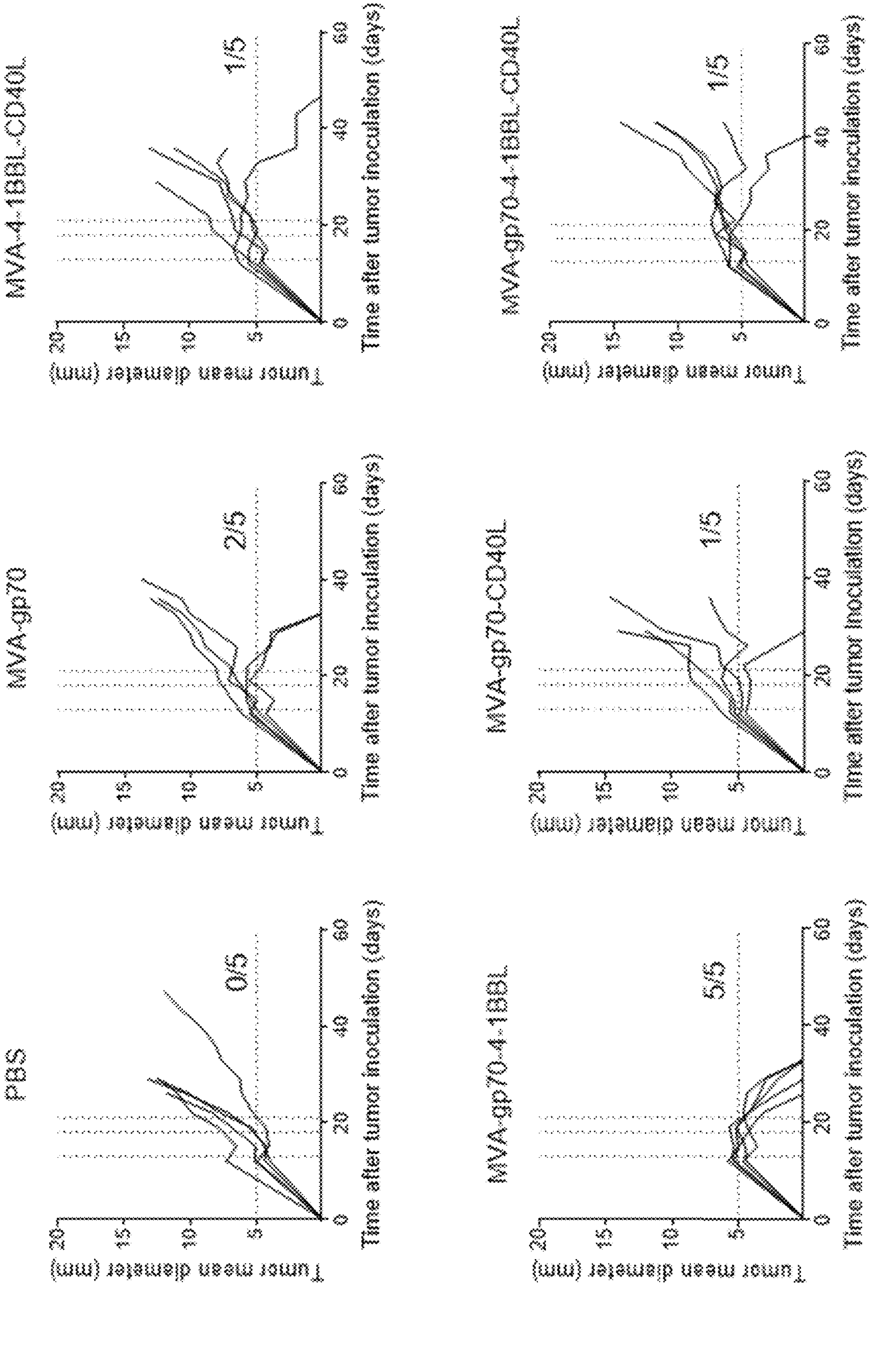
FIGS. 26A, 26B, and 26C: Anti-tumor efficacy of MVA-gp70 adjuvanted with CD40L or 4-1BBL in CT26 tumor-bearing mice. Balb/c mice received 5×10$^5$ Ct26 wt cells subcutaneously (s.c.). Thirteen days later, mice were grouped and injected intratumorally with PBS or 5×10$^7$ TCID50: MVA-gp70, MVA-gp70-4-1BBL, MVA-gp70-CD40L, MVA-gp70-4-1BBL-CD40L, MVA-4-1BBL, MVA-CD40L, and MVA-4-1BBL-CD40L (see Example 34). Treatment was repeated on day 5 and 8 after the first injection. Tumor growth was measured at regular intervals.
Figure 26B:
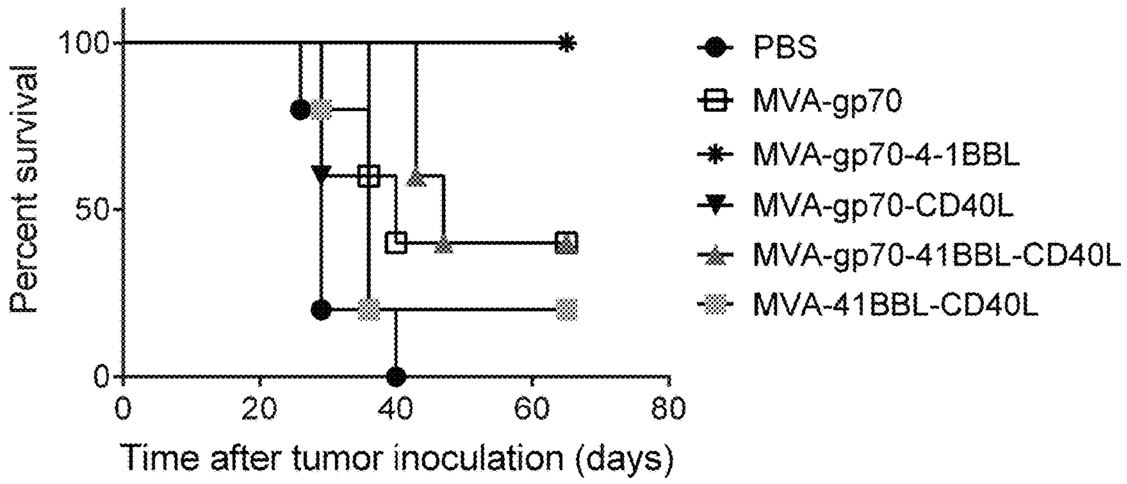

Immunization i.t. with MVA-gp70 induced transient and significant tumor growth control. This anti-tumor effect was not enhanced when the MVA expressed CD40L, but strikingly, immunization with MVA-gp70-4-1BBL led to the strongest therapeutic effects resulting in complete tumor clearance in all treated animals (FIG. 26A). However, treatment with MVA-gp70-4-1BBL-CD40L did not result in a better therapeutic efficacy. Of note, the viruses that only contained the co-stimulatory molecule but not gp70 also resulted in significant tumor growth delay, however could not compete with MVA-gp70-4-1BBL. These findings were reflected in the overall survival of treated mice (FIG. 26B).

Figure 26C:
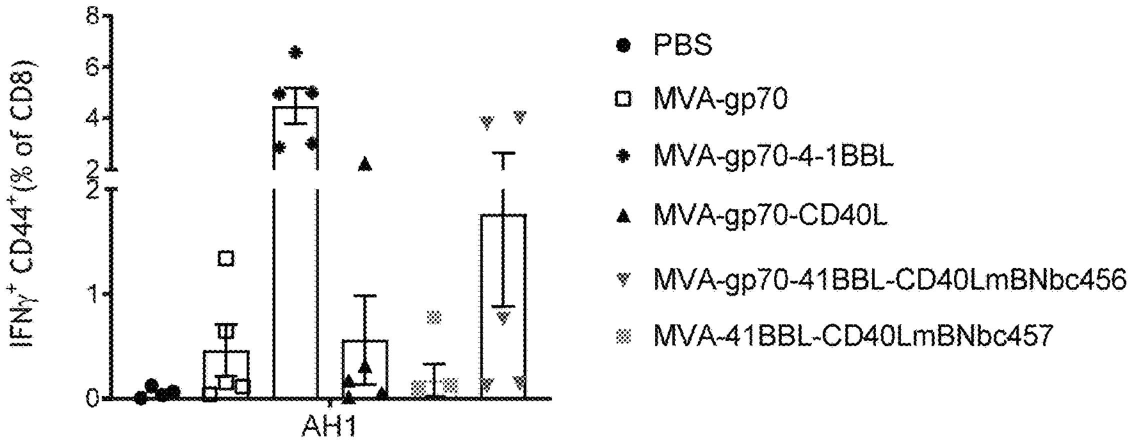

Gp70-specific T cell responses against the H2-Ld CD8+ T cell epitope AH-1 were readily detected in the blood of animals treated with MVA-gp70 and MVA-gp70-CD40L (FIG. 26C). This response was dramatically increased (>10 fold) in mice that received MVA-gp70-4-1BBL, which correlated with the therapeutic efficacy shown in FIGS. 26A and 26B. Treatment with MVA-gp70-4-1BBL-CD40L also enhanced AH-1-specific T cell responses in the blood (FIG. 26C).

Example 35: Comprehensive Analysis of the Tumor Microenvironment and the Tumor Draining LN after IT Injection of MVA-Gp70-4-1BBL-CD40L into B16.F10 Tumor Bearing Mice Data presented above showed that intratumoral treatment of B16.F10 tumor-bearing mice with MVA-gp70-4-1BBL-CD40L resulted in tumor rejection in 80% of treated mice (see FIG. 26A-26C). To study the tumor microenvironment (TME) and TdLN in this tumor model, B16.F10 tumor-bearing mice received either PBS or $5\times10^7$ TCID50 of MVA-gp70, MVA-gp70-4-1BBL, MVA-gp70-CD40L or MVA-gp70-4-1BBL-CD40L intratumorally (i.t.). Mice were sacrificed 3 days after prime immunization. Day 3 was selected based on previous experiments in the OVA system which showed changes in both, innate and adaptive components of the immune system at that timepoint (see FIG. 17). Tumors and TdLN were removed and digested with collagenase/DNase in order to analyze single cells using flow cytometry. The abundance of immune cell populations as well as their proliferative behavior and functional state were assessed.

Figure 27:
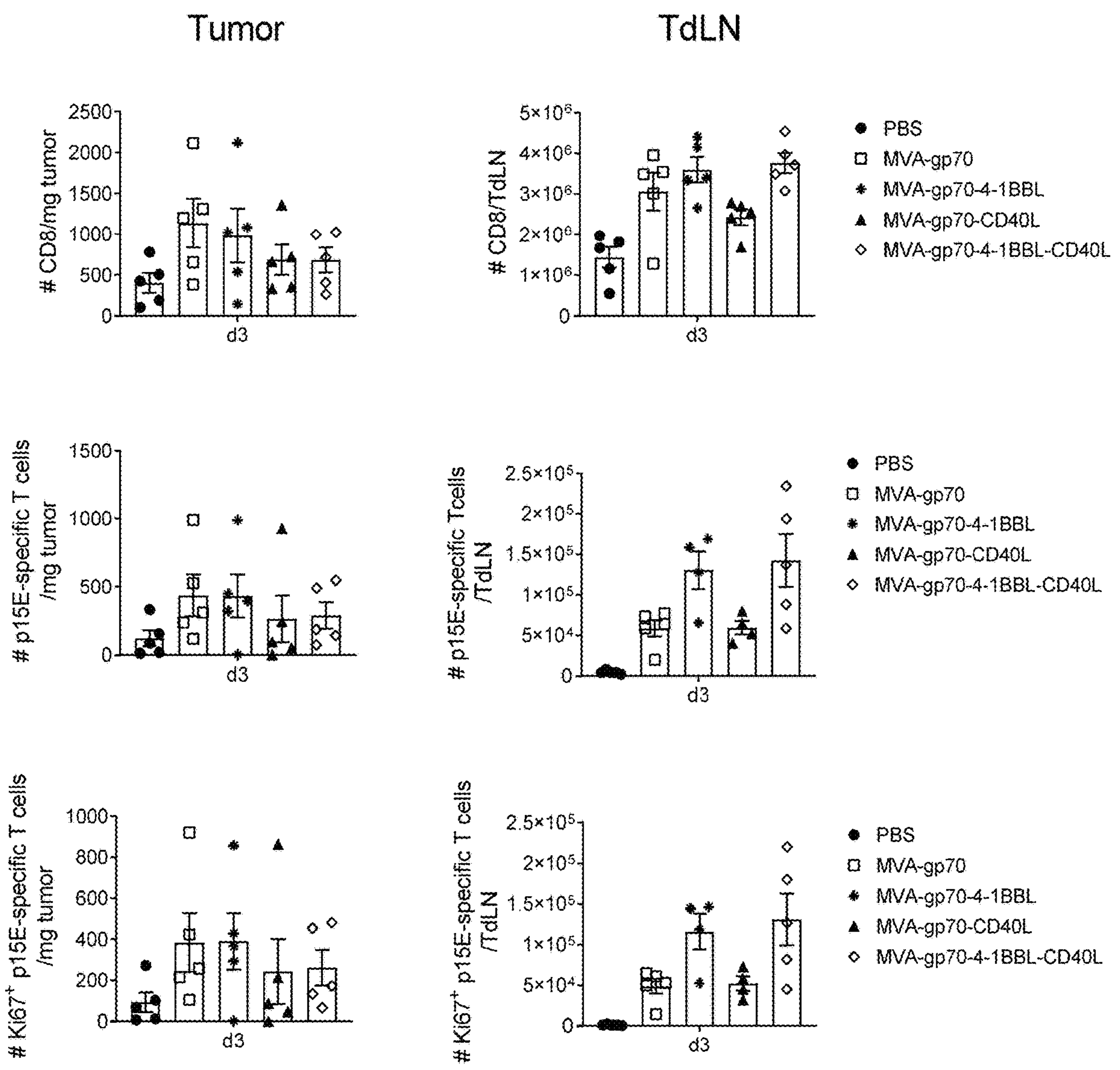
FIG. 27: Quantitative and qualitative T cell analysis of the tumor microenvironment (TME) and tumor draining lymph node (TdLN) after intratumoral injection of MVA-gp70 further comprising 4-1BBL and/or CD40L. C57BL/6 mice received 5×10$^5$ B16.F10 cells subcutaneously (s.c.). Nine days later when tumors measured above 5×5 mm, mice were grouped and injected intratumorally with either PBS or 5×10$^7$ TCID50 of MVA-gp70, MVA-gp70-4-1BBL, MVA-gp70-CD40L, or MVA-gp70-4-1BBL-CD40L (see Example 35). Three days after immunization, mice were sacrificed and tumors as well as tumor draining lymph nodes (TdLN) were collected, digested with collagenase/DNase, and analyzed by flow cytometry.

Intratumoral injection of 4-1BBL- and CD40L-adjuvanted MVAs did not confer an advantage at the day 3 timepoint in number of CD8 T cells or p15E-specific T cells in the tumor as determined by pentamer staining. However, in the TdLN, MVA-gp70 and MVA-gp70-CD40L produced an expansion of CD8 T cells, while the addition of 4-1BBL produced an even larger effect (FIG. 27, upper right). The increase produced by the addition of 4-1BBL was even more pronounced for p15E-specific CD8 T cells in the TdLN, for which i.t. immunization with either MVA-gp70-4-1BBL or MVA-gp70-4-1BBL-CD40L increased tumor-specific CD8 T cells (FIG. 27, middle right). The number of p15E-specific CD8 T cells also correlated with the proliferative state of those cells; for example, the addition of 4-1BBL along with gp70 and optionally CD40L to the MVA induced the highest numbers of Ki67+gp70-p15E CD8 T cells in the TdLN (FIG. 27, lower right).

These data demonstrate that intratumoral (i.t.) immunization with MVA-gp70 enhances the generation of adaptive immune responses on day 3 after treatment in the tumor and in the tumor draining lymph node, while adjuvantation with 4-1BBL or 4-1BBL plus CD40L specifically increased p15E-specific CD8 T cell responses in the TdLN.

Figure 28:
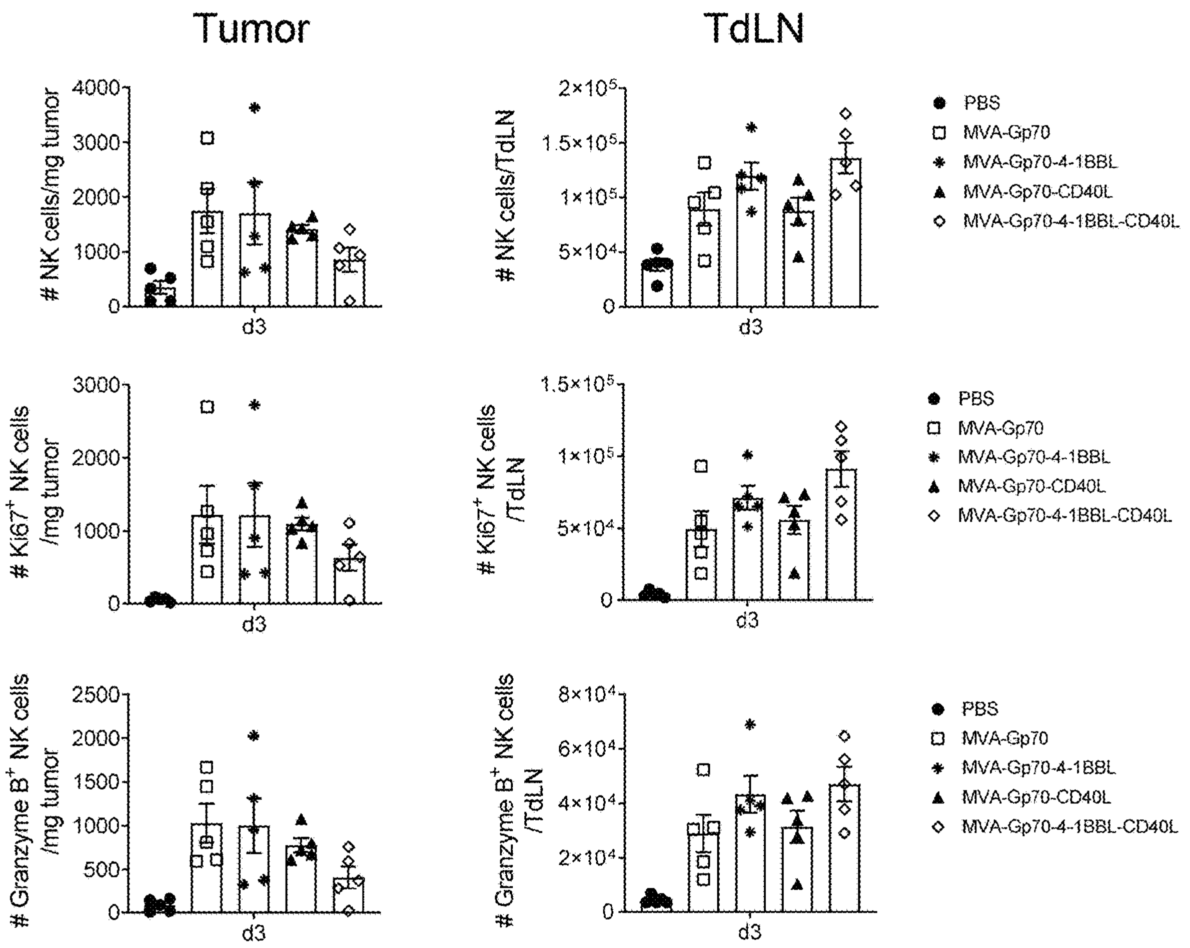
FIG. 28 shows quantitative and qualitative T cell analysis of the tumor microenvironment (TME) and tumor draining lymph node (TdLN) after intratumoral injection of MVA-gp70 further expressing 4-1BBL and/or CD40L. C57BL/6 mice received 5×10$^5$ B16.F10 cells subcutaneously (s.c.) (see Example 36). Nine days later when tumors measured above 5.5×5.5 mm, mice were grouped and intratumorally injected with either PBS or 5×10$^7$ TCID50 of: MVA-Gp70, MVA-gp70-4-1BBL, MVA-gp70-CD40L, and MVA-gp70-4-1BBL-CD40L. Three days after immunization, mice were sacrificed and tumors as well as TdLN were collected and digested with collagenase/DNase and resulting individual cells analyzed by flow cytometry. Number of NK cells, $Ki67^+$ NK cells and Granzyme $B^+$ NK cells per mg tumor and TdLN is shown. Data are shown as Mean±SEM.

Example 36: Induction of NK Cells in Tumor and TdLN after Intratumoral Injection of MVAs Intratumoral (i.t.) injection of MVA-OVA produced an activation and expansion of NK cells on day 1 and day 3, respectively (FIG. 19). We then examined NK cell infiltration, activation and expansion on day 3 after injection with different MVA constructs. Quantification of NK cells after i.t. immunization with recombinant MVAs showed an increase in NK cells infiltrating the tumor (FIG. 28, upper left) and the TdLN (FIG. 28, upper right). Infiltration was increased when the MVA encoded 4-1BBL (e.g., MVA-gp70-4-1BBL and MVA-gp70-4-1BBL-CD40L). Intratumoral (i.t.) injection of MVA-gp70 induced proliferation of NK cells (Ki67+) in the tumor (see FIG. 28, middle left) and the TdLN (FIG. 28, middle right), and adjuvantation with 4-1BBL or 4-1BBL and CD40L enhanced this effect in the TdLN.

Granzyme B is a marker for cytotoxicity of NK cells (see, e.g., Ida et al. (2005) *Mod. Rheumatol.* 15: 315-22). Granzyme B+NK cells were induced in the tumor and TdLN following intratumoral injection with recombinant MVAs (FIG. 28, lower left). Again, the addition of 4-1BBL or 4-1BBL-CD40L to the recombinant MVA mildly increased the number of cytotoxic NK cells in the TdLN (FIG. 28, lower right).

Altogether, these data highlight a significant role of MVA-encoded 4-1BBL-CD40L in the expansion and function of NK cells and TAA-specific T cells after intratumoral (i.t.) immunotherapy. Thus, intratumoral treatment with recombinant MVAs encoding gp70 and 4-1BBL or gp70, 4-1BBL, and CD40L can enhance T cell responses to an endogenous retroviral self-antigen such as gp70.

Example 37: Intravenous Immunotherapy with MVA-Gp70-4-1BBL-CD40L in CT26.WT Tumor-Bearing Mice Experiments discussed above showed that the novel MVA construct encoding the tumor antigen gp70 together with the costimulatory molecules 4-1BBL and CD40L was highly potent when applied intratumorally (FIGS. 25 and 26). In addition, Lauterbach et al. ((2013) *Front. Immunol.* 4: 251) found that MVA-encoded CD40L enhances innate and adaptive immune responses when given intravenously. Here, we asked whether intravenous (i.v.) immunization with MVA-gp70-4-1BBL-CD40L can also provide tumor growth control.

Figure 29A:
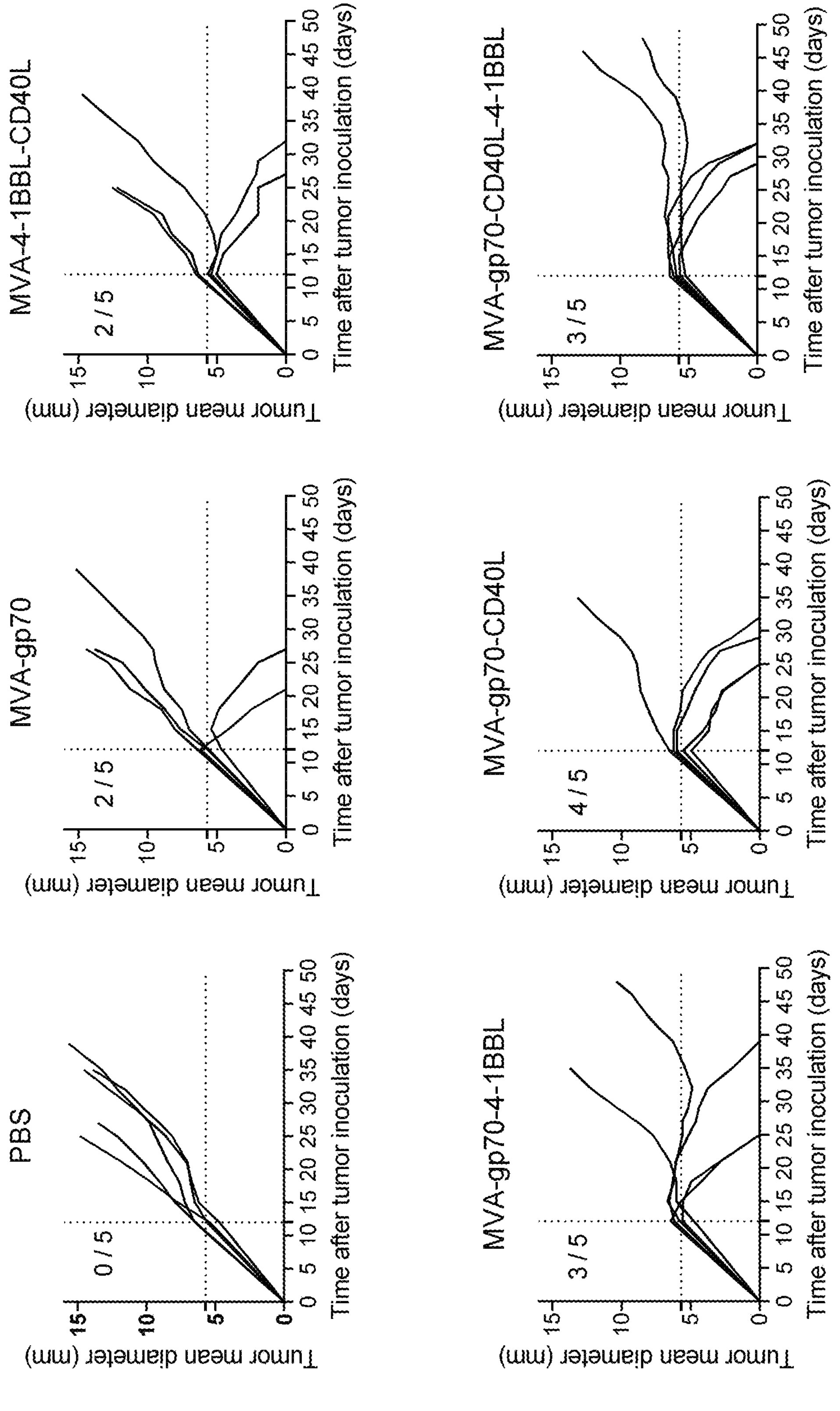
FIGS. 29A, 29B, and 29C: Anti-tumor efficacy of intravenous administration of MVA-gp70 adjuvanted with 4-1BBL and/or CD40L in CT26.WT tumor-bearing mice. Balb/c mice received 5×10$^5$ CT26.WT cells subcutaneously (s.c.). Twelve days later, mice were grouped and intravenously injected with PBS or 5×10$^7$ $TCID_{50}$ of MVA-Gp70, MVA-Gp70-4-1BBL, MVA-Gp70-CD40L, MVA-Gp70-4-1BBL-CD40L, and MVA-4-1BBL-CD40L (see Example 37).
Figure 29B:
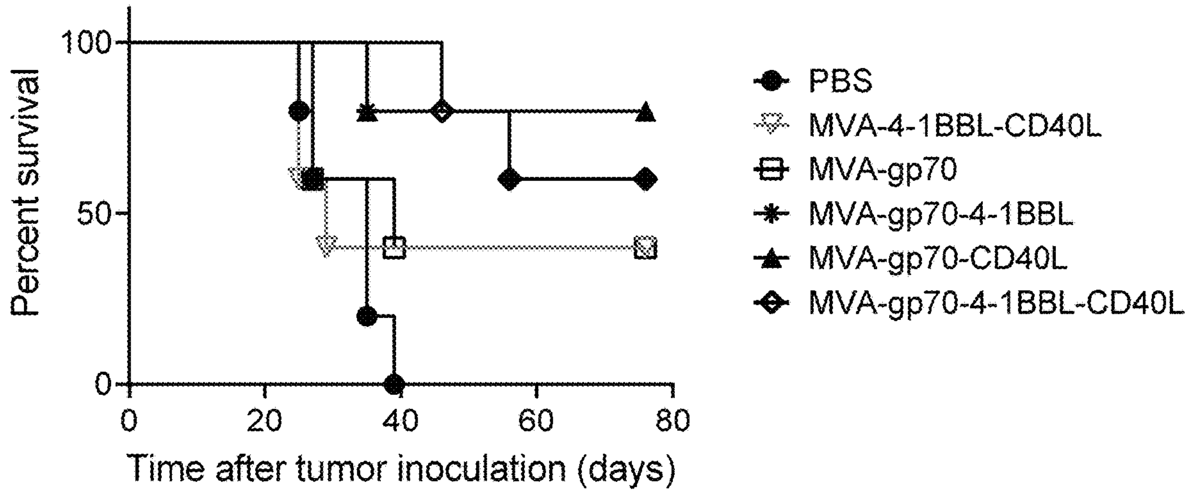

CT26.WT colon carcinoma cells were subcutaneously injected into Balb/c mice. When tumors reached ~60 mm3, mice were immunized intravenously with PBS or MVA-Gp70, MVA-Gp70-4-1BBL, MVA-Gp70-CD40L, MVA-gp70-4-1BBL-CD40L, and MVA-4-1BBL-CD40L (which lacks gp70). I.v. immunization with MVA-gp70 led to tumor clearance in 2/5 animals (FIG. 29A). Mice that were treated with gp70-expressing virus either containing 4-1BBL or CD40L showed a strongly improved anti-tumor response which resulted in 3/5 and 4/5 cured mice, respectively. Importantly, i.v. treatment with MVA-gp70-4-1BBL-CD40L led to a prolonged tumor growth control in all treated mice with 3/5 mice rejecting the tumor (FIG. 29A). Of note, the recombinant MVAs that only contained the co-stimulatory molecule but not gp70 also resulted in significant tumor growth delay, but did not lead to the same tumor rejection as observed with MVA-gp70-4-1BBL, MVA-gp70-CD40L or MVA-gp70-4-1BBL-CD40L (FIG. 29A). These findings were reflected in the overall survival of treated mice (FIG. 29B).

Figure 29C:
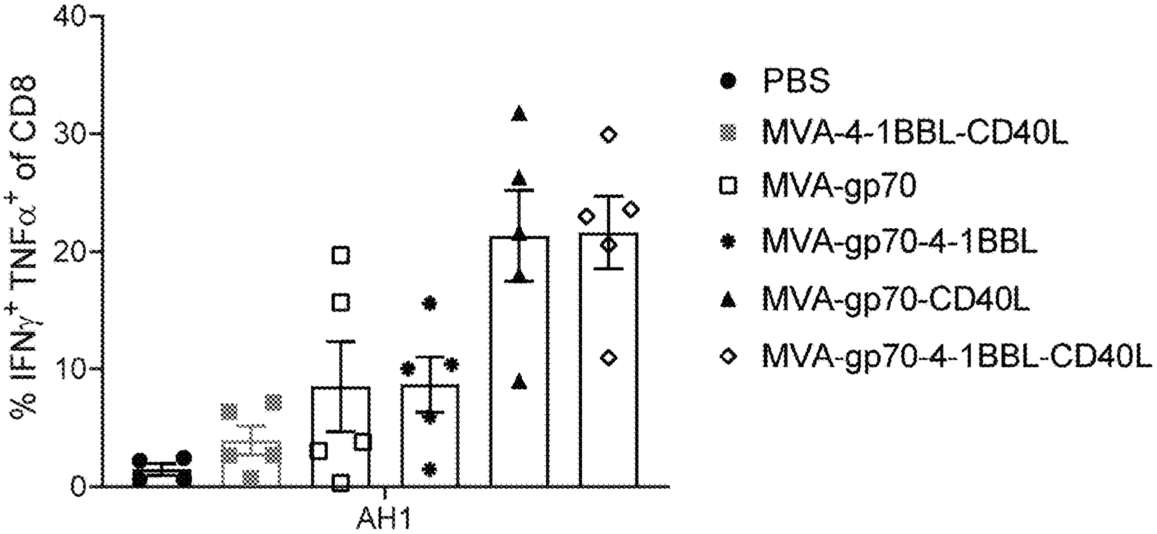

Analysis of tumor-directed CD8 T cell responses in the blood by peptide restimulation of PBLs revealed a significant induction of AH1-specific CD8 T cells in all MVA treatment groups, whereby this could be further increased in the presence of CD40L (i.e., MVA-gp70-CD40L and MVA-gp70-4-1BBL-CD40L) (FIG. 29C).

Example 38: Recombinant MVAs Comprising HERV-K Antigens

An MVA-based vector ("MVA-mBN489," also referred to as "MVA-HERV-Prame-FOLR1-4-1-BBL-CD40L") was designed comprising TAAs that are proteins of the K superfamily of human endogenous retroviruses (HERV-K), specifically, ERV-K-env and ERV-K-gag. The MVA also was designed to encode human FOLR1 and PRAME, and to express h4-1BBL and hCD40L.

Figure 30A:
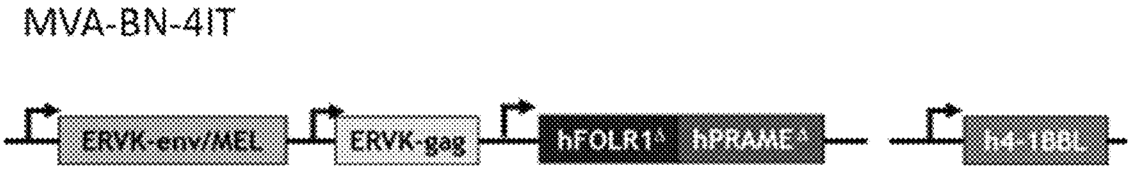
FIGS. 30A, 30B, and 30C illustrate MVA-based vector MVA-HERV-FOLR1-PRAME-h4-1-BBL ("MVA-mBN494" or "MVA-BN-4IT") (FIG. 30A) and furthermore shows the vector's capability of loading TAA into HLA of infected cells (FIG. 30B) as well as of expressing h4-1-BBL in a functional (i.e., h4-1-BB receptor binding) form (FIG. 30C). For more details, see Examples 38 and 39.

A similar MVA-based vector referred to as "MVA-HERV-Prame-FOLR1-4-1-BBL" was designed to express the TAAs ERV-K-env and ERV-K-gag and human FOLR1 and PRAME, and to express h4-1BBL. Specifically, vector "MVA-BN-4IT" ("MVA-mBN494" or "MVA-HERV-FOLR1-PRAME-h4-1-BBL") is schematically illustrated in FIG. 30A. HERV-K genes encoding the envelope (env) and group-specific antigen (gag) proteins are usually dormant in healthy human tissue but are activated in many tumors. FOLR1 and PRAME are genes that are specifically upregulated in cells of breast and ovarian cancers. The additional expression of co-stimulatory molecule 4-1-BBL intends to enhance the immune response against the TAAs.

Another MVA-based vector referred to as "MVA-HERV-Prame-FOLR-CD40L was designed to express the TAAs ERV-K-env and ERV-K-gag and human FOLR1 and PRAME, and to express hCD40L. Each of these constructs is useful in methods of the invention.

Exemplary sequences are known in the art and are also set forth in the sequence listing provided. Any sequence can be used in the compositions and methods of the invention so long as it provides the necessary function to the relevant MVA.

For the ERV-K env and gag sequences described above, an amino acid consensus sequence was produced from at least 10 representative sequences, and a potential immunosuppressive domain was inactivated by mutations and replaced in part with the immunodominant T-cell epitope HERV-K-mel as shown below. Suitable sequences are set forth in SEQ ID NO:5 (ERV-K-gag synthetic protein consensus sequence); SEQ ID NO:6 (ERV-K-gag synthetic nucleotide sequence); SEQ ID NO:7 (ERV-K-env/MEL synthetic protein sequence); and SEQ ID NO:8 (ERV-K-env/MEL nucleotide sequence).

MNPSEMQRKAPPRRRRHRNRAPLTHKMNKMVTSEEQMKLPSTKKAEPPTW

AQLKKLTQLATKYLENTKVTQTPESMLLAALMIVSMVVSLPMPAGAAAAN

YTYWAYVPFPPMIRAVTWMDNPIEVYVNDSVWVPGPIDDRCPAKPEEEGM

MINISIGYRYPPICLGRAPGCLMPAVQNWLVEVPTVSPISRFTYHMVSGM

SLRPRVNYLQDFSYQRSLKFRPKGKPCPKEIPKESKNTEVLVWEECVANS

AVILQNNEFGTIIDWAPRGQFYHNCSGQTQSCPSAQVSPAVDSDLTESLD

KHKHKKLQSFYPWEWGEKGISTPRPKIISPVSGPEHPELWRLTVASHHIR

IWSGNQTLETRDRKPFYTVDLNSSLTVPLQSCVKPPYMLVVGNIVIKPDS

QTITCENCRLLTCIDSTFNWQHRILLVRAREGVWIPVSMDRPWEASPSVH

ILTEVLKGVLNRSKRFIFTLIAVIMGLIAVTATAAVAGVALHSSVQSVNF

VNDWQKNSTRLWNSQSSIDQKMLAVISCAVQTVIWMGDRLMSLEHRFQLQ

CDWNTSDFCITPQIYNESEHHWDMVRRHLQGREDNLTLDISKLKEQIFEA

SKAHLNLVPGTEAIAGVADGLANLNPVTWVKTIGSTTIINLILILVCLFC

LLLVCRCTQQLRRDSDHRERAMMTMAVLSKRKGGNVGKSKRDQIVTVSV

Modified Consensus Amino Acid Sequence of ERVK-Env (Above):

A potential immunosuppressive domain was inactivated by mutations. The introduced mutations replace a substantial portion of the immunosuppressive domain by the immunodominant T-cell epitope HERVK-mel.

For some of these MVAs, hFOLR1 and PRAME were designed to be produced as a fusion protein. FOLR1 (folate receptor alpha) belongs to the family of folate receptors. It has a high affinity to folic acid and derivatives thereof, and is either secreted or expressed on the cell surface as a membrane protein. The transmembrane protein is anchored to the plasma membrane through a GPI (glycosylphosphatidylinositol) anchor which is most likely attached in the endoplasmic reticulum (ER) through a serine (Ser) residue in the C-terminal region of the protein. To avoid modification of FOLR1 with the GPI-anchor and full processing of the hFOLR1-hPRAME fusion protein in the ER, the C-terminal region from aa 234 to 257 (including the Ser residue) was deleted.

PRAME (Preferentially expressed antigen of melanoma) is a transcriptional regulator protein. It was first described as an antigen in human melanoma, which triggers autologous cytotoxic T cell-mediated immune responses and is expressed in variety of solid and hematological cancers. PRAME inhibits retinoic acid signaling via binding to retinoic acid receptors and thereby might provide a growth advantage to cancer cells. Functionality of PRAME requires nuclear localization, so potential nuclear localization signals (NLS) in PRAME were modified by targeted mutations in the hFOLR1-hPRAME fusion protein.

Thus, for the amino acid sequence of the hFOLR1-hPRAME fusion protein, FOLR1 was modified by deleting the C-terminal GPI anchor signal, while in PRAME, two potential nuclear localization signals were inactivated by amino acid substitutions. In this fusion protein, the N-terminal signal sequence of hFOLR1 should result in ER-targeting and incomplete processing of the fusion protein to serve as an additional safeguard to avoid nuclear localization of PRAME.

The protein sequences of human FOLR1 and human PRAME were based on NCBI RefSeq NP_000793.1 and NP_001278644.1, respectively. In addition to the modifications described above, the nucleotide sequence of the fusion protein was optimized for human codon usage, and poly-nt stretches, repetitive elements, and negative cis-acting elements were removed and the nucleotide sequence is set forth in SEQ ID NO:10 ("hFOLR1Δ_hPRAMEA fusion" nucleotide sequence), while the fusion protein sequence is set forth in SEQ ID NO:9.

MAQRMTTQLLLLLVWVAVVGEAQTRIAWARTELLNVCMNAKHHKEKPGPE

DKLHEQCRPWRKNACCSTNTSQEAHKDVSYLYRFNWNHCGEMAPACKRHF

IQDTCLYECSPNLGPWIQQVDQSWRKERVLNVPLCKEDCEQWWEDCRTSY

TCKSNWHKGWNWTSGFNKCAVGAACQPFHFYFPTPTVLCNEIWTHSYKVS

NYSRGSGRCIQMWFDPAQGNPNEEVARFYAAAM

~~SGAGPWAAWPFLLSLALMLLWLLSM~~

ERRRLWGSIQSRYISMSVWTSPRR

LVELAGQSLLKDEALAIAALELLPRELFPPLFMAAFDGRHSQTLKAMVQA

WPFTCLPLGVLMKGQHLHLETFKAVLDGLDVLLAQEVRPRRWKLQVLDLR

KNSHQDFWTVWSGNRASLYSFPEPEAAQPMTTKAKVDGLSTEAEQPFIPV

EVLVDLFLKEGACDELFSYLIEKVAAKKNVLRLCCKKLKIFAMPMQDIKM

ILKMVQLDSIEDLEVTCTWKLPTLAKFSPYLGQMINLRRLLLSHIHASSY

ISPEKEEQYIAQFTSQFLSLQCLQALYVDSLFFLRGRLDQLLRHVMNPLE

TLSITNCRLSEGDVMHLSQSPSVSQLSVLSLSGVMLTDVSPEPLQALLER

ASATLQDLVFDECGITDDQLLALLPSLSHCSQLTTLSFYGNSISISALQS

LLQHLIGLSNLTHVLYPVPLESYEDIHGTLHLERLAYLHARLRELLCELG

RPSMVWLSANPCPHCGDRTFYDPEPILCPCFMPN

Sequence of the hFOLR1-hPRAME Fusion Protein (Above):

Amino acid sequence of the hFOLR1-hPRAME fusion protein, a fusion of modified human FOLR1 (N-terminal portion) and PRAME (C-terminal portion). FOLR1 was modified by deleting the C-terminal GPI anchor signal (strikethrough letters). In PRAME (underlined letters), the initial Methionine was deleted, and two potential nuclear localization signals were inactivated by amino acid substitutions (bold, underlined letters).

The protein sequence of the membrane-bound human 4-1BBL used in this MVA shows 100% identity to NCBI RefSeq NP_003802.1, and the protein sequence of the membrane-bound human CD40L used shows 100% identity to NCBI RefSeq NP_000065.1. For both 4-1BBL and CD40L, the nucleotide sequence was optimized for human codon usage, and poly-nt stretches, repetitive elements, and negative cis-acting elements were removed.

The hCD40L amino acid sequence from NCBI RefSeq NP_000065.1. is set forth in SEQ ID NO:1, while the nucleotide sequence of hCD40L is set forth in SEQ ID NO:2. The h4-1BBL amino acid sequence from NCBI RefSeq NP_003802.1 is set forth in SEQ ID NO:3, while the nucleotide sequence of h4-1BBL is set forth in SEQ ID NO:4.

Each coding region was placed under the control of a different promoter, except that ERV-K-gag and h4-1BBL were both placed under the control of the Pr1328 promoter.

The Pr1328 promoter (100 bp in length) is an exact homologue of the Vaccinia Virus Promoter PrB2R. It drives strong immediate early expression as well as late expression at a lower level. In the recombinant MVA-mBN489, the Pr13.5long promoter drives expression of ERVK-env/MEL. This promoter compromises 124 bp of the intergenic region between 014 L/13.5 L driving the expression of the native MVA13.5L gene and exhibits a very strong early expression caused by two early promoter core sequences (see Wennier et al. (2013) *PLoS One* 8(8): e73511). The MVA1-40k promoter, used here to drive expression of hCD40L, was originally isolated as a 161 bp fragment from the vaccinia virus Wyeth Hind III H region in 1986. It compromises 158 bp of the Vaccinia Virus Wyeth and MVA genome within the intergenic region of 094L/095R driving the late gene transcription factor VLTF-4. The promoter PrH5m, used here to drive expression of the hFOLR1-hPRAME fusion protein, is a modified version of the Vaccinia virus H5 gene promoter. It consists of strong early and late elements resulting in expression during both early and late phases of infection of the recombinant MVA (see Wyatt et al. (1996) *Vaccine* 14: 1451-58).

Figure 31A:
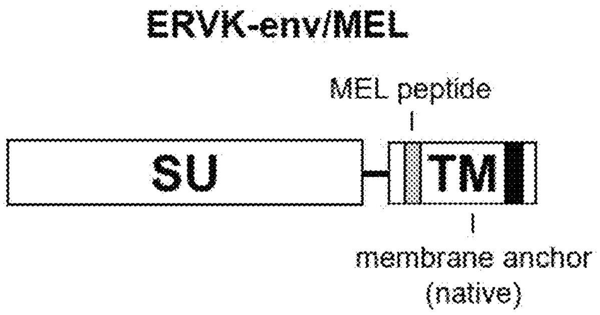
FIGS. 31A, 31B, and 31C illustrate MVA-based vector “MVA-mBN502” (FIG. 31C) and furthermore shows schematic maps of ERVK-env/MEL (FIG. 31A; as used in MVA-mBN494) and ERVK-env/MEL_03 (FIG. 31B; as used in MVA-mBN502).
Figure 31B:
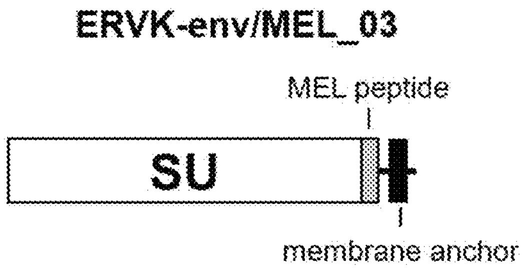
Figure 31C:
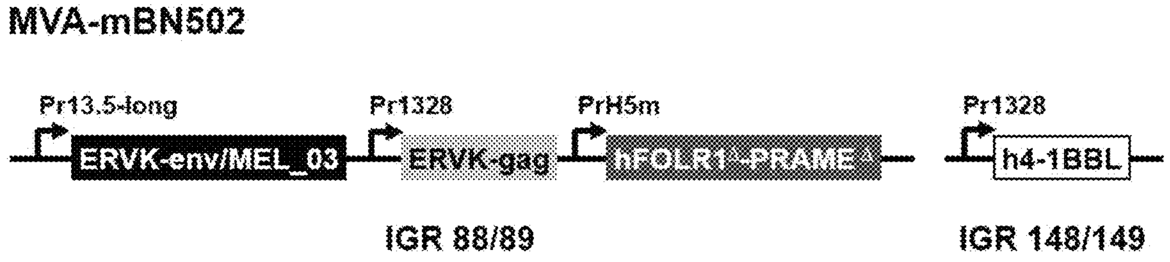

Based on MVA-mBN494 (see above) still another vector was designed to contain a modification in ERVK-env/MEL. The resulting vector was referred to as "MVA-mBN502" and is schematically illustrated in FIG. 31C. In addition to the modified ERVK-env/MEL, MVA-mBN502 also encodes ERVK-gag, the hFOLR1-hPRAME fusion protein, as well as h4-1BBL Natively, HERVK-env consists of a signal peptide, which is cleaved off post-translationally, a surface (SU) and a transmembrane unit (TM). Cleavage into the two domains is achieved by cellular proteases. An RSKR cleavage motif is required and sufficient for cleavage of the full-length 90 kDa protein into SU (ca. 60 kDa) and TM (ca. 40 kDa) domains. As described above for the preparation of MVA-mBN494, an amino acid consensus sequence for env derived from at least ten representative sequences was generated, and a potential immunosuppressive domain in the TM was inactivated by mutations. The introduced mutations replaced a substantial portion of the immunosuppressive domain by the immunodominant T-cell epitope HERV-K-mel. This transgene (used in MVA-mBN494) was termed ERVK-env/MEL (FIG. 31A).

As compared to MVA-mBN494, the TM domain in ERVK-env/MEL is deleted in MVA-mBN502. This ERVK-env/MEL variant was designated "ERVK-env/MEL_03" and consists of the entire SU domain except for the RSKR furin cleavage site, which was deleted. The MEL peptide was inserted at the C-terminal end, followed by 6 amino acids of the TM domain (excluding the fusion peptide sequence, which is strongly hydrophobic). In addition, this modified ERVK-env/MEL was targeted to the plasma membrane by adding a membrane anchor derived from the human PDGF (platelet-derived growth factor) receptor. This membrane anchor was attached to the SU domain via a flexible glycine-containing linker (FIG. 31B). The resulting ERVK-env/MEL variant, i.e. ERVK-env/MEL_03, is contained in MVA-mBN502 (FIG. 31C). Suitable sequences of the variant are set forth in SEQ ID NO:11 (ERV-K-env/MEL_03 synthetic protein sequence) and SEQ ID NO:12 (ERV-K-env/MEL_03 nucleotide sequence).

Example 39: Bioactivity of MVA-HERV-FOLR1-PRAME-h4-1-BBL (MVA-BN-41T)

It was investigated whether infection with MVA-BN-4IT (i.e., MVA-HERV-FOLR1-PRAME-h4-1-BBL; see also Example 38 above) would result in the presentation of vaccine-derived tumor antigens by HLA molecules on human cells. To this end, HLA-ABC peptide complexes on antigen presenting cells were immunoprecipitated, and it was analyzed which HLA-bound peptides could be identified by mass spectrometry.

Figure 30B:
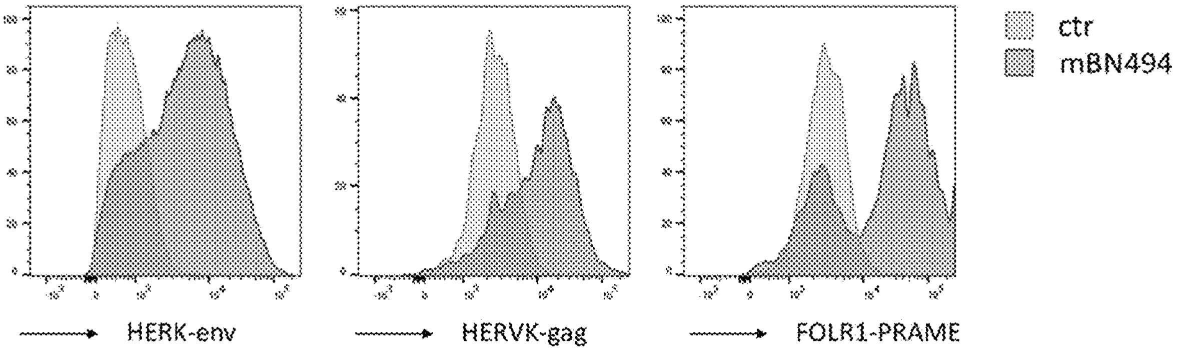

First, the human monocytic cell line THP-1 was differentiated into macrophages (Daigneault et al. *PLoS One,* 2010), which exert antigen presenting capabilities, since antigens can be loaded to HLA class I (Nyambura L. et al. *J. Immunol* 2016). Indeed, THP-1 cells express HLA-A*0201$^+$ which is one of the most frequent haplotypes in the USA and Europe (approximately 30% of the population). Apart of HLA-A*02:01:01G, THP-1 cells were reported to express HLA-B*15 and HLA-C*03 (Battle R. et al., Int. J. of Cancer). Here, $8\times10^5$/ml THP-1 cells were cultured in the presence of 200 ng/ml PMA (phorbol-12-myristate-13-acetate) for 3 days before medium was exchanged and cells were cultured for additional 2 days in the absence of PMA. On day 5 cells were infected with MVA-BN-4IT with an InfU (infectious unit) of 4 for 12 hours. As shown in FIG. 30B, HERVK-env/MEL, HERVK-gag and the fusion protein FOLR1-PRAME were expressed after infection of THP-1 cells with MVA-BN-4IT ("mBN494" in FIG. 30B). In contrast, the antigens were not endogenously expressed in uninfected THP-1 cells ("ctr" in FIG. 30B).

Next, a "ProPresent" HLA-ABC ligandome analysis (ProImmune) was performed. In MVA-BN-4IT infected cells, four tumor antigen-derived peptides were identified: The HERV-K env peptide ILTEVLKGV, the HERV-K gag peptide YLSFIKILL and the PRAME peptides ALQSLLQHL and SLLQHLIGL. The two identified PRAME peptides are largely overlapping and most likely share a common core epitope. Both peptides are predicted to bind very strongly to HLA-A*02:01, whereby ALQSLLQHL has almost a similar binding rank to HLA-B*15. Notably, the PRAME peptide SLLQHLIGL has already been described as an immunogenic HLA-A*0201-presented cytotoxic T lymphocyte epitope in human (Kessler J H. et al., *J Exp Med.,* 2001). Altogether, the data demonstrate that the antigens expressed by MVA-BN-4IT can be loaded into HLA of infected cells.

Figure 30C:
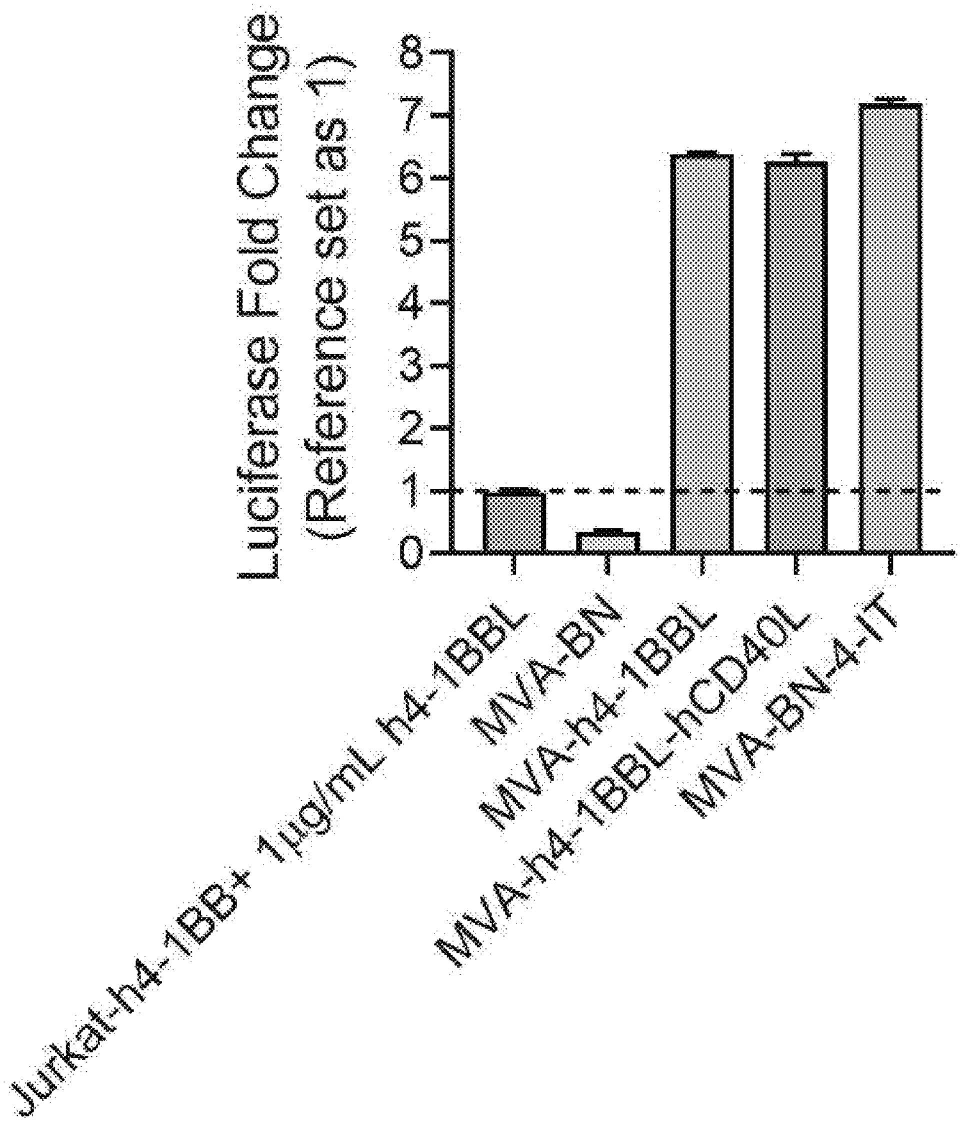

Furthermore, MVA-BN-4IT was tested for its capability of expressing 4-1-BBL in a functional form that binds to its receptor, 4-1-BB. For that purpose, a commercial kit ("4-1BB Bioassay", Promega) was used. The assay consists of a genetically engineered Jurkat T cell line expressing h4-1-BB and a luciferase reporter driven by a response element (RE) that can respond to 4-1-BB ligand stimulation. When h4-1-BB is stimulated by h4-1-BBL the RE activates cellular luciferase production within the cell. After cell lysis and addition of "Bio-Glo" reagent (Promega), luminescence is measured using a luminometer and quantified. Briefly, HeLa cells were plated ($1\times10^6$) and infected ($TCID_{50}$=2) each with the MVA-based constructs indicated in FIG. 30C, cultured overnight (37° C., 5% $CO_2$), and then co-cultured with the Jurkat-h4-1-BB cells (ratio of HeLa:Jurkat=4:1) for 6 hours. His-tagged h4-1BBL cross-linked with an Fc was used as a reference (positive control) and luciferase expression by Jurkat-h4-1BB cells cultured with 1 μg/ml of the cross-linked h4-1BB1 was set to 1 (FIG. 30C, dotted line). MVA-BN (i.e., not encoding h4-1-BBL) was used as a backbone control. As shown in FIG. 30C, HeLa cells infected with an MVA-based vector expressing h4-1-BBL induced a more than 6-fold higher luciferase production (through the co-cultured Jurkat-h4-1-BB cells) as compared to the reference. Notably, luciferase production mediated by MVA-BN-4IT was even higher than that mediated by the other two h4-1-BBL expressing MVA vectors. Thus, MVA-mBN494 expresses functional h4-1-BBL that effectively binds to its 4-1BB receptor.

Example 40: Intratumoral Immunization with MVA Encoding Brachyury Antigen

The highly attenuated, non-replicating vaccinia virus MVA-BN-Brachyury has been designed to consist of four human transgenes to elicit a specific and robust immune response to a variety of cancers. The vector co-expresses the brachyury human TAA and three human costimulatory molecules: B7.1 (also known as CD80), intercellular adhesion molecule-1 (ICAM-1, also known as CD54), and leukocyte function-associated antigen-3 (LFA-3, also known as CD58). The three costimulatory molecules (or TRIad of COstimulatory Molecules, TRICOM™) are included to maximize the immune response to the brachyury human TAA.

Brachyury is a transcription factor in the T-box family and is a driver of EMT, a process associated with cancer progression. It is overexpressed in cancer cells compared with normal tissue and has been linked to cancer cell resistance to several treatment modalities and metastatic potential. Cancers known to express brachyury include lung, breast, ovarian, chordoma, prostate, colorectal and pancreatic adenocarcinoma.

In vitro and clinical studies were conducted to demonstrate the safety and potential therapeutic efficacy of MVA encoding brachyury; see, e.g., Hamilton et al. (2013) *Oncotarget* 4: 1777-90 ("*Immunological targeting of tumor cells undergoing an epithelial-mesenchymal transition via a recombinant brachyury-yeast vaccine*"); Heery et al. (2015a) *J. Immunother. Cancer* 3: 132 ("*Phase I, dose escalation, clinical trial of MVA-brachyury-TRICOM vaccine demonstrating safety and brachyury-specific T cell responses*"); Heery et al. (2015b) *Cancer Immunol. Res.* 3: 1248-56 ("*Phase I trial of a yeast-based therapeutic cancer vaccine* (*GI*-6301) *targeting the transcription factor brachyury*"))

A GLP-compliant repeat-dose toxicity study is performed to evaluate any potential toxicity of MVA-BN-Brachyury (MVA-mBN240B) in NHP (cynomolgus macaques) in support of the use of the intravenous route in the Phase 1 clinical development. The toxicity study includes a biodistribution part evaluating spatial and temporal distribution of MVA-BN-Brachyury in NHP.

MVA-BN-Brachyury is used in a phase III trial in which cancer patients are treated with intratumoral injection of the MVA, optionally in conjunction with another treatment such as, for example, radiation and/or checkpoint inhibitors.

It will be apparent that the precise details of the methods or compositions described herein may be varied or modified without departing from the spirit of the described invention. We claim all such modifications and variations that fall within the scope and spirit of the claims below.

SEQUENCE LISTING

The nucleic and amino acid sequences listed in the accompanying sequence listing are shown using standard letter abbreviations for nucleotide bases, and either one letter code or three letter code for amino acids, as defined in 37 C.F.R. 1.822. Only one strand of each nucleic acid sequence is shown, but the complementary strand is understood as included by any reference to the displayed strand.

| Sequences in sequence listing: |
| --- |
| SEQ ID NO: 1:<br>hCD40L amino acid sequence from NCBI RefSeq NP_000065.1. (261 amino acids) |
| SEQ ID NO: 2:<br>hCD40L from NCBI RefSeq NP_000065.1 (792 nucleotides) |
| SEQ ID NO: 3:<br>h4-1BBL from NCBI RefSeq NP_003802.1 (254 amino acids) |
| SEQ ID NO: 4:<br>h4-1BBL from NCBI RefSeq NP_003802.1 |
| SEQ ID NO: 5:<br>ERV-K-gag (666 amino acids) synthetic consensus sequence |
| SEQ ID NO: 6:<br>ERV-K-gag; nt sequence |
| SEQ ID NO: 7:<br>ERV-K-env/MEL (699 amino acids) synthetic sequence |
| SEQ ID NO: 8:<br>ERV-K-env/MEL nt sequence |
| SEQ ID NO: 9:<br>hFOLR1Δ_hPRAMEΔ fusion (741 amino acids) |
| SEQ ID NO: 10:<br>hFOLR1Δ_hPRAMEΔ fusion (741 amino acids) nt sequence |
| SEQ ID NO: 11:<br>ERV-K-env/MEL_03 (517 amino acids) synthetic sequence |
| SEQ ID NO: 12:<br>ERV-K-env/MEL_03 nt sequence |

-continued

| Sequences in sequence listing: |
| --- |

SEQ ID NO: 1
hCD40L from NCBI RefSeq NP_000065.1. (261 amino acids)
MIETYNQTSPRSAATGLPISMKIFMYLLTVFLITQMIGSALFAVYLHRRLDKIEDERNLHE

DFVFMKTIQRCNTGERSLSLLNCEEIKSQFEGFVKDIMLNKEETKKENSFEMQKGDQNP

QIAAHVISEASSKTTSVLQWAEKGYYTMSNNLVTLENGKQLTVKRQGLYYIYAQVTFCS

NREASSQAPFIASLCLKSPGRFERILLRAANTHSSAKPCGQQSIHLGGVFELQPGASVFVN

VTDPSQVSHGTGFTSFGLLKL

SEQ ID NO: 2
hCD40L from NCBI RefSeq NP_000065.1. (792 nucleotides)
nt-Sequence:
atgatcgagacatacaaccagacaagccctagaagcgccgccacaggactgcctatcagcatgaagatcttcatgtacctgctgaccgtgtt cctgatcacccagatgatcggcagcgccctgtttgccgtgtacctgcacagacggctggacaagatcgaggacgagagaaacctgcacg aggacttcgtgttcatgaagaccatccagcggtgcaacaccggcgagagaagtctgagcctgctgaactgcgaggaaatcaagagccagt tcgagggcttcgtgaaggacatcatgctgaacaaagaggaaacgaagaaagagaactccttcgagatgcagaagggcgaccagaatcct cagatcgccgctcacgtgatcagcgaggccagcagcaagacaacaagcgtgctgcagtgggccgagaagggctactacaccatgagca acaacctggtcaccctggagaacggcaagcagctgacagtgaagcggcagggcctgtactacatctacgcccaagtgaccttctgcagca acagagaggccagctctcaggctcctttcatcgccagcctgtgcctgaagtctcctggcagattcgagcggattctgctgagagccgccaa cacacacagcagcgccaaaccttgtggccagcagtctattcacctcggcggagtgtttgagctgcagcctggcgcaagcgtgttcgtgaat gtgacagaccctagccaggtgtcccacggcaccggctttacatctttcggactgctgaagctgtgatgatag SEQ ID NO: 3
h4-1BBL from NCBI RefSeq NP_003802.1. (254 amino acids)
MEYASDASLDPEAPWPPAPRARACRVLPWALVAGLLLLLLLAAACAVFLACPWAVSG

ARASPGSAASPRLREGPELSPDDPAGLLDLRQGMFAQLVAQNVLLIDGPLSWYSDPGLA

GVSLTGGLSYKEDTKELVVAKAGVYYVFFQLELRRVVAGEGSGSVSLALHLQPLRSAA

GAAALALTVDLPPASSEARNSAFGFQGRLLHLSAGQRLGVHLHTEARARHAWQLTQGA

TVLGLFRVTPEIPAGLPSPRSE

SEQ ID NO: 4
h4-1BBL from NCBI RefSeq NP_003802.1.
nt sequence:
atggaatacgccagcgacgcctctctggaccctgaagctccttggcctccagctcctagagccagggcttgtagagtgctgccttgggctct tgtggctggacttctgcttctgttgctcctggctgctgcctgcgcagtgtttcttgcttgtccatgggctgtgtcaggagccagagcatctcctgg atctgccgcttctcccagactgagagagggacctgaactgagccctgatgatcctgctggactgctcgacctgagacagggcatgtttgccc agctggtggcccagaatgtgctgctgattgatggccctctgagctggtacagcgatcctggacttgctggcgttagcctgactggaggcctg agctacaaggaggacaccaaagaactggtggtggccaaggctggcgtgtactacgtgttctttcagctggaactgcggagagtggtggca ggcgaaggatctggatccgtgtctctggcactgcatctgcagcctctgagatctgctgctggtgcagctgccctggctctgacagttgatctg cctcctgcctccagcgaagccagaaacagcgcctttggcttccaaggcagactgctgcacctgtctgctggccagagactgggagtgcac ctccacacagaagcaagagcaagacacgcctggcagcttacacaaggcgctacagtgctgggcctgttcagagtgacacctgagattcca gctggcttgccatctcctcgcagcgagtaatga SEQ ID NO: 5
ERV-K-env/MEL (699 amino acids)
MNPSEMQRKAPPRRRRHRNRAPLTHKMNKMVTSEEQMKLPSTKKAEPPTWAQLKKLT

QLATKYLENTKVTQTPESMLLAALMIVSMVVSLPMPAGAAAANYTYWAYVPFPPMIR

AVTWMDNPIEVYVNDSVWVPGPIDDRCPAKPEEEGMMINISIGYRYPPICLGRAPGCLM

PAVQNWLVEVPTVSPISRFTYHMVSGMSLRPRVNYLQDFSYQRSLKFRPKGKPCPKEIP

KESKNTEVLVWEECVANSAVILQNNEFGTIIDWAPRGQFYHNCSGQTQSCPSAQVSPAV

-continued

| Sequences in sequence listing: |
|---|

DSDLTESLDKHKHKKLQSFYPWEWGEKGISTPRPKIISPVSGPEHPELWRLTVASHHIRI

WSGNQTLETRDRKPFYTVDLNSSLTVPLQSCVKPPYMLVVGNIVIKPDSQTITCENCRLL

TCIDSTFNWQHRILLVRAREGVWIPVSMDRPWEASPSVHILTEVLKGVLNRSKRFIFTLIA

VIMGLIAVTATAAVAGVALHSSVQSVNFVNDWQKNSTRLWNSQSSIDQKMLAVISCAV

QTVIWMGDRLMSLEHRFQLQCDWNTSDFCITPQIYNESEHHWDMVRRHLQGREDNLTL

DISKLKEQIFEASKAHLNLVPGTEAIAGVADGLANLNPVTWVKTIGSTTIINLILILVCLFC

LLLVCRCTQQLRRDSDHRERAMMTMAVLSKRKGGNVGKSKRDQIVTVSV

SEQ ID NO: 6
ERV-K-env/MEL
nt sequence
atgaaccctagcgagatgcagagaaaggctccacctagacggagaagacacagaaacagggctcctctgacacacaagatgaacaaga tggtcaccagcgaggaacagatgaaactgcccagcaccaagaaggccgagcctccaacatgggctcagctgaagaaactgacccagct ggccaccaagtacctggagaacaccaaagtgacccagacacctgagagcatgctgctggcagctctgatgatcgtgtccatggtggtgtc cctgcctatgcctgctggtgctgccgctgccaactacacatactgggcctacgtgccctttcctcctatgatcagagccgtgacctggatgga caaccctattgaggtgtacgtgaacgacagcgtgtgggtgccaggacctatcgacgatagatgtcctgccaaacctgaggaagagggcat gatgatcaacatcagcatcggctaccggtatcctccaatctgcctgggcagagcacctggctgtcttatgccagctgtgcagaattggctggt ggaagtgcctaccgtgtctcccatcagccggttcacctaccacatggtgtccggcatgagcctcagacctagagtgaactacttgcaggact tcagctatcagcggagcctgaagttcagacccaagggaaagccctgtcctaaagagattcccaaagagtccaagaacaccgaggtgctcg tgtgggaagagtgcgtggccaattctgccgtgatcctgcagaacaacgagttcggcaccatcattgactgggctcctagaggccagttctac cacaattgcagcggacagacacagagctgtcctagcgcacaagtgtcaccagccgtggatagcgatctgaccgagagcctggacaagca caaacacaagaaacttcagagcttctatccctgggagtggggagagaagggcatctctacaccaaggcctaagatcattagccctgtgtctg gaccagaacatcccgaactttggagactgacagtggccagccaccacatcagaatctggagcggcaatcagaccctggaaacacgggac agaaagcccttctacaccgtcgatctgaacagcagcctgaccgtgcctctccagagctgtgtgaagcctccttacatgctggtcgtgggcaa cattgtgatcaagcccgactcccagaccatcacatgcgagaactgcagactgctgacctgcatcgacagcaccttcaactggcagcaccg gatcctgctcgtgcgagctagagaaggcgtgtggatccctgtctctatggacaggccttgggaagccagccctagcgtgcacattctgaca gaggtgctgaagggcgtgctcaacagatccaagcggttcatcttcaccctgatcgccgtcatcatgggcctgattgctgtgacagccacagc tgctgttgctggcgtggccctgcatagctctgtgcagagcgtgaacttcgtgaacgattggcagaagaacagcacacggctgtggaacagc cagagcagcatcgaccagaagatgctggccgtgatctcctgtgccgtgcagacagttatctggatgggcgacagactgatgagcctggaa caccggttccagctgcagtgcgactggaataccagcgacttctgcatcacacctcagatctacaacgagagcgagcaccactgggatatg gtccgaaggcatctgcagggcagagaggacaacctgacactggacatcagcaagctgaaagagcagatcttcgaggccagcaaggctc acctgaatctggtgcctggaaccgaagctattgctggagttgcagatggcctggccaatctgaatcctgtgacctgggtcaagaccatcggc agcaccacaatcatcaacctgatcctgatcctcgtgtgcctgttttgcctgctgcttgtgtgcagatgcacccagcagctgagaagagacagc gaccatagagaaagagccatgatgaccatggccgtcctgagcaagagaaagggaggcaacgtgggcaagagcaagcgggatcagatc gtgaccgtgtccgtttgataa SEQ ID NO: 7
ERV-K-gag (666 amino acids)
MGQTKSKIKSKYASYLSFIKILLKRGGVKVSTKNLIKLFQIIEQFCPWFPEQGTLDLKDW

KRIGKELKQAGRKGNIIPLTVWNDWAIIKAALEPFQTEEDSVSVSDAPGSCIIDCNENTRK

KSQKETESLHCEYVAEPVMAQSTQNVDYNQLQEVIYPETLKLEGKGPELVGPSESKPRG

TSPLPAGQVPVTLQPQKQVKENKTQPPVAYQYWPPAELQYRPPPESQYGYPGMPPAPQ

GRAPYPQPPTRRLNPTAPPSRQGSELHEIIDKSRKEGDTEAWQFPVTLEPMPPGEGAQEG

-continued

| Sequences in sequence listing: |
|---|

EPPTVEARYKSFSIKMLKDMKEGVKQYGPNSPYMRTLLDSIAHGHRLIPYDWEILAKSS

LSPSQFLQFKTWWIDGVQEQVRRNRAANPPVNIDADQLLGIGQNWSTISQQALMQNEAI

EQVRAICLRAWEKIQDPGSTCPSFNTVRQGSKEPYPDFVARLQDVAQKSIADEKARKVI

VELMAYENANPECQSAIKPLKGKVPAGSDVISEYVKACDGIGGAMHKAMLMAQAITGV

VLGGQVRTFGGKCYNCGQIGHLKKNCPVLNKQNITIQATTGREPPDLCPRCKKGKHW

ASQCRSKFDKNGQPLSGNEQRGQPQAPQQTGAFPIQPFVPQGFQGQQPPLSQVFQGISQL

PQYNNCPPPQAAVQQ

SEQ ID NO: 8
ERV-K-gag
nt sequence
atgggacagaccaagagtaagatcaagtctaagtacgccagctacctcagcttcatcaagatcctgctgaagagaggaggcgtgaaagtgt ccaccaagaacctgatcaagctgttccagatcatcgagcagttctgtccctggtttcctgagcagggcaccctggatctgaaggactggaag cggatcggcaaagagctgaagcaggctggcagaaagggcaacatcatccctctgaccgtgtggaacgactgggccatcatcaaagcag ctctggaacccttccagaccgaagaggatagcgtgtccgtgtctgatgctcctggcagctgcatcatcgactgcaacgagaacacccggaa gaagtcccagaaagagacagagagcctgcactgcgagtacgtggccgaacctgtgatggctcagagcacccagaacgtggactacaac cagctccaagaagtgatctatcccgaaacactgaagctggaaggcaagggacctgaactcgtgggtccttctgagtctaagcccagaggc acatctcctctgcctgcaggacaggtgccagtgacactgcagcctcagaaacaagtgaaagagaacaagacccagcctcctgtggcctac cagtattggcctccagccgagctgcagtacagacctcctccagagagccagtacggctaccctggaatgcctcctgctcctcaaggcaga gctccttatcctcagcctcctaccagacggctgaaccctacagctcctcctagcagacagggctctgagctgcacgagatcattgacaagag ccggaaagagggcgacaccgaggcttggcagtttcccgttacactggaacccatgcctccaggcgaaggcgctcaagaaggcgaacct cctacagtggaagccaggtacaagagcttcagcatcaagatgctgaaggacatgaaggaaggcgtcaagcagtacggacctaacagccc atacatgcggaccctgctggattctattgcccacggccaccggctgatcccttacgattgggagatcctggctaagtcctctctgagccctag ccagttcctgcagttcaagacctggtggatcgacggcgtgcaagaacaagtgagacggaacagagctgccaatcctcctgtgaacatcga cgccgaccagctcctcggaatcggccagaattggagcaccatctctcagcaggctctgatgcagaacgaggccattgaacaagtcagagc catctgcctgagagcttgggagaagattcaggacccaggcagcacatgtcccagcttcaataccgttcggcagggcagcaaagagcccta tcctgactttgtggctagactgcaggatgtggcccagaagtctattgccgacgagaaggctcggaaagtgatcgtggaactgatggcctac gagaacgctaatccagagtgccagagcgccatcaagcccttgaagggcaaagtgcctgccggatccgatgtgatcagcgagtatgtgaa ggcctgcgacggaatcggaggtgccatgcacaaagccatgctgatggcacaggccatcactggcgttgtgctcggaggacaagttcgga cctttggaggcaagtgctacaactgtggccagatcggacacctgaagaagaactgccctgtgctgaacaagcagaacatcaccatccagg ccaccaccaccggcagagaacctccagatctgtgccctagatgcaagaagggcaagcactgggccagccagtgcagaagcaagttcga caagaacggccagcctctgagcggcaacgaacaaagaggacagcctcaggctcctcagcagactggcgcatttccaatccagcccttcg tgcctcaaggcttccagggacaacagcctccactgtctcaggtgttccagggcattagccagctccctcagtacaacaactgccctccacct caggctgctgtgcagcagtgatga SEQ ID NO: 9
hFOLR1Δ hPRAMEΔ fusion (741 amino acids)
MAQRMTTQLLLLLVWVAVVGEAQTRIAWARTELLNVCMNAKHHKEKPGPEDKLHEQ

CRPWRKNACCSTNTSQEAHKDVSYLYRFNWNHCGEMAPACKRHFIQDTCLYECSPNL

GPWIQQVDQSWRKERVLNVPLCKEDCEQWWEDCRTSYTCKSNWHKGWNWTSGFNKC

AVGAACQPFHFYFPTPTVLCNEIWTHSYKVSNYSRGSGRCIQMWFDPAQGNPNEEVAR

FYAAAMERRRLWGSIQSRYISMSVWTSPRRLVELAGQSLLKDEALAIAALELLPRELFPP

LFMAAFDGRHSQTLKAMVQAWPFTCLPLGVLMKGQHLHLETFKAVLDGLDVLLAQEV

Sequences in sequence listing:

RPRRWKLQVLDLRKNSHQDFWTVWSGNRASLYSFPEPEAAQPMTTKAKVDGLSTEAE

QPFIPVEVLVDLFLKEGACDELFSYLIEKVAAKKNVLRLCCKKLKIFAMPMQDIKMILK

MVQLDSIEDLEVTCTWKLPTLAKFSPYLGQMINLRRLLLSHIHASSYISPEKEEQYIAQFT

SQFLSLQCLQALYVDSLFFLRGRLDQLLRHVMNPLETLSITNCRLSEGDVMHLSQSPSVS

QLSVLSLSGVMLTDVSPEPLQALLERASATLQDLVFDECGITDDQLLALLPSLSHCSQLT

TLSFYGNSISISALQSLLQHLIGLSNLTHVLYPVPLESYEDIHGTLHLERLAYLHARLRELL

CELGRPSMVWLSANPCPHCGDRTFYDPEPILCPCFMPN

SEQ ID NO: 10
hFOLR1Δ hPRAMEΔ fusion (741 amino acids)
nt sequence
tggcccagagaatgaccacacaactgctgctgctcctggtgtgggttgccgttgttggagaggcccagaccagaattgcctgggccagaa ccgagctgctgaacgtgtgcatgaacgccaagcatcacaaagagaagcctggacctgaagacaagctgcatgaacagtgtcggccttgg agaaagaatgcttgctgtagcaccaacaccagccaagaggcccacaaggacgtgtcctacctgtaccggttcaactggaaccactgcgga gaaatggctcctgcctgcaagagacacttcatccaggatacctgcctgtacgagtgctctcccaatctcggaccttggatccagcaagtgga ccagagctggcggaaagaacgggtgctgaatgtgcccttgtgcaaagaggattgcgagcagtggtgggaagattgccggaccagctaca catgtaagagcaactggcacaaaggctggaactggaccagcggcttcaacaagtgtgccgtgggagctgcctgccagcctttccacttcta cttcccaacacctaccgtgctgtgcaacgaaatctggacccacagctacaaggtgtccaactacagcagaggcagcggcaggtgtatcca gatgtggttcgatcccgctcagggcaatcccaatgaggaagtggctagattctacgctgctgccatggaaagaagaaggctctggggcag catccagagccggtacattagcatgagcgtgtggacaagccctagacggctggttgaactggctggacagagcctgctcaaggatgaggc cctggccattgctgctctggagctgctgcctagagagctgttccctcctctgttcatggctgccttcgacggcagacacagccagacactgaa agccatggtgcaggcctggcctttcacctgtctgcctctgggagtgctgatgaagggccagcatctgcacctggaaaccttcaaggccgtg ctggacggcctggatgttctcctggctcaagaggtgaggcctcggcgttggaaactgcaggttctggatctgcggaagaactctcaccagg atttctggaccgtttggtccggcaacagagccagcctgtacagctttcctgaacctgaggctgcccagcccatgaccacaaaggccaaagt ggatggcctgagcacagaggccgagcagcctttcattcccgtcgaagtgctggtggacctgttcctgaaagaaggagcctgcgatgagct gttcagctacctgattgagaaggtggcagccaagaagaacgtgctgcggctgtgctgcaagaagctgaagatctttgccatgcctatgcag gatatcaagatgatcctgaagatggtgcagctggacagcatcgaggacctggaagtgacctgtacctggaagctgcccacactggccaag ttcagcccttacctgggacagatgattaacctgcggaggctgctgctgtctcacatccacgccagctcctacatcagccctgagaaagagga acagtatatcgcccagttcacaagccagtttctgagcctgcagtgtctgcaggccctgtacgtggacagcctgttctttctgagaggcaggct ggatcagctgctgcggcacgtgatgaaccctctggaaaccctgagcatcaccaactgtagactgagcgagggcgacgtgatgcacctgtc tcagagcccatctgtgtctcagctgagcgtgctgtctctgtctggcgtgatgctgaccgatgtgagccctgaacctctgcaggcactgctgga aagagcctccgctactctgcaggacctggtgttcgatgagtgcggcatcaccgatgaccagctgcttgctctgctgccaagcctgagccact gtagccagctgacaaccctgtccttctacggcaacagcatctccatctctgccctgcagtctctcctgcagcatctgatcggcctgtccaatct gacccacgtgctgtaccctgtgccactggaaagctacgaggacatccacggaaccctgcacctcgagagactggcctatctgcatgctcg gctgagagaactgctgtgcgaactgggcagacccagcatggtttggctgagcgccaatccatgtcctcactgtggcgaccggaccttctac gaccctgagcctatcctgtgtccttgcttcatgcccaactaatag SEQ ID NO: 11
ERV-K-env/MEL_03 (517 amino acids)
MNPSEMQRKAPPRRRRHRNRAPLTHKMNKMVTSEEQMKLPSTKKAEPPTWAQLKKLT

QLATKYLENTKVTQTPESMLLAALMIVSMVVSLPMPAGAAAANYTYWAYVPFPPMIR

AVTWMDNPIEVYVNDSVWVPGPIDDRCPAKPEEEGMMINISIGYRYPPICLGRAPGCLM

PAVQNWLVEVPTVSPISRFTYHMVSGMSLRPRVNYLQDFSYQRSLKFRPKGKPCPKEIP

-continued

| Sequences in sequence listing: |
| --- |
| KESKNTEVLVWEECVANSAVILQNNEFGTIIDWAPRGQFYHNCSGQTQSCPSAQVSPAV<br><br>DSDLTESLDKHKHKKLQSFYPWEWGEKGISTPRPKIISPVSGPEHPELWRLTVASHHIRI<br><br>WSGNQTLETRDRKPFYTVDLNSSLTVPLQSCVKPPYMLVVGNIVIKPDSQTITCENCRLL<br><br>TCIDSTFNWQHRILLVRAREGVWIPVSMDRPWEASPSVHILTEVLKGVLNMLAVISCAV<br><br>AGVALHGSAGSAAGSGEFVVISAILALVVLTIISLIILIMLWQKKPR |
| SEQ ID NO: 12<br>ERV-K-env/MEL 03<br>nt sequence<br>atgaaccctagcgagatgcagagaaaggctccacctagacggagaagacacagaaacagggctcctctgacacacaagatgaacaaga<br><br>tggtcaccagcgaggaacagatgaaactgcccagcaccaagaaggccgagcctccaacatgggctcagctgaagaaactgacccagct<br><br>ggccaccaagtacctggagaacaccaaagtgacccagacacctgagagcatgctgctggcagctctgatgatcgtgtccatggtggtgtc<br><br>cctgcctatgcctgctggtgctgccgctgccaactacacatactgggcctacgtgccctttcctcctatgatcagagccgtgacctggatgga<br><br>caaccctattgaggtgtacgtgaacgacagcgtgtgggtgccaggacctatcgacgatagatgtcctgccaaacctgaggaagagggcat<br><br>gatgatcaacatcagcatcggctaccggtatcctccaatctgcctgggcagagcacctggctgtcttatgccagctgtgcagaattggctggt<br><br>ggaagtgcctaccgtgtctcccatcagccggttcacctaccacatggtgtccggcatgagcctcagacctagagtgaactacttgcaggact<br><br>tcagctatcagcggagcctgaagttcagacccaagggaaagccctgtcctaaagagattcccaaagagtccaagaacaccgaggtgctcg<br><br>tgtgggaagagtgcgtggccaattctgccgtgatcctgcagaacaacgagttcggcaccatcattgactgggctcctagaggccagttctac<br><br>cacaattgcagcggacagacacagagctgtcctagcgcacaagtgtcaccagccgtggatagcgatctgaccgagagcctggacaagca<br><br>caaacacaagaaacttcagagcttctatccctgggagtggggagagaagggcatctctacaccaaggcctaagatcattagccctgtgtctg<br><br>gaccagaacatcccgaactttggagactgacagtggccagccaccacatcagaatctggagcggcaatcagaccctggaaacacgggac<br><br>agaaagcccttctacaccgtcgatctgaacagcagcctgaccgtgcctctccagagctgtgtgaagcctccttacatgctggtcgtgggcaa<br><br>cattgtgatcaagcccgactcccagaccatcacatgcgagaactgcagactgctgacctgcatcgacagcaccttcaactggcagcaccg<br><br>gatcctgctcgtgcgagctagagaaggcgtgtggatccctgtctctatggacaggccttgggaagccagccctagcgtgcacattctgaca<br><br>gaggtgctgaagggcgtgctcaacatgctggccgtgatctcctgtgccgtggctggcgtggccctgcatggctctgctggatctgctgctgg<br><br>aagcggcgagttcgtggtcatctctgccattctggctctggtggtgctgaccatcatcagcctgatcatcctgattatgctgtggcagaagaag<br><br>ccccggtgataa |

We claim:

1. A recombinant modified Vaccinia virus Ankara (MVA) comprising:

(i) a nucleic acid encoding HERV-K-env/MEL and having the nucleotide sequence set forth in SEQ ID NO:12 or encoding the amino acid sequence set forth in SEQ ID NO:11;

(ii) a nucleic acid encoding HERV-K gag;

(iii) a nucleic acid encoding FOLR1 and PRAME; and (iv) a nucleic acid encoding 4-1BBL.

2. The recombinant MVA according to claim 1 further comprising:

(v) a nucleic acid encoding CD40L.

3. The recombinant MVA of claim 1 that comprises MVA-BN as deposited at the European Collection of Cell Cultures (ECACC) under number V00083008.

4. A pharmaceutical preparation or composition comprising a recombinant MVA according to claim 1.

5. The pharmaceutical preparation or composition according to claim 4 which is adapted to intratumoral and/or intravenous administration.

6. The recombinant MVA of claim 1, wherein the nucleic acid of (iii) encodes FOLR1 and PRAME as a fusion protein.

7. The recombinant MVA of claim 1, wherein the nucleic acid encoding HERV-K-env/MEL encodes the protein sequence set forth in SEQ ID NO:11.

8. The recombinant MVA of claim 1, wherein the nucleic acid of (iii) encodes FOLR1 and PRAME as a fusion protein having the sequence set forth in SEQ ID NO:9.

* * * * *